US007501518B2

(12) United States Patent
Chen et al.

(10) Patent No.: US 7,501,518 B2
(45) Date of Patent: Mar. 10, 2009

(54) METHODS OF MAKING 2,6-DIARYL PIPERIDINE DERIVATIVES

(75) Inventors: Gang Chen, Langley (CA); Jason Crawford, Burnaby (CA); Renato Skerlj, Vancouver (CA)

(73) Assignee: Genzyme Corporation, Cambridge, MA (US)

( * ) Notice: Subject to any disclaimer, the term of this patent is extended or adjusted under 35 U.S.C. 154(b) by 539 days.

(21) Appl. No.: 10/977,221

(22) Filed: Oct. 28, 2004

(65) Prior Publication Data
US 2005/0154201 A1  Jul. 14, 2005

Related U.S. Application Data

(63) Continuation-in-part of application No. 10/831,098, filed on Apr. 22, 2004.

(60) Provisional application No. 60/505,230, filed on Sep. 22, 2003, provisional application No. 60/464,858, filed on Apr. 22, 2003.

(51) Int. Cl.
C07D 213/127 (2006.01)
(52) U.S. Cl. ...................... 546/193; 514/318
(58) Field of Classification Search ............ 514/318; 546/193
See application file for complete search history.

(56) References Cited

U.S. PATENT DOCUMENTS

| 5,021,409 | A | 6/1991 | Murrer et al. ............. 514/183 |
| 5,235,056 | A | 8/1993 | Cunkle et al. |
| 5,582,823 | A | 12/1996 | Souza ..................... 424/85.2 |
| 5,583,131 | A | 12/1996 | Bridger et al. ............ 514/183 |
| 5,698,546 | A | 12/1997 | Bridger et al. ............ 514/183 |
| 5,817,807 | A | 10/1998 | Bridger et al. ............ 540/474 |
| 6,001,826 | A | 12/1999 | Murrer et al. ............. 514/183 |
| 6,365,583 | B1 | 4/2002 | MacFarland et al. ....... 514/183 |
| 2004/0110304 | A1 | 6/2004 | Canary et al. |

FOREIGN PATENT DOCUMENTS

| WO | WO 00/56729 | 9/2000 |
| WO | WO 02/22599 | 3/2002 |
| WO | WO 02/22600 | 3/2002 |
| WO | WO 02/34745 | 5/2002 |
| WO | WO-02/076948 | 10/2002 |
| WO | WO-2006/138259 | 12/2006 |

OTHER PUBLICATIONS

Xu, Xiaodong "Design and Synthesis of Enantiosensors Based on Metal-Ligand Complexes" Ph.D. Dissertation, New York University, 2000.*
Jones, Maitland Organic Chemistry Norton: New York, 1997, p. 84-99.*
Daintith, J. A Dictionary of Chemistry, 3rd Edition Oxford: New York, 1996, p. 144.*
Greene and Wuts, Protective Groups in Organic Synthesis 3rd edition Wiley: New York, 1999 p. 601.*
Dorwald F. A. Side Reactions in Organic Synthesis, 2005, Wiley: VCH, Weinheim p. IX of Preface p. 1-15, 41.*
Database CA, No. 125:31527, Cohen et al. (1996).
Database Caplus, No. 64:27414, Haller (1966).
Database Caplus, No. 133:99145, Hendrix et al. (2000).
Database Caplus on STN, No. 138:82433, Borezel et al. (2002).
Dai et al., Chem Commun (2002) 1414-1415.
Kirkland et al., Blood (May 1996) 87(9):3963-3969.
Silverman, *Organic Chemistry of Drug Design and Drug Action*, Academic Press, Inc., 1993, p. 73.
Database Caplus on STN, No. 137:256911, Dai et al. (2002).
Database Caplus on STN, No. 112:56585, Khorlin et al. (1990).
Database Caplus on STN, No. 83:58606, Ram et al. (1974).
Database Caplus on STN, No. 50:1538, Baliah et al. (1954).
Database Caplus on STN, No. 120:191489, Pillay et al. (1993).
Database Caplus on STN, No. 140:16629, Mamutova et al. (2003).
Database Caplus on STN, No. 112:7331, Mobio et al. (1989).
Database Caplus on STN, No. 80:36962, Azerbaev et al. (1973).
Database Caplus on STN, No. 94:103485, Abiyurov et al. (1980).
Database Caplus on STN, No. 115:192267, Rajanarayanan et al. (1991).
Database Caplus on STN, No. 137:125068, Kim et al. (2002).
Database Caplus on STN, No. 88:62271, Abdullaev et al. (1977).
Database Caplus on STN, No. 79:42294, Radhakrisha et al. (1973).
Database Caplus on STN, No. 55:38053, Merz et al. (1960).
International Search Report for PCT/US05/34950, mailed on Oct. 4, 2006, 4 pages.
Written Opinion of the International Searching Authority for PCT/US05/34950, mailed on Oct. 4, 2006, 3 pages.
Database Caplus on STN, No. 52:25483, Potts et al., (1957), see RN 77898-87-4.
Database Caplus on STN, No. 134:326532, Sircar et al., PCT (2001), see RN 336813-07-1.
International Search Report for PCT/US04/12627, mailed on Jan. 13, 2005, 3 pages.
Abi-Younes, et al., Circ. Res. (2000) 86:131-138.
Aiuti, et al., J. Exp. Med. (1997) 185:111-120.
Alkhatib, et al., Science (1996) 272:1955-1958.
Arai, et al., Eur. J. Haematol. (2000) 64:323-332.
Blaak, et al., Proc. Natl. Acad. Sci. (2000) 97:1269-1274.
Blanco, et al., Antimicrobial Agents and Chemother. (2000) 44:51-56.
Bleul, et al., J. Exp. Med. (1998) 187:753-762.
Bleul, et al., Nature (1996) 382:829-833.
Bradstock, et al., Leukemia (2000) 14:882-888.
Bridger, et al., J. Med. Chem. (1999) 42:3971-3981.
Broxmeyer, et al., Exp. Hematol. (1995) 23:335-340.
Broxmeyer, et al., Blood Cells, Molecules and Diseases (1998) 24:14-30.
Burger, et al., Blood (1999) 94:3658-3667.
Carroll, et al., Science (1997) 276:273-276.
Cocchi, et al., Science (1995) 270:1811-1815.

(Continued)

*Primary Examiner*—Janet L Andres
*Assistant Examiner*—David K O'Dell
(74) *Attorney, Agent, or Firm*—Morrison & Foerster LLP

(57) ABSTRACT

Methods for preparing 2,6-diaryl piperidine derivatives are described. More particularly, 2,6-diaryl piperidines having formula 1-4 are prepared by cyclocondensation of an aryl or heteroaryl aldehyde with 1,3-acetonedicarboxylic acid.

6 Claims, No Drawings

OTHER PUBLICATIONS

Comba, et al., Eur. J. Inorg. Chem. (2003) 1711-1718.
Connor, J. Virol, et al. (1994) 68:4400-4408.
Dale, et al., Am J Hematol (1998) 57:7-15.
Deng, et al., Nature (1996) 381:661-666.
Diaz, et al., Spectrochimica Acta Part A (2000) 56:2191-2201.
Donzella, et al., Nature Medicine (1998) 4:72-77.
Dragic, et al., Nature (1996) 381:667-673.
Egberink, et al., J. Virol. (1999) 73:6346-6352.
Eitner, et al., Transplantation (1998) 66:1551-1557.
Fedyk, et al., J. Leukocyte Biol. (1999) 66:667-673.
Feng, et al., Science (1996) 272:872-877.
Glaspy, et al., Cancer Chemother. Pharmacol. (1996) 38 (suppl): S53-S57.
Glaspy, et al., Blood (1997) 90:2939-2951.
Gonzalo, et al., J. Immunol. (2000) 165:499-50.
Gupta, et al., J. Biolog. Chem. (1998) 273(7):4282-4287.
Haller, Archiv. Pharmaz. (1967) 300:119-125.
Ishii, et al., J. Immunol. (1999) 163:3612-3620.
King, et al., Blood (2001) 97:1534-1542.
Lataillade, et al., Blood (2000) 95:756-768.
Liu, et al., Cell (1996) 86:367-377.
Ma, et al., Immunity (1999) 10:463-471.
Maekawa, et al., Internal Medicine (2000) 39:90-100.
Michael, et al., Nature Med. (1997) 3:338-340.
Michael, et al., J. Virol. (1998) 72:6040-6047.
Miedema, et al., Immune. Rev. (1994) 140:35-72.
Moore, et al., J. Invest. Med. (1998) 46:113-120.
Moore, et al., Trends Cardiovasc. Med. (1998) 8:51-58.
Nagasawa, et al., Nature (1996) 382:635-638.
Nagase, J. Immunol. (2000) 164:5935-5943.
Nanki, et al., J. Immunol. (2000) 164:5010-5014.
Oberlin, et al., Nature (1996) 382:833-835.
O'Brien, et al., Lancet (1997) 349:1219.
Peled, et al., Science (1999) 283:845-848.
Peled, et al., Blood (2000) 95:3289-3296.
Ponath, Exp. Opin. Invest. Drugs (1998) 7:1-18.
Potts and Smith, J. Chem. Soc. (1957) 4018-4022.
Pruijt, et al., Cur. Op. in Hematol. (1999) 6:152-158.
Rana, et al., J. Virol. (1997) 71:3219-3227.
Rosenfeld, et al., Bone Marrow Transplantation (1996) 17:179-183.
Salcedo, et al., Am. J. Pathol. (1999) 154:1125-1135.
Samhammer, et al., Arch. Pharm. (Weinheim) (1998) 322:551-555.
Samson, et al., Nature (1996) 382:722-725.
Schols, et al., J. Exp. Med. (1997) 186:1383-1388.
Schols, et al., Antiviral Research (1997) 35:147-156.
Schuitemaker, et al., J. Virol. (1992) 66:1354-1360.
Seghal, et al., J. Surg. Oncol. (1998) 69:99-104.
Simmons, et al. J. Virol. (1996) 70:8355-8360.
Simmons, et al., J. Virol. (1988) 72:8453-8457.
Tachibana, et al., Nature (1998) 393:591-594.
Tersmette, et al., J. Virol. (1988) 62:2026-2032.
Theodorou, et al., Lancet (1997) 349:1219-1220.
Vadhan-Raj, et al., Ann. Intern. Med. (1997) 126:673-681.
Viardot, et al., Ann. Hematol. (1998) 77:193-197.
Wyatt, et al., Science (1998) 280:1884-1888.
Xia, et al., J. Neurovirology (1999) 5:32-41.
Yssel, et al., Clinical and Experimental Allergy (1998) 28:104-109.
Zhao, et al., J. Chem. Research (S) (1999), 312-313.
Zhang, et al., AIDS Res. Hum. Retroviruses (1997) 13:1357-1366.
Zhang, et al., J. Virol. (1998) 72:9307-9312.
Zhang, et al., J. Virol. (1999) 73:3443-3448.
Supplementary Partial European Search Report for EP 04814091.7, mailed Mar. 10, 2008, 4 pages.
Siener et al., J. Med. Chem. (2000) 43:3746-3751.
Supplementary Partial European Search Report for EP 04760161.2, mailed Jun. 10, 2008, 3 pages.
Database CA, No. 125:31527, Cohen et al. (1996).
Database CAPLUS, No. 64:27414, Haller (1966).
Database CAPLUS, No. 133:99145, Hendrix et al. (2000).
Database CAPLUS on STN, No. 138:82433, Borezel et al. (2002).
Bundgaard, ed., *Design of prodrugs*, Elsevier Science Publishers B.V., 1985, chapter 1, p. 1.
Dai et al., Chem Commun (2002) 1414-1415.
Kirkland et al., Blood (May 1996) 87(9):3963-3969.
Pike et al., *Nutrition An Integrated Approach*, 3rd Ed., John Wiley & Sons, 1984, pp. 538-539.
Silverman, *Organic Chemistry of Drug Design and Drug Action*, Academic Press, Inc., 1993, p. 73.
Database CAPLUS, No. 116:206551, Haanstra et al. (1992).

* cited by examiner

METHODS OF MAKING 2,6-DIARYL PIPERIDINE DERIVATIVES

CROSS-REFERENCE TO RELATED APPLICATIONS

This application is a continuation-in-part of U.S. patent application Ser. No. 10/831,098, filed Apr. 22, 2004, which claims priority to U.S. provisional patent application Ser. Nos. 60/505,230, filed Sep. 22, 2003, and 60/464,858, filed Apr. 22, 2003, which are incorporated by reference in this application.

TECHNICAL FIELD

This invention generally relates to methods of making 2,6-diaryl piperidine derivatives.

BACKGROUND ART

Certain diaryl piperidines have been shown to exhibit pharmacological properties (See, e.g., U.S. Pat. No. 4,707,486). The preparation of diaryl piperidines has also been described. (See, e.g., Haller, R., *Arch. Pharmaz.* (1965) 298:787; Davis, F. A., et al., *Org. Lett.* (2001) 3:3169; Pandiarajan, et al., *Indian J. Chem. Sect. B.* (1987) 26B:624; Galves, et al., *J. Heterocyclic Chem.* (1992) 29:1797; Ramalingam, et al., *J. Org. Chem.* (1979) 44:471; and Poerwono, et al., *Heterocycles* (1997) 46:385). Because of the utility of these compounds, there continues to be a need for new methods of preparing diaryl piperidines.

DISCLOSURE OF THE INVENTION

The present invention generally relates to methods of making 2,6-diaryl piperidine derivatives, and more particularly to compounds having formulas 1-4 and derivatives thereof.

In one aspect, the present invention provides a method for making a compound of formula (1)

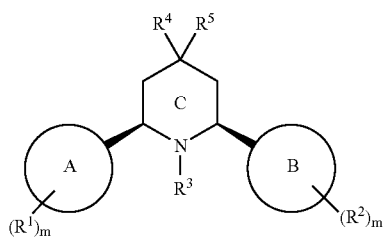

(1)

comprising contacting two equivalents of an aryl or heteroaryl carboxaldehyde with a primary amine or an ammonium salt, and 1,3-acetonedicarboxylic acid in an organic solvent to produce a compound having formula (2),

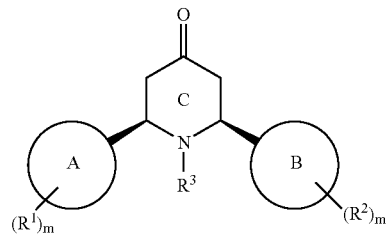

(2)

and optionally converting the carbonyl group in formula 2 to a carbonyl derivative obtainable by reduction or nucleophilic addition;

wherein in each compound having formula (1) and (2), each of rings A and B is an optionally substituted aryl or heteroaryl;

ring C is a saturated 6-membered ring;

m is 0-4;

$R^1$ and $R^2$ are independently H or a non-interfering substituent;

$R^3$ is H, alkyl, allyl or benzyl; and each $R^4$ and $R^5$ is H, halo, hydroxyl, alkoxyl, alkyl, cyano or aryl; or $R^4$ and $R^5$ together form a carbonyl, oxime or imine.

In one example, the method further comprises reacting the carbonyl group in formula 2 with a nucleophile.

In another example, the method further comprises reducing the carbonyl group in formula 2 using a reducing agent known in the art. For example, the carbonyl group may be reduced with a metal hydride or reduced using hydrazine and a base.

Examples of primary amine reagent for use in the above methods include but are not limited to methylamine, allylamine or benzylamine. Examples of ammonium salt for use in the above methods include but are not limited to ammonium acetate or ammonium hydroxide.

Examples of organic solvent for use in the above methods include but are not limited to methylene chloride, chloroform, or a lower alkyl alcohol such as methanol, ethanol, isopropanol or propanol.

In one example, the aryl or heteroaryl carboxaldehyde has a concentration between 0.1 M to 1 M. In other examples, the aryl or heteroaryl carboxaldehyde has a concentration of about 0.5 M.

In the above methods, the reaction may be conducted at a temperature between −20° C. and 25° C. For example, the reaction may be conducted at room temperature.

Furthermore, the present invention provides a method of making a compound of formula (3)

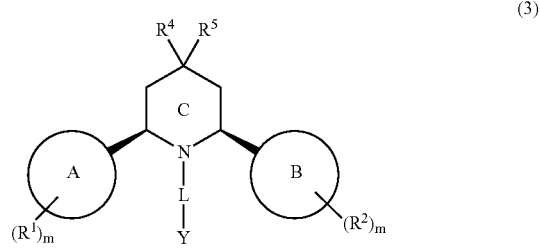

(3)

comprising contacting a compound having formula (4)

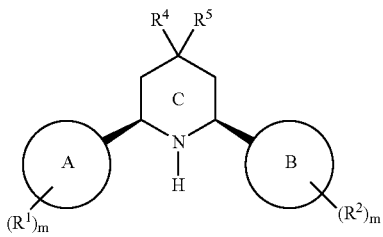

with a compound having the formula X-L-Y.
wherein X is a leaving group;
L is $(CR^6{}_2)_l$ wherein an alkyl bond may be replaced with an alkenyl or alkynyl bond, each $R^6$ is H or alkyl, and l is 1-6;
Y is H, a $C_{1-6}$ alkyl containing one or more heteroatoms, or an aryl, heteroaryl, or heterocyclic moiety, each of which is optionally substituted;
wherein in each compound having formulas (3) and (4), each of rings A and B is an optionally substituted aryl or heteroaryl;
ring C is a saturated 6-membered ring;
m is 0-4;
$R^1$ and $R^2$ are independently H or a non-interfering substituent; and
each $R^4$ and $R^5$ is H, halo, hydroxyl, alkoxyl, alkyl, cyano or aryl; or $R^4$ and $R^5$ together form a carbonyl, oxime or imine.

In the above formula X-L-Y, X may be halo, such as bromo, iodo, chloro or fluoro. Examples of Y substrates include but are not limited to phenyl, imidazole, pyridine, thiophene, pyrrolidine, pyrazole, piperidine, azetidine, benzimidazole, benzo[d]isoxazole, or thiazole.

In the above formula X-L-Y, Y may optionally be substituted with halo; cyano; nitro; hydroxy optionally substituted with alkyl or halogenated alkyl; substituted carbonyl; or an optionally substituted cyclic moiety, alkyl, alkenyl, or heteroalkyl moiety optionally containing one or more N, O, S, each of which is optionally in the form of oxides. In one example, the cyclic moiety is an optionally substituted aromatic or heteroaromatic moiety of 5-12 ring members. Examples of cyclic moieties include but are not limited to pyridine, phenyl, piperidine or 2H-tetrazole.

In the above formula X-L-Y, Y may be selected from the group consisting of,
—$(CR_2)_m NR_2$,
—$(CR_2)_m NR_2(CR_3)$,
—$(CR_2)_m NR(CR_2)_m NR_2$,
—$(CR_2)_m NR(CR_2)_m NR(CR_2)_m NR_2$,
—$(CR_2)_m OR$,
—$(CR_2)_m CO(CR_2)_m OR$,
—$(CR_2)_m CO(CR_2)_m NR_2$,
—$(CR_2)_m CO(CR_2)_m NR(CR_2)_m NR_2$,
—$(CR_2)_m NRCO(CR_2)_m NR_2$,
—$(CR_2)_m NR(CR_2)_m CO_2 R$,
—$(CR_2)_m NR(CR_2)_m COR$,
—$(CR_2)_m NR(CR_2)_m SO_2 R$,
—$(CR_2)_m NRCO(CR_2)_m NR(CR_2)_m NR_2$,
—$(CR_2)_m NRCO(CR_2)_m NR(CR_2)_m NR(CR_2)_m NR(CR_2)_m NR_2$,
—$(CR_2)_m NR(CR_2)_m OR$,
—$(CR_2)_m CR=NOH$,
—$(CR_2)_m CONR(CR_2)_m OR$,
—$(CR_2)_m N[(CR_2)_m CO_2 R]_2$,
—$(CR_2)_m ONRCONR_2$,
—$(CR_2)_m$-Z
—$(CR_2)_m NR$—$(CO)_m Z$,
—$(CR_2)_m NR$—$(CR_2)_m Z$, and
—$(CR_2)_m$—$CR=N=Z$;
each R is independently H or an non-interfering substituent,
each m is independently 0-4; and Z is an optionally substituted aromatic or heteroaromatic moiety containing 5-12 ring members.

In one example, Y is $(CH_2)_l NR_2$ where R is H or alkyl, and l is 1-10. In embodiments where Y includes Z, Z may be partially saturated nitrogen containing rings. In addition, an embodiment for Y includes, for example, an inorganic moiety. As used herein, "inorganic moiety" refers to a moiety that does not contain carbon. Examples include, but are not limited to, halo, hydroxyl, SH, $NO_2$ or $NH_2$.

In the above formula 1-4, the substituent on optionally substituted rings may be selected from the group consisting of inorganic moieties, alkyl ($C_{1-10}$), alkenyl ($C_{2-10}$), alkynyl ($C_{2-10}$), aryl (5-12 members), arylalkyl, arylalkenyl, and arylalkynyl, each of which may optionally contain one or more heteroatoms selected from O, S, and N and each of which may further be substituted.

In the above formula 1-3, $R^3$ may be H.

In the above formula 1-4, $R^1$ and $R^2$ may independently be H, alkyl, or halo. Each $R^1$ and $R^2$ may be at positions adjacent the bonds to ring C. Furthermore, each $R^1$ and $R^2$ may be identical.

In the above formula 1-4, each of rings A and B may be pyridine, pyrimidine, pyrazine, pyridazine, 1,2,3-triazine, 1,2,4-triazine, 1,3,5-triazine, 1,2,4,5-tetrazine, pyrrole, imidazole, pyrazole, 1,2,3-triazole, 1,2,4-triazole, tetrazole, thiazole, oxazole, isothiazole, isoxazole, 1,2,3-thiadiazole, 1,3,4-thiadiazole, 1,2,3-oxadiazole, 1,3,4-oxadiazole, quinoline, isoquinoline, quinoxaline, quinazoline, pthalazine, cinnoline, 1,2,3-benzotriazine, 1,2,4-benzotriazine, indole, benzimidazole, 1H-indazole, benzoxazole, benzthiazole, benz[d]isoxazole, benz[d]isothiazole, or purine. In particular examples, each of rings A and B may be pyridine, pyrimidine, imidazole or benzimidazole. Furthermore, each of rings A and B may be identical.

In the above formula 1-4, each ring C is piperidine.

In the above formula 1-4, each compound may be a cis-isomer. Furthermore, each compound in the above formula 1-4 may be a meso compound.

In the above formula 1-4, a "non-interfering substituent" generally refers to a substituent whose presence does not destroy the effectiveness of the compound. Examples of non-interfering substituents may include alkyl ($C_{1-10}$), alkenyl ($C_{2-10}$), alkynyl ($C_{2-10}$), aryl ("C"$_{5-12}$), arylalkyl, arylalkenyl, or arylalkynyl, each of which may optionally contain one or more heteroatoms selected from O, S, and N and each of which may further be substituted; or optionally substituted forms of acyl, arylacyl, alkyl-alkenyl-, alkynyl- or arylsulfonyl and forms thereof which contain heteroatoms in the alkyl, alkenyl, alkynyl or aryl moieties. Other noninterfering substituents include OR, SR, $NR_2$, COOR, $CONR_2$, where R is H or alkyl, alkenyl, alkynyl or aryl as defined above. Where the substituted atom is C, the substituents may include, in addition to the substituents listed above, halo, OOCR, NROCR, where an R is H or a substituent set forth above, or may be =O, or may be NO$_2$, SO$_2$R, SOR, CN, CF$_3$, OCF$_3$ or =NOR.

MODES OF CARRYING OUT THE INVENTION

The invention provides a method for preparing a compound of formula (1)

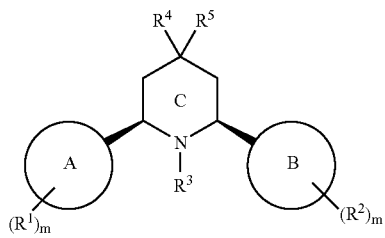

(1)

comprising contacting two equivalents of an aryl or heteroaryl carboxaldehyde with a primary amine or an ammonium salt, and 1,3-acetonedicarboxylic acid in an organic solvent to produce a compound having formula (2),

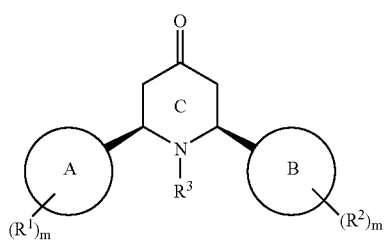

(2)

and optionally converting the carbonyl group in formula 2 to a carbonyl derivative obtainable by reduction or nucleophilic addition;
wherein in each compound having formula (1) and (2), each of rings A and B is an optionally substituted aryl or heteroaryl;
ring C is a saturated 6-membered ring;
m is 0-4;
R$^1$ and R$^2$ are independently H or a non-interfering substituent;
R$^3$ is H, alkyl, allyl or benzyl; and
each R$^4$ and R$^5$ is H, halo, hydroxyl, alkoxyl, alkyl, cyano or aryl; or R$^4$ and R$^5$ together form a carbonyl, oxime or imine.

In the above methods, the substituents on compounds having formulas (1) and (2) are as previously defined.

Scheme 1 illustrates the methods for efficient formation of compounds of formula (2) via a cyclocondensation reaction, followed by a spontaneous decarboxylation.

Scheme 1

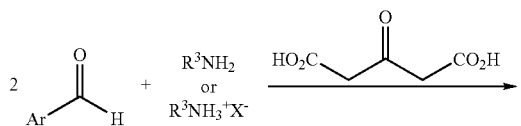

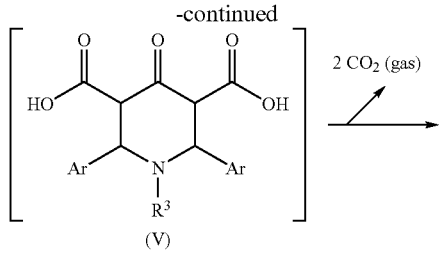

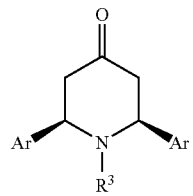

As shown in Scheme 1, two equivalents of an aryl carboxaldehyde are reacted with one equivalent of a primary amine reagent (R$^3$NH$_2$) or salt (R$^3$NH$_3^+$X$^-$) where X$^-$ is a counterion and each R$^3$ is independently H or alkyl, and one stoichiometric equivalent of 1,3-acetonedicarboxylic acid in such a way that gas evolution is controlled. In one example, the carboxaldehyde is contacted with the amine reagent in an organic solvent, followed by addition of the 1,3-acetonedicarboxylic acid. The reaction may be stirred over a duration of 1-24 hours before being concentrated.

Examples of organic solvents include but are not limited to dichloromethane, chloroform, and lower alkyl alcohols such as methanol, ethanol, isopropanol, or propanol. In one example, the organic solvent is methanol.

Examples of amine reagents include but are not limited to ammonium acetate, ammonium hydroxide, methylamine, allylamine, or benzylamine. In one example, the amine reagent is ammonium acetate.

Reaction concentrations typically range from 0.1 M to 1 M. In one example, the aryl carboxaldehyde reagent has a concentration in the 0.5 M range. Temperatures for the reaction are from −20° C. to ambient, with particular temperature being from 0° C. to ambient, or near 23° C.

Gas evolution during the addition of 1,3-acetonedicarboxylic acid is caused by spontaneous decarboxylation of the initial diacid intermediate formed during the cyclocondensation reaction. (See Scheme 1). The rate of addition of the 1,3-acetonedicarboxylic acid to the reaction is controlled, such that the rate of gas evolution can be controlled as well.

The stereochemical outcome of the cyclocondensation gives the cis-product preferentially or exclusively with respect to the spatial orientation of the two aryl groups (rings A and B). Confirmation of the stereochemical outcome is made by comparison of $^1$H Nuclear Magnetic Resonance (NMR) spectral data to analogous compounds in the literature (Fernandez, M. J., et al., *J. Heterocyclic Chem.* (1992) 29:1797; Poerwono, H., et al., *Heterocycles* (1997) 46:385). (See also, Mannich, et al., *Chem Ber.* (1930) 63:608; *J. Indian Chem. Soc.* (1951) p. 405; Holzgrabe, et al., *Arch. Pharm.* (1992) p. 657; *J. Med. Chem* (2000) p. 3746; *J. Chem. Soc. Perkin Trans.* (1999) 2:1827; *Chem. Ber.* (1965) 98:2317; *J. Indian Chem. Soc.* (1948) p. 437; *Acta Chem Acad Sci, Hung.* (1959) p. 97; *Arch. Pharm* (2000) p. 226; and *Eur. J. Inorg. Chem.* (2003) p. 1711).

The course of the cyclocondensation reaction can be followed by $^1$H NMR or by thin layer chromatography. When complete (as typically judged by the consumption of aldehyde), the reaction is concentrated, then taken up in dichloromethane and washed with an aqueous sodium carbonate or sodium bicarbonate solution. The organic layer is then dried, typically with anhydrous sodium sulfate or magnesium sulfate, and is then concentrated. The residue can be used in the next reaction without further purification, or can alternatively be purified by silica gel flash chromatography.

Furthermore, the carbonyl functionality in formula 2 may be converted to a carbonyl derivative using methods known in the art. (See, e.g., Wade, Jr., *Organic Chemistry*, Prentice Hall (1987) Chapter 18:778-844, incorporated herein by reference). For example, the carbonyl may also be reduced with a metal hydride reducing agent, as illustrated in Scheme 2. Examples of metal hydride reducing agents include, but are not limited to sodium borohydride, lithium borohydride, L-selectride. Alternatively, a chiral reducing agent, such as for example, Alpine Borane®, may be used for the reduction. Following the reduction, the alcohol may be further functionalized, such as with an alkylating agent via O-alkylation.

Scheme 2

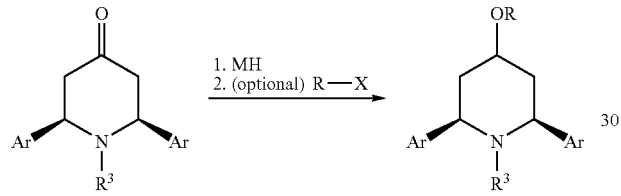

The carbonyl functionality may also be reacted with a nucleophile, such as a Grignard reagent, for example, to generate a tertiary alcohol, as illustrated in Scheme 3. Particular examples of nucleophiles include but are not limited to butyllithium, methylmagnesium chloride, methylmagnesium bromide, phenylmagnesium chloride, and phenyllithium. The tertiary alcohol may then be alkylated, if desired. Examples of alkylating agents include but are not limited to alkyl and aryl halides. In one example, the alkylating agent is methyl or ethyl iodide.

As shown in Scheme 3, the carbonyl functionality may also be reduced to a methylene functionality via established conditions, such as using hydrazine hydrate and a base such as "MOH" where M is an alkali metal as a reducing agent in a glycol solvent. In one example, the base is potassium hydroxide and the glycol solvent is ethylene glycol. (See, e.g., E. Baliah, *J. Indian Chem. Soc.* (1955) 274:276).

Scheme 3

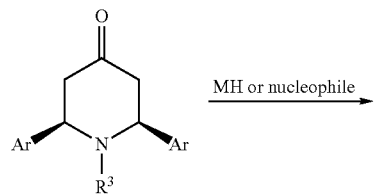

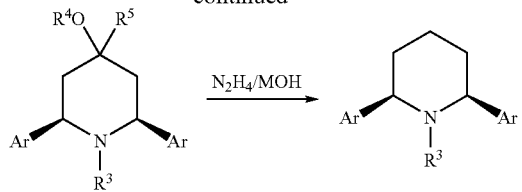

Furthermore, the present invention provides a method of making a compound of formula (3)

(3)

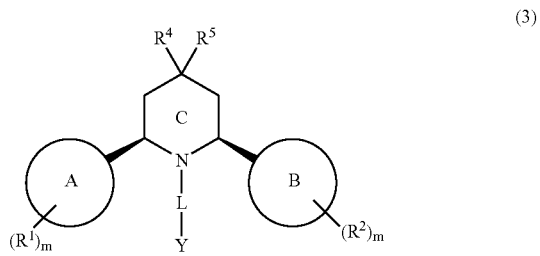

comprising contacting a compound having formula (4)

(4)

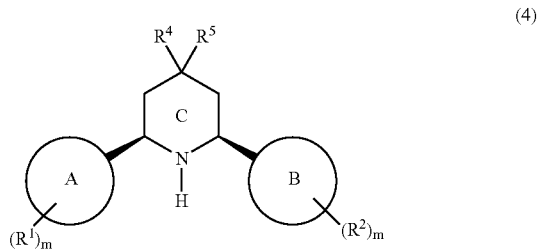

with a compound having the formula X-L-Y.

wherein X is a leaving group;

L is $(CR^6_2)_l$ wherein an alkyl bond may be replaced with an alkenyl or alkynyl bond, each $R^6$ is H or alkyl, and l is 1-6;

Y is H, a $C_{1-6}$ alkyl containing one or more heteroatoms, or an aryl, heteroaryl, or heterocyclic moiety, each of which is optionally substituted;

wherein in each compound having formula (3) and (4), each of rings A and B is an optionally substituted aryl or heteroaryl;

ring C is a saturated 6-membered ring;

m is 0-4;

$R^1$ and $R^2$ are independently H or a non-interfering substituent; and each $R^4$ and $R^5$ is H, halo, hydroxyl, alkoxyl, alkyl, cyano or aryl; or $R^4$ and $R^5$ together form a carbonyl, oxime or imine.

In the above methods, the substituents on compounds having formulas (3) and (4) are as previously defined.

In one example, a compound having formula (3) may be contacted with an alkyl or aryl halide to produce a compound having formula (4). For the cases where a protecting group exists on the L-Y fragment, standard deprotective methodologies, which would be readily apparent to those with skill in the art would be applied.

Typical electrophiles include alkyl bromides, alkyl chlorides, benzyl bromides, benzyl chlorides. The alkyl and aryl groups may contain various substitutions as described previously.

The alkylation reaction is typically carried out at ambient or elevated temperature in an organic solvent in the presence of a base for a duration of 2 to 48 hours. For example, the alkylation reaction may be carried out at elevated temperatures ranging from 40° C. to reflux, and more particularly at temperatures between 50-60° C. An iodide source may be used to accelerate the rate of reaction.

Solvents for the alkylation reaction include dichloromethane, tetrahydrofuran, toluene, acetonitrile and benzene. In one example, the solvent is acetonitrile.

Bases for the alkylation reaction include triethylamine, diisopropylethylamine, sodium carbonate, potassium carbonate and cesium carbonate. In particular example, the base is diisopropylethylamine or potassium carbonate.

Iodide sources include potassium iodide, sodium iodide, tetrabutylammonium iodide and cetylammonium iodide.

Utility and Administration

The invention relates to methods for preparing 2,6-diaryl piperidine derivatives, more particularly compounds having any of formulas 1-4. The compounds prepared by the described methods may modulate chemokine receptor activity. Chemokine receptors include but are not limited to CCR1, CCR2, CCR3, CCR4, CCR5, CXCR3 and CXCR4.

For example, the compounds may demonstrate protective effects on target cells from HIV infection by binding specifically to the chemokine receptor thus affecting the binding of a natural ligand to the CCR5 and/or CXCR4 of a target cell. The compounds may also be useful as agents which affect chemokine receptors, such as CCR1, CCR2, CCR3, CCR4, CCR5, CXCR3, CXCR4 where such chemokine receptors have been correlated as being important mediators of many inflammatory as well as immunoregulatory diseases.

Other diseases that are also implicated with chemokines as mediators include angiogenesis, and tumorigenesis such as brain, and breast tumors and tumors of prostate, lung or haematopoetic tissues. Thus, a compound that modulates the activity of such chemokine receptors is useful for the treatment or prevention of such diseases.

Compounds that inhibit chemokine receptor activity and function may be used for the treatment of diseases that are associated with inflammation, including but are not limited to, inflammatory or allergic diseases such as asthma, allergic rhinitis, hypersensitivity lung diseases, hypersensitivity pneumonitis, eosinophilic pneumonias, delayed-type hypersensitivity, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, systemic lupus erythematosus, myastenia gravis, juvenile onset diabetes; glomerulonephritis, autoimmune throiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In addition compounds that activate or promote chemokine receptor function may be used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round worms); Trichuriasis, Enterobiasis, Ascariasis, Hookworm, Strongyloidiasis, Trichinosis, filariasis; trematodes; visceral worms, visceral larva migrans (e.g., *Toxocara*), eosinophilic gastroenteritis (e.g., *Anisaki* spp., *Phocanema* ssp.), cutaneous larva migrans (*Ancylostona braziliense, Ancylostoma caninum*); the malaria-causing protozoan *Plasmodium vivax*, Human cytomegalovirus, Herpesvirus *saimiri*, and Kaposi's sarcoma herpesvirus, also known as human herpesvirus 8, and poxvirus *Moluscum contagiosum*.

The compounds may also be useful to stimulate the production and proliferation of stem cells and progenitor cells.

The compounds may be administered as sole active ingredients, as mixtures of various compounds, and/or in admixture with additional active ingredients that are therapeutically or nutritionally useful, such as antibiotics, vitamins, herbal extracts, anti-inflammatories, glucose, antipyretics, analgesics, granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoietin, growth related oncogene or chemotherapy and the like. In addition, the compounds of the invention may be administered in admixture with additional active ingredients that are therapeutically or nutritionally useful, such as antibiotics, vitamins, herbal extracts, anti-inflammatories, glucose, antipyretics, analgesics, and the like.

The compounds may be formulated for administration to using commonly understood formulation techniques well known in the art. Formulations which are suitable for particular modes of administration and for compounds prepared by described methods may be found in *Remington's Pharmaceutical Sciences*, latest edition, Mack Publishing Company, Easton, Pa.

In one example, the compounds may be administered by injection, most preferably by intravenous injection, but also by subcutaneous or intraperitoneal injection, and the like. Additional parenteral routes of administration include intramuscular and intraarticular injection. For intravenous or parenteral administration, the compounds are formulated in suitable liquid form with excipients as required. The compositions may contain liposomes or other suitable carriers. For injection intravenously, the solution is made isotonic using standard preparations such as Hank's solution.

Other routes of administration may also be used. For example, the compounds may be administered by oral, intramuscular, intraperitoneal, intravenous, intracisternal injection or infusion, subcutaneous injection, transdermal or transmucosal administration or by implant. They may also be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

The compounds may be formulated into tablets, capsules, syrups, powders, or other suitable forms for administration orally. By using suitable excipients, these compounds may also be administered through the mucosa using suppositories or intranasal sprays. Transdermal administration can also be effected by using suitable penetrants and controlling the rate of release.

The formulation and route of administration chosen will be tailored to the individual subject, the nature of the condition to be treated in the subject, and generally, the judgment of the attending practitioner.

Suitable dosage ranges for the compounds vary according to these considerations, but in general, the compounds are administered in the range of about 0.1 µg/kg-5 mg/kg of body weight; preferably the range is about 1 µg/kg-300 µg/kg of body weight; more preferably about 10 µg/kg-100 µg/kg of body weight. For a typical 70-kg human subject, thus, the dosage range is from about 0.7 µg-350 mg; preferably about 700 µg-21 mg; most preferably about 700 µg-7 mg. Dosages may be higher when the compounds are administered orally or transdermally as compared to, for example, i.v. administration.

The compounds may be administered as a single bolus dose, a dose over time, as in i.v. or transdermal administration, or in multiple dosages.

In addition to direct administration to the subject, the compounds may be used in ex vivo treatment protocols to prepare cell cultures which are then used to replenish the blood cells of the subject. Ex vivo treatment can be conducted on autologous cells harvested from the peripheral blood or bone marrow or from allografts from matched donors. The concentration of the compound alone or in combination with other agents, such as macrophage inflammatory protein is a matter of routine optimization.

The compounds may further be used in combination with any other active agents or pharmaceutical compositions where such combined therapy is useful to modulate chemokine receptor activity and thereby prevent and treat inflammatory and immunoregulatory diseases.

The compounds may further be used in combination with one or more agents useful in the prevention or treatment of HIV. Examples of such agents include:

(1) nucleotide reverse transcriptase inhibitor such as tenofovir disoproxil fumarate; lamivudine/zidovudine; abacavir/lamivudine/zidovudine; emtricitabine; amdoxovir; alovudine; DPC-817; SPD-756; SPD-754; GS7340; ACH-126,443 (beta)-L-F d4C; didanosine, zalcitabine, stavudine, adefovir, adefovir dipivoxil, fozivudine todoxil, etc.;

(2) non-nucleotide reverse transcriptase inhibitor (including an agent having anti-oxidation activity such as immunocal, oltipraz, etc.) such as nevirapine, delavirdine, efavirenz, loviride, immunocal, oltipraz, TMC-125; DPC-083; capravarine; calanolide A; SJ-3366 series, etc.;

(3) protease inhibitors such as saquinavir, lopinavir/ritonavir, atazanavir, fosamprenavir, tipranavir, TMC-114, DPC-684, indinavir, nelfinavir, amprenavir, palinavir, lasinavir, etc.;

(4) entry inhibitors such as T-20; T-1249; PRO-542; PRO-140; TNX-355; BMS-806 series; and 5-Helix;

(5) CCR5-receptor inhibitors such as Sch-C (or SCH351125); Sch-D, and/or SCH350634; TAK779; UK 427,857 and TAK 449;

(6) Integrase inhibitors such as L-870,810; GW-810781 (S-1360); and (7) Budding inhibitors such as PA-344; and PA-457.

Combinations of compounds of the present invention with HIV agents is not limited to (1), (2), and/or (3), but includes combination with any agent useful for the treatment of HIV.

Combinations the compounds of the invention and other HIV agents may be administered separately or in conjunction. The administration of one agent may be prior to, concurrent to, or subsequent to the administration of other agent(s).

The compounds of the invention may be prepared in the form of prodrugs, i.e., protected forms which release the compounds of the invention after administration to the subject. Typically, the protecting groups are hydrolyzed in body fluids such as in the bloodstream thus releasing the active compound or are oxidized or reduced in vivo to release the active compound. A discussion of prodrugs is found in *Smith and Williams Introduction to the Principles of Drug Design*, Smith, H. J.; Wright, $2^{nd}$ ed., London (1988).

The compounds of the invention, as they are polyamines, may be administered prepared in the forms of their acid addition salts or metal complexes thereof. Suitable acid addition salts include salts of inorganic acids that are biocompatible, including HCl, HBr, sulfuric, phosphoric and the like, as well as organic acids such as acetic, propionic, butyric and the like, as well as acids containing more than one carboxyl group, such as oxalic, glutaric, adipic and the like. Furthermore, acid addition salts including aromatic organic acids such as benzoic acid, 4-hydroxybenzoic acid, 4-aminobenzoic acid, benzenesulfonic acid and the like may be prepared. Typically, at physiological pH, the compounds of the invention will be in the forms of the acid addition salts. Particularly preferred are the hydrochlorides. In addition, when prepared as purified forms, the compounds may also be crystallized as the hydrates.

The compounds of the invention may be administered as sole active ingredients, as mixtures of various compounds of formula 1-4, and/or in admixture with additional active ingredients that are therapeutically or nutritionally useful, such as antibiotics, vitamins, herbal extracts, anti-inflammatories, glucose, antipyretics, analgesics, granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoietin, growth related oncogene or chemotherapy and the like.

The compounds may be used to treat animals, including mice, rats, horses, cattle, sheep, dogs, cats, and monkeys, and avians such as chickens and the like. The compounds may also be effective for use in humans.

In the treatment or prevention of conditions which require chemokine receptor modulation an appropriate dosage level will generally be about 0.01 to 500 mg per kg subject body weight per day which can be administered in singe or multiple doses. Preferably, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

Experimental

The following examples are intended to illustrate and not limit the described methods:

The intermediate N-(4-hydroxymethyl-benzyl)-2-nitro-N-pyridin-2-ylmethyl-benzenesulfonamide was prepared according to the procedures described in Bridger, et al., U.S. Pat. No. 6,506,770. The intermediate 2-bromomethyl-5-cyano-benzoic acid methyl ester was prepared according to the procedures described in WO 02/34745, both incorporated herein by reference.

General Procedures

General Procedure A: N-Alkylation of hexahydro-[2,2'; 6'2"]terpyridines

To a solution of the substituted-hexahydro-[2,2';6'2"] terpyridine] (1 equiv) in DMF or $CH_3CN$ (concentration ~0.1-0.2 M) was added the alkyl halide (1-1.4 equivalents), KI (0.05-0.16 equiv), and N,N-diisopropylethylamine (DIPEA) (1.5-2 equiv) and the mixture stirred at 60° C. overnight. The reaction mixture was cooled, diluted with $CH_2Cl_2$ (10 mL/mmol amine) and poured into either saturated aqueous $NaHCO_3$ (10 mL/mmol alcohol). The phases were separated and the aqueous phase extracted with $CH_2Cl_2$ (3×10 mL/mmol amine). The combined organic phases were dried ($Na_2SO_4$) and concentrated under reduced pressure. The crude material was purified by chromatography to afford the desired N-alkylated product.

General Procedure B: Salt Formation Using Saturated HBr (g) in HOAc

To a solution of the free base in glacial HOAc (2 mL) was added, a saturated solution of HBr(g) in HOAc (2 mL). A large volume of ether (25 mL) was then added to precipitate a solid, which was allowed to settle to the bottom of the flask and the supernatant solution was decanted. The solid was washed by decantation with ether (3×25 mL) and the remaining traces of solvent were removed under vacuum. For additional purification, the solid was dissolved in MeOH and re-precipitated with a large volume of ether. Washing the solid with ether by decantation, followed by drying of the solid in vacuo (0.1 Torr) gave the desired compound.

General Procedure C: Direct Reductive Amination with $NaBH(OAc)_3$ or $NaBH_4$

To a stirred solution of the amine (1 equivalent) in $CH_2Cl_2$ (concentration ~0.2 M), at room temperature, was added the carbonyl compound (~1-2 equivalents), glacial HOAc (0-2 equivalents) and $NaBH(OAc)_3$ (~1.5-3 equivalents) and the resultant solution stirred at room temperature. The reaction mixture was poured into either saturated aqueous $NaHCO_3$ or 1.0 M aqueous NaOH (10 mL/mmol amine). The phases separated and the aqueous phase extracted with $CH_2Cl_2$ (3×10 mL/mmol amine). The combined organic phases were dried ($Na_2SO_4$) and concentrated under reduced pressure. The crude material was purified by chromatography.

General Procedure D: Double-Step Mannich Condensation

To a solution of the appropriate pyridinecarboxaldehyde (2 equivalents) in MeOH (concentration ~0.1-1 M) at 0° C. was added $NH_4OAc$ (1.1 equivalents) followed by the slow addition (a period of approx. 15 minutes) of 1,3-acetonedicarboxylic acid (1 equivalents). After the vigorous bubbling subsided, the solution was allowed to stir for 1 hour while warming to room temperature. The solvent was then removed under reduced pressure and $CH_2Cl_2$ (10 mL/mmol amine) and saturated aqueous $Na_2CO_3$ (10 mL/mmol amine) were added. The layers were separated and the aqueous phase extracted with $CH_2Cl_2$ (2×10 mL/mmol amine). The combined organic extracts were dried ($Na_2SO_4$) and concentrated under reduced pressure. The crude product was purified by chromatography on silica gel.

General Procedure E: Wolff-Kishner Reduction

The following reaction was carried out under a flow of nitrogen in a 3-necked round bottom flask equipped with a condenser heated using a sand-filled Variac controlled heating mantle. To a solution of the appropriate substituted-tetrahydro-1'H-[2,2';6',2"]terpyridin-4'-one (1 equivalent) in diethylene glycol (concentration ~0.1-0.2 M) was added hydrazine monohydrate (40 equivalents) and potassium hydroxide pellets (20 equivalents) and the reaction stirred at 80° C. for 1-2 hours. The excess hydrazine was then distilled off (bath temperature of ~200° C.) by use of a short-path distillation apparatus and the remaining mixture was allowed to cool to room temperature. The reaction was diluted with $CH_2Cl_2$ (10 mL/mmol amine) and $H_2O$ (10 mL/mmol amine) and the layers separated. The aqueous phase was extracted with $CH_2Cl_2$ (10 mL/mmol amine) and the combined organic extracts dried ($Na_2SO_4$) and concentrated under reduced pressure. The crude product was purified by column chromatography on silica gel to afford the desired substituted tetrahydro-1'H-[2,2';6',2"]-terpyridine. (See also, *J. Org. Chem.* (1991) p. 4833).

General Procedure F: Reaction of Alcohols with Methanesulfonyl Chloride

To a stirred solution of the alcohol (1 equivalent) and $Et_3N$ (1.5-2 equivalents) in $CH_2Cl_2$ (or THF) (concentration ~0.1 M) at room temperature (or 0° C.) was added methanesulfonyl chloride (MsCl) (~1.5 equivalents) and the reaction stirred at room temperature for 0.5-1 h. The reaction mixture was poured into either saturated aqueous $NaHCO_3$ or saturated $NH_4Cl$ (10 mL/mmol alcohol). The phases were separated and the aqueous phase extracted with $CH_2Cl_2$ (3×10 mL/mmol amine). The combined organic phases were dried ($Na_2SO_4$) and concentrated under reduced pressure. The crude material was either purified by chromatography or used without further purification in the N-alkylation step.

General Procedure G: EDCI Coupling

To a stirred solution of a 1° or 2° amine (0.1-0.3 mmol), 1-[3-(dimethylamino)propyl]-3-ethylcarbodiimide hydrochloride (EDCI) (1.5 equiv.), 1-hydroxy-benzotriazole hydrate (HOBT) (1.5 equiv.), and DIPEA (2.0 equiv.) in $CH_2Cl_2$ or DMF (0.05 M), was added a carboxylic acid (1.0-2.0 equiv). The solution was stirred for 16 h at ambient temperature. The reaction was quenched with saturated $NaHCO_3$ solution and extracted three times with $CH_2Cl_2$. The combined organic layers were dried over $Na_2SO_4$, filtered, and concentrated. The resultant crude material was purified on a silica gel column (5% $MeOH/CH_2Cl_2$).

EXAMPLE 1

Cyclocondensation Formation of (2S, 6R)-4-oxo-2, 6-di-(1-methylimidazol-2-yl)-piperidine

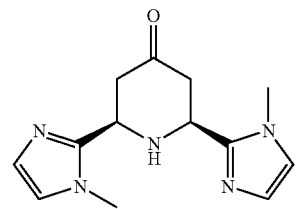

To a solution of 1-methyl-2-imidazole carboxaldehyde (2.60 g, 23.6 mmol) in methanol (60 mL) was added ammonium acetate (1.00 g, 13.0 mmol) followed by the slow addition (over a period of approx. 10 minutes) of 1,3-acetonedicarboxylic acid (1.73 g, 11.8 mmol). After the vigorous bubbling subsided, the solution was allowed to stir for 2 hours. The solvent was then removed under reduced pressure and $CH_2Cl_2$ (60 mL) and saturated aqueous solution of $Na_2CO_3$ (30 mL) was added. The layers were separated and the aqueous phase extracted with $CH_2Cl_2$ (2×40 mL). The combined organic extracts were dried over anhydrous MgSO$_4$ and were concentrated under reduced pressure. The crude product was purified by silica gel flash chromatography (5% methanol in dichloromethane as an eluent). The fractions containing the desired product were concentrated under reduced pressure to give the desired 4-oxo-2,6-di-(1-methylimidazol-2-yl)-piperidine (490 mg, 16%) as a pale yellow foam.

$^1$H NMR (CDCl$_3$) δ 2.52 (dd, 2H, J=13.8, 3.6 Hz), 2.83 (ddd, 2H, J=13.8, 11.7, 1.5 Hz), 4.22 (dd, 2H, J=10.7, 3.6 Hz), 6.82 (s, 2H), 6.95 (s, 2H). $^{13}$C NMR (CDCl$_3$) δ 25.01, 31.82, 46.41, 121.47, 127.40, 209.36. MS (m/z): 262.1 (M+H$^+$).

EXAMPLE 2

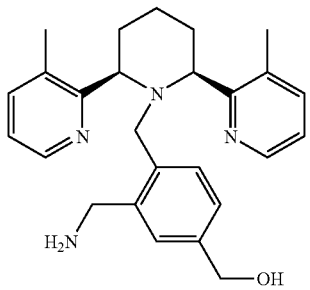

Compound 2: [3-Aminomethyl-4-meso-(3,3''-dimethyl-3',4',5',6'-tetrahydro-2'H-cis-[2,2';6',2'']terpyridin-1'-ylmethyl)-phenyl]-methanol To a solution of 3-methylpyridinecarbaldehyde (43.27 g, 357 mmol) in MeOH (179 mL) at 0° C. was added NH$_4$OAc (151.14 g, 197 mmol). 1,3-Acetonedicarboxylic acid (26.10 g, 178.6 mmol) was then slowly added to the reaction over a period of 15 minutes. After vigorous bubbling subsided, the solution was allowed to stir for 1 hour while warming to room temperature. The solvent was then removed under reduced pressure and CH$_2$Cl$_2$ (500 mL) was added. The solution was washed with saturated aqueous Na$_2$CO$_3$ (350 mL) and separated. The aqueous phase was then extracted with CH$_2$Cl$_2$ (2×400 mL) and the combined organic components dried (Na$_2$SO$_4$) and concentrated under reduced pressure to give, after flash chromatography through a plug of silica gel (2:0.5: 97.5 MeOH/NH$_4$OH/CH$_2$Cl$_2$), meso-3,3''-dimethyl-2',3',5', 6'-tetrahydro-1'H-cis-[2,2';6',2'']terpyridin-4'-one as a yellow solid (30.1 g, 60%). $^1$H NMR (CDCl$_3$) δ 2.37 (s, 6H), 2.55 (m, 2H), 2.82 (m, 2H), 3.37 (m, 1H, NH), 4.50 (t, 2H, J=9.0 Hz), 7.10 (m, 2H), 7.45 (d, 2H, J=7.5 Hz), 8.47 (d, 2H, J=4.5 Hz).

A solution of the above ketone (20.00 g, 71.1 mmol) in diethylene glycol (350 mL) was prepared in a 1L 3-neck round bottom flask. The vessel was purged under a flow of N$_2$ gas and also fitted with a condenser. Hydrazine monohydrate (138 mL, 2.84 mol) and KOH pellets (79.77 g, 1.42 mol) were added to the solution and an overhead mechanical stirrer was equipped to the flask. The reaction mixture was then stirred and heated to 80° C. for 2 hours using a Variac controlled heating mantle filled with sand in tin foil. The excess hydrazine was then distilled from the reaction at a bath temperature of ~200° C. Once all the hydrazine had been collected, the solution was allowed to slowly cool to room temperature. CH$_2$Cl$_2$ (500 mL) and H$_2$O (400 mL) were added and the organic phase separated. The aqueous phase was then extracted with CH$_2$Cl$_2$ (2×500 mL) and the combined organic components dried (Na$_2$SO$_4$) and concentrated under reduced pressure to afford, after column chromatography (NH$_3$/Et$_2$O ramping to 5% and then 10% MeOH in NH$_3$/Et$_2$O) meso-3, 3''-dimethyl-1',2',3',4',5',6'-hexahydro-cis-[2,2';6',2'']terpyridine as a pale yellow solid (15.0 g, 79%). $^1$H NMR (CDCl$_3$) δ 1.59 (dq, 2H, J=12.4, 3.6 Hz), 1.80 (m, 2H), 2.13 (m, 1H), 2.37 (s, 6H), 3.09 (br, 1H, NH), 4.20 (br d, 2H, J=11.1 Hz), 7.03 (m, 2H), 7.39 (d, 2H, J=7.5 Hz), 8.46 (d, 2H, J=4.5 Hz).

A solution of 4-methyl-3-nitrobenzoic acid (27.95 g, 154 mmol) in MeOH (550 mL) was treated with concentrated H$_2$SO$_4$ (10 mL, 188 mmol) and heated to reflux for 17 hours. The reaction was cooled and concentrated under reduced pressure. EtOAc (300 mL) and brine (400 mL) were added and the solution cooled to 0° C. 10N NaOH solution (40 mL) was slowly added until the acid content was neutralized and the solution basic. The organic phase was separated and the aqueous was then extracted with EtOAc (2×400 mL), and the combined organic phases dried (MgSO$_4$), filtered, and concentrated under reduced pressure to give 4—Methyl-3-nitrobenzoic acid methyl ester as a white solid (29.37 g, 98%).

The ester from above (29.37 g, 150 mmol) was added to a 2L Parr hydrogenation flask and dissolved in anhydrous MeOH (200 mL) plus EtOAc (25 mL). The solution was then treated with 10% Pd/C (2.25 g, 50% wet) and fitted to a hydrogenator apparatus. After purging the flask 3 times with hydrogen gas, the mixture was shaken for 1 hour at 30 psi. The flask was then removed, and filtered through a celite pad washing with MeOH. The solvent was then removed under reduced pressure to afford 3-amino-4-methyl-benzoic acid methyl ester as a white solid (25.0 g, 100%). $^1$H NMR (CDCl$_3$) δ 2.21 (s, 3H), 3.70 (br s, 2H, NH$_2$), 3.88 (s, 3H), 7.10 (d, 1H, J=7.5 Hz), 7.35 (s, 1H), 7.37 (d, 1H, J=8.4 Hz).

The above amine (25.00 g, 150 mmol) was suspended in water (140 mL) and treated with hydrochloric acid (41 mL) at 0° C. Upon dissolution, another portion of water (33 mL) was added. The substrate solution was then treated with NaNO$_2$ (11.39 g, 165 mmol) in water (26 mL) and stirred for half an hour. After neutralizing the acid content with K$_2$CO$_3$ (~20 g), the mixture was transferred via cannula to a solution of NaCN (17.64 g, 360 mmol) and CuCN (16.12 g, 180 mmol) in water (65 mL) at 60° C. The mixture was then heated to reflux for 1 hour. Upon cooling to room temperature, the mixture was partitioned between saturated aqueous NaHCO$_3$ solution (200 mL) and CH$_2$Cl$_2$ (400 mL) and the organic phase separated. The aqueous phase was the extracted with CH$_2$Cl$_2$ (3×300 mL) and the combined organic components dried (Na$_2$SO$_4$), filtered, and concentrated under reduced pressure to afford, after column chromatography with silica gel (5% EtOAc/hexanes) 3-cyano-4-methyl-benzoic acid methyl ester as a peach-colored solid (15.8 g, 60%). $^1$H NMR (CDCl$_3$) δ 2.62 (s, 3H), 3.94 (s, 3H), 7.41 (d, 1H, J=7.5 Hz), 8.13 (d, 1H, J=7.5 Hz), 8.27 (s, 1H).

To a solution of the above nitrile (5.08 g, 29.0 mmol) in CCl$_4$ (90 mL) was added N-bromosuccinimide (5.68 g, 32.0 mmol), and 1,1'-azobis(cyclohexanecarbonitrile) (1.06 g, 4.3 mmol). The solution was stirred at reflux for 2 hours and then a second portion of 1,1'-azobis(cyclohexanecarbonitrile) (0.35 g, 1.4 mmol) was added. After an additional 16 hours stirring at reflux the solution was allowed to cool, filtered through a medium glass fritted funnel, and concentrated under reduced pressure. This gave, after column chromatography with silica gel (5% EtOAc/hexanes ramping to 20% EtOAc/hexanes), 4-bromomethyl-3-cyano-benzoic acid methyl ester as pale orange solid. (3.94 g, 53%). $^1$H NMR (CDCl$_3$) δ 3.96 (s, 3H), 4.65 (s, 2H), 7.65 (d, 1H, J=7.5 Hz), 8.23 (d, 1H, J=7.5 Hz), 8.33 (s, 1H).

A solution of meso-3,3"-dimethyl-1',2',3',4',5',6'-hexahydro-cis-[2,2';6',2"]terpyridine (1.01 g, 3.8 mmol), 4-bromomethyl-3-cyano-benzoic acid methyl ester (1.25 g, 4.9 mmol), and KI (126 mg, 0.76 mmol) in anhydrous DMF (19 mL) was treated with DIPEA (1.32 mL, 7.6 mmol) and stirred at 60° C. for 16 hours. The mixture was then concentrated under reduced pressure and the residue dissolved in EtOAc (25 mL). The organic solution was washed with brine (5×20 mL), dried (MgSO$_4$), and concentrated under reduced pressure. This afforded, after purification by column chromatography with silica gel (2:0.5:97.5 MeOH/NH$_4$OH/CH$_2$Cl$_2$), 3-cyano-4-(meso-3,3"-dimethyl-3',4',5',6'-tetrahydro-2'H-cis-[2,2';6',2"]terpyridin-1'-ylmethyl)-benzoic acid methyl ester as a light beige-colored solid (1.52 g, 91%). $^1$H NMR (CDCl$_3$) δ 1.70 (m, 3H), 2.05 (m, 1H), 2.33 (m, 2H), 2.49 (s, 6H), 3.73 (s, 2H), 3.85 (s, 3H), 4.15 (br d, 2H, J=10.5 Hz), 6.85 (m, 2H), 7.25 (d, 2H, J=7.5 Hz), 7.67 (s, 1H), 7.77 (d, 1H, J=7.5 Hz), 7.85 (d, 1H, J=7.5 Hz), 8.25 (d, 2H, J=4.5 Hz).

The alkylated product from above (1.52 g, 3.45 mmol) was dissolved in THF (30 mL) and MeOH (30 mL), cooled to 0° C., and treated with solid LiBH$_4$ (0.90 g, 41.4 mmol). After vigorous bubbling subsided, the mixture was let warm to room temperature over 1 hour while stirring. The excess LiBH$_4$ was quenched with 1N NaOH solution (10 mL) plus brine (30 mL). The aqueous phase was then extracted with CH$_2$Cl$_2$ (3×60 mL), dried (Na$_2$SO$_4$), and concentrated under reduced pressure to give 2-(meso-3,3"-dimethyl-3',4',5',6'-tetrahydro-2'H-cis-[2,2';6',2"]terpyridin-1'-ylmethyl)-5-hydroxymethyl-benzonitrile as a fluffy white solid (1.42 g, 100%).

A solution of the above alcohol (0.69 g, 1.67 mmol) in MeOH (20 mL) was prepared in a 250 mL Parr hydrogenation flask and anhydrous solid Raney Nickel (~1 g) was added. The mixture was then saturated with ammonia gas and transferred to a hydrogenator apparatus. After purging the reaction vessel (flushing three times with hydrogen gas), the flask was pressurized to 50 psi H$_2$ and shaken for 16 hours. The flask was then removed from the hydrogenator, filtered through a celite pad (washing several times with MeOH), and the filtrate concentrated under reduced pressure to give a lightly green-colored solid that did not give a proper $^1$H NMR spectrum. The nickel impurity was then removed by dissolving the solid in MeOH (5 mL) and water (5 mL) and treating with NaCN (0.33 g, 6.7 mmol) at 50° C. for half an hour. After cooling, the solution was extracted with CH$_2$Cl$_2$ (3×15 mL), dried (Na$_2$SO$_4$), and concentrated under reduced pressure to give, after column chromatography with silica gel (1:1:10 MeOH:NH$_4$OH:CH$_2$Cl$_2$), COMPOUND 2 as a white solid (0.46 g, 65%). $^1$H NMR (CDCl$_3$) δ 1.67 (m, 3H), 2.04 (m, 1H), 2.26 (m, 2H), 2.42 (s, 6H), 2.58 (br, 3H), 3.48 (br s, 2H), 3.59 (s, 2H), 4.13 (br d, 2H, J=11.4 Hz), 4.40 (s, 2H), 6.75 (d, 1H, J=7.5 Hz), 6.86 (m, 3H), 7.00 (m, 1H), 7.18 (d, 2H, J=4.8 Hz), 8.29 (d, 2H, J=4.2 Hz). $^{13}$C NMR (CDCl$_3$) δ 18.87 (2C), 25.26 (2C), 28.79, 42.51, 53.43, 64.69 (2C), 66.34, 121.85 (2C), 124.41, 125.96, 129.24, 131.72 (2C), 137.47, 137.86 (2C), 138.71, 139.06, 146.35 (2C), 159.66 (2C). ES-MS m/z 417 (M$^+$H). Anal. Calcd. for C$_{26}$H$_{32}$N$_4$O.0.5CH$_2$Cl$_2$: C, 69.34; H, 7.25; N, 12.21. Found: C, 69.63; H, 7.54; N, 12.30.

EXAMPLE 3

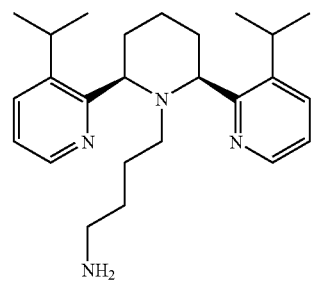

Compound 3: 4-(3,3"-Diisopropyl-3',4',5',6'-tetrahydro-2'H-cis-[2,2';6',2"]terpyridin-1'-yl)-butylamine (HBr Salt)

A 50% solution of hydrogen peroxide (24.89 mL) was slowly added to a solution of 3-isopropyl-2-methyl-pyridine (24.5 g, 183 mmol) (Ishiguro, et al., *Yakugaku Zasshi* (1958) 78:220) in HOAc (280 mL). The mixture was warmed to 70° C. and stirred for 18 h, then cooled to room temperature and concentrated in vacuo to remove the majority of HOAc. The mixture was basified with a saturated solution of NaHCO$_3$ to pH 12 and extracted with CH$_2$Cl$_2$ (3×150 mL). The combined organic layers were dried over Na$_2$SO$_4$ and concentrated in vacuo to afford 3-isopropyl-2-methyl-pyridine 1-oxide (26.05 g, 94%) as a yellow oil. $^1$H NMR (CDCl$_3$) δ 1.24 (d, 6H, J=7.0 Hz), 2.56 (s, 3H), 3.13 (sep, 1H, J=7.0 Hz), 7.06-7.17 (m, 2H), 8.17 (d, 1H, J=6.6 Hz).

To a stirred solution of 3-isopropyl-2-methyl-pyridine 1-oxide (26.05 g, 173 mmol) in CH$_2$Cl$_2$ (690 mL) was added dropwise TFAA (51.83 mL) over 30 min. under N$_2$ then stirred for an additional 3 h. Caution: exothermic reaction on addition of TFAA. The mixture was concentrated in vacuo to a minimum volume. Brine (200 mL) was added, basified to pH 9 with solid K$_2$CO$_3$ slowly, then the aqueous mixture was extracted with CH$_2$Cl$_2$ (3×100 mL). The combined organic layers were dried over Na$_2$SO$_4$ and concentrated in vacuo to afford (3-isopropyl-pyridin-2-yl)-methanol (26 g, 99%) as an orange oil. $^1$H NMR (CDCl$_3$) δ 1.24 (d, 6H, 7.0 Hz), 2.92 (sep, 1H, J=6.6 Hz), 4.79 (s, 2H), 7.02-7.25 (m, 1H), 7.61 (d, 1H, J=7.9 Hz), 8.41 (d, 1H, J=4.8 Hz).

To a vigorously stirred solution of (3-isopropyl-pyridin-2-yl)-methanol (26 g, 170 mmol) in CH$_2$Cl$_2$ (575 mL) was added MnO$_2$ (105 g, 1.20 mol) under N$_2$. The mixture was stirred for 18 h then filtered through a celite pad and concentrated in vacuo. Purification by column chromatography on silica gel (EtOAc/hexanes, 1:3) afforded 3-isopropyl-pyridine-2-carbaldehyde (15.65 g, 61%) as an orange oil. $^1$H NMR (CDCl$_3$) δ 1.26 (d, 6H, J=7.0 Hz), 4.17 (sep, 1H, J=6.6 Hz) 7.45 (dd, 1H, J=7.9, 4.4 Hz), 7.84 (d, 1H, J=7.9 Hz), 8.56 (dd, 1H, J=4.4, 1.3 Hz), 10.2 (s, 1H).

To a solution of 3-isopropyl-pyridine-2-carbaldehyde (235 mg, 1.57 mmol) in MeOH (10 mL) was added NH$_4$OAc (67 mg, 0.866 mmol) and 1,3-acetonedicarboxylic acid (115 mg, 0.787 mmol), and the mixture was stirred at room temperature for 2 h. The mixture was concentrated in vacuo and saturated NaHCO$_3$ (10 mL) followed by CH$_2$Cl$_2$ (20 mL) were added.

The layers were separated and the aqueous layer was extracted two more times with CH$_2$Cl$_2$ (2 times 20 mL). The organic extracts were dried (MgSO$_4$), filtered and concentrated. Purification of the crude material by flash column chromatography on silica gel (10:1 EtOAc:hexanes) provided 106 mg (40%) of 3,3"-diisopropyl-2',3',5',6'-tetrahydro-1'H-cis-[2,2';6',2"]terpyridin-4'-one as a solid. $^1$H NMR (CDCl$_3$) δ 1.25 (d, 6H, J=9.3 Hz), 2.54 (d, 2H, J=13.5 Hz), 2.88 (dd, 2H, J=12.0, 12.6 Hz), 3.16-3.26 (m, 2H), 3.46-3.55 (m, 1H), 4.59-4.63 (m, 2H), 7.16 (dd, 2H, J=7.8, 4.5 Hz), 7.57 (d, 2H, J=7.8 Hz), 8.48 (d, 2H, J=4.5 Hz).

To a solution of 3,3"-diisopropyl-2',3',5',6'-tetrahydro-1'H-[2,2';6',2"]terpyridin-4'-one (106 mg, 0.314 mmol) in diethylene glycol (3 mL) were added KOH (352 mg, 6.29 mmol) and hydrazine monohydrate (0.61 mL, 12.6 mmol). The reaction mixture was heated to ~100° C. for 1 h using a sand bath. After 1 h the temperature was raised to 200° C. for about 45 minutes. CH$_2$Cl$_2$ (50 mL) was added to the remaining mixture and was washed with water (3 times 50 mL). The organic layer was dried (MgSO$_4$), filtered and concentrated to provide 100 mg (99%) of 3,3"-diisopropyl-1',2',3',4',5',6'-hexahydro-cis-[2,2';6',2"]terpyridine (with some DEG). $^1$H NMR (CDCl$_3$) δ 1.25 (d, 6H, J=9.3 Hz), 1.57-1.65 (m, 2H), 1.68-1.89 (m, 3H), 2.10-2.14 (m, 1H), 3.19-3.30 (m, 3H), 4.33 (br s, 1H), 7.10 (dd, 2H, J=7.8, 4.5 Hz), 7.53 (d, 2H, J=7.8 Hz), 8.46 (d, 2H, J=4.5 Hz).

To a solution of 3,3"-diisopropyl-1',2',3',4',5',6'-hexahydro-cis-[2,2';6',2"]terpyridine (100 mg, 0.3141 mmol) in DMF (3 mL) were added 2-(4-bromo-butyl)-isoindole-1,3-dione (106 mg, 0.376 mmol), KI (4 mg, 0.03 mmol), DIPEA (0.10 mL, 0.62 mmol) and the mixture was stirred at 60° C. for 17 hours. Volatiles were removed on high vacuum rotovap. Saturated NaHCO$_3$ (10 mL) was added and the mixture was extracted with CH$_2$Cl$_2$ (20 mL). The organic extracts were dried (MgSO$_4$), filtered and concentrated. Purification of the crude material by column chromatography on silica gel (Et$_2$O saturated with NH$_4$OH) provided 81.3 mg (49%) of 2-[4-(3,3"-diisopropyl-3',4',5',6'-tetrahydro-2'H-cis-[2,2';6',2"]terpyridin-1'-yl)-butyl]-isoindole-1,3-dione as a white foam. By $^1$H NMR the product appeared to be a mixture of two rotamers in about 2.5:1 ratio. ES-MS m/z 525 (M$^+$H).

To a solution of 2-[4-(3,3"-diisopropyl-3',4',5',6'-tetrahydro-2'H-cis-[2,2';6',2"]terpyridin-1'-yl)-butyl]-isoindole-1,3-dione (80 mg, 0.153 mmol) in EtOH (25 mL) was added hydrazine monohydrate (0.3 mL), and the reaction mixture was stirred at room temperature for 17 h. The reaction mixture was concentrated, and purification of the crude material by radial chromatography on silica gel (1 mm plate, 20:1:1 CH$_2$Cl$_2$—MeOH—NH$_4$OH) provided 56 mg (93%) of 4-(3,3"-diisopropyl-3',4',5',6'-tetrahydro-2'H-cis-[2,2';6',2"]terpyridin-1'-yl)-butylamine as a colorless oil. $^1$H NMR showed that a mixture of isomers (~2:1) was obtained which separated on LCMS and had identical mass (m/z 395 (M$^+$H)).

To a solution of 4-(3,3"-diisopropyl-3',4',5',6'-tetrahydro-2'H-cis-[2,2';6',2"]terpyridin-1'-yl)-butylamine (53 mg, 0.134 mmol) in glacial HOAc (1.0 mL) was added HBr saturated HOAc (1.0 mL). The reaction mixture was stirred for 2 minutes then Et$_2$O was added (100 mL). The white precipitate was allowed to settle and the solvent was removed with a pipette. The solid was washed with Et$_2$O (100 mL) two more times. The resultant white powder was dried under reduced pressure to give 79.4 mg (88%) of COMPOUND 3. $^1$H NMR (D$_2$O) δ 1.14-1.23 (m, 3H), 1.32-1.36 (m, 7H), 1.54-1.76 (m, 3H), 1.93-1.96 (m, 1H), 2.05-2.16 (m, 2H), 2.25-2.33 (m, 2H), 2.69-2.75 (m, 2H), 3.45-3.56 (m, 2H), 7.95 (dd, 2H, J=8.4, 5.7 Hz), 8.60 (d, 2H, J=8.4 Hz), 8.67 (d, 2H, J=5.7 Hz); $^{13}$C NMR (D$_2$O) δ 20.2, 22.5, 22.7, 23.5, 25.0, 27.9, 34.0, 39.4, 52.2, 57.6, 126.6, 140.2, 146.0, 146.9, 153.1; ES-MS m/z 395.4 (M$^+$H). Anal. Calcd. for C$_{25}$H$_{38}$N$_4$.3HBr.2.2H$_2$O: C, 44.36; H, 6.76; N, 8.28; Br, 35.41. Found: C, 44.67; H, 6.69; N, 8.50; Br, 35.65.

EXAMPLE 4

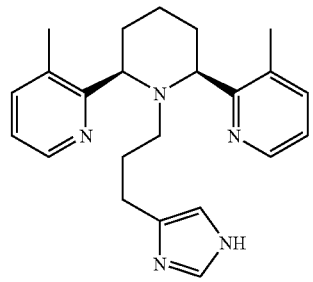

Compound 4: (2'R,6'S)-1'-[3-(1H-Imidazol-4-yl)-propyl]-3,3"-dimethyl-1',2',3',4',5',6'-hexahydro-cis-[2,2°;6',2"]terpyridine (HBr Salt)

To a solution of 4-(3-hydroxy-propyl)-imidazole-1-carboxylic acid tert-butyl ester (147 mg, 0.648 mmol) in anhydrous CH$_2$Cl$_2$ (5 mL) was added pyridine (0.080 mL, 0.98 mmol) followed by p-toluenesulfonyl chloride (247 mg, 1.30 mmol) and DMAP (8.0 mg, 0.065 mmol). The resultant mixture was stirred overnight at room temperature. The mixture was diluted with saturated aqueous NaHCO$_3$ (25 mL) and extracted with CH$_2$Cl$_2$ (3×15 mL). The combined organic extracts were dried (Na$_2$SO$_4$), filtered, and concentrated under reduced pressure. Purification by flash chromatography on silica gel (Hexanes/EtOAc, 60:40) afforded a regioisomeric mixture of 4-[3-(toluene-4-sulfonyloxy)-propyl]-imidazole-1-carboxylic acid tert-butyl ester (99 mg, 40%) as a colorless oil. $^1$H NMR (CDCl$_3$) of major regioisomer δ 1.59 (s, 9H), 1.99 (t, 2H, J=7.2 Hz), 2.43 (s, 3H), 2.57 (t, 2H, J=7.4 Hz), 4.04 (t, 2H, J=6.3 Hz), 7.00 (s, 1H), 7.33 (d, 2H, J=8.3 Hz), 7.77 (d, 2H, J=8.4 Hz), 7.93 (s, 1H).

To a solution of 4-[3-(toluene-4-sulfonyloxy)-propyl]-imidazole-1-carboxylic acid tert-butyl ester (99 mg, 0.26 mmol) in dry CH$_3$CN (2.5 mL) was added (2'R,6'S)-3,3"-dimethyl-1',2',3',4',5',6'-hexahydro-cis-[2,2';6',2"]terpyridine (104 mg, 0.389 mmol) and DIPEA (0.14 mL, 0.78 mmol). The resultant solution was heated to 60° C. overnight and then cooled to room temperature. The reaction mixture was concentrated and the residue was partitioned between CH$_2$Cl$_2$ (15 mL) and saturated aqueous NaHCO$_3$ (25 mL). The aqueous phase was separated and extracted with CH$_2$Cl$_2$ (2×15 mL). The combined organic extracts were dried (Na$_2$SO$_4$), filtered, and concentrated under reduced pressure. Purification by flash chromatography on silica gel (CH$_2$Cl$_2$/MeOH/NH$_4$OH, 92:4:4) afforded a mixture of the desired amine and (2'R,6'S)-3,3"-Dimethyl-1',2',3',4',5',6'-hexahydro-cis-[2,2';6',2"]terpyridine (93 mg). The mixture was dissolved in CH$_2$Cl$_2$ (2 mL) and treated with TFA (1 mL). The resultant solution was stirred at room temperature for 1.5 h and then concentrated. The residue was partitioned between CH$_2$Cl$_2$ (15 mL) and saturated aqueous NaHCO$_3$ (40 mL). The aqueous phase was separated and extracted with CH$_2$Cl$_2$ (2×10 mL). The combined organic extracts were dried (Na$_2$SO$_4$), filtered, and concentrated under reduced pressure. Purification by radial chromatography on a 1 mm silica gel plate (CH$_2$Cl$_2$/MeOH/

NH$_4$OH, 96:2:2, then 92:4:4) afforded the free base of the title compound (18 mg, 13% over 2 steps).

Using General Procedure B: Conversion of the free base from above (18 mg, 0.049 mmol) to a HBr salt followed by re-precipitation of the crude material from MeOH/ether gave COMPOUND 4 as a cream solid (25 mg, 77%). $^1$H NMR (D$_2$O) δ 1.43-1.83 (m, 5H), 1.88-2.04 (m, 1H), 2.07-2.19 (m, 2H), 2.19-2.29 (m, 2H), 2.29-2.39 (m, 2H), 2.52 (s, 6H), 4.59 (d, 2H, J=9.2 Hz), 6.90 (s, 1H), 7.80-7.93 (m, 2H), 8.38 (d, 2H, J=7.6 Hz), 8.49 (s, 1H), 8.67 (d, 2H, J=5.0 Hz); $^{13}$C NMR (D$_2$O) δ 17.08, 21.36, 22.22, 22.40, 32.42, 51.43, 58.39, 115.99, 126.03, 132.90, 133.38, 136.65, 140.35, 148.95, 154.36; ES-MS m/z 376 (M$^+$H). Anal. Calcd. for C$_{23}$H$_{29}$N$_5$.3.0 HBr.2.7H$_2$O: C, 41.42; H, 5.65; N, 10.50; Br, 35.94. Found: C, 41.58; H, 5.71; N, 10.45; Br, 35.82.

EXAMPLE 5

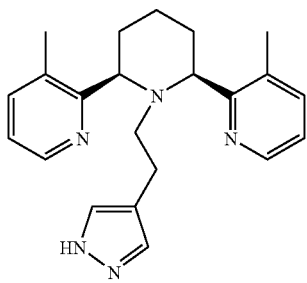

Compound 5: The (2'R,6'S)-3,3''-dimethyl-1'-[2-(1H-pyrazol-4-yl)-ethyl]-1',2',3',4',5',6'-hexahydro-[2,2';6',2'']terpyridine To a suspension of methoxymethyl-triphenyl-phosphonium chloride (2.06 g, 6.00 mmol) in dry THF (20 mL) cooled at −15° C. (ethyl glycol/dry ice) was added LDA (2.0 M in THF, 3.1 mL, 6.2 mmol) slowly. After the addition the mixture was stirred at −15° C. for 30 min, and a solution of 2-benzyl-1H-pyrazole-4-carbaldehyde (1.00 g, 5.37 mmol) (Werner, A., et al., *Tetrahedron* (1995) 51:4779-4800) in THF (15 mL) was added. The reaction mixture was stirred at room temperature for 16 h. Water (30 mL) was added, and the mixture was extracted with EtOAc (30 mL) and CH$_2$Cl$_2$ (2×30 mL). The extracts were combined and dried over Na$_2$SO$_4$. After filtration the solvent was removed by evaporation under vacuum, and the residue was purified by flash chromatography on a silica gel column (CH$_2$Cl$_2$) to afford a colorless oil. The oil was dissolved in THF (3 mL) and aqueous HCl (4 N, 15 mL) was added. After being stirred for 72 h, the mixture was neutralized with saturated aqueous K$_2$CO$_3$, and extracted with CH$_2$Cl$_2$ (3×30 mL). The extracts were combined and dried over Na$_2$SO$_4$. After filtration the solvent was removed by evaporation under vacuum, and the residue was purified by flash chromatography on a silica gel column (2:1 CH$_2$Cl$_2$/Et$_2$O), affording (2-benzyl-1H-pyrazol-4-yl)-acetaldehyde as a colorless oil (0.548 g, 51%). $^1$H NMR (CDCl$_3$) δ 3.56 (d, 2H, J=2.1 Hz), 5.29 (s, 2H), 7.21-7.24 (m, 2H), 7.28-7.39 (m, 4H), 7.45 (s, 1H), 9.70 (t, 1H, J=2.1 Hz).

(2-Benzyl-1H-pyrazol-4-yl)-acetaldehyde (0.548 g, 2.74 mmol) was dissolved in dry EtOH (20 mL) and cooled at 0° C.

NaBH$_4$ (0.104 g, 2.74 mmol) was added, and the mixture was stirred at room temperature for 2 h. Water (10 mL) was added, and MeOH was removed by evaporation under vacuum. The aqueous residue was neutralized with HCl (1 N), and then extracted with CH$_2$Cl$_2$ (3×30 mL). The extracts were combined and dried over Na$_2$SO$_4$. After filtration the solvent was removed by evaporation under vacuum to provide a pale yellow oil.

At 0° C., to a solution of the oil in CH$_2$Cl$_2$ (10 mL) was added MsCl (0.345 g, 3.01 mmol) and Et$_3$N (0.415 g, 4.11 mmol). The mixture was stirred at room temperature for 30 min. Water (10 mL) was added, and the mixture was extracted with CH$_2$Cl$_2$ (3×20 mL). The extracts were combined and dried over Na$_2$SO$_4$. After filtration the solvent was removed by evaporation under vacuum, and the residue was purified by flash chromatography on a silica gel column (4:1 CH$_2$Cl$_2$/Et$_2$O), affording methanesulfonic acid 2-(2-benzyl-1H-pyrazol-4-yl)-ethyl ester as a pale yellow oil (0.734 g, 96%). $^1$H NMR (CDCl$_3$) δ 2.84 (s, 3H), 2.87 (t, 2H, J=6.6 Hz), 4.27 (t, 2H, J=6.6 Hz), 5.22 (s, 2H), 7.17-7.20 (m, 2H), 7.27-7.35 (m, 4H), 7.40 (s, 1H).

A mixture of (2'R,6'S)-3,3''-dimethyl-1',2',3',4',5',6'-hexahydro-[2,2';6',2'']terpyridine (0.320 g, 1.20 mmol), methanesulfonic acid 2-(2-benzyl-1H-pyrazol-4-yl)-ethyl ester (0.540 g, 1.60 mmol) and 2,2,6,6-tetramethylpiperidine (0.255 g, 1.80 mmol) in CH$_3$CN (5 mL) was stirred and heated at reflux overnight. The solvent was then removed, water (20 mL) was added, and the mixture was extracted with CH$_2$Cl$_2$ (3×20 mL). The extracts were combined and dried over Na$_2$SO$_4$. After filtration the solvent was removed by evaporation under vacuum, and the residue was purified by flash chromatography on a silica gel column (500:15:1 CH$_2$Cl$_2$/CH$_3$OH/NH$_4$OH), affording (2'R,6'S)-1'-[2-(2-benzyl-1H-pyrazol-4-yl)-ethyl]-3,3''-dimethyl-1',2',3',4',5',6'-hexahydro-[2,2';6',2'']terpyridine as a pale yellow oil (0.420 g, 93%).

To a solution of (2'R,6'S)-1'-[2-(2-benzyl-1H-pyrazol-4-yl)-ethyl]-3,3''-dimethyl-1',2',3',4',5',6'-hexahydro-[2,2';6',2'']terpyridine (0.130 g, 0.288 mmol) in dry DMSO (0.70 mL) and THF (12 mL) was added 4 Å molecular sieve (~1 g) pre-heated at 140° C., and KO$^t$Bu (0.600 g, 5.35 mmol). The solution was bubbled with air (pre-dried by passing through a NaOH column) at room temperature for 1 h. Saturated aqueous NH$_4$Cl (20 mL) was then added. The mixture was filtered through a celite cake and the cake was washed with EtOAc throughout. The organic layer in the filtrate was collected, and the aqueous layer was extracted with CH$_2$Cl$_2$ (3×30 mL). The extracts were combined and dried over Na$_2$SO$_4$. After filtration the solvent was removed by evaporation under vacuum, and the residue was purified by flash chromatography on a silica gel column (200:10:1 CH$_2$Cl$_2$/CH$_3$OH/NH$_4$OH), affording a pale yellow solid (0.067 g, 64%) after precipitation from CH$_2$Cl$_2$/hexanes by evaporation under vacuum. $^1$H NMR (CDCl$_3$) δ 1.60-1.85 (4H), 2.00-2.15 (m, 2H), 2.25-2.62 (m, 10H), 4.10-4.20 (m, 2H), 6.73 (s, 2H), 7.07-7.12 (m, 2H), 7.43 (d, 2H, J=7.2 Hz), 8.45 (s, br. 2H); $^{13}$C NMR (CD$_2$Cl$_2$) δ 19.02, 21.33, 25.61, 30.31, 50.86, 64.12, 118.85, 122.40, 132.22, 132.65, 138.78, 147.03, 160.46. ES-MS m/z 362 (M+H). Anal. Calcd. for $C_{22}H_{27}N_5 \cdot 0.2H_2O$: C, 72.38; H, 7.56; N, 19.18. Found: C, 72.31; H, 7.70; N, 18.98.

EXAMPLES 6A AND 6B

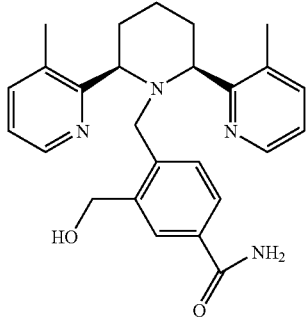

COMPOUND 6A

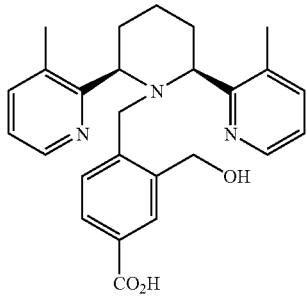

COMPOUND 6B

Compound 6A: 4-(3,3"-Dimethyl-3',4',5',6'-tetrahydro-2'H-cis-[2,2';6',2"]terpyridin-1'-ylmethyl)-3-hydroxymethyl-benzamide and COMPOUND 6B: 4-(3,3"-Dimethyl-3',4',5',6'-tetrahydro-2'H-cis-[2,2'; 6',2"]terpyridin-1'-ylmethyl)-3-hydroxymethyl-benzoic Acid Using General Procedure A: A solution of 3,3"-dimethyl-1',2',3',4',5',6'-hexahydro-cis-[2,2';6',2"]terpyridine (0.260 g, 0.98 mmol), 2-bromomethyl-5-cyano-benzoic acid methyl ester (0.360 g, 1.42 mmol), KI (37 mg, 0.22 mmol), and DIPEA (0.35 mL, 2.01 mmol) in DMF (5 mL) was heated at 60° C. for 17 hours. Purification of the crude material by column chromatography on silica gel (20:1:1 $CH_2Cl_2$—$CH_3OH$—$NH_4OH$) provided 415 mg (96%) of 5-cyano-2-(3, 3"-dimethyl-3',4',5',6'-tetrahydro-2'H-cis-[2,2';6',2"]terpyridin-1'-ylmethyl)-benzoic acid methyl ester as a tan solid.

To a cold (0° C.) solution of 5-cyano-2-(3,3"-dimethyl-3', 4',5',6'-tetrahydro-2'H-cis-[2,2';6',2"]terpyridin-1'-ylmethyl)-benzoic acid methyl ester (0.409 g, 0.937 mmol) in THF (4.5 mL) and MeOH (9 mL) was added $LiBH_4$ (229 mg, 10.52 mmol) and the mixture was allowed to warm to room temperature overnight. The mixture was diluted with 1.0 N NaOH (10 mL) and extracted with $CH_2Cl_2$ (5×25 mL). The combined organic extracts were dried ($Na_2SO_4$) and concentrated. Purification of the crude material by column chromatography on silica gel (20:1:1 $CH_2Cl_2$—$CH_3OH$—$NH_4OH$) provided 0.332 g (87%) of 4-(3,3"-dimethyl-3',4',5',6'-tetrahydro-2'H-cis-[2,2';6',2"]terpyridin-1'-ylmethyl)-3-hydroxymethyl-benzonitrile as a white foam. $^1H$ NMR ($CDCl_3$) δ 1.61-1.77 (m, 3H), 2.05-2.14 (m, 1H), 2.30-2.44 (m, 2H), 2.51 (s, 6H), 3.71 (s, 2H), 4.11 (d, 2H, J=10.8 Hz), 4.46 (s, 2H), 4.94 (br s, 1H), 6.87-6.96 (m, 4H), 7.22-7.27 (m, 3H), 8.21 (d, 2H, J=4.2 Hz).

To a solution of the 4-(3,3"-dimethyl-3',4',5',6'-tetrahydro-2'H-cis-[2,2';6',2"]terpyridin-1'-ylmethyl)-3-hydroxymethyl-benzonitrile (0.310 g, 0.75 mmol) in MeOH (4 mL) was added water (4 mL) and solid NaOH (0.315 g, 7.88 mmol). The resultant mixture was heated to reflux overnight then cooled to room temperature. The mixture was adjusted to pH ~4 with 4 N HCl (~2 mL) and extracted with $CH_2Cl_2$ (5×20 mL). The combined organic extracts were dried ($Na_2SO_4$) and concentrated. Purification of the crude material by radial chromatography on silica gel (1 mm plate, 5:1:1 $CH_2Cl_2$—$CH_3OH$—$NH_4OH$ followed by 5:1:1:1 $CH_2Cl_2$—$CH_3CN$—$CH_3OH$—$NH_4OH$) provided 24 mg (6%) of COMPOUND 6A as a pale yellow solid and 171 mg (45%) of COMPOUND 6B as a white solid.

Characterization data for COMPOUND 6A (24 mg, 6%), a pale yellow solid. $^1H$ NMR ($CDCl_3$) δ 1.60-1.75 (m, 3H), 1.80-2.15 (m, 1H), 2.23-2.43 (m, 2H), 2.51 (s, 6H), 3.68 (s, 2H), 4.06 (d, 2H, J=10.8 Hz), 4.44 (s, 2H), 5.45 (br s, 1H), 5.97 (br s, 1H), 6.83-6.96 (m, 3H), 7.19-7.32 (m, 4H), 8.19 (d, 2H, J=10.2 Hz); $^{13}C$ NMR ($CDCl_3$) δ 19.43, 25.69, 29.52, 53.39, 62.67, 67.47, 122.38, 126.18, 127.64, 129.20, 131.27, 131.95, 138.53, 139.05, 143.49, 146.83, 159.66, 169.56; ES-MS m/z 431 (M+H). Anal. Calcd. For $C_{26}H_{30}N_4O_2 \cdot 1.4CH_2Cl_2$: C, 59.90; H, 6.02; N, 10.20. Found: C, 60.22; H, 5.99; N, 10.38.

Characterization data for COMPOUND 6B (171 mg, 45%), a white solid. $^1H$ NMR ($CDCl_3$) δ 1.66-1.77 (m, 3H), 2.00-2.07 (m, 1H), 2.24-2.32 (m, 2H), 2.46 (s, 6H), 3.71 (s, 2H), 4.14 (d, 2H, J=10.8 Hz), 4.39 (s, 2H), 6.86 (dd, 2H, J=4.8, 7.5 Hz), 6.94 (d, 1H, J=7.8 Hz), 7.24 (d, 2H, J=7.5 Hz), 7.46 (d, 1H, J=7.8 Hz), 7.68 (s, 1H), 8.24 (d, 2H, J=4.8 Hz); $^{13}C$ NMR ($CDCl_3$) δ 19.17, 25.02, 30.39, 54.42, 62.52, 66.71, 122.66, 128.25, 129.40, 130.22, 130.80, 131.93, 138.97, 139.12, 142.19, 146.66, 159.27, 170.67; ES-MS m/z 432 (M+H). Anal. Calcd. For $C_{26}H_{29}N_3O_3 \cdot 0.5H_2O \cdot 0.7CH_2Cl_2$: C, 64.14; H, 6.33; N, 8.40. Found: C, 63.76; H, 6.24; N, 8.60.

EXAMPLE 7

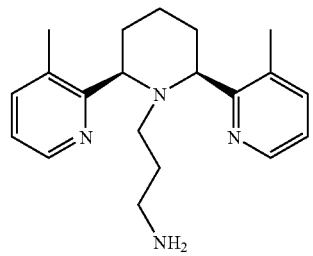

Compound 7: meso-2'β,6'β-[3-(3,3"-dimethyl-3',4', 5',6'-tetrahydro-2'H-cis-[2,2';6',2"]terpyridin-1'-yl)-propylamine]

To a solution of dibromopropane (0.61 mL, 6.0 mmol) in DMF (8 mL) was added potassium phthalimide (0.2756 g, 1.5 mmol), and was stirred at 90° C. for 17 hours. The mixture was concentrated, 1N NaOH (10 mL) was added, and extracted with $CH_2Cl_2$ (2×30 mL). The combined organic extracts were washed with water (1×15 mL), dried ($Na_2SO_4$), and concentrated. Purification of the crude material by column chromatography on silica gel (4:1 hexanes-EtOAc) provided 0.1977 g (49%) of 2-(3-bromo-propyl)-isoindole-1,3-dione as a white solid. $^1$H NMR (CDCl$_3$) δ 2.21-2.30 (m, 2H), 3.41 (t, 2H, J=6.0 Hz), 3.83 (t, 2H, J=6.0 Hz), 7.69-7.75 (m, 2H), 7.82-7.86 (m, 2H).

Following General Procedure A: A mixture of meso-2',6'-[3,3"-dimethyl-1',2',3',4',5',6'-hexahydro-cis-[2,2';6'2"]terpyridine] (0.1796 g, 0.67 mmol), 2-(3-bromo-propyl)-isoindole-1,3-dione (0.1977 g, 0.74 mmol), KI (0.0116 g, 0.07 mmol), DIPEA (0.23 mL, 1.34 mmol), and DMF (6.7 mL) were stirred at 60° C. for 18 hours. Purification of the crude material by column chromatography on silica gel (33:1:1 CH$_2$Cl$_2$—MeOH—NH$_4$OH) provided 0.2823 g (93%) of meso-2',6'-[2-[3-(3,3"-dimethyl-3',4',5',6'-tetrahydro-2'H-[2,2';6'2"]terpyridin-1'-yl)-propyl]-isoindole-1,3-dione] as an orange foam. $^1$H NMR (CDCl$_3$) δ 1.55-1.64 (m, 2H), 1.86-1.95 (m, 2H), 2.28-2.30 (m, 2H), 2.46-2.48 (m, 4H), 2.88-2.95 (m, 2H), 4.00-4.05 (m, 2H), 6.87-6.88 (m, 2H), 7.23-7.25 (m, 2H), 7.67-7.73 (m, 4H), 8.29-8.30 (m, 2H).

To a solution of meso-2',6'-[2-[3-(3,3"-dimethyl-3',4',5',6'-tetrahydro-2'H-cis-[2,2';6'2"]terpyridin-1'-yl)-propyl]-isoindole-1,3-dione] (0.2823 g, 0.62 mmol) in EtOH (6.2 mL) was added hydrazine monohydrate (0.30 mL, 6.21 mmol), and stirred at room temperature for 16 hours. The reaction mixture was concentrated, and purification of the crude material by column chromatography on silica gel (25:1:1 then 12:1:1 CH$_2$Cl$_2$—MeOH—NH$_4$OH) provided 0.1606 g (80%) of COMPOUND 7 as a pale yellow sticky oil. $^1$H NMR (CDCl$_3$) δ 0.69 (s, 1H), 1.53-1.66 (m, 3H), 2.01-2.02 (m, 5H), 2.29-2.30 (m, 2H), 2.52 (s, 6H), 2.52-2.53 (m, 1H), 4.04 (d, 2H, J=9.9 Hz), 7.04-7.08 (m, 2H), 7.41 (d, 2H, J=7.5 Hz), 8.43 (s, 2H). $^{13}$C NMR (CDCl$_3$) δ 19.03, 25.48, 29.67, 40.13, 46.71, 64.73, 71.53, 122.18, 131.97, 138.63, 146.81, 160.45. ES-MS m/z 325.4 (M$^+$H). Anal. Calcd. for C$_{20}$H$_{28}$N$_4$·0.7CH$_2$Cl$_2$: C, 64.76; H, 7.72; N, 14.59. Found: C, 64.51; H, 7.96; N, 14.65.

EXAMPLE 8

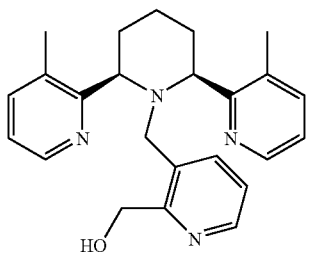

Compound 8: [3-(3,3"-Dimethyl-3',4',5',6'-tetrahydro-2'H-cis-[2,2';6',2"]terpyridin-1'-ylmethyl)-pyridin-2-yl]-methanol To a solution of 3-methylpicolinonitrile (700 mg, 5.93 mmol) in CCl$_4$ (15 mL) was added recrystallized N-bromosuccinimide (1.21 g, 6.82 mmol), followed by glacial HOAc (0.34 mL, 1.0 eq), and AIBN (97 mg, 0.60 mmol). The resultant mixture was heated to 65° C. for 3 hours, 80° C. for 2 hours, and then cooled to room temperature. The mixture was filtered through filter paper, and the filtrate was concentrated. Purification of the crude material by flash chromatography (Hexanes/EtOAc, 90:10 followed by 80:20) provided 3-bromomethyl-pyridine-2-carbonitrile (250 mg, 21%) as a white solid. $^1$H NMR (CDCl$_3$) δ 4.63 (s, 2H), 7.55 (dd, 1H, J=8.0, 4.6 Hz), 7.93 (dd, 1H, J=7.9, 1.2 Hz), 8.64 (dd, 1H, J=4.8, 1.4 Hz).

Using General Procedure A: A solution of 3,3"-dimethyl-1',2',3',4',5',6'-hexahydro-cis-[2,2';6',2"]terpyridine (0.104 g, 0.39 mmol), 3-bromomethyl-pyridine-2-carbonitrile (0.115 g, 0.58 mmol), KI (23 mg, 0.14 mmol), and DIPEA (0.15 mL, 0.86 mmol) in DMF (4 mL) was heated at 60° C. for 20 hours. Purification of the crude material by column chromatography on silica gel (20:1:1 CH$_2$Cl$_2$—CH$_3$OH—NH$_4$OH) provided 133 mg (88%) of 3-(3,3"-dimethyl-3',4',5',6'-tetrahydro-2'H-cis-[2,2';6',2"]terpyridin-1'-ylmethyl)-pyridine-2-carbonitrile as a tan solid.

To a solution of 3-(3,3"-dimethyl-3',4',5',6'-tetrahydro-2'H-cis-[2,2';6',2"]terpyridin-1'-ylmethyl)-pyridine-2-carbonitrile (0.127 g, 0.33 mmol) in MeOH (3 mL) was added water (3 mL) and solid NaOH (0.120 g, 2.99 mmol). The resultant mixture was heated to reflux overnight then cooled to room temperature. The mixture was adjusted to pH ~4 with 3 N HCl (~1 mL) and extracted with CH$_2$Cl$_2$ (5×10 mL). The combined organic extracts were dried (Na$_2$SO$_4$) and concentrated and provided 0.14 g of a white solid. The white solid (0.14 g) was dissolved in MeOH (10 mL), treated with concentrated H$_2$SO$_4$ (0.5 mL) and heated to reflux overnight. The mixture was cooled to room temperature and concentrated under reduced pressure. The residue was dissolved in CH$_2$Cl$_2$ (20 mL) and saturated aqueous Na$_2$CO$_3$ (5 mL). The phases were separated and the aqueous phase was extracted with CH$_2$Cl$_2$ (3×10 mL). The combined organic extracts were dried (Na$_2$SO$_4$) and concentrated. Purification of the crude material by radial chromatography on silica gel (1 mm plate, 20:1:1 CH$_2$Cl$_2$—CH$_3$OH—NH$_4$OH) gave 72.0 mg (52%) of 3-(3,3"-dimethyl-3',4',5',6'-tetrahydro-2'H-cis-[2,2';6',2"]terpyridin-1'-ylmethyl)-pyridine-2-carboxylic acid methyl ester as a white solid.

To a cold (0° C.) solution of 3-(3,3"-dimethyl-3',4',5',6'-tetrahydro-2'H-cis-[2,2';6',2"]terpyridin-1'-ylmethyl)-pyridine-2-carboxylic acid methyl ester (72 mg, 0.17 mmol) in THF (2 mL) and MeOH (2 mL) was added LiBH$_4$ (75 mg, 3.45 mmol) and the mixture was allowed to warm to room temperature overnight. The mixture was diluted with 1.0 N NaOH (10 mL) and extracted with CH$_2$Cl$_2$ (5×10 mL). The combined organic extracts were dried (Na$_2$SO$_4$) and concentrated. Purification of the crude material by column chromatography on silica gel (25:1:1 CH$_2$Cl$_2$—CH$_3$OH—NH$_4$OH) gave COMPOUND 8 (50 mg, 74%) as a white solid. $^1$H NMR (CDCl$_3$) δ 1.65-1.78 (m, 3H), 2.12-2.14 (m, 1H), 2.33-2.48 (m, 8H), 3.49 (s, 2H), 4.21 (d, 2H, J=11.1 Hz), 4.29 (s, 2H), 4.66 (br s, 1H), 6.74 (dd, 1H, J=4.8, 7.5 Hz), 6.86 (dd, 2H, J=4.5, 7.5 Hz), 7.20 (d, 2H, J=7.5 Hz), 7.45 (d, 1H, J=7.5 Hz), 7.96 (d, 1H, J=4.5 Hz), 8.28 (d, 2H, J=4.5 Hz); $^{13}$C NMR (CDCl$_3$) δ 19.15, 25.70, 27.29, 46.27, 61.30, 66.87, 121.16, 122.46, 132.32, 133.57, 136.63, 138.18, 144.84, 146.78, 154.48, 159.25; ES-MS m/z 389 (M$^+$H). Anal. Calcd. For C$_{24}$H$_{28}$N$_4$O·0.3H$_2$O: C, 73.18; H, 7.32; N, 14.22. Found: C, 73.17; H, 7.23; N, 14.17.

EXAMPLE 9

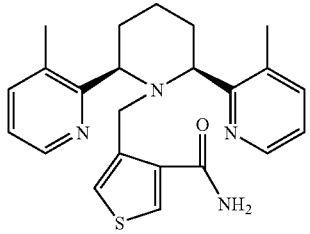

Compound 9: 4-(3,3"-Dimethyl-3',4',5',6'-tetrahydro-2'H-cis-[2,2';6',2"1]terpyridin-1'-ylmethyl)-thiophene-3-carboxylic Acid Amide Using General Procedure A: A solution of 3,3"-dimethyl-1',2',3',4',5',6'-hexahydro-cis-[2,2';6',2"]terpyridine (0.097 g, 0.37 mmol), 4-bromomethyl-thiophene-3-carbonitrile (0.168 g, 0.83 mmol) (Terpstra, J. W., et al., *J. Org. Chem.* (1986) 51:230-238), KI (21 mg, 0.13 mmol), and DIPEA (0.15 mL, 0.86 mmol) in DMF (3 mL) was heated at 60° C. for 21 hours. Purification of the crude material by column chromatography on silica gel (20:1:1 CH$_2$Cl$_2$—CH$_3$OH—NH$_4$OH) provided 118 mg (84%) of 4-(3,3"-dimethyl-3',4',5',6'-tetrahydro-2'H-[2,2';6',2"]terpyridin-1'-ylmethyl)-thiophene-3-carbonitrile as a tan solid.

To a solution of 4-(3,3"-dimethyl-3',4',5',6'-tetrahydro-2'H-cis-[2,2';6',2"]terpyridin-1'-ylmethyl)-thiophene-3-carbonitrile (0.118 g, 0.30 mmol) in MeOH (3 mL) was added water (3 mL) and solid NaOH (0.109 g, 2.72 mmol). The resultant mixture was heated to reflux overnight then cooled to room temperature. The mixture was adjusted to pH ~4 with 3 N HCl (~1 mL) and extracted with CH$_2$Cl$_2$ (5×10 mL). The combined organic extracts were dried (Na$_2$SO$_4$) and concentrated and provided 0.12 g of a tan solid. The tan solid (0.12 g) was dissolved in MeOH (10 mL), treated with concentrated H$_2$SO$_4$ (0.5 mL) and heated to reflux overnight. The mixture was cooled to room temperature and concentrated under reduced pressure. The residue was dissolved in CH$_2$Cl$_2$ (20 mL) and saturated aqueous Na$_2$CO$_3$ (5 mL). The phases were separated and the aqueous phase was extracted with CH$_2$Cl$_2$ (3×10 mL). The combined organic extracts were dried (Na$_2$SO$_4$) and concentrated. Purification of the crude material by radial chromatography on silica gel (1 mm plate, 25:1:1 CH$_2$Cl$_2$—CH$_3$OH—NH$_4$OH) gave COMPOUND 9 (43 mg, 31%) as a white solid. $^1$H NMR (CDCl$_3$) δ 1.53-1.64 (m, 1H), 1.69-1.74 (m, 2H), 1.91-1.98 (m, 1H), 2.08-2.22 (m, 2H), 2.34 (s, 6H), 3.56 (s, 2H), 3.82 (dd, 2H, J=11.4, 3.0 Hz), 5.55 (br s, 1H), 6.84-6.91 (m, 3H), 7.22 (d, 2H, J=7.5 Hz), 7.47 (d, 1H, J=2.7 Hz), 8.36 (d, 2H, J=3.6 Hz), 9.27 (br s, 1H); $^{13}$C NMR (CDCl$_3$) δ 19.34, 24.65, 33.00, 56.95, 66.39, 122.27, 125.11, 130.22, 132.84, 136.92, 137.16, 138.35, 147.33, 160.54, 164.99; ES-MS m/z 407 (M$^+$H). Anal. Calcd. For C$_{23}$H$_{26}$N$_4$OS.0.5CH$_2$Cl$_2$: C, 62.86; H, 6.06; N, 12.48; S, 7.14. Found: C, 63.08; H, 6.36; N, 12.31; S, 6.94.

EXAMPLE 10

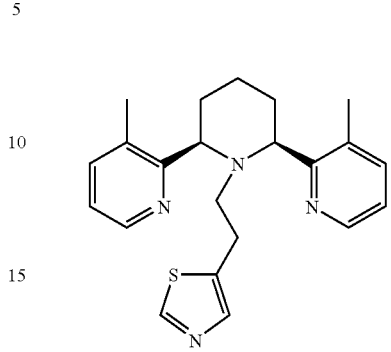

Compound 10: The (2'R,6'S)-3,3"-dimethyl-1'-(2-thiazol-5-yl-ethyl)-1',2',3',4',5',6'-hexahydro-[2,2';6',2"]terpyridine (HBr Salt)

A mixture of 5-methyl-thiazole (1.00 g, 10.1 mmol), NBS (2.06 g, 11.6 mmol) and 2,2'-azobisisobutyronitrile (0.164, 1.00 mmol) in CCl$_4$ (60 mL) was stirred and heated at reflux for 3 h. After the solution was cooled to room temperature NaS$_2$O$_3$ (5 g) in water (50 mL) was added, and the organic layer was collected. The aqueous layer was extracted with CH$_2$Cl$_2$ (3×60 mL). The organic layers were combined, washed with water (50 mL), and concentrated to ~150 mL by evaporation under vacuum. DMF (40 mL) and NaCN (1.00 g, 20.4 mmol) in water (20 mL) were then added, and the low boiling solvents (CH$_2$Cl$_2$ and CCl$_4$) were removed by evaporation under vacuum. The residue was then stirred overnight. Water (40 mL) was added, and the mixture was extracted with Et$_2$O (5×100 mL). The extracts were combined, washed with water (50 mL) and dried over Na$_2$SO$_4$. After filtration the solvent was removed by evaporation under vacuum, and the residue was purified by flash chromatography on a silica gel column (3:4 Et$_2$O/CH$_2$Cl$_2$) to afford thiazole-5-carbonitrile as a pale yellow liquid (0.550 g, 44%). $^1$H NMR (CDCl$_3$) δ 3.97 (s, 2H), 7.85 (s, 1H), 8.81 (s, 1H).

A suspension of thiazole-5-carbonitrile (0.550 g, 4.43 mmol) in aqueous NaOH (3 N, 20 mL) was stirred and heated at 50° C. for 2 h, and then cooed to room temperature. Aqueous HCl (4 N) was added to adjust the acidity of the solution to pH=~3, and the solution was extracted with EtOAc (10×50 mL). The extracts were combined and dried over Na$_2$SO$_4$. After filtration the solvent was removed by evaporation under vacuum to provide thiazol-5-yl-acetic acid as a pale yellow solid.

The solid was dissolved in dry THF (10 mL) and the solution was cooled to 0° C. BH$_3$ (1.0 M in THF, 10 mL, 10 mmol) was added slowly. After addition the mixture was stirred at room temperature for 20 h. MeOH (10 mL) was then added, and the mixture was heated at reflux for 2 h. At room temperature the mixture was concentrated by evaporation under vacuum, and the residue was purified by flash chromatography on a silica gel column ((EtOAc) to afford 2-thiazol-5-yl-ethanol as a pale yellow liquid (0.154 g, 27% two steps).

At 0° C., to a solution of 2-thiazol-5-yl-ethanol (0.154 g, 1.19 mmol) in CH$_2$Cl$_2$ (10 mL) was added MsCl (0.150 g, 1.31 mmol) and Et$_3$N (0.180 g, 1.79 mmol). The mixture was stirred at room temperature for 1 h. Water (20 mL) was added, and the mixture was extracted with CH$_2$Cl$_2$ (3×30 mL). The extracts were combined and dried over Na$_2$SO$_4$. After filtration the solvent was removed by evaporation under vacuum, and the residue was purified by flash chromatography on a silica gel column (EtOAc), affording methanesulfonic acid 2-thiazol-5-yl-ethyl ester as a pale yellow liquid (0.246 g, 100%). $^1$H NMR (CDCl$_3$) δ 2.99 (s, 3H), 3.33 (t, 2H, J=6.3 Hz), 4.42 (t, 2H, J=6.3 Hz), 7.73 (s, 1H), 8.74 (s, 1H).

A mixture of (2'R,6'S)-3,3"-dimethyl-1',2',3',4',5',6'-hexahydro-[2,2';6',2"]terpyridine (0.140 g, 0.523 mmol), methanesulfonic acid 2-thiazol-5-yl-ethyl ester (0.105 g, 0.505 mmol) and 2,2,6,6-tetramethylpiperidine (0.107 g, 0.758 mmol) in CH$_3$CN (2 mL) was stirred and heated at reflux overnight. The solvent was removed, saturated aqueous NaHCO$_3$ (10 mL) was added, and the mixture was extracted with CH$_2$Cl$_2$ (3×20 mL). The extracts were combined and dried over Na$_2$SO$_4$. After filtration the solvent was removed by evaporation under vacuum, and the residue was purified by flash chromatography on a silica gel column (500:25:1 CH$_2$Cl$_2$/CH$_3$OH/NH$_4$OH), affording a colorless oil (0.144 g, 75%).

Following General Procedure B the oil (0.115 g, 0.303 mmol) was treated with HBr/MeOH to afford an HBr salt as a yellow solid (0.210 g, 96%). $^1$H NMR (D$_2$O) δ 1.52-1.64 (2H), 1.72-1.86 (m, 1H), 1.95-2.00 (m, 1H), 2.17-2.22 (m, 2H), 2.59-2.70 (m, 8H), 3.07-3.13 (m, 2H), 4.70-4.76 (m, 2H), 7.78 (s, 1H), 7.92 (dd, 2H, J=5.4, 8.1 Hz), 8.45 (d, 2H, J=8.1 Hz), 8.70 (d, 2H, J=5.4 Hz), 9.65 (s, 1H); $^{13}$C NMR (D$_2$O) δ 17.41, 21.03, 22.35, 32.60, 52.84, 57.74, 126.34, 131.83, 137.08, 140.23, 140.77, 149.97, 153.75, 157.08. ES-MS m/z 379 (M$^+$H). Anal. Calcd. for C$_{22}$H$_{26}$N$_4$S.3.6HBr.1.8H$_2$O.0.3C$_4$H$_{10}$O: C, 38.46; H, 5.04; N, 7.73; Br, 39.70; S, 4.43. Found: C, 38.46; H, 5.07; N, 7.66; Br, 39.63; S, 4.37.

EXAMPLE 11

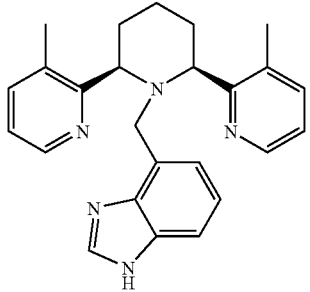

Compound 11: The (2'R,6'S)-1'-(1H-benzoimidazol-4-ylmethyl)-3,3"-dimethyl-1',2',3',4',5',6'-hexahydro-[2,2';6',2"]terpyridine Following General Procedure A using (2'R,6'S)-3,3"-dimethyl-1',2',3',4',5',6'-hexahydro-[2,2';6',2"]terpyridine (0.134 g, 0.501 mmol), 4-bromomethyl-benzoimidazole-1-carboxylic acid tert-butyl ester (0.168 g, 0.602 mmol), DIPEA (0.129 g, 1.00 mmol) and KI (0.0083 g, 0.050 mmol) in CH$_3$CN (5 mL). A white solid was obtained after purification by flash chromatography on a silica gel column (500:20:1 CH$_2$Cl$_2$/CH$_3$OH/NH$_4$OH).

The resulting white solid was treated with TFA (1 mL) in CH$_2$Cl$_2$ (2 mL) to remove the Boc protecting group. A white solid (0.109 g, 53% two steps) was obtained after purification by flash chromatography on a silica gel column (20:1:1 CH$_2$Cl$_2$/CH$_3$OH/NH$_4$OH). $^1$H NMR (CDCl$_3$) δ 1.62-1.78 (m, 4H), 1.92-2.20 (m, 8H), 3.65 (s, br. 2H), 3.87-3.92 (m, 2H), 6.05 (s, br. 1H), 6.51 (t, 1H, J=8.1 Hz), 6.85 (s, br. 2H), 7.07 (s, br. 2H), 7.29 (d, 1H, J=8.1 Hz), 8.13 (s, 1H), 8.24 (s, br. 2H); $^{13}$C NMR (CDCl$_3$) δ 18.78, 25.14, 32.57 (br.), 59.28, 117.21, 120.40, 120.93, 122.21, 124.38, 131.97 (br.), 132.88, 138.51, 140.13, 142.48, 146.01, 160.24. ES-MS m/z 398 (M$^+$Na). Anal. Calcd. for C$_{25}$H$_{27}$N$_5$.0.4CH$_2$Cl$_2$: C, 70.70; H, 6.49; N, 16.23. Found: C, 70.79; H, 6.61; N, 15.98.

EXAMPLE 12

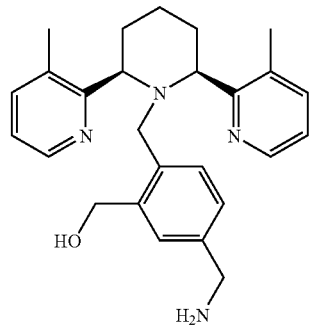

Compound 12: Meso-2',6'-[5-aminomethyl-2-(3,3"-dimethyl-3',4',5',6'-tetrahydro-2'H-cis-[2,2';6',2"]terpyridin-1'-ylmethyl)-phenyl]-methanol Following General Procedure A: To a solution of meso-2',6'-[3,3"-dimethyl-1',2',3',4',5',6'-hexahydro-cis-[2,2';6'2"]terpyridine] (0.4647 g, 1.7 mmol) in DMF (17 mL) was added 2-bromomethyl-5-cyano-benzoic acid methyl ester (0.5035 g, 2.0 mmol), KI (0.0309 g, 0.2 mmol), and DIPEA (0.62 mL, 3.6 mmol). The mixture stirred at 60° C. for 23 hours before it was concentrated. Saturated NaHCO$_3$ (50 mL) was added and was extracted with CH$_2$Cl$_2$ (3×75 mL). The combined organic extracts were washed with brine (1×50 mL), dried (Na$_2$SO$_4$), and concentrated. Purification of the crude material by column chromatography on silica gel (33:1:1 CH$_2$Cl$_2$—MeOH—NH$_4$OH) provided 0.6284 g (82%) of meso-2',6'-[5-cyano-2-(3,3"-dimethyl-3',4',5',6'-tetrahydro-2'H-cis-[2,2';6'2"]terpyridin-1'-ylmethyl)-benzoic acid methyl ester] as an orange solid. $^1$H NMR (CDCl$_3$) δ 1.61-1.74 (m, 3H), 2.06-2.10 (m, 1H), 2.26-2.38 (m, 2H), 2.44 (s, 6H), 3.85 (s, 3H), 3.98 (s, 2H), 4.14 (d, 2H, J=9.0 Hz), 6.83-6.88 (m, 2H), 7.19 (d, 2H, J=9.0 Hz), 7.34-7.38 (m, 1H), 7.56 (d, 1H, J=3.0 Hz), 7.90-7.93 (m, 1H), 8.22 (d, 2H, J=6.0 Hz).

To a solution of meso-2',6'-[5-cyano-2-(3,3"-dimethyl-3',4',5',6'-tetrahydro-2'H-cis-[2,2';6'2"]terpyridin-1'-ylmethyl)-benzoic acid methyl ester] (0.6284 g, 1.42 mmol) in MeOH (14 mL) under Ar was added LiBH$_4$ (0.3505 g, 14.2 mmol), and stirred at room temperature for 1 hour. The reaction mixture was concentrated, CH$_2$Cl$_2$ (50 mL) and 1N NaOH (15 mL) were added and separated, and the aqueous phase was extracted with CH$_2$Cl$_2$ (2×50 mL). The combined organic extracts were dried (Na$_2$SO$_4$), filtered, and concentrated to provided 0.5703 g (97%) of meso-2',6'-[4-(3,3"-dimethyl-3',4',5',6'-tetrahydro-2'H-cis-[2,2';6'2"]terpyridin-1'-ylmethyl)-3-hydroxymethylbenzonitrile] as a beige powder. $^1$H NMR (CDCl$_3$) δ 1.62-1.76 (m, 3H), 2.32-2.43 (m, 3H), 2.50 (s, 6H), 3.70 (s, 2H), 4.12 (d, 2H, J=9.0 Hz), 4.45 (d, 2H, J=6.0 Hz), 6.83-6.96 (m, 4H), 7.17-7.24 (m, 3H), 8.21 (d, 2H, J=3.0 Hz). $^{13}$C NMR (CDCl$_3$) δ 19.26, 25.61, 28.03, 51.97, 61.64, 66.92, 109.29, 119.57, 122.28, 129.19, 129.68, 131.03, 132.28, 138.44, 139.92, 144.92, 146.59.

To Raney Nickel, which had been washed with MeOH, was added meso-2',6'-[4-(3,3"-dimethyl-3',4',5',6'-tetrahydro-2'H-cis-[2,2';6'2"]terpyridin-1'-ylmethyl)-3-hydroxymethyl-benzonitrile] (0.5703 g, 1.38 mmol) in MeOH (10 mL). NH$_{3(g)}$ was bubbled through the solution for 10 minutes, then placed on the hydrogenator at 40 psi for 22 hours. The resulting mixture was flushed with Ar and filtered through a plug of celite with CH$_2$Cl$_2$ and concentrated. Purification of the crude material by column chromatography on silica gel (25:1:1 CH$_2$Cl$_2$—MeOH—NH$_4$OH) provided 0.2823 g (49%) of COMPOUND 12 as a white solid. $^1$H NMR (CDCl$_3$) δ1.61-1.70 (m, 3H), 2.00-2.01 (m, 1H), 2.29-2.33 (m, 2H), 2.48 (s, 6H), 3.54 (s, 2H), 3.61 (s, 2H), 4.00 (d, 2H, J=12.0 Hz), 4.32 (s, 2H), 6.59 (d, 1H, J=6.0 Hz), 6.73 (d, 1H, J=6.0 Hz), 6.80-6.84 (m, 3H), 7.22 (d, 2H, J=6.0 Hz), 8.22 (d, 2H, J=3.0 Hz). $^{13}$C NMR (CDCl$_3$) δ 19.32, 25.62, 29.36, 46.27, 52.37, 62.47, 67.08, 122.02, 125.09, 127.30, 129.26, 131.94, 137.32, 138.27, 139.23, 140.84, 146.61, 159.99. ES-MS m/z 417.3 (M$^+$H). Anal. Calcd. for C$_{26}$H$_{32}$N$_4$O.0.3CH$_2$Cl$_2$.0.5H$_2$O: C, 70.03; H, 7.51; N, 12.42. Found: C, 69.82; H, 7.55; N, 12.12.

EXAMPLE 13

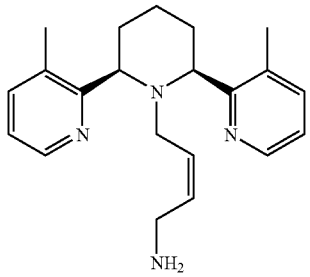

Compound 13: Meso-2',6'-[4-(3,3"-dimethyl-3',4',5',6'-tetrahydro-2'H-cis-2,2';6',2"]terpyridin-1'-yl)-but-2-enylamine] (HBr Salt)

Following General Procedure A: meso-2',6'-[3,3"-dimethyl-1',2',3',4',5',6'-hexahydro-cis-[2,2';6'2"]terpyridine] (0.1456 g, 0.54 mmol), (4-chloro-but-2-enyl)-carbamic acid tert-butyl ester (Casara, P, et al., *J. Am. Chem. Soc.* (1989) 111:9111-9113) (0.1358 g, 0.65 mmol), KI (0.0090 g, 0.05 mmol), DIPEA (0.2 mL, 1.08 mmol), and DMF (6 mL) were stirred at 60° C. for 18 hours. Purification of the crude material by column chromatography on silica gel (33:1:1 CH$_2$Cl$_2$—MeOH—NH$_4$OH) followed by radial chromatography on silica (50:1:1 CH$_2$Cl$_2$—MeOH—NH$_4$OH) provided 0.0968 g (41%) of meso-2',6'-[4-(3,3"-dimethyl-3',4',5',6'-tetrahydro-2'H-cis-[2,2';6'2"]terpyridin-1'-yl)-but-2-enyl]-carbamic acid tert-butyl ester as a beige solid. $^1$H NMR (CDCl$_3$) δ 1.37 (s, 9H), 1.87-1.89 (m, 6H), 2.46 (s, 6H), 2.93-2.95 (m, 2H), 3.12-3.14 (m, 2H), 4.22 (s, 1H), 4.50-4.51 (m, 2H), 5.41-5.43 (m, 1H), 7.10-7.14 (m, 2H), 7.46-7.48 (m, 2H), 8.43-8.44 (m, 2H).

Following General Procedure B: meso-2',6'-[4-(3,3"-dimethyl-3',4',5',6'-tetrahydro-2'H-cis-[2,2';6'2"]terpyridin-1'-yl)-but-2-enyl]-carbamic acid tert-butyl ester (0.0968 g, 0.22 mmol) was converted to the HBr salt followed by reprecipitation of the intermediate solid from MeOH/ether to give COMPOUND 13 (0.0879 g, 65%) as a white solid. $^1$H NMR (D$_2$O) δ 1.51-1.60 (m, 2H), 1.66-1.74 (m, 1H), 1.93-1.94 (m, 1H), 2.15 (d, 2H, J=13.2 Hz), 2.54 (s, 6H), 3.03-3.04 (s, 4H), 4.59 (d, 2H, J=10.8 Hz), 5.42-5.44 (m, 1H), 5.76-5.78 (m, 1H), 7.85-7.89 (m, 2H), 8.39 (d, 2H, J=7.5 Hz), 8.66 (d, 2H, J=4.2 Hz). $^{13}$C NMR (D$_2$O) δ 17.12, 22.37, 32.54, 35.84, 50.96, 59.22, 124.55, 126.17, 130.56, 137.00, 139.88, 149.51, 154.58. ES-MS m/z 337.4 (M$^+$H). Anal. Calcd. for C$_{21}$H$_{28}$N$_4$.3.0HBr.2.0H$_2$O: C, 41.00; H, 5.73; N, 9.11; Br, 38.96. Found: C, 41.17; H, 5.70; N, 8.78; Br, 38.88.

EXAMPLE 14

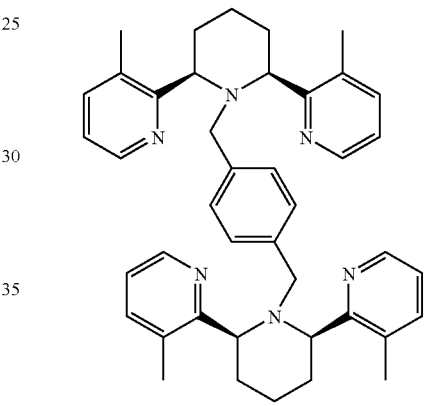

Compound 14: Meso-2',6'-[1,4-bis-N-(3,3"-Dimethyl-1',2',3',4',5',6'-hexahydro-cis-[2,2';6'2"]terpyridine)methyl-benzene]

Following General Procedure A: meso-2',6'-[3,3"-dimethyl-1',2',3',4',5',6'-hexahydro-cis-[2,2';6'2"]terpyridine] (0.2324 g, 0.87 mmol), 1,4-bis-bromomethyl-benzene (0.1148 g, 0.43 mmol), KI (0.0066 g, 0.04 mmol), DIPEA (0.22 mL, 1.29 mmol), and DMF (5 mL) were stirred at 60° C. for 18 hours. Purification of the crude material by column chromatography on silica gel (33:1:1 CH$_2$Cl$_2$—MeOH—NH$_4$OH) provided 0.1603 g (47%) of COMPOUND 14 as a beige solid. $^1$H NMR (CDCl$_3$) δ 1.65-1.70 (m, 4H), 1.95-2.03 (m, 6H), 2.33 (s, 12H), 3.42 (s, 4H), 3.91 (s, 4H), 4.98-5.00 (m, 2H), 6.21 (s, 4H), 6.97-7.01 (m, 4H), 7.30 (d, 4H, J=7.5 Hz), 8.44 (d, 4H, J=2.1 Hz). $^{13}$C NMR (CDCl$_3$) δ 19.18, 25.57, 29.94, 51.43, 64.60, 122.03, 128.19, 132.25, 136.41, 138.60, 146.80, 160.61. ES-MS m/z 637.8 (M$^+$H). Anal. Calcd. for C$_{42}$H$_{48}$N$_6$.1.8CH$_2$Cl$_2$: C, 66.61; H, 6.59; N, 10.64. Found: C, 66.47; H, 6.53; N, 10.73.

EXAMPLE 15

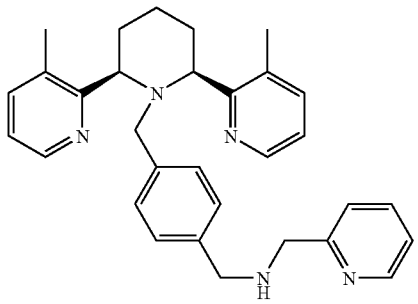

Compound 15: Meso-2',6'-[4-(3,3"-dimethyl-3',4',5', 6'-tetrahydro-2'H-cis-[2,2';6',2"]terpyridin-1'-ylmethyl)-benzyl]-pyridin-2-ylmethyl-amine To a stirring solution of N-(4-hydroxymethyl-benzyl)-2-nitro-N-pyridin-2-ylmethyl-benzenesulfonamide (Bridger, et al., U.S. Ser. No. 09/111,895) (0.2096 g, 0.51 mmol) in $CH_2Cl_2$ (5 mL) at 0° C. under Ar, was added $Et_3N$ (0.14 mL, 1.02 mmol) and MsCl (0.05 mL, 0.66 mmol). The mixture was stirred at 0° C. for 2 hours, then stirred at room temperature for 3 hours. Additional $Et_3N$ (0.30 mL, 2.16 mmol) and MsCl (0.10 mL, 1.32 mmol) were added, and stirred for 18 hours. Saturated $NaHCO_3$ (10 mL) was added and extracted with $CH_2Cl_2$ (3×30 mL). The combined organic extracts were dried ($Na_2SO_4$), filtered, and concentrated to provide 0.2383 g (95%) of methanesulfonic acid 4-{[(2-nitro-benzenesulfonyl)-pyridin-2-ylmethyl-amino]-methyl}-benzyl ester as a yellow oil. $^1H$ NMR ($CDCl_3$) δ 3.14 (s, 3H), 4.51 (s, 2H), 4.60 (s, 4H), 7.02-7.24 (m, 6H), 7.54-7.57 (m, 2H), 7.66 (d, 2H, J=3.0 Hz), 7.94 (d, 1H, J=9.0 Hz), 8.41-8.43 (m, 1H).

To a solution of meso-2',6'-[3,3"-dimethyl-1',2',3',4',5',6'-hexahydro-cis-[2,2';6'2"]terpyridine] (0.0997 g, 0.37 mmol) and methanesulfonic acid 4-{[(2-nitro-benzenesulfonyl)-pyridin-2-ylmethyl-amino]-methyl}-benzyl ester (0.2383 g, 0.48 mmol) in DMF (4 mL), were added KI (0.0066 g, 0.04 mmol) and DIPEA (0.13 mL, 0.74 mmol). The mixture was stirred at room temperature for 66 hours then concentrated. Saturated $NaHCO_3$ (10 mL) was added and extracted with $CH_2Cl_2$ (3×30 mL). The combined organic extracts were washed with brine (2×20 mL), dried ($Na_2SO_4$), filtered, and concentrated. Purification of the crude material by column chromatography on silica gel (50:1:1 $CH_2Cl_2$—MeOH—$NH_4OH$) provided 0.2005 g (82%) of meso-2',6'-N-[4-(3,3"-dimethyl-3',4',5',6'-tetrahydro-2'H-cis-[2,2';6',2"]terpyridin-1'-ylmethyl)-benzyl]-2-nitro-N-pyridin-2-ylmethyl-benzenesulfonamide as a beige solid. $^1H$ NMR ($CDCl_3$) δ 1.57-1.70 (m, 2H), 1.99-2.03 (m, 1H), 2.12-2.25 (m, 2H), 2.36 (s, 6H), 3.43-3.48 (m, 3H), 4.05 (d, 2H, J=9.0 Hz), 4.43 (d, 4H, J=9.0 Hz), 6.42 (d, 2H, J=6.0 Hz), 6.71 (d, 2H, J=6.0 Hz), 6.97-7.00 (m, 2H), 7.09-7.12 (m, 2H), 7.27-7.28 (m, 2H), 7.49-7.51 (m, 2H), 7.61-7.63 (m, 2H), 7.92 (d, 1H, J=6.0 Hz), 8.40-8.41 (m, 3H).

To a solution of meso-2',6'-N-[4-(3,3"-dimethyl-3',4',5',6'-tetrahydro-2'H-cis-[2,2';6',2"]terpyridin-1'-ylmethyl)-benzyl]-2-nitro-N-pyridin-2-ylmethyl-benzenesulfonamide (0.2005 g, 0.30 mmol) in $CH_3CN$ (3 mL) was added $K_2CO_3$ (0.2625 g, 1.80 mmol) and thiophenol (0.16 mL, 1.51 mmol). After stirring for 16 hours at room temperature, the mixture was concentrated, and $CH_2Cl_2$ (50 mL) was added and washed with brine (3×30 mL), dried ($Na_2SO_4$), filtered, and concentrated. Purification of the crude material by column chromatography on silica gel (25:1:1 $CH_2Cl_2$—MeOH—$NH_4OH$) provided 0.0763 g (49%) of COMPOUND 15 as a pale yellow oil. $^1H$ NMR ($CDCl_3$) δ 1.50-1.70 (m, 4H), 1.96-2.00 (m, 1H), 2.08-2.20 (m, 2H), 2.37 (s, 6H), 3.52 (s, 2H), 3.66 (s, 2H), 3.82 (s, 2H), 4.05 (d, 2H, J=10.8 Hz), 6.68 (d, 2H, J=7.2 Hz), 6.91 (d, 2H, J=7.5 Hz), 6.95-6.99 (m, 2H), 7.13-7.17 (m, 1H), 7.27-7.28 (m, 2H), 7.62-7.63 (m, 1H), 8.43 (d, 2H, J=3.3 Hz), 8.54 (d, 1H, J=4.5 Hz). $^{13}C$ NMR ($CDCl_3$) δ 19.17, 25.65, 29.56, 52.11, 53.51, 54.64, 65.13, 122.13, 122.26, 122.63, 127.42, 129.03, 130.38, 132.37, 136.74, 137.73, 138.46, 146.85, 149.69, 160.21, 160.53. ES-MS m/z 478.3 ($M^+H$). Anal. Calcd. for $C_{31}H_{35}N_5$·0.5$CH_2Cl_2$: C, 72.74; H, 6.98; N, 13.46. Found: C, 72.56; H, 6.94; N, 13.35.

EXAMPLE 16

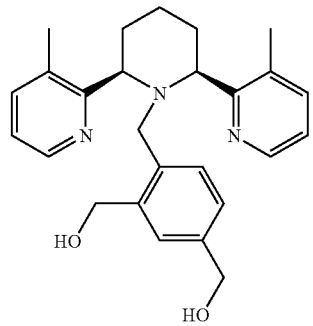

Compound 16: Meso-2',6'-[4-(3,3"-dimethyl-3',4',5', 6'-tetrahydro-2'H-cis-[2,2';6',2"]terpyridin-1'-ylmethyl)-3-hydroxymethyl-phenyl]-methanol Following General Procedure A: To a solution of meso-2', 6'-[3,3"-dimethyl-1',2',3',4',5',6'-hexahydro-cis-[2,2';6'2"]terpyridine] (0.1339 g, 0.50 mmol) in DMF (5 mL) was added 4-bromomethyl-isophthalic acid dimethyl ester (0.1438 g, 0.50 mmol), KI (0.0083 g, 0.05 mmol), and DIPEA (0.17 mL, 1.00 mmol). The mixture stirred at 60° C. for 16 hours before it was concentrated. Purification of the crude material by column chromatography on silica gel (50:1:1 $CH_2Cl_2$—MeOH—$NH_4OH$) provided 0.2473 g (100%) of meso-2'β, 6'β-[4-(3,3"-dimethyl-3',4',5',6'-tetrahydro-2'H-[2,2';6'2"]terpyridin-1'-ylmethyl)-isophthalic acid dimethyl ester] as a yellow solid. $^1H$ NMR ($CDCl_3$) δ 1.64-1.69 (m, 2H), 2.31-2.41 (m, 2H), 2.44 (s, 6H), 2.75 (s, 2H), 3.83 (s, 6H), 3.99 (s, 2H), 4.15 (d, 2H, J=12.0 Hz), 6.80-6.84 (m, 2H), 7.14-7.17 (m, 2H), 7.74 (s, 2H), 7.92 (s, 1H), 8.23 (d, 2H, J=3.0 Hz).

To a solution of meso-2',6'-[4-(3,3"-dimethyl-3',4',5',6'-tetrahydro-2'H-cis-[2,2';6'2"]terpyridin-1'-ylmethyl)-isophthalic acid dimethyl ester] (0.2273 g, 0.48 mmol) in THF (5 mL) at 0° C. under Ar was added $LiAlH_4$ (0.3100 g, 4.80 mmol). The mixture was stirred at room temperature for 2 hours, then distilled water (0.3 mL) was added, followed by 15% NaOH (1 mL), and distilled water (3 mL), and stirred for 15 minutes. The mixture was filtered through celite with $CH_2Cl_2$ and concentrated. Purification of the crude material by column chromatography on silica gel (25:1:1 $CH_2Cl_2$—MeOH—$NH_4OH$) provided 0.1282 g (59%) of COMPOUND 16 as a white solid. $^1H$ NMR ($CDCl_3$) δ 1.61-1.65

(m, 3H), 2.01-2.02 (m, 1H), 2.30-2.34 (m, 2H), 2.49 (s, 6H), 3.63 (s, 2H), 4.02 (d, 2H, J=11.1 Hz), 4.33 (s, 2H), 4.38 (s, 2H), 6.65-6.68 (m, 1H), 6.74-6.77 (m, 1H), 6.80-6.85 (m, 2H), 6.90 (s, 1H), 7.22 (d, 2H, J=7.5 Hz), 8.20 (d, 2H, J=3.9 Hz). $^{13}$C NMR (CDCl$_3$) δ 19.44, 25.67, 29.69, 53.70, 62.82, 64.86, 67.61, 122.15, 125.24, 127.71, 129.23, 131.93, 138.00, 138.45, 138.90, 139.44, 146.72, 159.97. ES-MS m/z 418.5 (M$^+$H). Anal. Calcd. for C$_{26}$H$_{31}$N$_3$O$_2$.0.4CH$_2$Cl$_2$: C, 70.15; H, 7.09; N, 9.29. Found: C, 70.17; H, 7.05; N, 9.19.

EXAMPLE 17

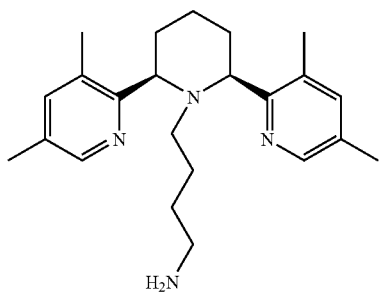

Compound 17: Meso-2',6'-[4-(3,5,3",5"-tetramethyl-3',4',5',6'-tetrahydro-2'H-cis-[2,2°;6',2"]terpyridin-1'-yl)-butylamine] (HBr Salt)

To a solution of (3,5-dimethyl-pyridin-2-yl)-methanol (2.12 g, 15.45 mmol) (Weidmann, K., et al., *J. Med. Chem.* (1992) 35:438-450) in CH$_2$Cl$_2$ (50 mL) was added MnO$_2$ (9.41 g, 108.18 mmol) and the reaction mixture was refluxed overnight. Then it was cooled and the mixture was filtered through a layer of celite. The filtrate was concentrated to afford a brown/yellow oil. Purification by flash column chromatography on silica gel using 30% EtOAc/hexane afforded 3,5-dimethyl-pyridine-2-carbaldehyde as a yellow oil (960 mg, 31% over 3 steps). $^1$H NMR (CDCl$_3$) δ 2.39 (s, 3H), 2.62 (s, 3H), 7.41 (s, 1H), 8.47 (s, 1H), 10.15 (s, 1H).

Following General Procedure D: To a solution of 3,5-dimethyl-pyridine-2-carbaldehyde (0.6551 g, 4.9 mmol) in MeOH (24 mL) was added NH$_4$OAc (0.2172 g, 2.6 mmol) and 1,3-acetonedicarboxylic acid (0.3533 g, 2.4 mmol), and stirred at room temperature for 4 hours. Purification of the crude material by column chromatography on silica gel (200:1:1 CH$_2$Cl$_2$—MeOH—NH$_4$OH) provided 0.4526 g (61%) of meso-2',6'-[3,5,3",5"-tetramethyl-2',3',5',6'-tetrahydro-1'H-cis-[2,2';6'2"]terpyridin-4'-one] as a yellow solid. $^1$H NMR (CDCl$_3$) δ 2.27 (s, 6H), 2.32 (s, 6H), 2.46-2.55 (m, 2H), 2.78-2.86 (m, 2H), 3.24 (t, 1H, J=12.0 Hz), 4.40-4.47 (m, 2H), 7.25 (s, 2H), 8.28 (s, 2H).

Following General Procedure E: meso-2',6'-[3,5,3",5"-tetramethyl-2',3',5',6'-tetrahydro-1'H-cis-[2,2';6'2"]terpyridin-4'-one] (0.4526 g, 1.5 mmol), KOH (1.64 g, 29.3 mmol), hydrazine monohydrate (2.84 mL, 58.5 mmol), and diethylene glycol (10 mL) were used. Purification of the crude material by column chromatography on silica gel (50:1:1 CH$_2$Cl$_2$—MeOH—NH$_4$OH) provided 0.3521 g (79%) of meso-2'β,6'β-[3,5,3",5"-tetramethyl-1',2',3',4',5',6'-hexahydro-[2,2';6'2"]terpyridine] as a dark orange oil. $^1$H NMR (CDCl$_3$) δ 1.55-1.63 (m, 2H), 1.79-1.84 (m, 3H), 2.09-2.13 (m, 1H), 2.24 (s, 6H), 2.33 (s, 6H), 4.16-4.19 (m, 2H), 7.20 (s, 2H), 8.27 (s, 2H).

Following General Procedure A: meso-2',6'-[3,5,3",5"-tetramethyl-1',2',3',4',5',6'-hexahydro-cis-[2,2';6'2"]terpyridine] (0.0939 g, 0.32 mmol), 2-(4-bromo-butyl)-isoindole-1,3-dione (0.0913 g, 0.32 mmol), KI (0.0053 g, 0.03 mmol), DIPEA (0.11 mL, 0.64 mmol), and DMF (3.2 mL) were stirred at 60° C. for 17 hours. Purification of the crude material by column chromatography on silica gel (50:1:1 CH$_2$Cl$_2$—MeOH—NH$_4$OH) provided 0.0951 g (60%) of meso-2',6'-[2-[4-(3,5,3",5"-tetramethyl-3',4',5',6'-tetrahydro-2'H-cis-[2,2';6'2"]terpyridin-1'-yl)-butyl]-isoindole-1,3-dione] as a white solid. $^1$H NMR (CDCl$_3$) δ 0.92-0.94 (m, 2H), 1.63-1.64 (m, 2H), 1.94-2.04 (m, 2H), 2.22 (s, 6H), 2.23-2.26 (m, 2H), 2.40 (s, 6H), 2.49-2.58 (m, 2H), 2.95-3.03 (m, 2H), 3.20-3.25 (m, 2H), 3.99-4.00 (m, 2H), 7.13 (s, 2H), 7.68-7.71 (m, 2H), 7.77-7.82 (m, 2H), 8.23 (s, 2H).

To a solution of meso-2',6'-[2-[4-(3,5,3",5"-tetramethyl-3',4',5',6'-tetrahydro-2'H-cis-[2,2';6'2"]terpyridin-1'-yl)-butyl]-isoindole-1,3-dione] (0.0951 g, 0.19 mmol) in EtOH (2 mL) was added hydrazine monohydrate (0.1 mL, 1.90 mmol), and stirred at room temperature for 17 hours. The reaction mixture was concentrated, and purification of the crude material by column chromatography on silica gel (25:1:1 then 12:1:1 CH$_2$Cl$_2$—MeOH—NH$_4$OH) provided 0.0474 g (68%) of meso-2',6'-[4-(3,5,3",5"-tetramethyl-3',4',5',6'-tetrahydro-2'H-cis-[2,2';6'2"]terpyridin-1'-yl)-butylamine] as a colorless oil. $^1$H NMR (CDCl$_3$) δ 0.76-0.91 (m, 2H), 1.58-1.62 (m, 4H), 1.91-2.04 (m, 3H), 2.18-2.23 (m, 4H), 2.26 (s, 6H), 2.45 (s, 6H), 2.58-2.59 (m, 1H), 3.98 (d, 2H, J=12.0 Hz), 7.22 (s, 2H), 8.26 (s, 2H).

Following General Procedure B: meso-2',6'-[4-(3,5,3",5"-tetramethyl-3',4',5',6'-tetrahydro-2'H-cis-[2,2';6'2"]terpyridin-1'-yl)-butylamine] was converted to the HBr salt followed by reprecipitation of the intermediate solid from MeOH/ether to give COMPOUND 17 (0.0621 g, 68%) as a white solid. $^1$H NMR (D$_2$O) δ 1.14-1.15 (m, 2H), 1.28-1.29 (m, 2H), 1.39-1.50 (m, 2H), 1.59-1.67 (m, 1H), 1.87-1.91 (m, 1H), 2.03-2.10 (m, 2H), 2.17-2.20 (m, 2H), 2.45 (s, 6H), 2.51 (s, 6H), 2.69-2.70 (m, 2H), 4.51 (d, 2H, J=10.2 Hz), 8.22 (s, 2H), 8.46 (s, 2H). $^{13}$C NMR (D$_2$O) δ 16.92, 17.53, 19.99, 22.41, 25.16, 32.63, 39.31, 52.07, 57.49, 135.99, 137.37, 139.18, 150.04, 151.71. EMS m/z 367.4 (M$^+$H). Anal. Calcd. for C$_{23}$H$_{34}$N$_4$.3.3HBr.2.1CH$_4$O: C, 43.02; H, 6.57; N, 7.99; Br, 37.62. Found: C, 42.96; H, 6.44; N, 8.23; Br, 37.49.

EXAMPLE 18

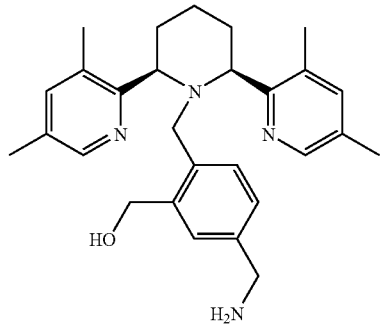

Compound 18: Meso-2',6'-[5-aminomethyl-2-(3,5,3",5"-tetramethyl-3',4',5',6'-tetrahydro-2'H-cis-[2,2°;6',2"]terpyridin-1'-ylmethyl)-phenyl]-methanol Following General Procedure D: To a solution of 3,5-dimethyl-pyridine-2-carbaldehyde (0.6551 g, 4.9 mmol) in MeOH (24 mL) was added NH₄OAc (0.2172 g, 2.6 mmol) and 1,3-acetonedicarboxylic acid (0.3533 g, 2.4 mmol), and stirred at room temperature for 4 hours. Purification of the crude material by column chromatography on silica gel (200:1:1 CH₂Cl₂—MeOH—NH₄OH) provided 0.4526 g (61%) of meso-2',6'-[3,5,3",5"-tetramethyl-2',3',5',6'-tetrahydro-1'H-cis-[2,2';6'2"]terpyridin-4'-one] as a yellow solid. ¹H NMR (CDCl₃) δ 2.27 (s, 6H), 2.32 (s, 6H), 2.46-2.55 (m, 2H), 2.78-2.86 (m, 2H), 3.24 (t, 1H, J=12.0 Hz), 4.40-4.47 (m, 2H), 7.25 (s, 2H), 8.28 (s, 2H).

Following General Procedure E: meso-2',6'-[3,5,3",5"-tetramethyl-2',3',5',6'-tetrahydro-1'H-cis-[2,2';6'2"]terpyridin-4'-one] (0.4526 g, 1.5 mmol), KOH (1.64 g, 29.3 mmol), hydrazine monohydrate (2.84 mL, 58.5 mmol), and diethylene glycol (10 mL) were used. Purification of the crude material by column chromatography on silica gel (50:1:1 CH₂Cl₂—MeOH—NH₄OH) provided 0.3521 g (79%) of meso-2'β,6'β-[3,5,3",5"-tetramethyl-1',2',3',4',5',6'-hexahydro-[2,2';6'2"]terpyridine] as a dark orange oil. ¹H NMR (CDCl₃) δ 1.55-1.63 (m, 2H), 1.79-1.84 (m, 3H), 2.09-2.13 (m, 1H), 2.24 (s, 6H), 2.33 (s, 6H), 4.16-4.19 (m, 2H), 7.20 (s, 2H), 8.27 (s, 2H).

Following General Procedure A: meso-2',6'-[3,5,3",5"-tetramethyl-1',2',3',4',5',6'-hexahydro-cis-[2,2';6'2"]terpyridine] (0.1903 g, 0.64 mmol), 2-bromomethyl-5-cyano-benzoic acid methyl ester (0.1630 g, 0.64 mmol), KI (0.0100 g, 0.06 mmol), DIPEA (0.22 mL, 1.29 mmol), and DMF (6.4 mL) were stirred at 60° C. for 17 hours. Purification of the crude material by column chromatography on silica gel (50:1:1 CH₂Cl₂—MeOH—NH₄OH) provided 0.2682 g (89%) of meso-2',6'-[5-cyano-2-(3,5,3",5"-tetramethyl-3',4',5',6'-tetrahydro-cis-[2,2';6'2"]terpyridin-1'-ylmethyl)-benzoic acid methyl ester] as a brown oil. ¹H NMR (CDCl₃) δ 1.63-1.67 (m, 3H), 2.00-2.05 (m, 1H), 2.12 (s, 6H), 2.21-2.31 (m, 2H), 2.36 (s, 6H), 3.84 (s, 3H), 3.90-3.94 (m, 2H), 4.05-4.08 (m, 2H), 6.96 (s, 2H), 7.37 (d, 1H, J=9.0 Hz), 7.56 (d, 1H, J=3.0 Hz), 7.90 (s, 1H), 8.02 (s, 2H).

To a solution of meso-2',6'-[5-cyano-2-(3,5,3",5"-tetramethyl-3',4',5',6'-tetrahydro-cis-[2,2';6'2"]terpyridin-1'-ylmethyl)-benzoic acid methyl ester] (0.2682 g, 0.57 mmol) in THF (6 mL) at 0° C. under Ar was added dropwise 1.0 M LiAlH₄ in THF (5.7 mL, 5.72 mmol). The mixture was stirred at room temperature for 2 hours, then distilled water (0.3 mL) was added, followed by 15% NaOH (1 mL), and distilled water (3 mL), and stirred for 15 minutes. The mixture was filtered through celite with CH₂Cl₂ and concentrated. Purification of the crude material by column chromatography on silica gel (25:1:1 CH₂Cl₂—MeOH—NH₄OH) provided 0.1435 g (54%) of COMPOUND 18 as a white solid. ¹H NMR (CDCl₃) δ 1.58-1.62 (m, 4H), 2.01-2.07 (m, 2H), 2.10 (s, 6H), 2.31-2.35 (m, 2H), 2.45 (s, 6H), 3.58 (d, 4H, J=10.8 Hz), 4.36 (s, 2H), 6.57-6.67 (m, 2H), 6.85 (s, 1H), 7.02 (s, 2H), 8.01 (s, 2H). ¹³C NMR (CDCl₃) δ 18.08, 19.26, 25.84, 29.08, 46.30, 52.52, 62.98, 67.18, 125.22, 125.72, 127.84, 129.13, 131.23, 131.41, 138.04, 138.94, 140.91, 146.94, 157.02. ES-MS m/z 445.5 (M⁺H). Anal. Calcd. for C₂₈H₃₆N₄·0.2CH₂Cl₂·0.3H₂O: C, 72.53; H, 7.99; N, 12.00. Found: C, 72.91; H, 8.07; N, 11.91.

EXAMPLE 19

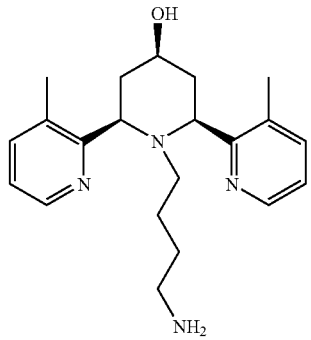

Compound 19: Meso-2'β,4'α,6'β-[1'-(4-amino-butyl)-3,3"-dimethyl-1',2',3',4',5',6'-hexahydro-[2,2';6',2"]terpyridin-4'-ol]

To a solution of meso-2',6'-[3,3"-dimethyl-2',3',5',6'-tetrahydro-1'H-cis-[2,2';6'2"]terpyridin-4'-one] (0.1666 g, 0.59 mmol) in MeOH (6 mL) under Ar was added NaBH₄ (0.0552 g, 1.48 mmol), and stirred at room temperature for 1 hour. The mixture was then concentrated, and saturated NaHCO₃ (10 mL) was added and extracted with CH₂Cl₂ (3×40 mL). The combined organic extracts were dried (Na₂SO₄), filtered, and concentrated. Purification of the crude material by column chromatography on silica gel (25:1:1 CH₂Cl₂—MeOH—NH₄OH) provided 0.1462 g (82%) of meso-2'β,4'β,6'β-[3,3"-dimethyl-1',2',3',4',5',6'-hexahydro-[2,2';6'2"]terpyridin-4'-ol] as a yellow solid. ¹H NMR (CDCl₃) δ1.43-1.55 (m, 2H), 1.81-1.97 (m, 2H), 2.14-2.18 (m, 2H), 2.36 (s, 6H), 3.97-4.07 (m, 1H), 4.19-4.20 (m, 2H), 7.00-7.07 (m, 2H), 7.38-7.42 (m, 2H), 8.44 (d, 2H), J=6.0 Hz).

Following General Procedure A: To a solution of meso-2'β,4'α,6'β'-[3,3"-dimethyl-1',2',3',4',5',6'-hexahydro-[2,2';6'2"]terpyridin-4'-ol] (0.1462 g, 0.49 mmol) in DMF (5 mL) was added 2-(4-bromo-butyl)-isoindole-1,3-dione (0.1466 g, 0.49 mmol), KI (0.0081 g, 0.05 mmol), and DIPEA (0.17 mL, 0.97 mmol). The mixture stirred at 60° C. for 17 hours before it was concentrated. Purification of the crude material by column chromatography on silica gel (33:1:1 CH₂Cl₂—MeOH—NH₄OH) provided 0.1144 g (47%) of meso-2'β,4'β,6'β-[2-[4-(4'-hydroxy-3,3"-dimethyl-3',4',5',6'-tetrahydro-2'H-[2,2';6'2"]terpyridin-1'-yl)-butyl]-isoindole-1,3-dione] as a beige solid. ¹H NMR (CDCl₃) δ 0.78-0.83 (m, 2H), 1.50-1.58 (m, 1H), 1.98-2.04 (m, 2H), 2.14-2.23 (m, 4H), 2.30-2.46 (m, 2H), 2.46 (s, 6H), 3.11-3.15 (m, 2H), 3.92 (s, 1H), 4.08-4.18 (m, 2H), 6.92-6.96 (m, 2H), 7.23-7.25 (m, 2H), 7.73-7.80 (m, 4H), 8.38 (d, 2H, J=3.0 Hz).

To a solution of meso-2'β,4'α,6'β-[2-[4-(4'-hydroxy-3,3"-dimethyl-3',4',5',6'-tetrahydro-2'H-[2,2';6'2"]terpyridin-1'-yl)-butyl]-isoindole-1,3-dione] (0.1144 g, 0.23 mmol) in EtOH (3 mL) was added hydrazine monohydrate (0.11 mL, 2.28 mmol), and stirred at room temperature for 18 hours. The reaction mixture was concentrated, and purification of the crude material by column chromatography on silica gel (13:1:1 CH₂Cl₂—MeOH—NH₄OH) provided 0.0537 g (62%) of COMPOUND 19 as a white solid. ¹H NMR (CDCl₃) δ 0.52-0.55 (m, 1H), 0.72 (t, 2H, J=6.9 Hz), 2.02-2.24 (m, 10H), 2.48

(s, 6H), 2.65 (s, 2H), 3.84-3.89 (m, 1H), 4.13 (d, 2H, J=9.9 Hz), 7.06-7.10 (m, 2H), 7.44 (d, 2H, J=7.5 Hz), 8.42 (d, 2H, J=3.0 Hz). $^{13}$C NMR (CDCl$_3$) δ 19.06, 23.81, 30.78, 38.81, 41.42, 47.56, 62.01, 69.75, 122.46, 132.04, 138.76, 146.92, 159.38. ES-MS m/z 355.4 (M$^+$H). Anal. Calcd. for C$_{21}$H$_{30}$N$_4$O.0.1CH$_2$Cl$_2$.0.5CH$_4$O: C, 68.45; H, 8.56; N, 14.78. Found: C, 68.11; H, 8.48; N, 14.61.

EXAMPLE 20

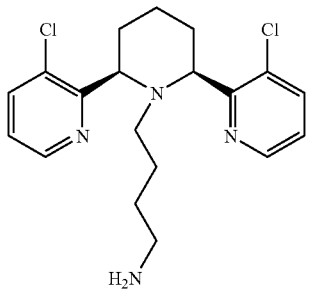

Compound 20: Meso-2',6'-[4-(3,3''-dichloro-3',4',5', 6'-tetrahydro-2'H-cis-[2,2';6',2'']terpyridin-1'-yl)-butylamine]

Following General Procedure D: To a solution of 3-chloro-pyridine-2-carbaldehyde (0.6151 g, 4.35 mmol) in MeOH (22 mL) was added NH$_4$OAc (0.1841 g, 2.39 mmol) and 1,3-acetonedicarboxylic acid (0.3211 g, 2.17 mmol), and stirred at room temperature for 2.5 hours. Purification of the crude material by column chromatography on silica gel (3:2 then 1:1 hexanes-EtOAc) provided 0.2018 g (29%) of meso-2',6'-[3,3''-dichloro-3',4',5',6'-tetrahydro-1'H-cis-[2,2';6',2'']terpyridin-4'-one] as a white solid. $^1$H NMR (CDCl$_3$) δ 2.55-2.63 (m, 2H), 2.70-2.76 (m, 2H), 3.42-3.43 (m, 1H), 4.84 (t, 2H, J=9.0 Hz), 7.16-7.20 (m, 2H), 7.66-7.69 (m, 2H), 8.54-8.56 (m, 2H).

Following General Procedure E: meso-2',6'-[3,3''-dichloro-3',4',5',6'-tetrahydro-1'H-cis-[2,2';6',2'']terpyridin-4'-one] (0.3667 g, 1.14 mmol), KOH (1.2943 g, 22.76 mmol), hydrazine monohydrate (2.21 mL, 45.52 mmol), and diethylene glycol (6 mL) were used to provide 0.4004 g (100%) of meso-2',6'-[3,3''-dichloro-1',2',3',4',5',6'-hexahydro-cis-[2,2';6',2'']terpyridine] as a yellow oil. $^1$H NMR (CDCl$_3$) δ 1.70 (s, 2H), 1.89-1.98 (m, 4H), 3.12-3.21 (m, 1H), 3.61-3.66 (m, 1H), 3.75-3.78 (m, 1H), 4.50-4.53 (m, 2H), 7.09-7.14 (m, 2H), 7.62-7.68 (m, 2H), 8.52-8.54 (m, 2H).

Following General Procedure A: meso-2',6'-[3,3''-dichloro-1',2',3',4',5',6'-hexahydro-cis-[2,2';6',2'']terpyridine] (0.4004 g, 1.3 mmol), 2-(4-bromo-butyl)-isoindole-1,3-dione (0.4815 g, 1.7 mmol), KI (0.0216 g, 0.1 mmol), DIPEA (0.45 mL, 2.6 mmol), and DMF (13 mL) were stirred at 60° C. for 22 hours. Purification of the crude material by column chromatography on silica gel (100:1:1 CH$_2$Cl$_2$—MeOH—NH$_4$OH) provided 0.4142 g (63%) of meso-2',6'-[2-[4-(3,3''-dichloro-3',4',5',6'-tetrahydro-2'H-cis-[2,2';6',2'']terpyridin-1'-yl)-butyl]-isoindole-1,3-dione] as an orange oil. $^1$H NMR (CDCl$_3$) δ 1.06-1.08 (m, 4H), 1.56-1.62 (m, 2H), 1.89-2.03 (m, 3H), 2.12-2.17 (m, 2H), 3.32-3.36 (m, 2H), 4.37 (d, 2H, J=9.0 Hz), 7.06-7.10 (m, 2H), 7.55-7.58 (m, 2H), 7.68-7.70 (m, 2H), 7.77-7.78 (m, 2H), 8.52-8.54 (m, 2H).

To a solution of meso-2',6'-[2-[4-(3,3''-dichloro-3',4',5',6'-tetrahydro-2'H-cis-[2,2';6',2'']terpyridin-1'-yl)-butyl]-isoindole-1,3-dione] (0.4142 g, 0.81 mmol) in EtOH (8 mL) was added hydrazine monohydrate (0.4 mL, 8.13 mmol), and stirred at room temperature for 16 hours. The reaction mixture was concentrated, and purification of the crude material by column chromatography on silica gel (100:1:1, then 50:1:1, then 20:1:1 CH$_2$Cl$_2$—MeOH—NH$_4$OH) provided 0.1399 g (44%) of COMPOUND 20 as a white solid. $^1$H NMR (CDCl$_3$) δ0.78-0.88 (m, 2H), 1.05-1.15 (m, 2H), 1.53-1.62 (m, 1H), 1.72 (d, 2H, J=11.4 Hz), 1.92-1.99 (m, 3H), 2.14 (t, 2H, J=8.1 Hz), 2.30 (t, 2H, J=6.9 Hz), 4.39 (d, 2H, J=10.5 Hz), 7.09-7.13 (m, 2H), 7.64 (d, 2H, J=8.1 Hz), 8.57 (d, 2H, J=3.6 Hz). $^{13}$C NMR (CDCl$_3$) δ 20.83, 24.83, 31.46, 31.78, 41.69, 50.27, 61.97, 122.82, 130.62, 137.29, 147.80, 159.07. EMS m/z 379.3 (M$^+$H). Anal. Calcd. for C$_{19}$H$_{24}$N$_4$Cl$_2$.0.7H$_2$O: C, 58.23; H, 6.53; N, 14.29; Cl, 18.09. Found: C, 58.30; H, 6.33; N, 14.07; Cl, 18.23.

EXAMPLE 21

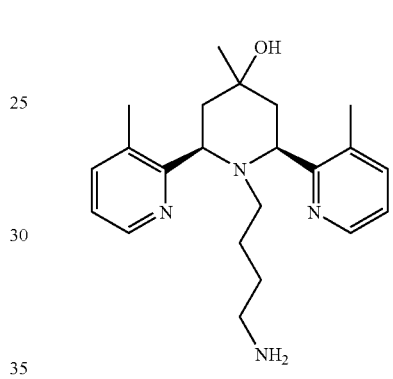

Compound 21: A 1:1 mixture of meso-2'β,4'α,6'β-[1'-(4-amino-butyl)-3,4',3''-trimethyl-1',2',3',4',5',6'-hexahydro-[2,2';6',2'']terpyridin-4'-ol] and meso-2'β, 4'β,6'β-[1'-(4-amino-butyl)-3,4',3''-trimethyl-1',2',3', 4',5',6'-hexahydro-[2,2';6',2'']terpyridin-4'-ol]

To a solution of meso-2',6'-[3,3''-dimethyl-2',3',5',6'-tetrahydro-1'H-[2,2';6'2'']terpyridin-4'-one] (2.0601 g, 7.32 mmol) in THF (50 mL) were added Et$_3$N (2.04 mL, 14.64 mmol) and Boc$_2$O (1.6083 g, 7.32 mmol) in THF (20 mL). The mixture was stirred at 70° C. for 18 hours, then concentrated. Saturated NaHCO$_3$ (30 mL) was added and extracted with CH$_2$Cl$_2$ (2×50 mL). The combined organic extracts were washed with brine (2×30 mL), dried (Na$_2$SO$_4$), filtered, and concentrated. Purification of the crude material by column chromatography on silica gel (1:1 hexanes-EtOAc) provided 1.9598 g (70%) of meso-2',6'-[3,3''-dimethyl-4'-oxo-3',4',5', 6'-tetrahydro-2'H-[2,2';6'2'']terpyridine-1'-carboxylic acid tert-butyl ester] as an orange solid. $^1$H NMR (CDCl$_3$) δ 1.27 (s, 9H), 2.37 (s, 6H), 2.50-2.58 (m, 2H), 3.16-3.24 (m, 2H), 5.78 (t, 2H, J=6.0 Hz), 6.93-6.98 (m, 2H), 7.35 (d, 2H, J=9.0 Hz), 8.07 (d, 2H, J=6.0 Hz).

To a solution of meso-2',6'-[3,3''-dimethyl-4'-oxo-3',4',5', 6'-tetrahydro-2'H-[2,2';6'2'']terpyridine-1'-carboxylic acid tert-butyl ester] (1.1179 g, 2.9 mmol) in THF (30 mL) at 0° C. under Ar was added dropwise 3.0 M MeMgBr in Et$_2$O (4.88 mL, 14.7 mmol). The mixture was stirred at 70° C. for 20 hours, then cooled to 0° C. and distilled water (30 mL) was slowly added, and stirred for 15 minutes. Next, it was concentrated to remove the THF and extracted with EtOAc (3×100 mL). The combined organic extracts were dried (Na$_2$SO$_4$), filtered, and concentrated. Purification of the crude material by column chromatography on silica gel (25:1:1CH$_2$Cl$_2$—MeOH—NH$_4$OH) followed by another column (1:1 hexanes-EtOAc) provided 0.1256 g (11%) of meso-2'β,6'β-[4'-hydroxy-3,4',3''-trimethyl-3',4',5',6'-tetrahydro-2'H-[2,2';6'2'']terpyridine-1'-carboxylic acid tert-butyl ester] as a colorless oil and 0.1606 g (19%) of meso-2'β,6'β-[3,4',3''-trimethyl-1',2',3',4',5',6'-hexahydro-[2,2';6',2'']terpyridin-4'-ol as a beige solid. $^1$H NMR (CDCl$_3$) δ 1.19 (s, 9H), 1.22-1.40 (m, 2H), 1.47 (s, 3H), 1.86-1.92 (m, 2H), 2.35-2.38 (m, 2H), 2.42 (s, 6H), 5.37-5.39 (m, 2H), 6.97-7.01 (m, 2H), 7.38 (d, 2H, J=6.0 Hz), 8.13 (d, 2H, J=3.0 Hz) and $^1$H NMR (CDCl$_3$) δ 1.51 (s, 3H), 1.56-1.64 (m, 2H), 1.82-1.94 (m, 3H), 2.36 (s, 6H), 3.09-3.11 (m, 1H), 4.15-4.21 (m, 2H), 7.00-7.06 (m, 2H), 7.40 (d, 2H, J=6.0 Hz), 8.45 (d, 2H, J=3.0 Hz) respectively.

To a solution of meso-2'β,6'β-[3,4',3''-trimethyl-1',2',3',4',5',6'-hexahydro-[2,2';6',2'']terpyridin-4'-ol (0.2499 g, 0.84 mmol) in DMF (9 mL) was added 2-(4-bromo-butyl)-isoindole-1,3-dione (0.2605 g, 0.92 mmol), KI (0.0142 g, 0.08 mmol), and DIPEA (0.29 mL, 1.68 mmol), and stirred at 60° C. for 24 hours. The mixture was concentrated, and saturated NaHCO$_3$ (30 mL) was added and extracted with CH$_2$Cl$_2$ (3×35 mL). The combined organic extracts were washed with brine (2×20 mL), dried (Na$_2$SO$_4$), filtered, and concentrated. Purification of the crude material by column chromatography on silica gel (50:1:1 CH$_2$Cl$_2$—MeOH—NH$_4$OH) provided 0.3144 g (75%) of meso-2'β,6'β-[2-[4-(4'-hydroxy-3,4',3''-trimethyl-3',4',5',6'-tetrahydro-2'H-[2,2';6',2'']terpyridin-1'yl)-butyl]-isoindole-1,3-dione as a white solid. $^1$H NMR (CDCl$_3$) δ 0.48 (s, 1H), 0.86 (s, 2H), 1.42 (s, 3H), 1.68-1.72 (m, 2H), 2.18-2.38 (m, 6H), 2.45 (s, 6H), 3.15 (t, 2H, J=6.0 Hz), 4.13 (d, 2H, J=12.0 Hz), 6.94-7.03 (m, 2H), 7.25-7.34 (m, 2H), 7.67-7.70 (m, 2H), 7.75-7.78 (m, 2H), 8.32-8.34 (m, 2H).

To a solution of meso-2'β,6'β-[2-[4-(4'*-hydroxy-3,4',3''-trimethyl-3',4',5',6'-tetrahydro-2'H-[2,2';6',2'']terpyridin-1'yl)-butyl]-isoindole-1,3-dione] (0.3144 g, 0.63 mmol) in EtOH (6 mL) was added hydrazine monohydrate (0.31 mL, 6.31 mmol), and stirred for 19 hours, then concentrated. Purification of the crude material by column chromatography on silica gel (20:1:1 CH$_2$Cl$_2$—MeOH—NH$_4$OH) provided 0.1324 g (52%) of COMPOUND 21 as a white solid. $^1$H NMR (CDCl$_3$) δ 0.72-0.76 (m, 4H), 1.42 (s, 3H), 1.42 (d, 2H, J=12.0 Hz), 2.19-2.73 (m, 6H), 2.45 (s, 6H), 2.46-4.48 (m, 1H), 4.12 (d, 2H, J=11.4 Hz), 7.03-7.07 (m, 2H), 7.41 (d, 2H, J=7.2 Hz), 8.37-8.38 (m, 2H). $^{13}$C NMR (CDCl$_3$) δ 18.98, 22.71, 25.31, 31.15, 41.47, 44.21, 48.20, 61.01, 69.41, 122.29, 131.23, 138.75, 146.95, 159.68. ES-MS m/z 369.4 (M$^+$H). Anal. Calcd. for C$_{22}$H$_{32}$N$_4$O.0.2CH$_2$Cl$_2$.0.7CH$_4$O: C, 67.43; H, 8.70; N, 13.73. Found: C, 67.25; H, 8.57; N, 13.66.

EXAMPLE 22

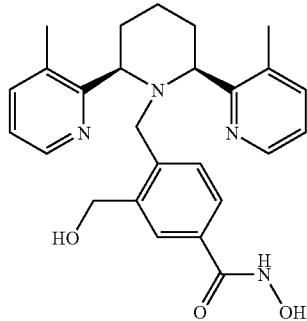

Compound 22: 4-(3,3-Dimethyl-3',4',5',6'-tetrahydro-2'H-[2,2';6',2'']terpyridin-1'-ylmethyl)-N-hydroxy-3-hydroxymethyl-benzamide Following General Procedure A: 3,3''-dimethyl-1',2',3',4',5',6'-hexahydro-[2,2';6',2'']terpyridine (1.6 g, 6.0 mmol) was reacted with 2-bromomethyl-5-cyano-benzoic acid methyl ester (1.5 g, 6.0 mmol) to give 5-cyano-2-(3,3''-dimethyl-3',4',5',6'-tetrahydro-2'H-[2,2';6',2'']terpyridin-1'-ylmethyl)-benzoic acid methyl ester (2.05 g, 78%), as a pale-yellow solid.

To a stirred, room temperature solution of the ester from above (2.05 g, 4.6 mmol) in MeOH (50 mL) was added LiBH$_4$ (1.0 g, 50 mmol) in three portions. Effervescence was observed, and the mixture was stirred for 3.5 hours. The mixture was concentrated and 1 N NaOH (50 mL) was added to the resultant residue. The aqueous mixture was extracted with CH$_2$Cl$_2$ (3×50 mL). The organic extracts were combined, dried (Na$_2$SO$_4$), and concentrated. Purification of the crude material by column chromatography on silica gel (40 g, eluted with 5% NH$_4$OH/5% MeOH/CH$_2$Cl$_2$) provided 4-(3,3''-dimethyl-3',4',5',6'-tetrahydro-2'H-[2,2';6',2'']terpyridin-1'-ylmethyl)-3-hydroxymethyl-benzonitrile (1.63 g, 86%) as a pale yellow solid.

The nitrile from above (1.13 g, 2.7 mmol) was stirred in refluxing 50% H$_2$SO$_4$ (50 mL) for 16 hours. The solution was cooled to room temperature and concentrated to remove water. The residue was taken up in MeOH (50 mL) and concentrated three times. MeOH was added to the resultant residue and the solution was refluxed for 2 hours. The solution was concentrated to remove MeOH. The residue was basified with 10 N NaOH (final pH=10) and extracted with CH$_2$Cl$_2$ (3×100 mL). The combined organic extracts were dried (Na$_2$SO$_4$) and concentrated. Purification of the crude material by silica gel column chromatography (30 g, eluted with 5% NH$_4$OH/5% MeOH/CH$_2$Cl$_2$) gave two products: 4-(3,3''-dimethyl-3',4',5',6'-tetrahydro-2'H-[2,2';6',2'']terpyridin-1'-ylmethyl)-3-hydroxymethyl-benzoic acid methyl ester (700 mg, 58%), and 4-(3,3''-dimethyl-3',4',5',6'-tetrahydro-2'H-[2,2';6',2'']terpyridin-1'-ylmethyl)-3-methoxymethyl-benzoic acid methyl ester (210 mg, 17%).

To a stirred solution of sodium (320 mg, 14 mmol) in anhydrous MeOH (15 mL) was added NH$_2$OH.H$_2$O (550 mg, 7.9 mmol) followed by a solution of 4-(3,3''-dimethyl-3',4', 5',6'-tetrahydro-2'H-[2,2';6',2"]terpyridin-1'-ylmethyl)-3-hydroxymethyl-benzoic acid methyl ester (700 mg, 1.6 mmol) in anhydrous MeOH (7 mL). The mixture was stirred for 2 h, at which time TLC indicated that the reaction had stalled. A solution of sodium (320 mg, 14 mmol) and $NH_2OH \cdot H_2O$ (550 mg, 7.9 mmol) in anhydrous MeOH (8 mL) was added to the reaction mixture and stirring was continued for 2 hours. The reaction mixture was diluted with $CHCl_3$ (100 mL) and poured into a saturated $NaHCO_3$ solution (100 mL). The aqueous layer was extracted with $CHCl_3$ (5×100 mL). The combined organic portions were concentrated to 100 mL, washed once with saturated $NaHCO_3$ solution (20 mL), dried over $Na_2SO_4$, concentrated, and dried under high vacuum to give COMPOUND 22 (647 mg, 92%) as an off-white solid. $^1H$ NMR (DMSO-$d_6$) δ 1.46 (d, 2H, J=12.0 Hz), 1.69-1.84 (m, 1H), 2.01-2.11 (m, 1H), 2.48 (s, 6H), 3.59 (s, 2H), 4.13 (d, 2H, J=3.8 Hz), 4.40 (d, 2H, J=10.8 Hz), 4.79-4.85 (m, 1H), 5.74 (s, 1H), 6.84-6.91 (m, 3H), 7.06 (d, 1H, J=7.5 Hz), 7.18-7.28 (m, 3H), 8.14 (d, 2H, J=3.3 Hz), 8.75 (s br, 1H), 10.82 (s br, 1H); $^{13}C$ NMR ($D_2O$) δ 18.38 (2), 24.40, 25.32 (2), 55.27, 60.85 (2), 64.75, 122.31 (2), 123.64, 124.88, 126.82, 132.62, 137.64 (2), 138.08, 143.18, 145.86 (2), 158.58, 164.49; ES-MS m/z 447 ($M^+H$). Anal. Calcd. For $C_{26}H_{30}N_4O_3 \cdot 1.1H_2O$: C, 66.96; H, 6.96; N, 12.01. Found: C, 66.95; H, 6.71; N, 11.66.

EXAMPLE 23

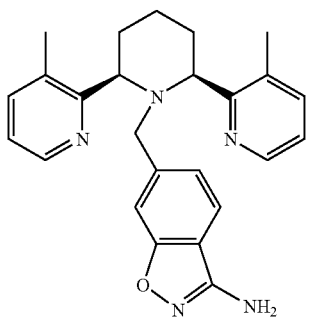

Compound 23: The 6-((2'S,6'R)-3,3"-dimethyl-3',4', 5',6'-tetrahydro-2'H-2,2';6',2"-terpyridin-1'-ylmethyl)-1,2-benzisoxazol-3-ylamine (HBr Salt)

Under $N_2$, to a suspension of 1-bromo-2-fluoro-4-methyl-benzene (2.59 g, 13.7 mmol) and $Zn(CN)_2$ (1.60 g, 13.7 mmol) in dry DMF (50 mL) was added 1,1'-bis(diphenylphosphino)ferrocene (DPPF) (0.0753 g, 0.136 mmol) and $Pd_2(dba)_3$ (dba=di(benzylidene)acetone) (0.0623 g, 0.0681 mmol). After the mixture was heated at 130° C. for 2 days, the solvent was removed by evaporation under vacuum, and saturated aqueous $NaHCO_3$ (40 mL) was added. The aqueous suspension was extracted with $CH_2Cl_2$ (3×40 mL), and the extract was dried over $Na_2SO_4$. After filtration the solvent was removed by evaporation under vacuum, and the residual solid was purified by flash chromatography on silica gel (1:20 EtOAc/hexanes), affording 2-fluoro-4-methyl-benzonitrile as a pale yellow solid (1.21 g, 65%). $^1H$ NMR ($CDCl_3$) δ 2.43 (s, 3H), 7.01-7.07 (m, 2H), 7.48-7.52 (m, 1H).

To a solution of 2-fluoro-4-methyl-benzonitrile (1.45 g, 10.7 mmol) in $CCl_4$ (100 mL) was added 1,1'-azobis(cyclohexanecarbonitrile) (0.240 g, 0.982 mmol) and NBS (2.19 g, 12.3 mmol). The mixture was stirred and heated at reflux overnight, and then cooled to room temperature. A solution of $Na_2S_2O_3$ (5 g) in $H_2O$ (100 mL) was added, and the organic layer was collected. The aqueous layer was extracted with $CH_2Cl_2$ (3×50 mL), and the extracts were combined and dried over $Na_2SO_4$. After filtration the solvent was removed by evaporation under vacuum, and the residue was purified on silica gel column (1:10 EtOAc/hexanes), affording 4-bromomethyl-2-fluoro-benzonitrile as a pale yellow oil (1.49 g, 65%). $^1H$ NMR ($CDCl_3$) δ 4.45 (s, 2H), 7.24-7.30 (m, 2H), 7.60 (dd, 1H, J=6.3, 8.1 Hz).

A mixture of (2'R,6'S)-3,3"-dimethyl-1',2',3',4',5',6'-hexahydro-[2,2';6',2"]terpyridine (0.267 g, 1.00 mmol), 4-bromomethyl-2-fluoro-benzonitrile (0.321 g, 0.1.50 mmol), DIPEA (0.259 g, 2.00 mmol) and KI (0.017 g, 0.10 mmol) in dry $CH_3CN$ (10 mL) was stirred at 60° C. for 16 h. After that period of time the $CH_3CN$ was removed by evaporation under vacuum, and saturated aqueous $NaHCO_3$ (20 mL) was added. The aqueous mixture was extracted with $CH_2Cl_2$ (3×30 mL), and the extract was dried over $Na_2SO_4$. After filtration the solvent was removed by evaporation under vacuum, and the residue was purified on a silica gel column (1000:30:1, $CH_2Cl_2/CH_3OH/NH_4OH$), affording 4-((2'R,6'S)-3,3"-dimethyl-3',4',5',6'-tetrahydro-2'H-[2,2';6',2"]terpyridin-1'-ylmethyl)-2-fluoro-benzonitrile as a white foam (0.400 g, 100%). $^1H$ NMR ($CDCl_3$) δ 1.65-1.80 (m, 3H), 2.09-2.14 (m, 1H), 2.20-2.38 (m, 2H), 2.44 (s, 6H), 3.58 (s, 2H), 4.16 (s, 1H), 4.20 (s, 1H), 6.37-6.43 (m, 2H), 6.93-7.03 (m, 3H), 7.23 (d, 2H, J=7.5 Hz), 8.35 (dd, 2H, J=0.9, 4.5 Hz).

To a solution of potassium tert-butoxide (0.140 g, 1.25 mmol) in dry DMF (5 mL) was added acetone oxime (0.0877 g, 1.20 mmol), and the mixture was stirred for 30 min. A solution of 4-((2'R,6'S)-3,3"-dimethyl-3',4',5',6'-tetrahydro-2'H-[2,2';6',2"]terpyridin-1'-ylmethyl)-2-fluoro-benzonitrile (0.400 g, 1.00 mmol) in dry DMF (5 mL) was then added, and the mixture was stirred overnight. The solvent was then removed by evaporation under vacuum, and saturated aqueous $NaHCO_3$ (10 mL) was added. The mixture was extracted with EtOAc (3×30 mL), and the extract was dried over $Na_2SO_4$. After filtration the solvent was removed by evaporation under vacuum, and the residue was purified on silica gel column (1000:25:1 $CH_2Cl_2/CH_3OH/NH_4OH$), affording 4-((2'R,6'S)-3,3"-dimethyl-3',4',5',6'-tetrahydro-2'H-[2,2';6', 2"]terpyridin-1'-ylmethyl)-2-isopropylideneamineooxy-benzonitrile as a pale yellow solid (0.311 g, 69%). $^1H$ NMR ($CDCl_3$) δ 1.65-1.75 (m, 3H), 2.06 (s, 3H), 2.07 (s, 3H), 2.09-2.14 (m, 1H), 2.20-2.40 (m, 2H), 2.45 (s, 6H), 3.58 (s, 2H), 4.19 (s, 1H), 4.23 (s, 1H), 6.14 (d, 1H, J=7.8 Hz), 6.68 (s, 1H), 6.91-6.96 (m, 3H), 7.22 (d, 2H, J=7.2 Hz), 8.35 (d, 2H, J=3.9 Hz).

To a solution of 4-((2'R,6'S)-3,3"-dimethyl-3',4',5',6'-tetrahydro-2'H-[2,2';6',2"]terpyridin-1'-ylmethyl)-2-isopropylideneamineooxy-benzonitrile (0.145 g, 0.320 mmol) in EtOH (4 mL) was added aqueous HCl (3 N, 4 mL), and the mixture was stirred and heated at reflux overnight. The mixture was then cooled to room temperature, EtOH was removed, and saturated aqueous $NaHCO_3$ (20 mL) was added. The mixture was extracted with $CH_2Cl_2$ (4×40 mL), and the combined extract was dried over $Na_2SO_4$. After filtration the solvent was removed by evaporation under vacuum, and the residue was purified on silica gel column (100:5:2 $CH_2Cl_2/CH_3OH/NH_4OH$), affording 6-((2'S,6'R)-3,3"-dimethyl-3', 4',5',6'-tetrahydro-2'H-2,2';6',2"-terpyridin-1'-ylmethyl)-1,2-benzisoxazol-3-ylamine as a white solid (0.082 g, 62%).

Following General Procedure B the white solid (0.060 g, 0.15 mmol) was treated with HBr/MeOH to afford an HBr salt as a yellow solid (0.099 g, 96%). $^1H$ NMR ($CD_3OD$) δ 1.83-1.94 (m, 3H), 2.03-2.16 (m, 3H), 2.63 (s, 6H), 3.77 (s, 2H), 4.57-4.60 (m, 2H), 6.99 (d, 1H, J=8.1 Hz), 7.03 (s, 1H), 7.43 (d, 1H, J=8.1 Hz), 7.76 (dd, 2H, J=5.7, 7.8 Hz), 8.29 (d, 2H, J=7.8 Hz), 8.69 (d, 2H, J=5.7 Hz). $^{13}$C NMR (CD$_3$OD/D$_2$O) δ 16.98, 22.07, 38.37, 61.33, 61.83, 110.25, 114.90, 122.14, 124.69, 125.39, 136.38, 138.93, 139.65, 148.66, 154.78, 157.50, 161.07. ES-MS m/z 414 (M$^+$H). Anal. Calcd. for C$_{25}$H$_{27}$N$_5$O.3.4HBr.1.1H$_2$O: C, 42.39; H, 4.64; N, 9.89; Br, 38.35. Found: C, 42.22; H, 4.55; N, 9.60; Br, 38.54.

EXAMPLE 24

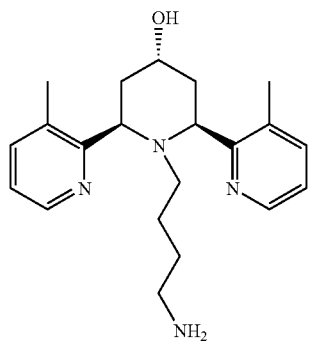

Compound 24: Meso-2'β,4'α,6'β-[1'-(4-amino-butyl)-3,3"-dimethyl-1',2',3',4',5',6'-hexahydro-[2,2';6',2"]terpyridin-4'-ol]

To a solution of meso-2'β,6'β-[3,3"-dimethyl-2',3',5',6'-tetrahydro-1'H-[2,2';6'2"]terpyridin-4'-one] (3.5417 g, 12.6 mmol) in THF (90 mL) under Ar at −78° C. was slowly added L-selectride (13.8 mL, 13.8 mmol), and was stirred for 30 minutes (*Tetrahedron: Asymmetry* (1999) 10:2225-2235). MeOH (35 mL) was added, and at room temperature distilled water (70 mL) was added and extracted with CH$_2$Cl$_2$ (3×150 mL). The combined organic extracts were dried (Na$_2$SO$_4$), filtered, and concentrated to provide 5.37 g (100%) of a 1:1 mixture of meso-2'β,4'β,6'β-[3,3"-dimethyl-1',2',3',4',5',6'-hexahydro-[2,2';6'2"]terpyridin-4'-ol] and meso-2'β,4'α,6'β-[3,3"-dimethyl-1',2',3',4',5',6'-hexahydro-[2,2';6'2"]terpyridin-4'-ol] as a sticky orange oil. $^1$H NMR (CDCl$_3$) δ 1.43-1.55 (m, 2H), 1.81-1.97 (m, 2H), 2.14-2.18 (m, 2H), 2.36 (s, 6H), 3.97-4.07 (m, 1H), 4.19-4.20 (m, 1H), 7.00-7.07 (m, 2H), 7.38-7.42 (m, 2H), 8.44-8.45 (m, 2H).

To a solution of a 1:1 mixture of meso-2'β,4'β,6'β-[3,3"-dimethyl-1',2',3',4',5',6'-hexahydro-[2,2';6'2"]terpyridin-4'-ol] and meso-2'β,4'α,6'β-[3,3"-dimethyl-1',2',3',4',5',6'-hexahydro-[2,2';6'2"]terpyridin-4'-ol] in THF (90 mL) was added DIPEA (4.36 mL, 25.2 mmol) and Boc$_2$O (3.3407 g, 15.1 mmol) and stirred at 50° C. for 16 hours. The mixture was concentrated, and saturated NaHCO$_3$ (75 mL) was added and extracted with CH$_2$Cl$_2$ (3×100 mL). The combined organic extracts were washed with brine (2×75 mL), dried (Na$_2$SO$_4$), filtered, and concentrated. Purification of the crude material by column chromatography on silica gel (1:1 hexanes-EtOAc) provided 1.2984 g (27%) of meso-2'β,4'β,6β'-[4'-hydroxy-3,3"-dimethyl-3',4',5',6'-tetrahydro-2'H-[2,2';6'2"]terpyridine-1'-carboxylic acid tert-butyl ester as a yellow solid and 0.8605 g (18%) of meso-2'β,4'α,6'β-[4'-hydroxy-3,3"-dimethyl-3',4',5',6'-tetrahydro-2'H-[2,2';6'2"]terpyridine]-1'-carboxylic acid tert-butyl ester a pale yellow solid. $^1$H NMR (CDCl$_3$) δ 1.17 (s, 9H), 2.19 (t, 4H, J=6.6 Hz), 2.40 (s, 6H), 4.17-4.20 (m, 1H), 5.38 (t, 2H, J=6.3 Hz), 6.05 (d, 1H, J=10.2 Hz), 6.94-6.98 (m, 2H), 7.34-7.36 (m, 2H), 8.11 (d, 2H, J=3.9 Hz) and $^1$H NMR (CDCl$_3$) δ 1.50 (s, 9H), 1.67-1.76 (m, 2H), 2.21 (s, 6H), 2.69-2.76 (m, 2H), 5.62-5.67 (m, 1H), 5.80-5.83 (m, 2H), 6.68-6.72 (m, 2H), 6.97-7.05 (m, 2H), 7.99 (d, 2H, J=3 Hz), respectively.

To a solution of meso-2'β,4'α,6'β-[4'-hydroxy-3,3"-dimethyl-3',4',5',6'-tetrahydro-2'H-[2,2';6'2"]terpyridine]-1'-carboxylic acid tert-butyl ester (0.2508 g, 0.66 mmol) in CH$_2$Cl$_2$ (5 mL) was added TFA (5 mL), and stirred at room temperature for 3.5 hours. The mixture was concentrated, and distilled water (2 mL) and 10 N NaOH (2 mL) were added and extracted with CH$_2$Cl$_2$ (3×50 mL). The combined organic extracts were dried (Na$_2$SO$_4$), filtered, and concentrated to provide 0.2182 g (100%) of meso-2'β,4'α,6'β-[3,3"-dimethyl-1',2',3',4',5',6'-hexahydro-[2,2';6'2"]terpyridin-4'-ol] as a beige solid. $^1$H NMR (CDCl$_3$) δ 1.82-1.97 (m, 4H), 2.39 (s, 6H), 4.46-4.48 (m, 1H), 4.90-4.93 (m, 2H), 7.04-7.08 (m, 2H), 7.40-7.43 (m, 2H), 8.44 (d, 2H, J=3.0 Hz).

Following General Procedure A: To a solution of meso-2'β,4'α,6'β-[3,3"-dimethyl-1',2',3',4',5',6'-hexahydro-[2,2';6'2"]terpyridin-4'-ol] (0.2182 g, 0.77 mmol) in DMF (5 mL) was added 2-(4-bromo-butyl)-isoindole-1,3-dione (0.2389 g, 0.85 mmol), KI (0.0128 g, 0.08 mmol), and DIPEA (0.27 mL, 1.54 mmol). The mixture stirred at 60° C. for 21 hours before it was concentrated. Purification of the crude material by column chromatography on silica gel (25:1:1 CH$_2$Cl$_2$—MeOH—NH$_4$OH) provided 0.2356 g (61%) of meso-2'β,4'α,6'β-2-[4-(4'-hydroxy-3,3"-dimethyl-3',4',5',6'-tetrahydro-2'H-[2,2';6',2"]terpyridin-1'-yl)-butyl]-isoindole-1,3-dione. $^1$H NMR (CDCl$_3$) δ 0.46-0.47 (m, 2H), 0.85-0.89 (m, 2H), 1.72 (d, 2H, J=12.0 Hz), 2.34-2.40 (m, 2H), 2.48 (s, 6H), 2.49-2.50 (m, 2H), 3.16 (t, 2H, J=6.0 Hz), 4.44-4.45 (m, 1H), 4.71 (d, 2H, J=6.0 Hz), 6.94-6.98 (m, 2H), 7.27-7.29 (m, 2H), 7.69-7.72 (m, 2H), 7.78-7.81 (m, 2H), 8.38 (d, 2H, J=6.0 Hz).

To a solution of meso-2'β,4'α,6'β-2-[4-(4'-hydroxy-3,3"-dimethyl-3',4',5',6'-tetrahydro-2'H-[2,2';6',2"]terpyridin-1'-yl)-butyl]-isoindole-1,3-dione (0.2356 g, 0.47 mmol) in EtOH (5 mL) was added hydrazine monohydrate (0.23 mL, 4.70 mmol), and stirred at room temperature for 17 hours. The reaction mixture was concentrated, and purification of the crude material by column chromatography on silica gel (15:1:1 CH$_2$Cl$_2$—MeOH—NH$_4$OH) provided 0.1297 g (72%) of COMPOUND 24 as a white solid. $^1$H NMR (CDCl$_3$) δ 0.40-0.42 (m, 2H), 0.66-0.71 (m, 2H), 1.72 (d, 2H, J=15.0 Hz), 2.13-2.14 (m, 2H), 2.27-2.32 (m, 2H), 2.49-2.54 (m, 2H), 2.55 (s, 6H), 4.44 (s, 1H), 4.70 (d, 2H, J=9.0 Hz), 7.06-7.10 (m, 2H), 7.43 (d, 2H, J=9.0 Hz), 8.43 (d, 2H, J=3.0 Hz). $^{13}$C NMR (CDCl$_3$) δ19.02, 24.67, 28.82, 35.26, 41.38, 46.36, 57.34, 64.78, 122.19, 132.69, 138.41, 146.53, 160.21. ES-MS m/z 355.3 (M+H). Anal. Calcd. for $C_{21}H_{30}N_4O \cdot 0.2CH_2Cl_2 \cdot 0.8H_2O$: C, 65.99; H, 8.36; N, 14.52. Found: C, 66.22; H, 8.28; N, 14.88.

EXAMPLE 25

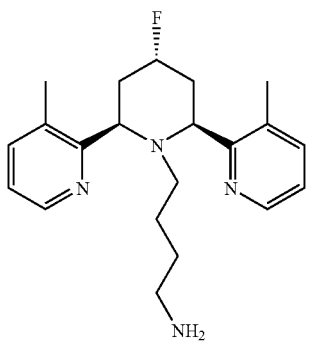

Compound 25: Meso-2'β,4'α,6'β-[4-(4'-fluoro-3,3"-dimethyl-3',4',5',6'-tetrahydro-2'H-[2,2';6',2"]terpyridin-1'-yl)-butylamine]

To a solution of meso-2'β,4'β,6'β-[4'-hydroxy-3,3"-dimethyl-3',4',5',6'-tetrahydro-2'H-[2,2';6'2"]terpyridine]-1'-carboxylic acid tert-butyl ester (0.5022 g, 1.31 mmol) in $CH_2Cl_2$ (13 mL) at 0° C. under Ar was added dropwise (diethylamino)sulfur trifluoride (0.19 mL, 1.44 mmol) and stirred for 20 minutes, then stirred at room temperature for 40 minutes. Saturated $NaHCO_3$ (20 mL) was added and extracted with $CH_2Cl_2$ (3×30 mL). The combined organic extracts were washed with brine (1×20 mL), dried ($Na_2SO_4$), filtered, and concentrated. Purification of the crude material by column chromatography on silica gel (1:1 hexanes-EtOAc, then EtOAc) provided 0.1524 g (30%) of meso-2'β,4'α,6'β-[4'-fluoro-3,3"-dimethyl-3',4',5',6'-tetrahydro-2'H-[2,2';6'2"]terpyridine]-1'-carboxylic acid tert-butyl ester as an amber oil. $^1$H NMR (CDCl$_3$) δ 1.43 (s, 9H), 1.44-1.45 (m, 1H), 1.88-2.01 (m, 2H), 2.25 (s, 6H), 2.78-2.88 (m, 2H), 5.78 (t, 2H, J=5.1 Hz), 6.75-6.79 (m, 2H), 7.11 (d, 2H, J=7.7 Hz), 8.00 (d, 2H, J=4.8 Hz).

To a solution of meso-2'β,4'α,6'β-[4'-fluoro-3,3"-dimethyl-3',4',5',6'-tetrahydro-2'H-[2,2';6'2"]terpyridine]-1'-carboxylic acid tert-butyl ester in $CH_2Cl_2$ (5 mL) was added TFA (5 mL), and stirred at room temperature for 18 hours. The mixture was concentrated, and distilled water (2 mL) and 10 N NaOH (2 mL) were added and extracted with $CH_2Cl_2$ (3×40 mL). The combined organic extracts were dried ($Na_2SO_4$), filtered, and concentrated to provide 0.0834 g (73%) of meso-2'β,4'α,6'β-[4'-fluoro-3,3"-dimethyl-1',2',3',4',5',6'-hexahydro-[2,2';6'2"]terpyridine] as an amber oil. $^1$H NMR (CDCl$_3$) δ 1.81-1.90 (m, 1H), 1.96-2.18 (m, 4H), 2.40 (s, 6H), 2.71-3.00 (m, 1H), 4.68 (d, 2H, J=10.2 Hz), 7.03-7.07 (m, 2H), 7.41 (d, 2H, J=7.7 Hz), 8.43 (d, 2H, J=4.5 Hz).

Following General Procedure A: To a solution of meso-2'β,4'α,6'β-[4'-fluoro-3,3"-dimethyl-1',2',3',4',5',6'-hexahydro-[2,2';6'2"]terpyridine] (0.0834 g, 0.29 mmol) in DMF (5 mL) was added 2-(4-bromo-butyl)-isoindole-1,3-dione (0.0946 g, 0.32 mmol), KI (0.0048 g, 0.03 mmol), and DIPEA (0.10 mL, 0.58 mmol). The mixture stirred at 60° C. for 21 hours before it was concentrated. Purification of the crude material by column chromatography on silica gel (100:1:1 $CH_2Cl_2$—MeOH—$NH_4OH$) provided 0.0839 g (63%) of meso-2'β,4'α,6'β-[4-(4'-fluoro-3,3"-dimethyl-3',4',5',6'-tetrahydro-2'H-[2,2';6'2"]terpyridin-1'-yl)-butylamine]. $^1$H NMR (CDCl$_3$) δ 0.74-0.84 (m, 2H), 1.87 (s, 6H), 2.34-2.44 (m, 3H), 2.48 (s, 6H), 3.12 (t, 2H, J=7.0 Hz), 4.67 (d, 2H, J=11.4 Hz), 6.92-6.96 (m, 2H), 7.23-7.25 (m, 2H), 7.71-7.73 (m, 2H), 7.78-7.82 (m, 2H), 8.36 (d, 2H, J=6.0 Hz).

To a solution of meso-2'β,4'α,6'β-[4-(4'-fluoro-3,3"-dimethyl-3',4',5',6'-tetrahydro-2'H-[2,2';6'2"]terpyridin-1'-yl)-butylamine] (0.0839 g, 0.18 mmol) in EtOH (2 mL) was added hydrazine monohydrate (0.10 mL, 1.83 mmol), and stirred at room temperature for 20 hours. The reaction mixture was concentrated, and purification of the crude material by column chromatography on silica gel (75:1:1 then 25:1:1 $CH_2Cl_2$—MeOH—$NH_4OH$) provided 0.0482 g (73%) of COMPOUND 25 as a white solid. $^1$H NMR (CDCl$_3$) δ 0.36-0.38 (m, 2H), 0.61-0.71 (m, 3H), 1.97 (t, 2H, J=12.0 Hz), 2.10 (t, 2H, J=6.3 Hz), 2.30 (t, 2H, J=7.8 Hz), 2.41-2.61 (m, 4H), 2.53 (s, 6H), 4.66 (d, 2H, J=11.7 Hz), 7.07-7.12 (m, 2H), 7.44 (d, 2H, J=7.5 Hz), 8.43 (d, 2H, J=4.2 Hz). $^{13}$C NMR (CDCl$_3$) δ 18.94, 25.73, 31.18, 31.64, 31.90, 41.76, 44.59, 57.59, 122.87, 133.03, 138.37, 146.68, 159.05. ES-MS m/z 357.3 (M+H). Anal. Calcd. for $C_{21}H_{29}N_4F \cdot 0.1CH_2Cl_2$: C, 69.44; H, 8.06; N, 15.35; F, 5.21. Found: C, 69.57; H, 8.12; N, 15.04; F, 5.06.

EXAMPLE 26

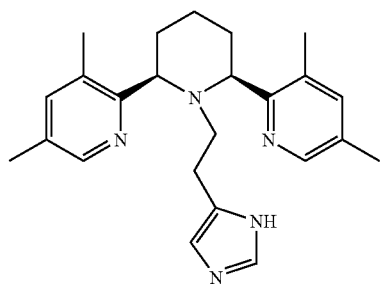

Compound 26: Meso-2'β,6'β-[2-(3,5,3",5"-tetramethyl-3',4',5',6'-tetrahydro-2'H-[2,2';6',2"]terpyridin-1'-ylmethyl)-benzonitrile]

To a solution of meso-2'β,6'β-[3,5,3",5"-tetramethyl-1',2',3',4',5',6'-hexahydro-[2,2';6',2"]terpyridine (0.2860 g, 0.97 mmol) in DMF (10 mL) was added 5-(2-chloro-ethyl)-1H-imidazole (0.1896 g, 1.45 mmol), KI (0.0161 g, 0.10 mmol), and DIPEA (0.34 mL, 1.94 mmol). The reaction was stirred at 80° C. for 18 hours, then concentrated. Saturated $NaHCO_3$ (25 mL) was added and extracted with $CH_2Cl_2$ (3×50 mL). The combined organic extracts were washed with brine (3×30 mL), dried ($Na_2SO_4$), filtered, and concentrated. Purification of the crude material by column chromatography on silica gel (100:1:1 then 50:1:1 $CH_2Cl_2$—MeOH—$NH_4OH$) provided 76.7 mg (19%) of COMPOUND 26 as a beige solid. $^1$H NMR (CDCl$_3$) δ 1.53-1.67 (m, 4H), 1.84-2.06 (m, 4H), 2.21 (s, 6H), 2.34 (s, 6H), 2.46-2.57 (m, 2H), 3.86 (d, 2H, J=6.0 Hz), 6.14 (s, 1H), 7.18 (s, 2H), 7.39 (s, 1H), 8.17 (s, 2H). $^{13}$C NMR (CDCl$_3$) 17.44, 18.22, 22.51, 24.67, 31.07, 50.85, 64.51, 119.07, 130.19, 130.81, 133.62, 138.86, 140.08, 146.54, 157.06. ES-MS m/z 390.3 (M+H). Anal. Calcd. for C$_{24}$H$_{31}$N$_5$.0.4CH$_2$Cl$_2$: C, 69.20; H, 7.57; N, 16.54. Found: C, 69.05; H, 7.75; N, 16.46.

EXAMPLE 27

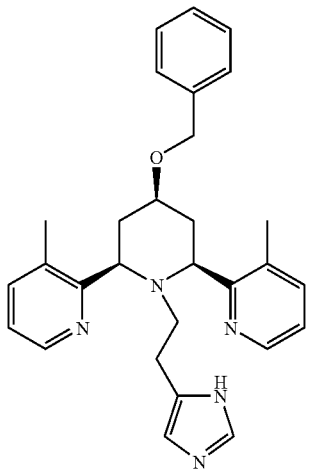

Compound 27: Meso-2'β,4'β,6'β-[4'-benzyloxy-1'-[2-(3H-imidazol-4-yl)-ethyl]-3,3"-dimethyl-1',2',3',4',5',6'-hexahydro-[2,2';6',2"]terpyridine To a solution of meso-2'β,4'β,6'β-[4'-hydroxy-3,3"-dimethyl-3',4',5',6'-tetrahydro-2'H-[2,2';6'2"]terpyridine-1'-carboxylic acid tert-butyl ester] (0.7035 g, 1.8 mmol) in DMF (18 mL) was added NaH, 60% dispersion in mineral oil (0.1440 g, 3.6 mmol), and stirred at room temperature for 1 hour. Benzyl bromide (1.07 mL, 9.0 mmol) and KI (0.0664 g, 0.4 mmol) were added, and stirred at 80° C. for 20 hours. The mixture was concentrated, and saturated NaHCO$_3$ (30 mL) was added and extracted with CH$_2$Cl$_2$ (3×50 mL). The combined organic extracts were washed with brine (3×50 mL), dried (Na$_2$SO$_4$), filtered, and concentrated. Purification of the crude material by column chromatography on silica gel (100:1:1 CH$_2$Cl$_2$—MeOH—NH$_4$OH) provided a 1:1 mixture of recovered starting material meso-2'β,4'β,6'β-[4'-hydroxy-3,3"-dimethyl-3',4',5',6'-tetrahydro-2'H-[2,2';6'2"]terpyridine-1'-carboxylic acid tert-butyl ester] and product meso-2'β,4'β,6'β-[4'-benzyloxy-3,3"-dimethyl-3',4',5',6'-tetrahydro-2'H-[2,2';6'2"]terpyridine-1'-carboxylic acid tert-butyl ester] as a dark red oil.

To a solution of the above in CH$_2$Cl$_2$ (10 mL) was added TFA (10 mL) and stirred at room temperature for 1 hour. The reaction was concentrated, and water (5 mL) and CH$_2$Cl$_2$ (40 mL) were added. 10N NaOH was slowly added (10 mL) until basic, and the phases were separated. The aqueous phase was extracted with CH$_2$Cl$_2$ (2×40 mL), and the combined organic extracts were dried (Na$_2$SO$_4$), filtered, and concentrated. Purification of the crude material by column chromatography on silica gel (50:1:1 CH$_2$Cl$_2$—MeOH—NH$_4$OH) followed by another column (100:1:1 CH$_2$Cl$_2$—MeOH—NH$_4$OH) provided 0.1282 g (19%, 2 steps) of meso-2'β,4'β,6'β-[4'-benzyloxy-3,3"-dimethyl-1',2',3',4',5',6'-hexahydro-[2,2';6'2"]terpyridine as a yellow oil. $^1$H NMR (CDCl$_3$) δ 2.19-2.31 (m, 2H), 2.37 (s, 3H), 2.42 (s, 3H), 3.84-3.89 (m, 1H), 4.20 (d, 2H, J=9.0 Hz), 4.63 (s, 2H), 5.39 (t, 1H, J=7.5 Hz), 7.01-7.07 (m, 4H), 7.29-7.42 (m, 5H), 8.45 (d, 2H, J=3.0 Hz).

To a solution of meso-2'β,4'β,6'β-[4'-benzyloxy-3,3"-dimethyl-1',2',3',4',5',6'-hexahydro-[2,2';6'2"]terpyridine (0.1282 g, 0.34 mmol) in DMF (4 mL) were added 2-(2-chloro-ethyl)-1H-imidazole (0.0672 g, 0.51 mmol), DIPEA (0.12 mL, 0.68 mmol), and KI (0.0056 g, 0.03 mmol). The reaction was stirred at 80° C. for 65 hours, then concentrated. Saturated NaHCO$_3$ (15 mL) was added and extracted with CH$_2$Cl$_2$ (3×20 mL). The combined organic extracts were washed with brine (2×30 mL), dried (Na$_2$SO$_4$), filtered, and concentrated. Purification of the crude material by column chromatography on silica gel (50:1:1, 25:1:1, then 10:1:1 CH$_2$Cl$_2$—MeOH—NH$_4$OH) followed by radial chromatography on silica (20:1:1 CH$_2$Cl$_2$—MeOH—NH$_4$OH) provided 24.4 mg (13%) of COMPOUND 27 as a white solid. $^1$H NMR (CDCl$_3$) δ 2.09-2.28 (m, 4H), 2.40 (s, 6H), 2.53-2.65 (m, 2H), 2.95-3.04 (m, 1H), 3.71-3.77, 4.02 (d, 2H, J=11.7 Hz), 4.20 (t, 1H, J=6.9 Hz), 4.59 (s, 2H), 6.15 (s, 1H), 7.05-7.09 (m, 2H), 7.28-7.33 (m, 5H), 7.36-7.42 (m, 3H), 8.38-8.39 (m, 2H). $^{13}$C NMR (CDCl$_3$) 19.10, 24.07, 30.27, 32.30, 36.52, 44.46, 47.36, 50.02, 166.68, 122.72, 127.85, 128.76, 131.88, 134.38, 135.70, 137.17, 139.09, 140.39, 146.59, 147.05, 159.32. ES-MS m/z 468.5 (M+H). Anal. Calcd. for C$_{29}$H$_{33}$O.0.6CH$_2$Cl$_2$.0.6H$_5$NO: C, 65.89; H, 6.95; N, 14.54. Found: C, 66.08; H, 6.79; N, 14.75.

EXAMPLE 28

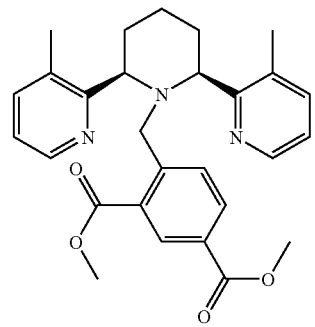

Compound 28: 4-(3,3"-Dimethyl-3',4',5',6'-tetrahydro-2'H-[2,2';6',2"]terpyridin-1'-ylmethyl)-isophthalic Acid Dimethyl Ester 5-Cyano-2-methyl-benzoic acid methyl ester (1.09 g, 6.22 mmol) was suspended in a mixture of water (25 mL) and concentrated sulfuric acid (10 mL). The yellow solution was stirred at 150° C. for 4 hours to give a pale yellow slurry. The reaction mixture was cooled to room temperature and the precipitate was isolated via suction filtration, washed with water (2×10 mL) and dried in vacuo to yield 4-methyl-isophthalic acid as a tan solid. The diacid was then suspended in MeOH (25 mL) and concentrated sulfuric acid (10 mL) and the resulting mixture was stirred at 90° C. for 14 hours to give a bright yellow solution. The MeOH was removed under reduced pressure and the remaining aqueous solution was diluted with brine (60 mL) and EtOAc (50 mL) and then neutralized with 3M NaOH until pH of aqueous layer was approximately 10. The mixture was extracted with EtOAc (3×100 mL), dried (Na$_2$SO$_4$), filtered, and concentrated in vacuo to give pure 4-methyl-isophthalic acid dimethyl ester as a pale orange solid (1.06 g, 82%, 2-steps). $^1$H NMR (CDCl$_3$) δ 2.66 (s, 3H), 3.92 (s, 3H), 3.93 (s, 3H), 7.33 (d, 1H, J=9.0 Hz), 8.05 (dd, 1H, J=9.0, 3.0 Hz), 8.57 (d, 1H, J=3.0 Hz).

4-Methyl-isophthalic acid dimethyl ester (1.06 g, 5.10 mmol), N-bromosuccinimide (1.00 g, 5.61 mmol) and 1,1'-azobis(cyclohexanecarbonitrile) (0.31 g, 1.27 mmol) were suspended in carbon tetrachloride (22 mL) and the resulting mixture was refluxed for 16 hours under N$_2$. The orange solution was concentrated under reduced pressure and the resulting orange residue was purified via column chromatography on silica gel (hexanes:EtOAc, 7:1, v/v). 4-Bromomethyl-isophthalic acid dimethyl ester was isolated as a yellow crystalline solid (1.05 g, 72%). $^1$H NMR (CDCl$_3$) δ 3.95 (s, 3H), 3.97 (s, 3H), 4.96 (s, 2H), 7.57 (d, 1H, J=9.0 Hz), 8.13 (dd, 1H, J=9.0, 3.0 Hz), 8.62 (d, 1H, J=3.0 Hz).

Using General Procedure A: A solution of 3,3"-dimethyl-1',2',3',4',5',6'-hexahydro-[2,2';6',2"]terpyridine (0.402 g, 1.50 mmol), 4-bromomethyl-isophthalic acid dimethyl ester (0.603 g, 2.10 mmol), KI (63 mg, 0.38 mmol), and DIPEA (0.60 mL, 3.44 mmol) in DMF (7.5 mL) was heated at 60° C. for 24 hours. Purification of the crude material by column chromatography on silica gel (20:1:1 CH$_2$Cl$_2$—CH$_3$OH—NH$_4$OH) provided 710 mg (99%) of COMPOUND 28 as a white solid. $^1$H NMR (CDCl$_3$) δ 1.63-1.77 (m, 3H), 2.09 (br s, 1H), 2.34-2.52 (m, 8H), 3.84 (s, 6H), 4.02 (s, 2H), 4.18 (d, 2H, J=11.1 Hz), 6.82 (dd, 2H, J=4.8, 7.5 Hz), 7.14 (d, 2H, J=7.5 Hz), 7.72 (s, 2H), 7.92 (s, 1H), 8.22 (d, 2H, J=4.8 Hz); $^{13}$C NMR (CDCl$_3$) δ 19.32, 25.66, 28.30, 50.13, 52.23, 52.36, 67.14, 122.20, 126.83, 128.07, 130.49, 131.08, 131.33, 132.14, 138.08, 146.90, 149.71, 159.50, 166.88, 167.23; ES-MS m/z 474 (M$^+$H). Anal. Calcd. For C$_{28}$H$_{31}$N$_3$O$_4$.0.3H$_2$O: C, 70.21; H, 6.65; N, 8.77. Found: C, 70.17; H, 6.60; N, 8.72.

EXAMPLE 29

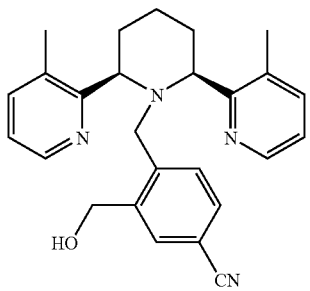

Compound 29: 4-(3,3"-Dimethyl-3',4',5',6'-tetrahydro-2'H-[2,2';6',2"]terpyridin-1'-ylmethyl)-3-hydroxymethyl-benzonitrile Using General Procedure A: A solution of 3,3"-dimethyl-1',2',3',4',5',6'-hexahydro-[2,2';6',2"]terpyridine (0.260 g, 0.98 mmol), 2-bromomethyl-5-cyano-benzoic acid methyl ester (0.360 g, 1.42 mmol), KI (37 mg, 0.22 mmol), and DIPEA (0.35 mL, 2.01 mmol) in DMF (5 mL) was heated at 60° C. for 17 hours. Purification of the crude material by column chromatography on silica gel (20:1:1 CH$_2$Cl$_2$—CH$_3$OH—NH$_4$OH) provided 415 mg (96%) of 5-cyano-2-(3,3"-dimethyl-3',4',5',6'-tetrahydro-2'H-[2,2';6',2"]terpyridin-1'-ylmethyl)-benzoic acid methyl ester as a tan solid. To a cold (0° C.) solution of 5-cyano-2-(3,3"-dimethyl-3',4',5',6'-tetrahydro-2'H-[2,2';6',2"]terpyridin-1'-ylmethyl)-benzoic acid methyl ester (0.409 g, 0.937 mmol) in THF (4.5 mL) and MeOH (9 mL) was added LiBH$_4$ (229 mg, 10.52 mmol) and the mixture was allowed to warm to room temperature overnight. The mixture was diluted with 1.0 N NaOH (10 mL) and extracted with CH$_2$Cl$_2$ (5×25 mL). The combined organic extracts were dried (Na$_2$SO$_4$) and concentrated. Purification of the crude material by column chromatography on silica gel (20:1:1 CH$_2$Cl$_2$—CH$_3$OH—NH$_4$OH) provided 0.332 g (87%) of COMPOUND 29 as a white foam. $^1$H NMR (CDCl$_3$) δ 1.61-1.77 (m, 3H), 2.05-2.14 (m, 1H), 2.30-2.44 (m, 2H), 2.51 (s, 6H), 3.71 (s, 2H), 4.11 (d, 2H, J=10.8 Hz), 4.46 (s, 2H), 4.94 (br s, 1H), 6.87-6.96 (m, 4H), 7.22-7.27 (m, 3H), 8.21 (d, 2H, J=4.2 Hz). $^{13}$C NMR (CDCl$_3$) δ 19.35, 25.70, 28.19, 51.31, 62.24, 67.36, 109.58, 119.48, 122.56, 129.25, 130.02, 132.00, 132.24, 138.53, 139.79, 145.29, 146.76, 159.25; ES-MS m/z 413 (M$^+$H). Anal. Calcd. For C$_{26}$H$_{28}$N$_4$O.1.0H$_2$O$_2$: C, 72.53; H, 7.02; N, 13.01. Found: C, 72.46; H, 6.73; N, 12.91.

EXAMPLE 30

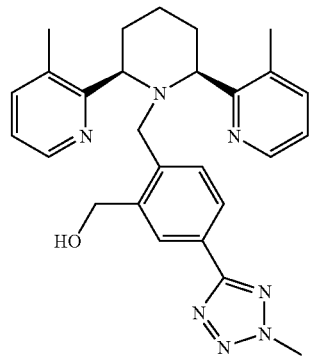

Compound 30: [2-(3,3"-Dimethyl-3',4',5',6'-tetrahydro-2'H-[2,2';6',2"]terpyridin-1'-ylmethyl)-5-(2-methyl-2H-tetrazol-5-yl)-phenyl]-methanol To a solution of 5-cyano-2-methylbenzoic acid methyl ester (1.069 g, 6.10 mmol) in 2-methoxyethanol (6 mL) was added NaN$_3$ (0.400 g, 6.16 mmol) followed by LiCl (0.421 g, 9.94 mmol). The resultant mixture was heated to reflux for 6 hours then cooled to room temperature. The mixture was poured onto ice (~25 g) and treated with 37% HCl (2 mL). The mixture was extracted with CH$_2$Cl$_2$ (4×25 mL). The combined organic extracts were dried (Na$_2$SO$_4$) and concentrated and provided 1.43 g of an orange solid. To a cold (0° C.) solution of the orange solid (1.43 g) in DMF (6 mL) and 1,4-dioxane (6 mL) was added K$_2$CO$_3$ (2.52 g, 18.23 mmol) followed by MeI (1.0 mL, 16.06 mmol). The mixture was warmed to room temperature. After 4 hours, the mixture was diluted with water (10 mL) and EtOAc (60 mL). The phases were separated and the organic phase was washed with brine (3×10 mL), dried (Na$_2$SO$_4$) and concentrated. Purification of the crude material by column chromatography on silica gel (8:1:hexanes-EtOAc) provided 0.50 g (30%) of 5-(2-methyl-2H-tetrazol-5-yl)-2-methylbenzoic acid 2-methoxyethyl ester as a white solid. $^1$H NMR (CDCl$_3$) δ 2.66 (s, 3H), 3.44 (s, 3H), 3.75 (t, 2H, J=6.6 Hz), 4.41 (s, 3H), 4.49 (t, 2H, J=6.6 Hz), 7.37 (d, 1H, J=7.5 Hz), 8.15 (dd, 1H, J=7.5, 2.4 Hz).

To a solution of 5-(2-methyl-2H-tetrazol-5-yl)-2-methylbenzoic acid 2-methoxyethyl ester in CCl$_4$ (6 mL) was added N-bromosuccinimide (0.366 g, 2.06 mmol) followed by 1,1'- azobis(cyclohexanecarbonitrile) (74 mg, 0.30 mmol). The resultant mixture was refluxed for 6 hours then cooled to room temperature, filtered through filter paper, and concentrated. Purification of the crude material by column chromatography on silica gel (4:1:hexanes-EtOAc) provided 0.35 g of a white solid. Using General Procedure A: A solution of 3,3"-dimethyl-1',2',3',4',5',6'-hexahydro-[2,2';6',2"]terpyridine (0.140 g, 0.52 mmol), the white solid (0.35 g), KI (16 mg, 0.10 mmol), and DIPEA (0.18 mL, 1.03 mmol) in DMF (5 mL) was heated at 60° C. for 23 hours. Purification of the crude material by column chromatography on silica gel (40:1:1 $CH_2Cl_2$—$CH_3OH$—$NH_4OH$) provided 0.28 g (99%) of 5-(2-methyl-2H-tetrazol-5-yl) 2-(3,3"-dimethyl-3',4',5',6'-tetrahydro-2'H-[2,2';6',2"]terpyridin-1'-ylmethyl)-benzoic acid 2-methyoxyethyl ester as a tan solid. To a cold solution of the ester (0.280 g, 0.52 mmol) in THF (10 mL) was added $LiBH_4$ (168 mg, 7.72 mmol) and the mixture was refluxed overnight. The mixture was cooled to room temperature, diluted with 1.0 N NaOH (5 mL) and extracted with $CH_2Cl_2$ (4×20 mL). The combined organic extracts were dried ($Na_2SO_4$) and concentrated. Purification of the crude material by column chromatography on silica gel (20:1:1 $CH_2Cl_2$—$CH_3OH$—$NH_4OH$) provided 0.215 g (85%) of COMPOUND 30 as a white solid. $^1$H NMR ($CDCl_3$) δ 1.63-1.77 (m, 3H), 2.06-2.13 (m, 1H), 2.38-2.47 (m, 2H), 2.54 (s, 6H), 3.75 (s, 2H), 4.12 (d, 2H, J=12.0 Hz), 4.34 (s, 3H), 4.48 (s, 2H), 4.98 (br s, 1H), 6.82 (dd, 2H, J=7.5, 4.8 Hz), 6.90 (d, 1H, J=7.5 Hz), 7.23 (d, 2H, J=7.5 Hz), 7.44 (dd, 1H, J=7.5, 1.5 Hz), 7.66 (d, 1H, J=1.5 Hz), 8.22 (d, 2H, J=4.8 Hz). $^{13}$C NMR ($CDCl_3$) δ 19.42, 25.72, 28.99, 39.75, 52.92, 63.08, 67.58, 122.31, 124.98, 125.19, 127.58, 129.53, 132.08, 138.49, 139.38, 141.98, 146.80, 159.69, 165.44; ES-MS m/z 470 ($M^+H$). Anal. Calcd. For $C_{27}H_{31}N_7O.0.8H_2O$: C, 67.00; H, 6.79; N, 20.26. Found: C, 66.68; H, 6.39; N, 19.93.

EXAMPLE 31

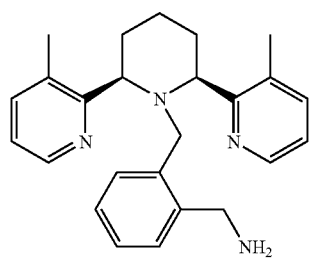

Compound 31: 2-(3,3"-Dimethyl-3',4',5',6'-tetrahydro-2'H-[2,2';6',2"]terpyridin-1'-ylmethyl)-benzylamine (HBr Salt)

Using General Procedure A: A solution of 3,3"-dimethyl-1',2',3',4',5',6'-hexahydro-[2,2';6',2"]terpyridine (0.602 g, 2.25 mmol), α-bromo-o-tolunitrile (0.668 g, 3.41 mmol), KI (100 mg, 0.60 mmol), and DIPEA (0.80 mL, 4.59 mmol) in DMF (11 mL) was heated at 60° C. for 23 hours. Purification of the crude material by column chromatography on silica gel (40:1:1 $CH_2Cl_2$—$CH_3OH$—$NH_4OH$) provided 0.78 g (91%) of 2-(3,3"-dimethyl-3',4',5',6'-tetrahydro-2'H-[2,2';6',2"] terpyridin-1'-ylmethyl)-benzonitrile as a tan solid. $^1$H NMR ($CDCl_3$) δ 1.63-1.73 (m, 3H), 2.02-2.07 (m, 1H), 2.26-2.38 (m, 2H), 2.48 (s, 6H), 3.69 (s, 2H), 4.12 (d, 2H, J=10.8 Hz), 6.83-6.89 (m, 3H), 6.99 (d, 1H, J=7.2 Hz), 7.19-7.26 (m, 3H), 7.64 (d, 1H, J=7.8 Hz), 8.27 (d, 2H, J=3.9 Hz). $^{13}$C NMR ($CDCl_3$) δ 19.44, 25.53, 29.42, 52.72, 67.05, 109.86, 118.06, 122.19, 125.90, 130.68, 131.41, 131.54, 132.02, 138.18, 145.77, 147.23, 159.61; ES-MS m/z 383 ($M^+H$). Anal. Calcd. For $C_{25}H_{26}N_4C$, 78.50; H, 6.852; N, 14.65. Found: C, 78.28; H, 6.93; N, 14.57.

A solution of 2-(3,3"-dimethyl-3',4',5',6'-tetrahydro-2'H-[2,2';6',2']terpyridin-1'-ylmethyl)-benzonitrile (0.129 g, 0.34 mmol) in $NH_3$ saturated MeOH (5 mL) was treated with Raney nickel (60 mg) and placed under 50 psi $H_2$, on a Parr shaker, for 3.5 hours. The mixture was filtered through Celite and the cake was washed with MeOH. The eluant was concentrated under reduced pressure. Purification of the crude material by column chromatography on silica gel (10:1:1 $CH_2Cl_2$—$CH_3OH$—$NH_4OH$) provided 96 mg (73%) of the free base of the title compound as a white solid. Using General Procedure B: Conversion of the white solid (92 mg) to the HBr salt gave COMPOUND 31 (152 mg, 96%) as a white solid. $^1$H NMR ($D_2O$) δ 1.49-1.61 (m, 2H), 1.71-1.84 (m, 1H), 1.96-2.03 (m, 1H), 2.14-2.20 (m, 2H), 2.54 (s, 6H), 3.82 (s, 2H), 3.96 (s, 2H), 4.57 (dd, 2H J=11.4, 3.0 Hz), 6.96 (d, 1H, J=7.8 Hz), 7.08-7.13 (m, 1H), 7.18-7.26 (m, 2H), 7.73 (dd, 2H, J=7.8, 5.7 Hz), 8.26 (d, 2H, J=7.8 Hz), 8.53 (d, 2H, J=5.7 Hz); $^{13}$C NMR ($D_2O$) δ 17.25, 22.25, 33.11, 39.91, 58.88, 61.96, 125.96, 129.91, 130.13, 130.57, 131.21, 132.11, 134.86, 136.53, 139.49, 149.14, 155.32;ES-MS m/z 387 ($M^+H$). Anal. Calcd. For $C_{25}H_{30}N_4.3.0HBr.2.0H_2O$: C, 45.13; H, 5.61; N, 8.42; Br, 36.03. Found: C, 45.07; H, 5.71; N, 8.23; Br, 36.20.

EXAMPLE 32

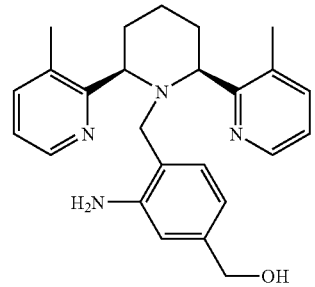

Compound 32: [3-Amino-4-(3,3"-dimethyl-3',4',5',6'-tetrahydro-2'H-[2,2';6',2"]terpyridin-1'-ylmethyl)-phenyl]-methanol To a solution of 4-methyl-3-nitrobenzoic acid (5.52 g, 30.5 mmol) in MeOH (100 mL) was added 98% sulfuric acid (2 mL) and the resultant mixture was refluxed overnight, then cooled to room temperature. The mixture was concentrated and the residue was dissolved in CH$_2$Cl$_2$ (50 mL) and water (20 mL). Solid Na$_2$CO$_3$ was added until the aqueous phase was basic to litmus paper. The phases were separated and the aqueous phase was extracted with CH$_2$Cl$_2$ (5×20 mL). The combined organic extracts were dried (Na$_2$SO$_4$) and concentrated and provided 5.79 g (97%) of 4-methyl-3-nitrobenzoic acid methyl ester as a white solid. To a solution of 4-methyl-3-nitrobenzoic acid methyl ester (5.01 g, 25.7 mmol) in CCl$_4$ (65 mL) was added N-bromosuccinimide (5.04 g, 28.3 mmol) followed by 1,1'-azobis(cyclohexanecarbonitrile) (1.21 g, 4.96 mmol). The resultant mixture was refluxed for 24 hours then cooled to room temperature, filtered through filter paper, and concentrated. Purification of the crude material by column chromatography on silica gel (9:1:hexanes-EtOAc) provided 4.30 g (61%) of 4-bromomethyl-3-nitrobenzoic acid methyl ester as a yellow oil. $^1$H NMR (CDCl$_3$) δ 3.98 (s, 3H), 4.85 (s, 2H), 7.67 (d, 1H, J=7.8 Hz), 8.25 (d, 1H, J=7.8, 1.5 Hz), 8.66 (d, 1H, J=1.5 Hz).

Using General Procedure A: A solution of 3,3"-dimethyl-1',2',3',4',5',6'-hexahydro-[2,2';6',2"]terpyridine (0.829 g, 3.10 mmol), 4-bromomethyl-3-nitrobenzoic acid methyl ester (1.26 g, 4.61 mmol), KI (115 mg, 0.69 mmol), and DIPEA (1.20 mL, 6.89 mmol) in DMF (16 mL) was heated at 60° C. for 18 hours. Purification of the crude material by column chromatography on silica gel (40:1:1 CH$_2$Cl$_2$—CH$_3$OH—NH$_4$OH) provided 1.40 g (98%) of 4-(3,3"-dimethyl-3',4',5',6'-tetrahydro-2'H-[2,2';6',2"]terpyridin-1'-ylmethyl)-3-nitro-benzoic acid methyl ester as a tan solid. To a solution of 4-(3,3"-dimethyl-3',4',5',6'-tetrahydro-2'H-[2,2';6',2"]terpyridin-1'-ylmethyl)-3-nitro-benzoic acid methyl ester (1.40 g, 3.03 mmol) in MeOH (15 mL) and EtOAc (15 mL) was added palladium (50% wet with water), 10 wt. % on activated carbon (0.30 g). The resultant mixture was hydrogenated at 30 psi on a Parr shaker for 3 hours. The mixture was vacuum filtered through celite and the cake was washed with MeOH and EtOAc. The solvent was removed from the filtrate under reduced pressure and the thus obtained oil was purified by column chromatography on silica gel (40:1:1 CH$_2$Cl$_2$—CH$_3$OH—NH$_4$OH) and provided 0.90 g (69%) of 3-amino-4-(3,3"-dimethyl-3',4',5',6'-tetrahydro-2'H-[2,2';6',2"]terpyridin-1'-ylmethyl)-benzoic acid methyl ester.

To a solution of 3-amino-4-(3,3"-dimethyl-3',4',5',6'-tetrahydro-2'H-[2,2';6',2"]terpyridin-1'-ylmethyl)-benzoic acid methyl ester (0.61 g, 1.42 mmol) in THF (14 mL) was added LiBH$_4$ (430 mg, 19.74 mmol) and the mixture was heated to reflux overnight. The mixture was cooled to room temperature, diluted with 1.0 N NaOH (20 mL) and extracted with CH$_2$Cl$_2$ (5×30 mL). The combined organic extracts were dried (Na$_2$SO$_4$) and concentrated. Purification of the crude material by radial chromatography on silica gel (2 mm plate, 20:1:1 CH$_2$Cl$_2$—CH$_3$OH—NH$_4$OH) provided 0.220 g (37%) of COMPOUND 32 as a white solid. $^1$H NMR (CDCl$_3$) δ 1.23 (br s, 1H), 1.47-1.72 (m, 3H), 1.88-1.95 (m, 1H), 2.04-2.18 (m, 2H), 2.35 (s, 6H), 3.32 (s, 2H), 3.73 (dd, 2H, J=11.7, 3.0 Hz), 4.26 (d, 2H, J=3.3 Hz), 4.53 (br s, 2H), 6.03 (s, 1H), 6.07 (d, 1H, J=7.8 Hz), 6.48 (d, 1H, J=7.2 Hz), 6.86 (dd, 2H, J=7.8, 4.8 Hz), 7.15 (d, 2H, J=7.5 Hz), 8.33 (d, 2H, J=3.9 Hz). $^{13}$C NMR (CDCl$_3$) δ 19.44, 25.02, 32.92, 60.69, 65.60, 68.25, 112.98, 115.09, 122.09, 122.80, 129.96, 131.38, 138.18, 140.42, 146.89, 147.51, 161.18; ES-MS m/z 403 (M$^+$H). Anal. Calcd. For C$_{25}$H$_{30}$N$_4$O.1.0H$_2$O: C, 71.40; H, 7.67; N, 13.32. Found: C, 71.31; H, 7.55; N, 13.22.

EXAMPLE 33

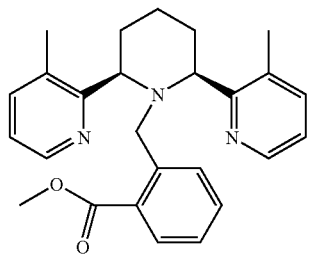

Compound 33: 2-(3,3"-Dimethyl-3',4',5',6'-tetrahydro-2'H-[2,2';6',2"]terpyridin-1'-ylmethyl)-benzoic Acid Methyl Ester To a solution of 2-methyl-benzoic acid methyl ester (4.58 g, 30.5 mmol) in CCl$_4$ (75 mL) was added N-bromosuccinimide (5.79 g, 32.5 mmol) followed by 1,1'-azobis(cyclohexanecarbonitrile) (1.42 g, 5.80 mmol). The resultant mixture was refluxed for 6 hours then cooled to room temperature, filtered through filter paper, and concentrated. Purification of the crude material by column chromatography on silica gel (20:1:hexanes-EtOAc) provided 5.44 g (78%) of 2-bromomethyl-benzoic acid methyl ester as a colorles oil. $^1$H NMR (CDCl$_3$) δ 3.95 (s, 3H), 4.96 (s, 2H), 7.36-7.50 (m, 3H), 7.97 (d, 1H, J=7.8 Hz).

Using General Procedure A: A solution of 3,3"-dimethyl-1,2',3',4',5',6'-hexahydro-[2,2';6',2"]terpyridine (0.901 g, 3.37 mmol), 2-bromomethyl-benzoic acid methyl ester (1.17 g, 5.13 mmol), KI (121 mg, 0.73 mmol), and DIPEA (1.50 mL, 8.61 mmol) in DMF (17 mL) was heated at 60° C. for 23 hours. Purification of the crude material by column chromatography on silica gel (40:1:1 CH$_2$Cl$_2$—CH$_3$OH—NH$_4$OH) provided 1.19 g (85%) of COMPOUND 33 as a tan solid. $^1$H NMR (CDCl$_3$) δ 1.58-1.72 (m, 3H), 2.02-2.06 (m, 1H), 2.31-2.42 (m, 8H), 3.80 (s, 3H), 3.94 (s, 2H), 4.11 (d, 2H, J=10.5 Hz), 6.79-6.91 (m, 3H), 7.09-7.26 (m, 4H), 7.63 (d, 1H, J=7.5 Hz), 8.26 (d, 2H, J=3.6 Hz). $^{13}$C NMR (CDCl$_3$) δ 19.39, 25.69, 28.76, 50.43, 51.98, 67.31, 122.06, 124.90, 128.02, 129.03, 130.54, 131.20, 132.11, 138.04, 143.92, 146.89, 159.83, 168.12; ES-MS m/z 416 (M$^+$H). Anal. Calcd. For C$_{26}$H$_{29}$N$_3$O$_2$.0.2H$_2$O: C, 74.51; H, 7.07; N, 10.03. Found: C, 74.56; H, 7.08; N, 9.99.

EXAMPLE 34

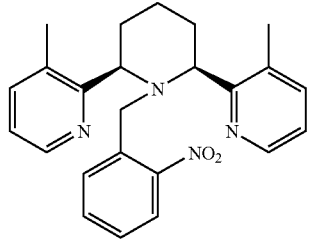

Compound 34: 3,3"-Dimethyl-1'-(2-nitro-benzyl)-1',2',3',4',5',6'-hexahydro-[2,2°;6',2"]terpyridine Using General Procedure A: A solution of 3,3"-dimethyl-1',2',3',4',5',6'-hexahydro-[2,2';6',2"]terpyridine (0.431 g, 1.61 mmol), 2-nitrobenzyl bromide (0.509 g, 2.75 mmol), KI (60 mg, 0.36 mmol), and DIPEA (0.6 mL, 3.44 mmol) in DMF (8 mL) was heated at 60° C. for 24 hours. Purification of the crude material by column chromatography on silica gel (40:1:1 $CH_2Cl_2$—$CH_3OH$—$NH_4OH$) provided 0.58 g (90%) of COMPOUND 34 as a yellow solid. $^1H$ NMR ($CDCl_3$) δ 1.63-1.70 (m, 3H), 2.04-2.08 (m, 1H), 2.31-2.43 (m, 8H), 3.85 (s, 2H), 4.12 (d, 2H, J=11.1 Hz), 6.83-6.91 (m, 3H), 7.18-7.29 (m, 4H), 7.78 (d, 1H, J=7.5 Hz), 8.24 (d, 2H, J=3.9 Hz); ES-MS m/z 403 ($M^+H$).

EXAMPLE 35

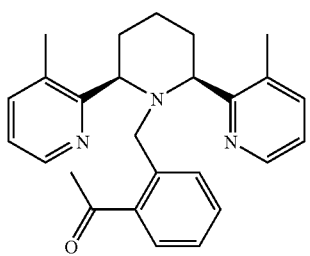

Compound 35: 1-[2-(3,3''-Dimethyl-3',4',5',6'-tetrahydro-2'H-[2,2';6',2'']terpyridin-1'-ylmethyl)-phenyl]-ethanone To a solution of 2'-methyl-acetophenone (2.68 g, 20.0 mmol) in benzene (100 mL) was added ethylene glycol (2.0 mL, 35.9 mmol) followed by p-toluenesulfonic acid monohydrate (0.39 g, 2.10 mmol). The reaction flask was topped with a Dean-Stark trap, and the mixture was heated to reflux overnight. The mixture was cooled to room temperature, diluted with $Et_2O$ (100 mL), washed with saturated aqueous $NaHCO_3$ (5×20 mL) and brine (3×25 mL), dried ($MgSO_4$), and concentrated. The resultant colorless oil (3.6 g) was dissolved in $CCl_4$ (50 mL) and to this solution was added N-bromosuccinimide (3.76 g, 21.1 mmol) followed by 1,1'-azobis(cyclo-hexanecarbonitrile) (0.98 g, 3.99 mmol). The resultant mixture was refluxed for 5 hours then cooled to room temperature, filtered through filter paper, and concentrated. Purification of the crude material by column chromatography on silica gel (20:1:hexanes-EtOAc) provided 4.09 g (80%) of 2-(2-bromomethyl-phenyl)-2-methyl-[1,3]dioxolane as a colorless oil. $^1H$ NMR ($CDCl_3$) δ 1.74 (s, 3H), 3.75-3.81 (m, 2H), 4.04-4.08 (m, 2H), 4.89 (s, 2H), 7.24-7.31 (m, 2H), 7.44-7.57 (m, 2H).

Using General Procedure A: A solution of 3,3''-dimethyl-1',2',3',4',5',6'-hexahydro-[2,2';6',2'']terpyridine (0.547 g, 2.04 mmol), 2-(2-bromomethyl-phenyl)-2-methyl-[1,3]dioxolane (1.03 g, 3.99 mmol), KI (73 mg, 0.42 mmol), and DIPEA (0.70 mL, 4.02 mmol) in DMF (10 mL) was heated at 60° C. for 24 hours. Purification of the crude material by column chromatography on silica gel (40:1:1 $CH_2Cl_2$—$CH_3OH$—$NH_4OH$) provided 0.81 g (90%) of 3,3''-dimethyl-1'-[2-(2-methyl-[1,3]dioxolan-2-yl)-benzyl]-1',2',3',4',5',6'-hexahydro-[2,2';6',2'']terpyridine as a white solid. $^1H$ NMR ($CDCl_3$) δ 1.46 (s, 3H), 1.60-1.83 (m, 3H), 2.15-2.20 (m, 1H), 2.47-2.57 (m, 8H), 3.26-3.31 (m, 2H), 3.82-3.87 (m, 2H), 4.01 (s, 2H), 4.44 (d, 2H, J=10.8 Hz), 6.72-6.82 (m, 4H), 7.05 (dd, 1H, J=7.2, 1.5 Hz), 7.21 (d, 2H, J=7.2 Hz), 7.46 (d, 1H, J=6.9 Hz), 8.19 (d, 2H, J=4.8 Hz); ES-MS m/z 444 ($M^+H$).

To a solution of 3,3''-dimethyl-1'-[2-(2-methyl-[1,3]dioxolan-2-yl)-benzyl]-1',2',3',4',5',6'-hexahydro-[2,2';6',2''] terpyridine (0.78 g, 1.76 mmol) in THF (8 mL) was added 1.0 N HCl (18 mL, 18.0 mmol) and the mixture was stirred at room temperature overnight. The mixture was diluted with 10 N NaOH (2 mL) and extracted with $CH_2Cl_2$ (4×50 mL). The combined organic extracts were dried ($Na_2SO_4$) and concentrated. Purification of the crude material by column chromatography on silica gel (30:1:1 $CH_2Cl_2$—$CH_3OH$—$NH_4OH$) provided 0.64 g (91%) of COMPOUND 35 as a white solid. $^1H$ NMR ($CDCl_3$) δ 1.58-1.71 (m, 3H), 2.02-2.12 (m, 1H), 2.30-2.37 (m, 5H), 2.44 (s, 6H), 3.82 (s, 2H), 4.09 (d, 2H, J=11.1 Hz), 6.81-6.85 (m, 3H), 7.04-7.18 (m, 4H), 7.76 (d, 1H, J=7.8 Hz), 8.26 (d, 2H, J=3.6 Hz); ES-MS m/z 400 ($M^+H$).

EXAMPLE 36

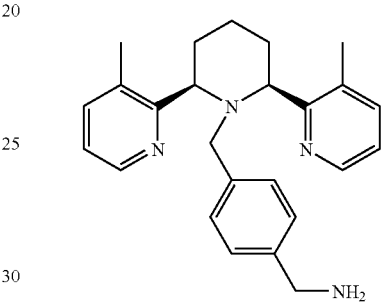

Compound 36: 4-(3,3''-Dimethyl-3',4',5',6'-tetrahydro-2'H-[2,2';6',2'']terpyridin-1'-ylmethyl)-benzylamine Using General Procedure A: A solution of 3,3''-dimethyl-1',2',3',4',5',6'-hexahydro-[2,2';6',2'']terpyridine (0.502 g, 1.83 mmol), α-bromo-p-tolunitrile (0.538 g, 2.75 mmol), KI (65 mg, 0.40 mmol), and DIPEA (0.72 mL, 4.13 mmol) in DMF (9 mL) was heated at 60° C. for 16 hours. Purification of the crude material by column chromatography on silica gel (40:1:1 $CH_2Cl_2$—$CH_3OH$—$NH_4OH$) provided 0.66 g (94%) of 4-(3,3''-dimethyl-3',4',5',6'-tetrahydro-2'H-[2,2';6',2''] terpyridin-1'-ylmethyl)-benzonitrile as a white solid. $^1H$ NMR ($CDCl_3$) δ 1.60-1.73 (m, 3H), 2.02-2.12 (m, 1H), 2.18-2.34 (m, 2H), 2.41 (s, 6H), 3.56 (s, 2H), 4.14 (d, 2H, J=10.5 Hz), 6.64 (d, 2H, J=8.1 Hz), 6.95 (dd, 2H, J=7.5, 4.8 Hz), 7.10 (d, 2H, J=7.8 Hz), 7.22 (d, 2H, J=7.2 Hz), 8.37 (d, 2H, J=3.9 Hz); ES-MS m/z 383 ($M^+H$).

A solution of 4-(3,3''-dimethyl-3',4',5',6'-tetrahydro-2'H-[2,2';6',2'']terpyridin-1'-ylmethyl)-benzonitrile (0.122 g, 0.32 mmol) in $NH_3$ saturated MeOH (3 mL) was treated with Raney nickel (100 mg) and placed under 50 psi $H_2$, on a Parr shaker, for 4 hours. The mixture was filtered through Celite and the cake was washed with MeOH. The eluant was concentrated under reduced pressure. Purification of the crude material by column chromatography on silica gel (20:1:1 $CH_2Cl_2$—$CH_3OH$—$NH_4OH$) provided 93 mg (76%) of COMPOUND 36 as a white solid. $^1$H NMR (CDCl$_3$) δ 1.44-1.57 (m, 1H), 1.66-1.72 (m, 2H), 1.90-2.11 (m, 3H), 2.34 (s, 6H), 3.51 (s, 2H), 3.71 (s, 2H), 3.98 (d, 2H J=10.5 Hz), 6.54 (d, 2H, J=7.8 Hz), 6.93 (d, 2H, J=7.8 Hz), 7.01 (dd, 2H, J=7.5, 4.8 Hz), 7.34 (d, 2H, J=7.5 Hz), 8.47 (d, 2H, J=3.9 Hz); ES-MS m/z 387 (M$^+$H).

EXAMPLE 37

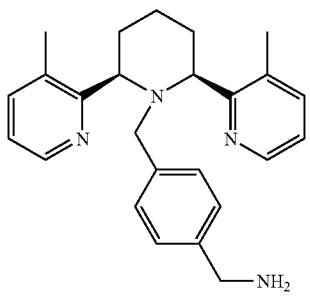

Compound 37: 3-(3,3''-Dimethyl-3',4',5',6'-tetrahydro-2'H-[2,2';6',2'']terpyridin-1'-ylmethyl)-benzylamine Using General Procedure A: A solution of 3,3''-dimethyl-1',2',3',4',5',6'-hexahydro-[2,2';6',2'']terpyridine (0.414 g, 1.55 mmol), α-bromo-m-toluinitrile (0.466 g, 2.38 mmol), KI (53 mg, 0.32 mmol), and DIPEA (0.55 mL, 3.16 mmol) in DMF (8 mL) was heated at 60° C. for 18 hours. Purification of the crude material by column chromatography on silica gel (40:1:1 CH$_2$Cl$_2$—CH$_3$OH—NH$_4$OH) provided 0.447 g (75%) of 3-(3,3''-dimethyl-3',4',5',6'-tetrahydro-2'H-[2,2';6',2'']terpyridin-1'-ylmethyl)-benzonitrile as a beige solid. $^1$H NMR (CDCl$_3$) δ 1.56-1.72 (m, 3H), 2.05-2.10 (m, 1H), 2.18-2.34 (m, 2H), 2.41 (s, 6H), 3.53 (s, 2H), 4.10 (d, 2H, J=11.1 Hz), 6.71 (s, 1H), 6.83 (d, 1H, J=7.8 Hz), 6.93-7.00 (m, 3H), 7.13 (d, 1H, J=7.5 Hz), 7.25-7.27 (m, 2H), 8.39 (dd, 2H, J=4.8, 1.2 Hz); ES-MS m/z 383 (M$^+$H).

A solution of 3-(3,3''-dimethyl-3',4',5',6'-tetrahydro-2'H-[2,2';6',2'']terpyridin-1'-ylmethyl)-benzonitrile (0.107 g, 0.28 mmol) in NH$_3$ saturated MeOH (5 mL) was treated with Raney nickel (100 mg) and placed under 50 psi H$_2$, on a Parr shaker, for 4 hours. The mixture was filtered through Celite and the cake was washed with MeOH. The eluant was concentrated under reduced pressure. Purification of the crude material by column chromatography on silica gel (10:1:1 CH$_2$Cl$_2$—CH$_3$OH—NH$_4$OH) provided 62 mg (58%) of COMPOUND 37 as a white solid. $^1$H NMR (CDCl$_3$) δ 1.49-1.71 (m, 3H), 1.95-2.23 (m, 3H), 2.36 (s, 6H), 3.52 (s, 2H), 3.61 (s, 2H), 4.01 (d, 2H J=10.2 Hz), 6.42-6.48 (m, 2H), 6.91-7.02 (m, 4H), 7.24-7.31 (m, 2H), 8.45 (d, 2H, J=3.9 Hz); ES-MS m/z 387 (M$^+$H).

EXAMPLE 38

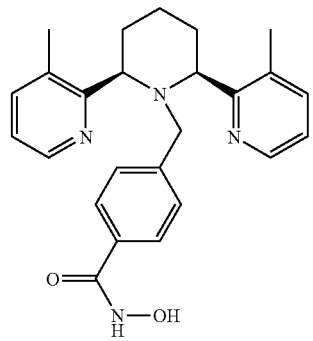

Compound 38: 4-(3,3''-Dimethyl-3',4',5',6'-tetrahydro-2'H-[2,2';6',2'']terpyridin-1'-ylmethyl)-N-hydroxy-benzamide Using General Procedure A: A solution of 3,3''-dimethyl-1',2',3',4',5',6'-hexahydro-[2,2';6',2'']terpyridine (0.485 g, 1.81 mmol), 4-bromomethyl-benzoic acid methyl ester (0.642 g, 2.80 mmol), KI (64 mg, 0.38 mmol), and DIPEA (0.65 mL, 3.73 mmol) in DMF (9 mL) was heated at 60° C. for 23 hours. Purification of the crude material by column chromatography on silica gel (40:1:1 CH$_2$Cl$_2$—CH$_3$OH—NH$_4$OH) provided 0.67 g (89%) of 4-(3,3''-dimethyl-3',4',5', 6'-tetrahydro-2'H-[2,2';6',2'']terpyridin-1'-ylmethyl)-benzoic acid methyl ester as a white solid. $^1$H NMR (CDCl$_3$) δ 1.54-1.72 (m, 3H), 2.02-2.08 (m, 1H), 2.20-2.34 (m, 2H), 2.40 (s, 6H), 3.58 (s, 2H), 3.83 (s, 3H), 4.12 (d, 2H, J=11.4 Hz), 6.57 (d, 2H, J=7.8 Hz), 6.96 (dd, 2H, J=7.5, 4.5 Hz), 7.23 (d, 2H, J=7.5 Hz), 7.53 (d, 2H, J=7.8 Hz), 8.26 (d, 2H, J=4.5 Hz); ES-MS m/z 416 (M$^+$H).

To a solution of 4-(3,3''-dimethyl-3',4',5',6'-tetrahydro-2'H-[2,2';6',2'']terpyridin-1'-ylmethyl)-benzoic acid methyl ester (0.420 g, 1.01 mmol) in MeOH (5 mL) was added water (5 mL) and solid NaOH (0.448 g, 11.21 mmol). The resultant mixture was heated to reflux overnight then cooled to room temperature. The mixture was adjusted to pH ~5 with 6 N HCl (~2 mL) and extracted with CH$_2$Cl$_2$ (5×20 mL). The combined organic extracts were dried (Na$_2$SO$_4$) and concentrated and provided 0.440 g (quantitative yield) of 4-(3,3''-dimethyl-3',4',5',6'-tetrahydro-2'H-[2,2';6',2'']terpyridin-1'-ylmethyl)-benzoic acid as a white solid. $^1$H NMR (CDCl$_3$) δ 1.80-2.05 (m, 6H), 2.42 (s, 6H), 3.83 (br s, 2H), 4.55 (br s, 2H) 6.79 (d, 2H, J=8.1 Hz), 7.02 (dd, 2H, J=7.5, 5.1 Hz), 7.34 (d, 2H, J=7.5 Hz), 7.65 (d, 2H, J=7.8 Hz), 8.42 (d, 2H, J=3.9 Hz); ES-MS m/z 402 (M$^+$H).

To a cold (0° C.) solution of 4-(3,3''-dimethyl-3',4',5',6'-tetrahydro-2'H-[2,2';6',2'']terpyridin-1'-ylmethyl)-benzoic acid (0.124 g, 0.31 mmol) in CH$_2$Cl$_2$ (3 mL) and DMF (5 drops) was added oxalyl chloride (0.11 mL, 1.26 mmol). After 15 minutes, the mixture was concentrated and provided a beige solid. The solid was dissolved in DMF (3 mL) and treated with DIPEA (0.50 mL, 2.87 mmol) followed by NH$_2$OH.H$_2$O (72 mg, 1.04 mmol). The resultant mixture was stirred at room temperature overnight. The mixture was diluted with saturated aqueous NH$_4$Cl (5 mL) and extracted with CH$_2$Cl$_2$ (5×10 mL). The combined organic extracts were dried (Na$_2$SO$_4$) and concentrated. Purification of the crude material by radial chromatography on silica gel (1 mm plate, 5:1:1 CH$_2$ClN—CH$_3$OH—NH$_4$OH) provided 21 mg (16%) of COMPOUND 38 as a white solid. $^1$H NMR (CDCl$_3$) δ 1.48-1.67 (m, 3H), 1.88-2.13 (m, 3H), 2.31 (s, 6H), 3.46 (s, 2H), 3.94 (d, 2H, J=10.5 Hz), 6.54 (d, 2H, J=6.9 Hz), 6.93 (dd, 2H, J=7.5, 4.5 Hz), 7.26-7.39 (m, 4H), 8.28 (d, 2H, J=3.3 Hz); ES-MS m/z 417 (M$^+$H).

EXAMPLE 39

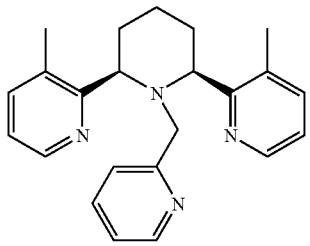

Compound 39: (2'R,6'S)-3,3"-Dimethyl-1'-pyridin-2-ylmethyl-1',2',3',4',5',6'-hexahydro-[2,2';6',2"]terpyridine A solution of (2'R,6'S)-3,3"-dimethyl-1',2',3',4',5',6'-hexahydro-[2,2';6',2"]terpyridine (166 mg, 0.621 mmol), 2-(bromomethyl)pyridine hydrobromide (189 mg, 0.745 mmol), DIPEA (265 μL, 1.52 mmol) and KI (10 mg, 0.060 mmol) in CH$_3$CN (6 mL) was warmed to 50° C. and stirred for 15.5 h according to General Procedure A. Purification by flash chromatography on silica gel using CH$_2$Cl$_2$/MeOH/NH$_4$OH (94:5:1) afforded COMPOUND 39 (127 mg, 57%) as an orange solid. $^1$H NMR (CDCl$_3$) δ 1.75-1.85 (m, 3H), 1.93-2.02 (m, 1H), 2.09-2.21 (m, 2H), 2.42 (s, 6H), 3.80 (bs, 2H), 6.81-6.85 (m, 2H), 6.96 (dd, 2H, J=7.7, 3.9 Hz), 7.23-7.30 (m, 3H), 8.18 (d, 1H, J=4.8 Hz), 8.40 (d, 2H, J=4.4 Hz); ES-MS m/z 359 (M$^+$H).

EXAMPLE 40

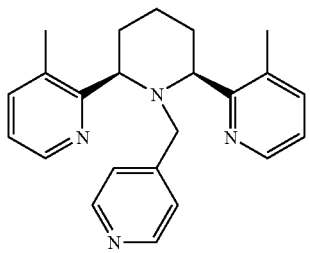

Compound 40: (2'R,6'S)-3,3"-Dimethyl-1'-pyridin-4-ylmethyl-1',2',3',4',5',6'-hexahydro-[2,2';6',2"]terpyridine A solution of (2'R,6'S)-3,3"-dimethyl-1',2',3',4',5',6'-hexahydro-[2,2';6',2"]terpyridine (163 mg, 0.609 mmol), 4-(bromomethyl)pyridine hydrobromide (185 mg, 0.730 mmol), DIPEA (265 μL, 1.52 mmol) and KI (10 mg, 0.060 mmol) in CH$_3$CN (6 mL) was warmed to 50° C. and stirred for 15.5 h according to General Procedure A. Purification by flash chromatography on silica gel using CH$_2$Cl$_2$/MeOH/NH$_4$OH (94:5:1) afforded COMPOUND 40 (110 mg, 37%) as an orange oily solid. $^1$H NMR (CDCl$_3$) δ 1.63-1.73 (m, 3H), 2.08-2.20 (m, 2H), 2.28-2.42 (m, 2H), 2.46 (s, 6H), 3.56 (s, 2H), 4.22 (d, 2H, J=11.8 Hz), 6.14 (d, 2H, J=5.3 Hz), 6.96 (dd, 2H, J=7.5, 4.8 Hz), 7.22 (d, 2H, J=7.9 Hz), 8.00 (d, 2H, J=4.4 Hz), 8.37 (d, 2H, J=4.4 Hz); ES-MS m/z 359 (M$^+$H).

EXAMPLE 41

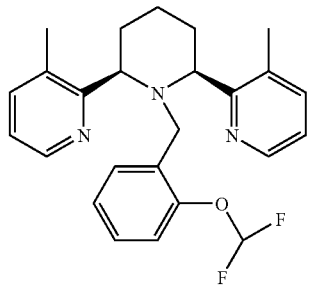

Compound 41: (2'R,6'S)-1'-(2-Difluoromethoxy-benzyl)-3,3"-dimethyl-1',2',3',4',5',6'-hexahydro-[2,2';6',2"]terpyridine A solution of (2'R,6'S)-3,3"-dimethyl-1',2',3',4',5',6'-hexahydro-[2,2';6',2"]terpyridine (169 mg, 0.624 mmol), 2-(difluoromethoxy)benzyl bromide (114 μL, 0.745 mmol), DIPEA (160 μL, 0.936 mmol) and KI (10 mg, 0.060 mmol) in CH$_3$CN (6 mL) was warmed to 50° C. and stirred for 15.5 h according to General Procedure A. Purification by flash chromatography on silica gel using CH$_2$Cl$_2$/MeOH/NH$_4$OH (94:5:1) afforded COMPOUND 41 (238 mg, 90%) as an white solid. $^1$H NMR (CDCl$_3$) δ 1.65-1.70 (m, 3H), 2.05-2.07 (m, 2H), 2.30-2.45 (m, 3H), 3.63 (s, 2H), 4.16 (d, 2H, J=10.2 Hz), 6.50 (s, 1H), 6.78-6.83 (m, 4H), 7.20-7.30 (m, 3H), 8.30 (d, 2H, J=3.1 Hz); ES-MS m/z 424 (M$^+$H).

EXAMPLE 42

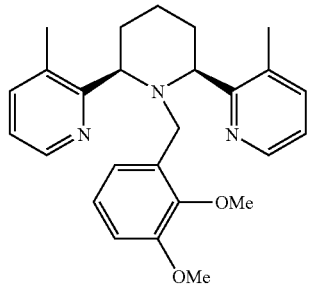

Compound 42: (2'R,6'S)-1'-(2,3-Dimethoxy-benzyl)-3,3"-dimethyl-1',2',3',4',5',6'-hexahydro-[2,2';6',2"]terpyridine A solution of (2'R,6'S)-3,3"-dimethyl-1',2',3',4',5',6'-hexahydro-[2,2';6',2"]terpyridine (164 mg, 0.613 mmol), 2,3- dimethoxybenzy chloride (136 mg, 0.731 mmol), DIPEA (160 μL, 0.936 mmol) and KI (10 mg, 0.060 mmol) in CH$_3$CN (6 mL) was warmed to 50° C. and stirred for 15.5 h according to General Procedure A. Purification by flash chromatography on silica gel using CH$_2$Cl$_2$/MeOH/NH$_4$OH (94:5:1) afforded COMPOUND 42 (61 mg, 24%) as an white solid. $^1$H NMR (CDCl$_3$) δ 1.61-1.76 (m, 3H), 2.16-2.23 (m, 3H), 2.45 (s, 6H), 3.68 (s, 6H), 4.16 (d, 2H, J=9.1 Hz), 6.45-6.48 (m, 1H), 6.62-6.65 (m, 2H), 6.89-6.73 (m, 2H), 7.26-7.29 (m, 2H), 8.38 (d, 2H, J=3.1 Hz); ES-MS m/z 418 (M$^+$H).

EXAMPLE 43

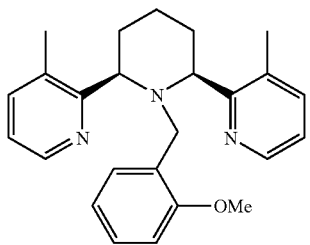

Compound 43: (2'R,6'S)-1'-(2-Methoxy-benzyl)-3,3''-dimethyl-1',2',3',4',5',6'-hexahydro-[2,2';6',2'']terpyridine A solution of (2'R,6'S)-3,3''-dimethyl-1',2',3',4',5',6'-hexahydro-[2,2';6',2'']terpyridine (197.6 mg, 0.739 mmol), 2-methoxybenzy chloride (125 μL, 0.898 mmol), DIPEA (195 μL, 1.12 mmol) and KI (10 mg, 0.060 mmol) in CH$_3$CN (6 mL) was warmed to 50° C. and stirred for 26 h according to General Procedure A. Purification by flash chromatography on silica gel using CH$_2$Cl$_2$/MeOH/NH$_4$OH (94:5:1) afforded COMPOUND 43 (78 mg, 31%) as an white solid. $^1$H NMR (CDCl$_3$) δ 1.20-1.30 (m, 3H), 1.65-1.72 (m, 1H), 2.15-2.25 (m, 2H), 2.40 (s, 6H), 3.59 (s, 3H), 4.05-4.15 (m, 2H), 6.32 (bs, 1H), 6.55-6.60 (m, 1H), 6.81-6.91 (m, 4H), 7.23-7.25 (m, 2H), 8.36 (bs, 2H); ES-MS m/z 388 (M$^+$H).

EXAMPLE 44

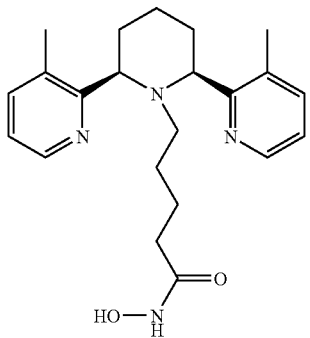

Compound 44: 5-((2'R,6'S)-3,3''-Dimethyl-3',4',5',6'-tetrahydro-2'H-[2,2';6',2'']terpyridin-1'-yl)-pentanoic Acid Hydroxyamide A solution of (2'R,6'S)-3,3''-dimethyl-1',2',3',4',5',6'-hexahydro-[2,2';6',2'']terpyridine (306 mg, 1.12 mmol), 5-bromo-pentanoic acid ethyl ester (263 mg, 1.12 mmol), DIPEA (260 μL, 1.49 mmol) and KI (10 mg, 0.060 mmol) in CH$_3$CN (12 mL) was warmed to 60° C. and stirred for 23 h according to General Procedure A. Purification by flash chromatography on silica gel using CH$_2$Cl$_2$/MeOH/NH$_4$OH (94:5:1) afforded 5-((2'R,6'S)-3,3''-dimethyl-3',4',5',6'-tetrahydro-2'H-[2,2';6',2'']terpyridin-1'-yl)-pentanoic acid ethyl ester (417 mg, 90%) as a yellow oil. $^1$H NMR (CDCl$_3$) δ 0.75-0.94 (m, 3H), 1.17 (t, 3H, J=7.1 Hz), 1.55-2.01 (m 8H), 2.20-2.35 (m, 6H), 2.47 (s, 6H), 3.99 (q, 2H, J=7.2 Hz), 7.05-7.09 (m, 2H), 7.43 (d, 2H, J=7.6 Hz), 8.46 (bs, 2H).

A warmed (50° C.) solution of KOH (1.36 g, 28.9 mmol) in MeOH (6.0 mL) was added to a warmed (50° C.) solution of NH$_2$OH.H$_2$O (1.00 g, 14.3 mmol) in MeOH (10.2 mL). Stirred for 5 min. during which time a white precipitate formed immediately. Cooled in an ice bath and decanted clear hydroxylamine freebase solution.

The freshly prepared solution of hydroxylamine in MeOH (5.3 mL) was added to a 5-((2'R,6'S)-3,3''-dimethyl-3',4',5',6'-tetrahydro-2'H-[2,2';6',2'']terpyridin-1'-yl)-pentanoic acid ethyl ester (228 mg, 0.575 mmol) and stirred for 23 h at ambient temperature. The mixture was concentrated to remove volatiles. Taken up in CH$_2$Cl$_2$ (50 mL) was washed with a saturated solution of NaHCO$_3$ (30 mL) to pH 8. Separated and the aqueous layer was extracted with CH$_2$Cl$_2$ (2×50 mL). Combine organic layers were dried over Na$_2$SO$_4$ and concentrated in vacuo. Purification by flash chromatography on silica gel using CH$_2$Cl$_2$/MeOH/NH$_4$OH (89:10:1) afforded COMPOUND 44 (121.3, 55%) as a white solid. $^1$H NMR (CDCl$_3$) δ 0.85-0.95 (m, 4H), 1.55-2.00 (m, 14H), 2.40 (s, 6H), 3.85-3.93 (bs, 2H), 7.03-7.06 (m, 2H), 7.47 (d, 2H, J=Hz), 8.31 (bs, 2H); $^{13}$C NMR (CDCl$_3$) δ 18.86, 22.73, 23.59, 32.31, 32.76, 53.44, 62.23, 122.17, 130.73, 139.26, 146.78, 169.62; ES-MS m/z 383 (M$^+$H). Anal Calcd. For C$_{22}$H$_{30}$N$_4$O$_2$.0.5(CH$_2$Cl$_2$): C, 63.59; H, 7.35; N, 13.18. Found: C, 63.69; H, 7.51; N, 13.36.

EXAMPLE 45

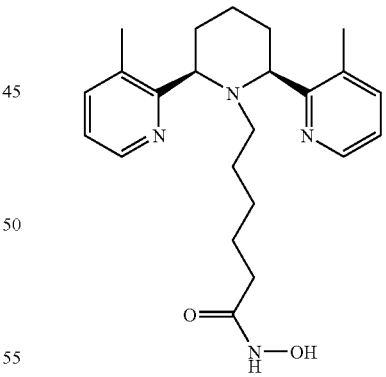

Compound 45: 6-((2'R,6'S)-3,3''-Dimethyl-3',4',5',6'-tetrahydro-2'H-[2,2';6',2'']terpyridin-1'-yl)-hexanoic Acid Hydroxyamide A solution of (2'R,6'S)-3,3''-dimethyl-1',2',3',4',5',6'-hexahydro-[2,2';6',2'']terpyridine (308 mg, 1.15 mmol), 6-bromo-hexanoic acid ethyl ester (283 mg, 1.27 mmol), DIPEA (260 μL, 1.49 mmol) and KI (10 mg, 0.060 mmol) in CH$_3$CN (12 mL) was warmed to 60° C. and stirred for 23 h according to General Procedure A. Purification by flash chromatography on silica gel using $CH_2Cl_2$/MeOH/$NH_4OH$ (94:5:1) afforded 6-((2'R,6'S)-3,3"-dimethyl-3',4',5',6'-tetrahydro-2'H-[2,2';6',2"]terpyridin-1'-yl)-hexanoic acid ethyl ester (425 mg, 90%) as a yellow oil. $^1H$ NMR ($CDCl_3$) δ 0.60-0.68 (m, 2H), 0.79-0.85 (m, 1H), 1.13-1.25 (m, 5H), 1.58-1.70 (m, 3H), 1.94-1.98 (m, 4H), 2.08-2.25 (m, 7H), 2.48 (bs, 6H), 1.50-2.63 (m, 2H), 4.03 (q, 2H, J=7.1 Hz), 7.05-7.08 (m, 2H), 7.43 (d, 2H, J=7.3 Hz), 8.47 (bs, 2H).

A warmed (50° C.) solution of KOH (1.36 g, 28.9 mmol) in MeOH (6.0 mL) was added to a warmed (50° C.) solution of $NH_2OH \cdot H_2O$ (1.00 g, 14.3 mmol) in MeOH (10.2 mL). Stirred for 5 min. during which time a white precipitate formed immediately. Cooled in an ice bath and decanted clear hydroxylamine freebase solution.

The freshly prepared solution of hydroxylamine in MeOH (5.8 mL) was added to a 5-((2'R,6'S)-3,3"-dimethyl-3',4',5',6'-tetrahydro-2'H-[2,2';6',2"]terpyridin-1'-yl)-pentanoic acid ethyl ester (262 mg, 0.638 mmol) and stirred for 23 h at ambient temperature. The mixture was concentrated to remove volatiles. Taken up in $CH_2Cl_2$ (50 mL) was washed with a saturated solution of $NaHCO_3$ (30 mL) to pH 8. Separated and the aqueous layer was extracted with $CH_2Cl_2$ (2×50 mL). Combine organic layers were dried over $Na_2SO_4$ and concentrated in vacuo. Purification by flash chromatography on silica gel using $CH_2Cl_2$/MeOH/$NH_4OH$ (89:10:1) afforded COMPOUND 45 (152, 60%) as a white solid. $^1H$ NMR ($CDCl_3$) δ 0.20-0.30 (m, 2H), 0.70-0.78 (m, 2H), 1.14-1.19 (m, 2H), 1.50-1.63 (m, 2H), 1.85-1.95 (m, 6H), 2.39 (s, 6H), 3.86 (bs, 2H), 7.02-7.06 (m, 2H), 7.46 (d, 2H, J=6.7 Hz), 8.48 (d, 2H, J=3.0 Hz); $^{13}C$ NMR ($CDCl_3$) δ 19.03, 23.29, 24.69, 25.93, 32.47, 33.05, 53.44, 62.82, 121.91, 130.74, 139.15, 146.71, 160.24, 169.87; ES-MS m/z 383 (M+H). Anal Calcd. For $C_{23}H_{32}N_4O_2O_2 \cdot 0.4(CH_2Cl_2)$: C, 65.29; H, 7.68; N, 13.01. Found: C, 65.59; H, 7.78; N, 13.21.

EXAMPLE 46

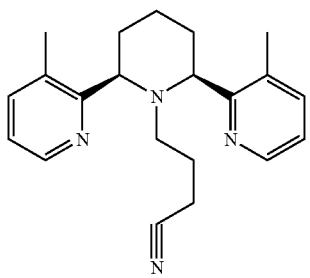

Compound 46: 4-(3,3"-Dimethyl-3',4',5',6'-tetrahydro-2'H-cis-[2,2';6',2"]terpyridin-1'-yl)-butyronitrile (HBr Salt)

Following General Procedure A: A solution of 3,3"-dimethyl-1',2',3',4',5',6'-hexahydro-cis-[2,2';6',2"]terpyridine (0.293 g, 1.10 mmol), 4-bromobutyronitrile (0.15 mL, 1.51 mmol), KI (10 mg), and DIPEA (0.30 mL, 1.73 mmol) in DMF (3 mL) was heated at 65° C. for 17 hours. Purification of the crude material by column chromatography on silica gel ($CH_2Cl_2$—$CH_3OH$, 96:4) provided 290 mg (79%) of 4-(3,3"-dimethyl-3',4',5',6'-tetrahydro-2'H-cis-[2,2';6',2"]terpyridin-1'-yl)-butyronitrile as a colorless oil.

Using General Procedure B: Conversion of the free base from above (60 mg, 0.18 mmol) to a HBr salt followed by reprecipitation of the crude material from MeOH/ether gave COMPOUND 46 as a yellow solid (86 mg, 90%). $^1H$ NMR ($D_2O$) δ 1.50-1.80 (m, 5H), 1.95-2.00 (m, 1H), 2.12-2.18 (m, 4H), 2.30-2.40 (m, 2H), 2.61 (s, 6H), 4.63 (dd, 2H, J=11.4, 3.0 Hz), 7.91 (dd, 2H, J=8.1, 6 Hz), 8.44 (d, 2H, J=8.1 Hz), 8.69 (d, 2H, J=5.7 Hz); $^{13}C$ NMR ($D_2O$) δ 14.88, 17.19, 19.02, 22.39, 32.55, 51.34, 57.89, 120.71, 126.16, 137.16, 139.92, 149.716, 154.27; ES-MS m/z 335 (M+H). Anal. Calcd. for $C_{21}H_{26}N_4 \cdot 2.1$ HBr$\cdot 1.4 H_2O$: C, 47.63; H, 5.88; N, 10.58; Br, 31.68. Found: C, 47.64; H, 5.85; N, 10.60; Br, 31.61.

EXAMPLE 47

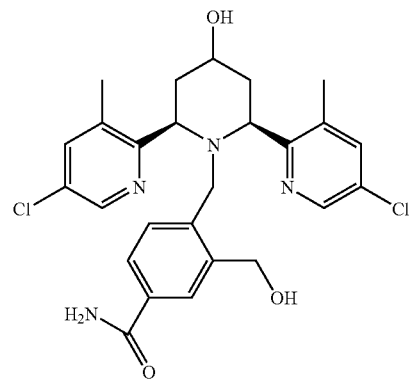

Compound 47: 4-(5,5"-Dichloro-4'-hydroxy-3,3"-dimethyl-3',4',5',6'-tetrahydro-2'H-cis-[2,2';6',2"]terpyridin-1'-ylmethyl)-3-hydroxymethyl-benzamide To a solution of 5-chloro-3-methyl-pyridine-2-carbaldehyde (1.99 g, 12.81 mmol) in MeOH (30 mL) was added $NH_4OAc$ (530 mg, 6.88 mmol) and 1,3-acetonedicarboxylic acid (913 mg, 6.25 mmol), and the mixture was stirred at room temperature for 29 h. The mixture was concentrated in vacuo and saturated $NaHCO_3$ (50 mL) followed by $CH_2Cl_2$ (75 mL) were added. The layers were separated and the aqueous layer was extracted with $CH_2Cl_2$ (2×30 mL). The organic extracts were dried ($Na_2SO_4$), filtered and concentrated. Purification of the crude material by flash column chromatography on silica gel (EtOAc:hexanes, 1:3 then 1:1) provided 5,5"-dichloro-3,3"-dimethyl-1',2',3',4',5',6'-hexahydro-cis-[2,2';6',2"]terpyridin-4'-one as a yellow foam.

To a solution of the ketone from above (1.12 g) in MeOH (20 mL) at 0° C. was added $NaBH_4$ (260 mg, 6.87 mmol) and the reaction stirred at 0° C. for 30 min. then warmed to room temperature and stirred 5 h. The mixture was concentrated in vacuo then diluted with $CH_2Cl_2$ (40 mL) and saturated, aqueous $NaHCO_3$ (30 mL). The aqueous layer was extracted with $CH_2Cl_2$ (2×10 mL) and the combined organic extracts dried ($Na_2SO_4$) and concentrated. Purification of the crude orange oil (369 mg) by column chromatography on silica gel ($CH_2Cl_2$/MeOH, 96:4 then 92:8) afforded 5,5"-dichloro-3,3"-dimethyl-1',2',3',4',5',6'-hexahydro-cis-[2,2';6',2"]terpyridin-4'-ol (590 mg, 27% 2 steps). $^1H$ NMR ($CDCl_3$) δ 1.30 (q, 2H, J=11.7 Hz), 1.98 (d, 2H, J=12 Hz), 2.31 (s, 6H), 2.72-2.82 (m, 2H), 3.84-3.89 (m, 1H), 4.05 (t, 2H, J=11.1 Hz), 7.40 (s, 2H), 8.35 (s, 2H).

Using General Procedure A: A solution of 5,5"-dichloro-3,3"-dimethyl-1',2',3',4',5',6'-hexahydro-cis-[2,2';6',2"]terpyridin-4'-ol (590 mg, 1.68 mmol), 2-bromomethyl-5-cyano-benzoic acid methyl ester (U.S. patent application Attorney Docket No. 391442005900) (512 mg, 2.02 mmol), KI (15 mg), and DIPEA (0.45 mL, 2.59 mmol) in DMF (4 mL) was heated at 70° C. for 17 hours. Purification of the crude material by column chromatography on silica gel ($CH_2Cl_2$—$CH_3OH$, 99:1 then 96:4) provided 779 mg (88%) of the desired alkylated material as a brown foam.

To a cold (0° C.) solution of the methyl ester form above (152 mg, 0.29 mmol) in THF (5 mL) was added $LiBH_4$ (51 mg, 2.34 mmol) and the mixture was allowed to warm to room temperature before being heated to 65° C. for 4 h 15 min. The mixture was diluted with 1 N NaOH (10 mL) and extracted with $CH_2Cl_2$ (3×15 mL). The combined organic extracts were dried ($Na_2SO_4$) and concentrated and the resultant alcohol was used without further purification in the next reaction.

To a solution of the nitrile from above in $MeOH/H_2O$ (2:1, 6 mL) was added $NaBO_3.4H_2O$ (121 mg, 0.79 mmol) and the reaction heated to 55° C. for 2.5 d. The mixture was concentrated and purified by radial chromatography on silica gel (1 mm plate, $CH_2Cl_2$—$CH_3OH$—$NH_4OH$, 100:1:1 then 50:1:1) to afford COMPOUND 47 as a white solid (25 mg, 17% 2 steps). $^1H$ NMR (DMSO-$d_6$) δ 1.70-1.75 (m, 2H), 2.22 (q, 2H, J=12 Hz), 2.50 (s, 6H), 3.48 (s, 2H), 3.84-3.90 (m, 1H), 4.18 (d, 2H, J=4.8 Hz), 4.41 (br d, 2H, J=11.7 Hz), 4.82 (d, 2H, J=4.5 Hz), 6.79 (d, 1H, J=7.8 Hz), 7.02 (s, 1H), 7.25 (d, 1H, J=7.8 Hz), 7.37 (s, 1H), 7.43 (s, 2H), 7.59 (s, 1H), 8.18 (s, 2H); $^{13}C$ NMR (DMSO-$d_6$) δ 17.96, 33.68, 41.65, 61.10, 61.73, 68.61, 124.71, 125.84, 126.51, 129.64, 130.88, 135.14, 137.00, 138.04, 142.85, 144.15, 156.53, 168.02; ES-MS m/z 537 ($M^+Na$). Anal. Calcd. for $C_{26}H_{28}N_4O_3Cl_2.1.8H_2O$: C, 57.00; H, 5.81; N, 10.23; Cl, 12.94. Found: C, 56.98; H, 5.79; N, 9.88; Cl, 12.95.

EXAMPLE 48

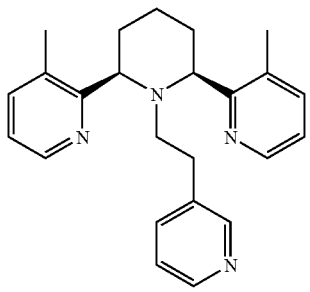

Compound 48: (3,3"-Dimethyl-1'-(2-pyridin-3-yl-ethyl)-1',2',3',4',5',6'-hexahydro-cis-[2,2';6',2"]terpyridine To a solution of ethyl 3-pyridylacetate (983 mg, 5.95 mmol) in THF (10 mL) at 0° C. was added a solution of $LiAlH_4$ (1.0 M in THF, 9.0 mL, 9.0 mmol) and the reaction stirred for 15 min. before quenching at 0° C. with $H_2O$ (0.35 mL) then 15% aqueous NaOH (0.35 mL) then $H_2O$ (1.0 mL). The mixture was stirred 10 min. then filtered, washing with $Et_2O$ and EtOAc. The filtrate was concentrated and purified by column chromatography on silica gel ($CH_2Cl_2$/MeOH, 96:4) to afford the desired alcohol (0.47 g, 64%) as a colorless oil.

To a solution of the alcohol from above (366 mg, 2.98 mmol) in $CH_2Cl_2$ (10 mL) at −78° C. was added $Et_3N$ (0.85 mL, 6.11 mmol) and mesyl chloride (0.35 mL, 4.52 mmol) and the reaction stirred at −78° C. for 25 min. The mixture was diluted with $CH_2Cl_2$ (25 mL) and saturated aqueous $NaHCO_3$ (25 mL) and the aqueous phase was extracted with $CH_2Cl_2$ (2×10 mL). The combined organic phase was dried ($Na_2SO_4$) and concentrated to afford methanesulfonic acid 2-pyridin-3-yl-ethyl ester, used without further purification in the next reaction.

Using General Procedure A: A solution of 3,3"-dimethyl-1',2',3',4',5',6'-hexahydro-cis-[2,2';6',2"]terpyridine (0.219 g, 0.82 mmol), methanesulfonic acid 2-pyridin-3-yl-ethyl ester (approx. 3 mmol), KI (15 mg), and DIPEA (0.25 mL, 1.44 mmol) in DMF (3 mL) was heated at 80° C. for 17 hours. Purification of the crude material by column chromatography on silica gel ($CH_2Cl_2$—$CH_3OH$—$NH_4OH$, 94:4:2) followed by radial chromatography on silica gel (1 mm plate, $CH_2Cl_2$—$CH_3OH$—$NH_4OH$, 50:1:1) provided 193 mg (63%) of COMPOUND 48 as a colorless oil. $^1H$ NMR ($CDCl_3$) δ 1.61-1.70 (m, 4H), 2.00-2.22 (m, 4H), 2.51 (s, 6H), 2.51-2.55 (m, 2H), 4.14-4.18 (m, 2H), 6.55-6.60 (m, 1H), 6.85 (dd, 1H, J=7.5, 4.8 Hz), 7.09-7.12 (m, 2H), 7.42 (d, 2H, J=6.9 Hz), 7.54-7.60 (m, 1H), 8.18 (dd, 1H, J=4.8, 1.5 Hz), 8.42-8.46 (m, 2H); $^{13}C$ NMR ($CDCl_3$) δ 17.59, 22.43, 24.32, 26.23, 28.85, 30.67, 47.26, 51.85, 63.52, 70.06, 121.05, 121.87, 131.24, 134.51, 137.16, 138.57, 145.34, 145.73, 148.78, 158.55; ES-MS m/z 373 ($M^+H$). Anal. Calcd. for $C_{24}H_{28}N_4.0.3H_2O$: C, 76.28; H, 7.63; N, 14.83. Found: C, 76.14; H, 7.78; N, 14.82.

EXAMPLE 49

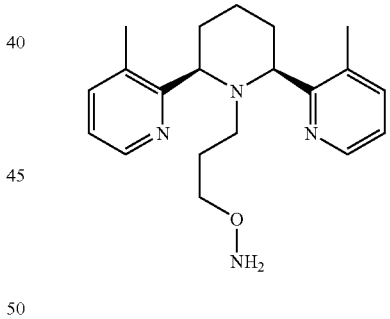

Compound 49: O-[3-(3,3"-Dimethyl-3',4',5',6'-tetrahydro-2'H-cis-[2,2';6',2"]terpyridin-1'-yl)-propyl]-hydroxylamine Using General Procedure A: A solution of 3,3"-dimethyl-1',2',3',4',5',6'-hexahydro-cis-[2,2';6',2"]terpyridine (253 mg, 0.95 mmol), 2-(3-bromo-propoxy)-isoindole-1,3-dione (Canne, L. E, et al., J. Am. Chem. Soc. (1996) 118:5891-5896) (334 mg, 1.18 mmol), KI (15 mg), and DIPEA (0.35 mL, 2.01 mmol) in DMF (3 mL) was heated at 70° C. for 17 hours. Purification of the crude material by column chromatography on silica gel ($CH_2Cl_2$—$CH_3OH$—$NH_4OH$, 96:4:0 then 94:4:2) afforded the alkylated material (260 mg, 58%) as a brown foam.

To a solution of the phthalimide from above (181 mg, 0.385 mmol) in MeOH (5 mL) was added hydrazine monohydrate (0.10 mL, 2.06 mmol) and the reaction stirred overnight at room temperature. The mixture was filtered, concentrated and purified by radial chromatography on silica gel (1 mm plate, $CH_2Cl_2$—$CH_3OH$—$NH_4OH$, 50:1:1 then 25:1:1) to afford COMPOUND 49 as a colorless oil (88 mg, 67%). $^1H$ NMR (CDCl$_3$) δ 0.91-0.97 (m, 1H), 1.55-1.66 (m, 3H), 1.94-2.08 (m, 3H), 2.29 (t, 2H, J=6 Hz), 2.50 (s, 6H), 2.95-3.04 (m, 2H), 4.04 (br d, 2H, J=12 Hz), 4.83 (br s, 3H), 7.05 (dd, 1H, J=7.5, 4.8 Hz), 7.40 (d, 2H, J=7.5 Hz), 8.41-8.43 (m, 2H); $^{13}C$ NMR (CDCl$_3$) δ 21.06, 26.85, 27.52, 31.84, 47.27, 49.48, 66.12, 73.32, 76.51, 124.11, 140.54, 141.82, 148.93, 162.55; ES-MS m/z 341 (M$^+$H). Anal. Calcd. for $C_{20}H_{28}N_4O\cdot0.7H_2O$: C, 68.04; H, 8.39; N, 15.87. Found: C, 68.04; H, 8.34; N, 15.62.

EXAMPLE 50

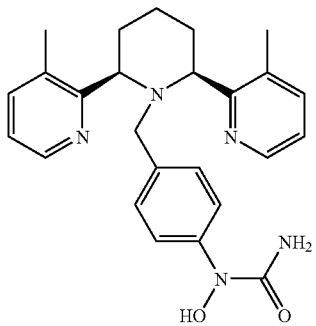

Compound 50: [4-(3,3"-Dimethyl-3',4',5',6'-tetrahydro-2'H-cis-[2,2';6',2"]terpyridin-1'-ylmethyl)-phenyl]-N-hydroxyurea Using General Procedure A: A solution of 3,3"-dimethyl-1',2',3',4',5',6'-hexahydro-cis-[2,2';6',2"]terpyridine (558 mg, 2.09 mmol), 4-nitrobenzyl bromide (547 mg, 2.53 mmol), KI (15 mg), and DIPEA (0.60 mL, 3.45 mmol) in $CH_3CN$ (10 mL) was heated at 65° C. for 17 hours. Purification of the crude material by column chromatography on silica gel ($CH_2Cl_2$—$CH_3OH$, 96:4 then 92:8) afforded the N-alkylated material (0.73 g, 87%) as a yellow foam.

To a solution of 3,3"-dimethyl-1'-(4-nitro-benzyl)-1',2',3',4',5',6'-hexahydro-cis-[2,2';6',2"]terpyridine (245 mg, 0.61 mmol) in THF (3 mL) was added rhodium (5% on carbon, 15 mg) followed by hydrazine hydrate (0.30 mL, 6.15 mmol) and the reaction stirred 6.5 h. The mixture was filtered through Celite, washing with MeOH and $CH_2Cl_2$ and the filtrate concentrated. To a solution of the resultant residue in $CH_2Cl_2$ (6 mL) was added trimethylsilyl isocyanate (0.13 mL, 0.96 mmol) and the reaction stirred overnight. The mixture was concentrated and purified by radial chromatography on silica gel (1 mm plate, $CH_2Cl_2$—$CH_3OH$—$NH_4OH$, 50:1:1 to 10:1:1) to afford COMPOUND 50 as a yellow foam (37 mg, 14%). $^1H$ NMR (CDCl$_3$/CD$_3$OD) δ 1.34-1.42 (m, 1H), 1.59-1.81 (m, 5H), 2.24 (s, 6H), 3.15 (s, 2H), 3.24-3.46 (m, 3H), 3.82 (br d, 2H, J=9 Hz), 6.28 (d, 2H, J=7.5 Hz), 7.00 (dd, 2H, J=7.2, 4.8 Hz), 7.16 (d, 2H, J=8.1 Hz), 7.34 (d, 2H, J=7.2 Hz), 8.29 (d, 2H, J=3 Hz); $^{13}C$ NMR (CDCl$_3$/CD$_3$OD) δ 18.79, 24.68, 32.36, 53.94, 62.16, 119.82, 122.59, 129.65, 130.42, 131.67, 138.70, 141.42, 146.67, 158.98, 159.94; ES-MS m/z 432 (M$^+$H). Anal. Calcd. for $C_{25}H_{29}N_5O_2\cdot1.9H_2O$: C, 64.47; H, 7.10; N, 15.04. Found: C, 64.43; H, 6.77; N, 15.05.

EXAMPLE 51

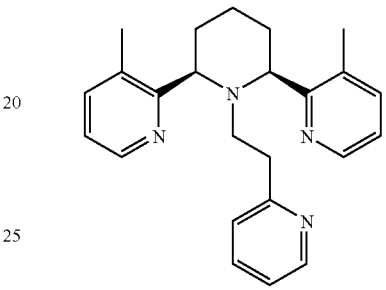

Compound 51: Preparation of (3,3"-Dimethyl-1'-(2-pyridin-2-yl-ethyl)-1',2',3',4',5',6'-hexahydro-cis-[2,2°;6',2"]terpyridine To a solution of 2-(2-hydroxyethyl)pyridine (602 mg, 4.89 mmol) in $CH_2Cl_2$ (10 mL) at −78° C. was added Et$_3$N (1.0 mL, 7.20 mmol) and mesyl chloride (0.45 mL, 5.8 mmol) and the reaction warmed to room temperature and stirred for 15 min. The mixture was diluted with $CH_2Cl_2$ (25 mL) and saturated aqueous NaHCO$_3$ (25 mL) and the aqueous phase was extracted with $CH_2Cl_2$ (2×10 mL). The combined organic phase was dried (Na$_2$SO$_4$) and concentrated to afford the desired mesylate (1.01 g), used without further purification in the next reaction.

Using General Procedure A: A suspension of 3,3"-dimethyl-1',2',3',4',5',6'-hexahydro-cis-[2,2';6',2"]terpyridine (252 mg, 0.94 mmol), methanesulfonic acid 2-pyridin-2-yl-ethyl ester (approx. 4.9 mmol) and K$_2$CO$_3$ (1.30 g, 9.42 mmol) in DMF (5 mL) was heated at 85° C. for 2.5 d. Purification of the crude material by column chromatography on silica gel ($CH_2Cl_2$—$CH_3OH$—$NH_4OH$, 96:4:0 then 94:4:2) followed by radial chromatography on silica gel (1 mm plate, $CH_2Cl_2$—$CH_3OH$—$NH_4OH$, 25:1:1) provided 152 mg (43%) of COMPOUND 51 as a pale yellow oil. $^1H$ NMR (CDCl$_3$) δ 1.60-1.72 (m, 3H), 1.96-2.23 (m, 5H), 2.51 (s, 6H), 2.61-2.66 (m, 2H), 4.15 (d, 2H, J=12 Hz), 6.33-6.38 (m, 1H), 6.85 (dd, 1H, J=7.2, 5.1 Hz), 7.07 (dd, 2H, J=7.5, 4.8 Hz), 7.27 (dt, 1H, J=7.5, 1.5 Hz), 7.40 (d, 2H, J=7.5 Hz), 8.19 (d, 1H, J=4.8 Hz), 8.42-8.47 (m, 2H); $^{13}C$ NMR (CDCl$_3$) δ 19.18, 25.52, 30.76, 34.77, 49.87, 63.61, 120.80, 122.22, 122.76, 131.72, 136.15, 138.83, 147.10, 149.18, 160.47, 161.42; ES-MS m/z 373 (M+H). Anal. Calcd. for C$_{24}$H$_{28}$N$_4$.1.6H$_2$O: C, 71.83; H, 7.84; N, 13.96. Found: C, 71.84; H, 7.53; N, 13.65.

EXAMPLE 52

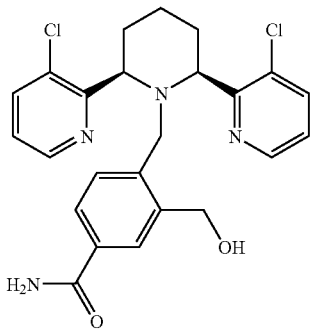

Compound 52: 4-(3,3"-Dichloro-3',4',5',6'-tetrahydro-2'H-[2,2';6',2"]terpyridin-1'-ylmethyl)-3-hydroxymethyl-benzamide Using General Procedure A: 3,3"-dichloro-1',2',3',4',5',6'-hexahydro-[2,2';6',2"]terpyridine (304 mg, 0.987 mmol), 2-bromomethyl-5-cyano-benzoic acid methyl ester (351 mg, 1.38 mmol), KI (32.7 mg, 0.197 mmol), DIPEA (0.34 mL, 1.97 mmol), and DMF (5 mL) were stirred at 60° C. for 3 h. Purification of the crude material by flash chromatography on silica gel (CH$_2$Cl$_2$/MeOH, 98:2) afforded 5-cyano-2-(3,3"-dichloro-3',4',5',6'-tetrahydro-2'H-[2,2';6',2"]terpyridin-1'-ylmethyl)-benzoic acid methyl ester (391 mg, 82%) as a yellow oil. $^1$H NMR (CDCl$_3$) δ 1.63-1.78 (m, 3H), 2.01-2.14 (m, 1H), 2.18-2.38 (m, 2H), 3.87 (s, 3H), 3.95 (s, 2H), 4.52 (dd, 2H, J=11.4, 1.6 Hz), 6.89 (dd, 2H, J=8.4, 4.9 Hz), 7.38-7.48 (m, 3H), 7.57 (d, 1H, J=1.7 Hz), 8.22-8.32 (m, 3H).

To a cold (0° C.) solution of 5-cyano-2-(3,3"-dichloro-3',4',5',6'-tetrahydro-2'H-[2,2';6',2"]terpyridin-1'-ylmethyl)-benzoic acid methyl ester (391 mg, 0.813 mmol) in THF (4 mL) and MeOH (4 mL) was added LiBH$_4$ (88 mg, 4.1 mmol), and the mixture was warmed to room temperature and stirred for 3.5 h. The mixture was diluted with 1.0 N NaOH (20 mL) and extracted with CH$_2$Cl$_2$ (4×10 mL). The combined organic extracts were dried (Na$_2$SO$_4$), filtered, and concentrated in vacuo to provide 4-(3,3"-Dichloro-3',4',5',6'-tetrahydro-2'H-[2,2';6',2"]terpyridin-1'-ylmethyl)-3-hydroxymethyl-benzonitrile (367 mg) without any further purification. To a solution of the crude material (160 mg) in MeOH (4.5 mL) was added H$_2$O (2.5 mL) and NaBO$_3$.4H$_2$O (108 mg, 0.707 mmol). The resultant mixture was heated to 50° C. for 5 h and stirred at room temperature overnight. The reaction mixture was concentrated and the residue was purified by flash chromatography on silica gel (CH$_2$Cl$_2$/MeOH/NH$_4$OH, 90:5:5 then 85:10:5) to afford COMPOUND 52 (54 mg, 32% over 2 steps) as a white solid. $^1$H NMR (CDCl$_3$) δ 1.63-1.79 (m, 3H), 1.93-2.06 (m, 1H), 2.11-2.30 (m, 2H), 2.33-2.47 (m, 2H), 3.63 (s, 2H), 4.59 (d, 2H, J=9.92 Hz), 4.41 (s, 2H), 4.99 (br s, 1H), 5.67 (br s, 1H), 6.15 (br s, 1H), 6.85-6.96 (m, 2H), 7.04 (d, 1H, J=7.8 Hz), 7.24 (d, 1H, J=1.8 Hz), 7.38 (d, 1H, J=1.5 Hz), 7.48 (dd, 2H, J=7.8, 1.5 Hz), 8.30 (dd, 2H, J=4.5, 1.2 Hz); $^{13}$C NMR (CDCl$_3$) δ 24.98, 31.59, 57.28, 62.72, 66.56, 123.45, 126.39, 128.11, 129.90, 131.55, 131.70, 137.47, 140.08, 142.64, 147.77, 158.55, 169.17; ES-MS m/z 473 (M+1+H). Anal. Calcd. for C$_{24}$H$_{24}$N$_4$Cl$_2$O$_2$.0.5H$_2$O: C, 60.01; H, 5.25; N, 11.66. Found: C, 60.00; H, 5.15; N, 11.49.

EXAMPLE 53

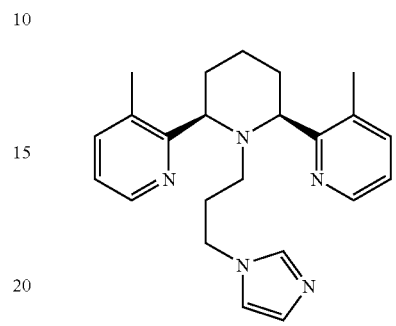

Compound 53: 1'-(3-Imidazol-1-yl-propyl)-3,3"-dimethyl-1',2',3',4',5',6'-hexahydro-[2,2';6',2"]terpyridine (HBr Salt)

To a stirred solution of imidazole (500 mg, 7.35 mmol) and 1,3-dibromopropane (2.2 mL, 22.0) in THF (35 mL) was added 60% NaH (356 mg, 8.82 mmol), and the resultant mixture was refluxed for 1 h and stirred at room temperature overnight. The mixture was quenched with H$_2$O (25 mL) and diluted with CH$_2$Cl$_2$ (40 mL). The aqueous phase was separated and extracted with CH$_2$Cl$_2$ (3×15 mL). The combined organic extracts were dried (Na$_2$SO$_4$), filtered, and concentrated to dryness. Purification by flash chromatography on silica gel (CH$_2$Cl$_2$/MeOH, 97:3) provided 1-(3-Bromo-propyl)-1H-imidazole (410 mg, 30%) as a colorless oil. $^1$H NMR (CDCl$_3$) δ 2.20-2.34 (m, 2H), 3.31 (t, 2H, J=6.3 Hz), 4.16 (t, 2H, J=6.2 Hz), 6.93 (s, 1H), 7.08 (s, 1H), 7.51 (s, 1H).

Using General Procedure A: 3,3"-dimethyl-1',2',3',4',5',6'-hexahydro-[2,2';6',2"]terpyridine (91.3 mg, 0.341 mmol), 1-(3-bromo-propyl)-1H-imidazole (129 mg, 0.680 mmol), KI (5.6 mg, 0.034 mmol), DIPEA (0.18 mL, 1.02 mmol), and DMF (3.4 mL) were stirred at 60° C. overnight. Purification of the crude material by flash chromatography on silica gel (CH$_2$Cl$_2$/MeOH/NH$_4$OH, 90:5:5) followed by radial chromatography on a 1 mm TLC grade silica gel plate (CH$_2$Cl$_2$/MeOH/NH$_4$OH, 96:2:2) afforded the free base of the title compound (48 mg, 38%) as a colorless oil.

Using General Procedure B: Conversion of the free base from above (48 mg, 0.13 mmol) to a HBr salt followed by reprecipitation of the crude material from MeOH/ether gave COMPOUND 53 as an off-white solid (84 mg, 94%). $^1$H NMR (D$_2$O) δ 1.42-1.61 (m, 2H), 1.63-2.00 (m, 4H), 2.07-2.25 (m, 4H), 2.55 (s, 6H), 3.93 (t, 2H, J=6.3 Hz), 4.57 (d, 2H, J=11.1 Hz), 7.32 (d, 1H, J=15.9 Hz), 7.91 (dd, 2H, J=7.8, 6.0 Hz), 8.42 (d, 2H, J=8.1 Hz), 8.53 (s, 1H), 8.69 (d, 2H, J=5.4 Hz); $^{13}$C NMR (D$_2$O) δ 17.30, 22.39, 24.10, 32.50, 47.16, 49.25, 57.97, 120.62, 121.91, 126.23, 134.97, 136.96, 140.10, 149.71, 153.99; ES-MS m/z 376 (M+H). Anal. Calcd.

for C$_{23}$H$_{29}$N$_5$.3.3 HBr.2.8H$_2$O: C, 39.87; H, 5.51; N, 10.11; Br, 38.05. Found: C, 39.82; H, 5.45; N, 9.97; Br, 38.30.

EXAMPLE 54

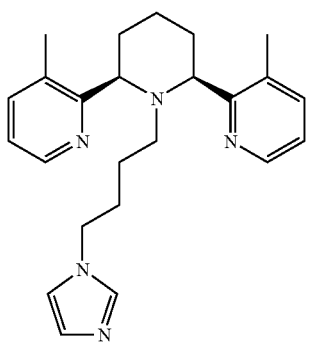

Compound 54: 1'-(4-Imidazol-1-yl-butyl)-3,3''-dimethyl-1',2',3',4',5',6'-hexahydro-[2,2';6',2'']terpyridine (HBr Salt)

To a stirred solution of imidazole (500 mg, 7.35 mmol) and 1,4-dibromobutane (2.6 mL, 22.0) in THF (50 mL) was added 60% NaH (356 mg, 8.81 mmol), and the resultant mixture was refluxed for 2 h and stirred at room temperature overnight. The mixture was quenched with H$_2$O (50 mL) and diluted with CH$_2$Cl$_2$ (75 mL). The aqueous phase was separated and extracted with CH$_2$Cl$_2$ (3×15 mL). The combined organic extracts were dried (Na$_2$SO$_4$), filtered, and concentrated to dryness. Purification by flash chromatography on silica gel (CH$_2$Cl$_2$/MeOH, 97:3) resulted in partial decomposition of 1-(4-bromo-butyl)-1H-imidazole. This material was used without any further purification. Using General Procedure A: 3,3''-dimethyl-1',2',3',4',5',6'-hexahydro-[2,2';6',2''] terpyridine (94.4 mg, 0.353 mmol), impure 1-(4-bromo-butyl)-1H-imidazole (145 mg), KI (6.0 mg, 0.035 mmol), DIPEA (0.18 mL, 1.02 mmol), and DMF (3.5 mL) were stirred for 48 h at 60° C. Purification of the crude material by radial chromatography on a 1 mm TLC grade silica gel plate (CH$_2$Cl$_2$/MeOH/NH$_4$OH, 96:2:2) afforded the free base of the title compound (47 mg, 34% over 2 steps) as a colorless oil.

Using General Procedure B: Conversion of the free base from above (48 mg, 0.13 mmol) to a HBr salt followed by re-precipitation of the crude material from MeOH/ether gave COMPOUND 54 as an off-white solid (85 mg, 92%). $^1$H NMR (D$_2$O) δ 1.01-1.19 (m, 2H), 1.35-1.56 (m, 4H), 1.58-1.80 (m, 1H), 1.82-1.95 (m, 1H), 1.96-2.15 (m, 2H), 2.16-2.32 (m, 2H), 2.51 (s, 6H), 4.02 (t, 2H, J=6.9 Hz), 4.52 (d, 2H, J=11.1 Hz), 7.31 (s, 1H), 7.41 (s, 1H), 7.87 (dd, 2H, J=7.8, 6.0 Hz), 8.39 (d, 2H, J=7.8 Hz), 8.58 (s, 1H), 8.65 (d, 2H, J=5.7 Hz); $^{13}$C NMR (D$_2$O) δ 17.21, 20.16, 20.89, 22.43, 27.26, 32.59, 49.06, 52.95, 58.22, 120.30, 122.01, 126.05, 134.75, 136.82, 139.80, 149.59, 154.67; ES-MS m/z 390 (M$^+$H). Anal. Calcd. for C$_{24}$H$_{31}$N$_5$.3.9 HBr.2.9H$_2$O: C, 38.06; H, 5.42; N, 9.25; Br, 41.15. Found: C, 37.99; H, 5.14; N, 9.30; Br, 41.29.

EXAMPLE 55

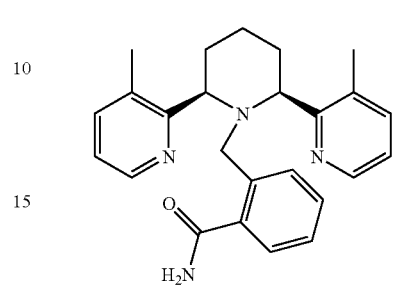

Compound 55: 2-meso-(3,3''-Dimethyl-3',4',5' 6'-tetrahydro-2'H-[2,2';6',2'']terpyridin-1'-ylmethyl)-benzamide A solution of meso-3,3''-dimethyl-1',2',3',4',5',6'-hexahydro-[2,2';6',2'']terpyridine (107 mg, 0.40 mmol), 2-bromomethyl-benzonitrile (102 mg, 0.52 mmol), and KI (13 mg, 0.08 mmol) in anhydrous DMF (2.0 mL) was treated with DIPEA (0.14 mL, 0.80 mmol) and stirred at 60° C. for 16 hours. EtOAc (10 mL) was added and the organic solution was washed with brine (5×5 mL), dried (MgSO$_4$), and concentrated under reduced pressure. This afforded, after purification by column chromatography with silica gel (50:1:0.1 CH$_2$Cl$_2$/MeOH/NH$_4$OH), 2-meso-(3,3''-dimethyl-3',4',5',6'-tetrahydro-2'H-[2,2';6',2'']terpyridin-11'-ylmethyl)-benzonitrile as a light beige-colored solid (143 mg, 93%).

The above nitrile (143 mg, 0.37 mmol) in MeOH (3.0 mL) was added to a solution of 50% H$_2$O$_2$ (0.11 mL, 1.9 mmol) and 3N NaOH (0.6 mL, 1.9 mmol). The reaction was heated to 80° C. for 16 hours and cooled to ambient temperature. Water (2 mL) was added and the media extracted with CH$_2$Cl$_2$ (3×15 mL). The combined organics were then dried (Na$_2$SO$_4$) and concentrated under reduced pressure to afford, after radial chromatographic purification on a silica gel plate (33:1:0.1 CH$_2$Cl$_2$/MeOH/NH$_4$OH), COMPOUND 55 as a white solid (61 mg, 40%). $^1$H NMR (CDCl$_3$) δ 1.64 (m, 3H), 2.02 (m, 1H), 2.28 (q, 2H, J=13.8 Hz), 2.46 (s, 6H), 3.72 (s, 2H), 4.07 (d, 2H, J=11.1 Hz), 5.72 (br, 1H(NH)), 6.79-6.90 (m, 4H), 7.06 (d, 1H, J=7.8 Hz), 7.19 (d, 3H, J=7.5 Hz), 8.24 (d, 2H, J=3.9 Hz), 9.44 (br, 1H(NH)). $^{13}$C NMR (CDCl$_3$) δ 18.86 (2C), 24.81, 29.62 (2C), 55.81, 65.95 (2C), 121.92 (2C), 126.60, 128.55, 128.78 (2C), 129.83, 130.88, 135.19, 136.33, 137.94 (2C), 146.45 (2C), 159.77 (2C), 170.68. ES- MS m/z 401 (M+H). Anal. Calcd. for C$_{25}$H$_{28}$N$_4$O.0.3CH$_2$Cl$_2$.0.1H$_2$O: C, 71.03; H, 6.79; N, 13.10. Found: C, 70.75; H, 6.81; N, 12.95.

EXAMPLE 56

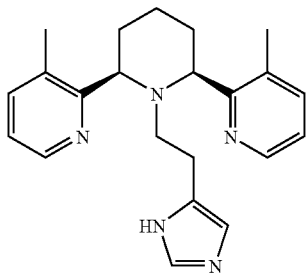

Compound 56: 1'-[2-(3H-imidazol-4-yl)-ethyl]-3,3"-dimethyl-1',2',3',4',5',6'-hexahydro-[2,2';6',2"]terpyridine (HBr Salt)

To a solution of 4-imidazoleacetic acid hydrochloride (499 mg, 3.07 mmol) in MeOH (10 mL) was added concentrated sulfuric acid (1 mL) and the mixture was heated to 80° C. overnight. Then the mixture was cooled and concentrated. The residue was dissolved in CH$_2$Cl$_2$ (30 mL) and washed with saturated NaHCO$_3$ (30 mL). The aqueous layer was saturated with NaCl (s) and extracted with EtOAc (3×30 mL). The combined organic layers were dried (MgSO$_4$), filtered, and concentrated to afford (1H-imidazol-4-yl)-acetic acid methyl ester as a yellow oil (330 mg, 66%). $^1$H NMR (CDCl$_3$) δ 3.70 (s, 2H), 3.72 (s, 3H), 6.97 (s, 1H), 7.59 (s, 1H).

To a solution of the ester (330 mg, 2.35 mmol) in DMF (5 mL) was added DIPEA (1.2 mL, 7.05 mmol) and Sem-chloride (0.49 mL, 2.83 mmol) and the reaction mixture was stirred overnight. The mixture was concentrated in vacuo and the residue was dissolved in EtOAc (30 mL) and washed with H$_2$O (25 mL) and brine (2×25 mL). The combined aqueous layers were extracted with CH$_2$Cl$_2$ (2×30 mL). The combined organic layers were dried (MgSO$_4$), filtered, and concentrated to afford a yellow oil. Purification by flash column chromatography on silica gel using 2% CH$_3$OH/CH$_2$Cl$_2$ afforded [1-(2-trimethylsilanyl-ethoxymethyl)-1H-imieazol-4-yl]-acetic acid methyl ester as a yellow oil (240 mg, 73%). $^1$H NMR (CDCl$_3$) δ −0.03 and −0.02 (s, total 9H), 0.85-0.93 (m, 2H), 3.40-3.50 (m, 2H), 3.71 and 3.72 (s, total 3H), 5.22 and 5.29 (s, total 2H), 6.98 and 7.00 (s, total 2H), 7.52 (s, 1H).

To a solution of the above ester (240 mg, 0.89 mmol) in THF (3 mL) at 0° C. was added LiAlH$_4$ (1.2 mL, 1.15 mmol) and the reaction mixture was stirred for 1 h. The mixture was quenched with H$_2$O (0.2 mL), 15% NaOH (0.2 mL), and H$_2$O (0.6 mL), and extracted with CH$_2$Cl$_2$ (4×20 mL). The combined organic layers were dried (MgSO$_4$), filtered, and concentrated to afford a pale yellow oil. Purification by flash column chromatography on silica gel using 2% CH$_3$OH/CH$_2$Cl$_2$ afforded 2-[1-(2-trimethylsilanyl-ethoxymethyl)-1H-imidazol-4-yl]-ethanol as a pale yellow oil (154 mg, 71%). $^1$H NMR (CDCl$_3$) δ 0.88 (td, 2H, J=7.5, 3.0 Hz), 2.78 and 2.87 (t, total 2H, J=6.0 Hz), 3.45 (td, 2H, J=7.5, 3.0 Hz), 3.80-3.88 (m, 2H), 5.19 and 5.24 (s, total 2H), 6.82 and 6.84 (s, 1H), 7.46 and 7.47 (s, 1H).

To a solution of the above alcohol (152 mg, 0.63 mmol) in CH$_2$Cl$_2$ (5 mL) at −78° C. was added Et$_3$N (0.18 mL, 1.26 mmol) and MsCl (0.07 mL, 0.94 mmol) according to General Procedure F. No further purification was attempted before proceeding onto the next step.

A solution of the above mesylate (190 mg, 0.59 mmol), meso-4-(3,3'-dimethyl-3',4',5',6'-tetrahydro-2'H-[2,2';6',2"]terpyridin-1'-yl)-butylamine (132 mg, 0.49 mmol), N,N,-diisoproylethylamine (0.13 mL, 0.74 mmol), and KI (9 mg, 0.05 mmol) in DMF (5 mL) according to General Procedure A. Purification by radial chromatography on silica gel(2 mm plate; using CH$_2$Cl$_2$/CH$_3$OH/NH$_4$OH; 50:1:1→25:1:1) afforded the product as a yellow oil (50 mg, 20%).

A solution of the above amine (58 mg, 0.12 mmol) in 6N HCl (4 mL) was stirred at 60° C. After 3 h, the reaction mixture was cooled and quenched with K$_2$CO$_3$ (s) to pH=9. The mixture was extracted with CH$_2$Cl$_2$ (4×20 mL). The combined organic layers were dried (MgSO$_4$), filtered, and concentrated to afford a pale yellow oil. Purification by radial chromatography on silica gel (1 mm plate; using CH$_2$Cl$_2$/CH$_3$OH/NH$_4$OH; 50:1:1→25:1:1→10:1:1) afforded the product as a pale yellow oil (38 mg, 88%). $^1$H NMR (CDCl$_3$) δ 1.60-1.67 (m, 2H), 1.93-1.97 (m, 2H), 2.06-2.14 (m, 2H), 2.40 (s, 6H), 2.50 9t, 2H, J=6.0 Hz), 2.86 (br s, 2H), 3.92 (d, 2H, J=6.0 Hz), 6.13 (s, 1H), 7.02 (t, 2H, J=6.0 Hz), 7.37-7.40 (m, 3H), 8.37 (d, 2H, J=6.0 Hz).

To a solution of the above amine (38 mg, 0.11 mmol) in HOAc (2 mL) was added HBr saturated HOAc (2 mL) according to General Procedure B. After drying in vacuo overnight, COMPOUND 56 was isolated as a yellow solid (49 mg). $^1$H NMR (D$_2$O) δ 1.54-1.58 (m, 2H), 1.70-1.83 (m, 1H), 1.93-1.96 (m, 1H), 2.19 (d, 2H, J=13.5 Hz), 2.60 (s, 6H), 2.63-2.65 (m, 2H), 2.77-2.82 (m, 2H), 4.73-4.74 (m, 2H), 6.92 (s, 1H), 7.91 (dd, 2H, J=8.0, 6.0 Hz), 8.43 (d, 2H, J=3.3 Hz), 8.46 (s, 1H), 8.69 (d, 2H, 94=5.7 Hz). $^{13}$C NMR (D$_2$O) δ 17.13, 18.51, 22.32, 32.57, 50.80, 57.70, 115.85, 126.22, 130.71, 133.69, 137.13, 140.04, 149.78, 154.01. ES-MS m/z 362 [M+H]+. Anal. Calcd. for C$_{22}$H$_{27}$N$_5$.3.3HBr.2.6H$_2$O.0.3C$_4$H$_{10}$O: C, 39.95; H, 5.56; N, 10.04; Br, 37.80. Found: C, 39.95; H, 5.46; N, 9.96; Br, 37.85.

EXAMPLE 57

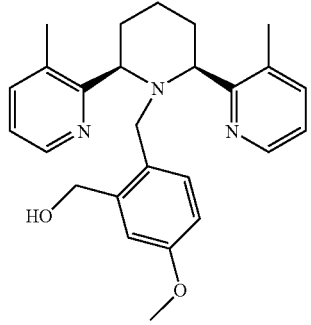

Compound 57: [2-meso-(3,3"-Dimethyl-3',4',5',6'-tetrahydro-2'H-[2,2';6',2"]terpyridin-1'-ylmethyl)-5-methoxy-phenyl]-methanol A solution of 4-methyl-3-nitrophenol (1.92 g, 12.5 mmol) in acetone (60 mL) was treated with dimethyl sulfate (1.42 mL, 15.0 mmol) and K$_2$CO$_3$ (2.59 g, 18.8 mmol) for 18 hours. The solvent was removed under reduced pressure and the solids dissolved in H$_2$O (50 mL). The aqueous was then extracted with CH$_2$Cl$_2$ (3×50 mL) and the combined organics were dried (Na$_2$SO$_4$) and concentrated under reduced pressure. This gave, after column chromatographic purification with silica gel (20:1 hexanes/EtOAc) 4-methoxy-1-methyl-2-nitrobenzene as a light yellow liquid (1.91 g, 91%).

The above compound (1.91 g, 11.4 mmol) was dissolved in MeOH (15 mL) and 10% Pd/C (50% wet, 400 mg) was added. The reagents were then agitated under an atmosphere of hydrogen (30 psi) for 1.5 hours. The reaction mixture was filtered through celite and the solvent removed under reduced pressure. This afforded 5-methoxy-2-methyl-phenylamine as a brown liquid (1.57 g, 100%). $^1$H NMR (CDCl$_3$) δ 2.11 (s, 3H), 3.61 (br, 2H(NH$_2$)), 3.75 (s, 3H), 6.27 (s, 1H), 6.29 (d, 1H, J=7.8 Hz), 6.94 (d, 1H, J=7.8 Hz).

The amine from above (1.57 g, 11.4 mmol) was suspended in H$_2$O (3 mL) and concentrated HCl (3 mL). An additional 8 mL of H$_2$O was then added, and the temperature chilled to 0° C. A solution of NaNO$_2$ (0.87 g, 12.6 mmol) in H$_2$O (2 mL) was slowly added and the mixture stirred for 0.5 hour. The acid was then neutralized with K$_2$CO$_3$ (1.9 g, 3.8 mmol) and the mixture poured into a solution of sodium cyanate (1.35 g, 27.5 mmol) and copper (I) cyanide (1.23 g, 13.7 mmol) in H$_2$O (7.5 mL) stirring at 60° C. The temperature was increased to 110° C. and the reaction stirred for 1 hour. CH$_2$Cl$_2$ (50 mL) and brine (50 mL) were then added, and the organic phase separated. The aqueous phase was then extracted with CH$_2$Cl$_2$ (2×50 mL), and the combined organic phases were dried (Na$_2$SO$_4$) and concentrated under reduced pressure to give, after purification by column chromatography with silica gel (10:1 hexanes/EtOAc), 5-methoxy-2-methyl-benzonitrile as a brown liquid (0.93 g, 55%).

The compound above (0.93 g, 6.3 mmol) was dissolved in H$_2$O (12 mL) and concentrated H$_2$SO$_4$ (18 mL) at 160° C. After 4 hours, the solution was cooled and filtered through a medium glass-fritted funnel, washing the residue with Et$_2$O. The filtrate was then extracted with Et$_2$O (3×50 mL), dried (MgSO$_4$) and concentrated under reduced pressure to afford a black solid (0.47 g). This material was dissolved in anhydrous MeOH (10 mL) and c. H$_2$SO$_4$ (0.5 mL), heating to reflux and stirring for 16 hours. The solution was cooled to room temperature and partitioned between Et$_2$O (15 mL) and brine (10 mL). After separating, the organic phase was washed with brine (3×10 mL). The organic was then dried (MgSO$_4$), filtered, and concentrated under reduced pressure to afford, after column chromatography with silica gel (5:1 hexanes/EtOAc), 5-hydroxy-2-methyl-benzoic acid methyl ester as a pale brown solid (0.28 g, 27%). Note the methoxyl group had been lost. $^1$H NMR (CDCl$_3$) δ 2.51 (s, 3H), 3.89 (s, 3H), 4.94 (s, 1H(OH)), 6.91 (dd, 1H, J=1.5, 7.5 Hz), 7.12 (d, 1H, J=7.8 Hz), 7.41 (d, 1H, J=1.5 Hz).

A solution of the above ester (0.28 g, 1.7 mmol) in acetone (9 mL) was treated with dimethyl sulfate (0.19 mL, 2.0 mmol) and K$_2$CO$_3$ (0.35 g, 2.5 mmol) for 18 hours. The solvent was removed under reduced pressure and the solids dissolved in H$_2$O (5 mL). The aqueous was then extracted with CH$_2$Cl$_2$ (3×10 mL) and the combined organics were dried (Na$_2$SO$_4$) and concentrated under reduced pressure. This gave, after column chromatographic purification with silica gel (20:1 hexanes/EtOAc) 5-methoxy-2-methyl-benzoic acid methyl ester as a light yellow liquid (0.24 g, 80%).

To a solution of the above ester (0.24 g, 1.3 mmol) in CCl$_4$ (5 mL) was added N-bromosuccinimide (0.26 g, 1.5 mmol), and 1,1'-azobis(cyclohexanecarbonitrile) (64 mg, 0.26 mmol). The solution was stirred at reflux for 16 hours and then cooled to room temperature, filtered through a medium glass fritted funnel, and concentrated under reduced pressure. This gave, after column chromatography with silica gel (100:1 hexanes/EtOAc), 2-bromomethyl-5-methoxy-benzoic acid methyl ester as a colorless liquid. (0.24 g, 70%). $^1$H NMR (CDCl$_3$) δ 3.85 (s, 3H), 3.95 (s, 3H), 4.93 (s, 2H), 7.01 (dd, 1H, J=1.5, 7.5 Hz), 7.37 (d, 1H, J=7.5 Hz), 7.48 (d, 1H, J=1.5 Hz).

A solution of meso-3,3"-dimethyl-1',2',3',4',5',6'-hexahydro-[2,2';6',2"]terpyridine (185 mg, 0.69 mmol), 2-bromomethyl-5-methoxy-benzoic acid methyl ester (235 mg, 0.90 mmol), and KI (23 mg, 0.14 mmol) in anhydrous DMF (3.5 mL) was treated with DIPEA (0.24 mL, 1.4 mmol) and stirred at 60° C. for 16 hours. The mixture was then concentrated under reduced pressure and the residue dissolved in EtOAc (15 mL). The organic solution was washed with brine (5×10 mL), dried (MgSO$_4$), and concentrated under reduced pressure. This afforded, after purification by column chromatography with silica gel (2:0.5:97.5 MeOH/NH$_4$OH/CH$_2$Cl$_2$), meso-2-(3,3"-dimethyl-3',4',5',6'-tetrahydro-2'H-[2,2';6',2"]terpyridin-1'-ylmethyl)-5-methoxy-benzoic acid methyl ester as a light beige-colored solid (0.29 g, 93%).

The alkylated product from above (0.29 g, 0.65 mmol) was dissolved in THF (6 mL) and MeOH (6 mL), cooled to 0° C., and treated with solid LiBH$_4$ (0.16 g, 7.8 mmol). After vigorous bubbling subsided, the mixture was let warm to room temperature over 1 hour while stirring. The excess LiBH$_4$ was quenched with 1N NaOH solution (5 mL) plus brine (15 mL). The aqueous phase was then extracted with CH$_2$Cl$_2$ (3×20 mL), dried (Na$_2$SO$_4$), and concentrated under reduced pressure to give, after radial chromatographic purification on a silica gel plate (50:1:0.1 CH$_2$Cl$_2$/MeOH/NH$_4$OH), COMPOUND 57 as a fluffy white solid (77 mg, 29%). $^1$H NMR (CDCl$_3$) δ 1.64 (br d, 3H, J=10.8 Hz), 2.00 (br, 1H), 2.30 (m, 2H), 2.49 (s, 6H), 3.56 (s, 2H), 3.60 (s, 3H), 3.95 (br d, 2H, J=11.4 Hz), 4.30 (s, 2H), 6.18 (d, 1H, J=8.1 Hz), 6.50 (s, 1H), 6.62 (d, 1H, J=8.4 Hz), 6.86 (m, 2H), 7.25 (d, 2H, J=8.4 Hz), 8.25 (d, 2H, J=3.9 Hz). $^{13}$C NMR (CDCl$_3$) 19.14 (2C), 25.27, 30.23 (2C), 55.20 (2C), 62.76, 67.78 (2C), 112.24 (2C), 114.22, 121.67 (2C), 130.02, 130.72, 131.23, 138.07 (2C), 140.20, 146.54 (2C), 157.82, 160.00 (2C). ES-MS m/z 418 (M$^+$H). Anal. Calcd. for C$_{26}$H$_{31}$N$_3$O$_2$.0.1NH$_4$OH.1.0H$_2$O: C, 71.12; H, 7.69; N, 9.89. Found: C, 71.25; H, 7.41; N, 10.23.

EXAMPLE 58

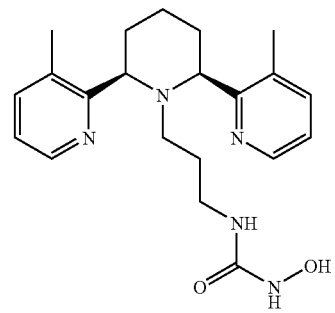

Compound 58: N-[3-meso-(3,3"-Dimethyl-3',4',5',6'-tetrahydro-2'H-[2,2';6',2"]terpyridin-1'-yl)-propyl]-N'-hydroxyurea A solution of meso-3,3"-dimethyl-1',2',3',4',5',6'-hexahydro-[2,2';6',2"]terpyridine (235 mg, 0.88 mmol), 2-(3-bromopropyl)-isoindole-1,3-dione (306 mg, 1.14 mmol), and KI (29 mg, 0.18 mmol) in anhydrous DMF (4.0 mL) was treated with DIPEA (0.31 mL, 1.8 mmol) and stirred at 60° C. for 16 hours. The mixture was then concentrated under reduced pressure and the residue dissolved in EtOAc (15 mL). The organic solution was washed with brine (5×10 mL), dried (MgSO$_4$), and concentrated under reduced pressure. This afforded, after purification by column chromatography with silica gel (20:1:0.2 CH$_2$Cl$_2$/MeOH/NH$_4$OH), 2-[3-meso-3,3"-dimethyl-3',4',5',6'-tetrahydro-2'H-[2,2';6',2"]terpyridin-1'-yl)-propyl]-isoindole-1,3-dione as a pale yellow solid (0.40 g, 100%). $^1$H NMR (CDCl$_3$) δ 0.95 (br, 2H), 1.58 (m, 2H), 1.86 (m, 1H), 2.07 (m, 1H), 2.32 (br, 2H), 2.50 (s, 8H), 2.90 (br, 2H), 4.06 (d, 2H), 6.89 (m, 2H), 7.26 (br, 2H), 7.70 (m, 4H), 8.27 (br, 2H).

A solution of the above compound (400 mg, 0.88 mmol) in EtOH (9 mL) was treated with hydrazine monohydrate (0.48 mL, 8.8 mmol) and stirred at room temperature for 16 hours. CH$_2$Cl$_2$ (10 mL) was added and the white mixture filtered to remove the solids. The filtrate was then concentrated under reduced pressure and dried in vacuo. This afforded, after radial chromatography with silica gel (10:1:0.1 CH$_2$Cl$_2$/CH$_3$OH/NH$_4$OH), 3-meso-(3,3"-dimethyl-3',4',5',6'-tetrahydro-2'H-[2,2';6',2"]terpyridin-1'-yl)-propylamine as a pale yellow solid (233 mg, 82%).

A solution of the above compound (233 mg, 0.71 mmol) and 1,1-carbonyldiimidazole (115 mg, 0.71 mmol) in THF (7 mL) was stirred for 30 minutes at room temperature. The solvent was then removed under reduced pressure and the residue dissolved in DMF (3.5 mL). The solution was then treated with NH$_2$OH.H$_2$O (200 mg, 2.8 mmol) and DIPEA (0.62 mL, 3.5 mmol) and stirred at room temperature for 18 hours. The reaction was then partitioned between CH$_2$Cl$_2$ (15 mL) and brine (10 mL) and separated. The organic phase was then washed several times with brine (4×10 mL) and the organic phase dried (Na$_2$SO$_4$) and concentrated under reduced pressure to afford, after column chromatography with silica gel (50:1:0.1 CH$_2$Cl$_2$/MeOH/NH$_4$OH), COMPOUND 58 as a white solid (81 mg, 30%). $^1$H NMR (CDCl$_3$) δ 1.55 (m, 1H), 1.67 (d, 2H, J=11.7 Hz), 1.94 (m, 1H), 2.06 (q, 2H, J=10.5 Hz), 2.35 (br, 2H), 2.44 (s, 6H), 2.60 (br d, 2H, J=12.0 Hz), 6.94 (br, 1H), 7.10 (m, 2H), 7.44 (d, 2H, J=7.8 Hz), 7.70 (br, 1H), 8.48 (br, 2H), 10.14 (br, 1H). $^{13}$C NMR (CDCl$_3$) δ 19.01 (2C), 25.03, 26.34, 32.12 (2C), 38.23, 51.04, 64.37 (2C), 122.09 (2C), 130.95 (2C), 138.84 (2C), 146.89 (2C), 160.05 (2C), 161.86. ES-MS m/z 384 (M$^+$H). Anal. Calcd. for C$_{21}$H$_{29}$N$_5$O$_2$.0.4CH$_2$Cl$_2$: C, 61.57; H, 7.19; N, 16.78. Found: C, 61.23; H, 7.35; N, 16.43.

succinimide (0.27 g, 1.5 mmol), and 1,1'-azobis(cyclohexanecarbonitrile) (68 mg, 0.28 mmol). The solution was stirred at reflux for 16 hours and then cooled to room temperature and concentrated under reduced pressure. This gave, after column chromatography with silica gel (60:1 hexanes/EtOAc), 4-bromomomethyl-3-methoxy-benzoic acid methyl ester plus a minor impurity (~15%) as a colorless liquid. (0.39 g, excess). $^1$H NMR (CDCl$_3$) δ 3.92 (s, 3H), 3.95 (s, 3H), 4.55 (s, 2H), 7.39 (d, 1H, J=7.5 Hz), 7.55 (s, 1H), 7.61 (d, 1H, J=7.5 Hz).

A solution of meso-3,3"-dimethyl-1',2',3',4',5',6'-hexahydro-[2,2';6',2"]terpyridine (0.25 g, 0.93 mmol), the above methyl ester (0.36 g, 1.4 mmol), and KI (31 mg, 0.20 mmol) in anhydrous DMF (4.7 mL) was treated with DIPEA (0.32 mL, 1.9 mmol) and stirred at 60° C. for 16 hours. The mixture was then concentrated under reduced pressure and the residue dissolved in EtOAc (15 mL). The organic solution was washed with brine (5×10 mL), dried (MgSO$_4$), and concentrated under reduced pressure. This afforded, after purification by column chromatography with silica gel (saturated NH$_3$/Et$_2$O), 4-meso-(3,3"-dimethyl-3',4',5',6'-tetrahydro-2'H-[2,2';6',2"]terpyridin-1'-ylmethyl)-3-methoxy-benzoic acid methyl ester as a colorless solid (0.26 g, 63%).

The alkylated product from above (0.25 g, 0.56 mmol) was dissolved in THF (6 mL) and treated with solid LiBH$_4$ (0.20 g, 7.8 mmol). The mixture was then heated to 75° C. for 16 hours. The excess LiBH$_4$ was quenched with 1N NaOH solution (4 mL) plus brine (15 mL). The aqueous phase was then extracted with CH$_2$Cl$_2$ (3×20 mL), dried (Na$_2$SO$_4$), and concentrated under reduced pressure to give, after column chromatographic purification on a silica gel plate (20:1:0.1 CH$_2$Cl$_2$/MeOH/NH$_4$OH), COMPOUND 59 white solid (200 mg, 87%). $^1$H NMR (CDCl$_3$) δ 1.49 (m, 1H), 1.66 (m, 3H), 1.98 (m, 1H), 2.17 (m, 2H), 2.39 (s, 6H), 3.46 (s, 3H), 3.57 (s, 2H), 4.08 (br d, 2H, J=11.4 Hz), 4.46 (s, 2H), 6.39 (s, 1H), 6.54 (d, 1H, J=7.2 Hz), 6.89 (m, 2H), 6.99 (d, 1H, J=7.2 Hz), 7.22 (d, 2H, J=7.5 Hz), 8.34 (d, 2H, J=3.9 Hz). $^{13}$C NMR (CDCl$_3$) δ 18.84 (2C), 25.12, 30.09 (2C), 46.91 (2C), 54.53, 65.18 (2C), 107.56, 117.77, 121.41 (2C), 127.30, 131.05, 131.59 (2C), 137.66 (2C), 139.80, 146.17 (2C), 156.52, 160.44 (2C). ES-MS m/z 418 (M$^+$H). Anal. Calcd. for C$_{26}$H$_{31}$N$_3$O$_2$.0.4CH$_2$Cl$_2$: C, 70.23; H, 7.10; N, 9.31. Found: C, 70.46; H, 7.33; N, 9.34.

EXAMPLE 59

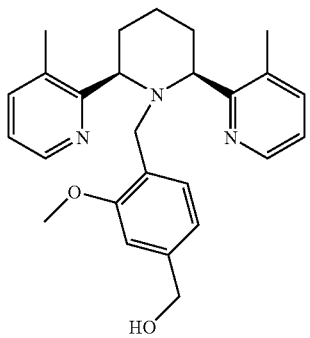

Compound 59: [4-meso-(3,3"-Dimethyl-3',4',5',6'-tetrahydro-2'H-[22';6',2"]terpyridin-1'-ylmethyl)-3-methoxy-phenyl]-methanol To a solution of 3-methoxy-4-methyl-benzoic acid methyl ester (0.25 g, 1.4 mmol) in CCl$_4$ (5 mL) was added N-bromo-

EXAMPLE 60

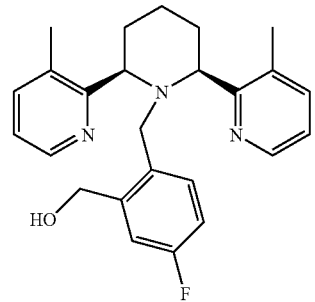

Compound 60: [2-meso-(3,3"-Dimethyl-3',4',5',6'-tetrahydro-2'H-[2,2';6',2"]terpyridin-1'-ylmethyl)-5-fluoro-phenyl]-methanol 5-Fluoro-2-methyl-benzoic acid (0.29 g, 1.9 mmol) was dissolved in anhydrous MeOH (7 mL) and c. H$_2$SO$_4$ (0.12 mL, 2.3 mmol) was added, heating to reflux for 16 hours. The solution was cooled to room temperature and partitioned between EtOAc (15 mL) and brine (10 mL). After separating, the aqueous phase was extracted with EtOAc (2×10 mL), dried (MgSO$_4$), filtered, and concentrated under reduced pressure to afford 5-fluoro-2-methyl-benzoic acid methyl ester as a pale brown liquid. (0.25 g, 78%).

To a solution of the above ester (0.25 g, 1.5 mmol) in CCl$_4$ (5 mL) was added N-bromosuccinimide (0.29 g, 1.6 mmol), and 1,1'-azobis(cyclohexanecarbonitrile) (73 mg, 0.30 mmol). The solution was stirred at reflux for 16 hours and then cooled to room temperature and concentrated under reduced pressure. This gave, after column chromatographic purification with silica gel (50:1 hexanes/EtOAc), 2-bromomethyl-5-fluoro-benzoic acid methyl ester as a pale yellow liquid. (0.23 g, 62%). $^1$H NMR (CDCl$_3$) δ 3.94 (s, 3H), 4.93 (s, 2H), 7.20 (dt, 1H, J=7.5, 1.5 Hz), 7.45 (m, 1H), 7.67 (dd, 1H, J=7.5, 1.5 Hz).

A solution of meso-3,3"-dimethyl-1',2',3',4',5',6'-hexahydro-[2,2';6',2"]terpyridine (190 mg, 0.72 mmol), the above bromide (235 mg, 0.90 mmol), and KI (23 mg, 0.14 mmol) in anhydrous DMF (3.5 mL) was treated with DIPEA (0.24 mL, 1.4 mmol) and stirred at 60° C. for 16 hours. The mixture was then concentrated under reduced pressure and the residue dissolved in EtOAc (15 mL). The organic solution was washed with brine (5×10 mL), dried (MgSO$_4$), and concentrated under reduced pressure. This afforded, after purification by column chromatography with silica gel (50:1:0.1 CH$_2$Cl$_2$/MeOH/NH$_4$OH), 2-meso-(3,3"-dimethyl-3',4',5',6'-tetrahydro-2'H-[2,2';6',2"]terpyridin-1'-ylmethyl)-5-fluorobenzoic acid methyl ester as a white solid. (0.28 g, 90%).

The alkylated product from above (0.28 g, 0.65 mmol) was dissolved in THF (6 mL) and treated with solid LiBH$_4$ (0.17 g, 7.7 mmol). The mixture was then heated to 75° C. for 16 hours. The excess LiBH$_4$ was quenched with 1N NaOH solution (4 mL) plus brine (15 mL). The aqueous phase was then extracted with CH$_2$Cl$_2$ (3×20 mL), dried (Na$_2$SO$_4$), and concentrated under reduced pressure to give COMPOUND 60 as a white solid (239 mg, 92%). $^1$H NMR (CDCl$_3$) δ 1.66 (m, 3H), 2.05 (m, 1H), 2.31 (m, 2H), 2.50 (s, 6H), 3.59 (s, 2H), 4.00 (br d, 2H, J=10.8 Hz), 4.34 (s, 2H), 5.10 (br, 1H(OR)), 6.32 (dt, 1H, J=8.4, 2.4 Hz), 6.63 (dd, 1H, J=9.6, 2.7 Hz), 6.69 (t, 1H, J=7.2 Hz), 6.88 (m, 2H), 7.25 (d, 2H, J=6.0 Hz), 8.25 (d, 2H, J=3.9 Hz). $^{13}$C NMR (CDCl$_3$) δ 19.06 (2C), 25.22, 29.76 (2C), 54.06, 62.13, 67.44 (2C), 112.57 (d, 1C, J=83 Hz), 115.25 (d, 1C, J=84 Hz), 121.84 (2C), 130.24, 131.31 (2C), 134.00, 138.11 (2C), 141.13, 146.51 (2C), 159.71 (2C), 161.08 (d, 1C, J=971 Hz). ES-MS m/z 406 (M$^+$H). Anal. Calcd. for C$_{25}$H$_{28}$N$_3$OF.0.2CH$_2$Cl$_2$: C, 71.64; H, 6.77; N, 9.95. Found: C, 71.45; H, 6.85; N, 9.95.

EXAMPLE 61

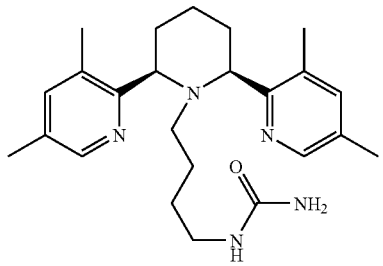

Compound 61: [4-meso-(3,5,3",5"-Tetramethyl-3',4',5',6'-tetrahydro-2'H-[2,2';6',2"]terpyridin-1'-yl)-butyl]-urea (HBr Salt)

Using General Procedure A, a solution of the above compound (356 mg, 1.2 mmol) in DMF (6 mL) was added 2-(4-bromo-butyl)-isoindole-1,3-dione (442 mg, 1.6 mmol), KI (40 mg, 0.24 mmol), and DIPEA (0.42 mL, 2.4 mmol) and the mixture stirred at 60° C. overnight. This gave, after work-up and column chromatography with silica gel (20:1:0.2 CH$_2$Cl$_2$/MeOH/NH$_4$OH), 2-[4-meso-(3,5,3",5"-tetramethyl-3',4',5',6'-tetrahydro-2'H-[2,2';6',2"]terpyridine-1'-yl)-butyl]-isoindole-1,3-dione (515 mg, 86%).

A solution of the above compound (515 mg, 1.04 mmol) in EtOH (10 mL) was treated with hydrazine monohydrate (0.50 mL, 10.4 mmol) and stirred at room temperature for 16 hours. CH$_2$Cl$_2$ (10 mL) was added and the white mixture filtered to remove the solids. The filtrate was then concentrated under reduced pressure and dried in vacuo. This afforded, after column chromatography with silica gel (20:1:0.1 CH$_2$Cl$_2$/CH$_3$OH/NH$_4$OH), 4-meso-(3,5,3",5"-tetramethyl-3',4',5',6'-tetrahydro-2'H-[2,2';6',2"]terpyridine-1'-yl)-butylamine as a sticky white solid (0.25 g, 66%). $^1$H NMR (CDCl$_3$) δ 0.80 (br, 3H), 1.54 (m, 1H), 1.62 (d, 2H, J=12.0 Hz), 1.97 (m, 3H), 2.16 (t, 2H, J=7.5 Hz), 2.27 (s, 6H), 2.40 (br, 1H), 2.47 (s, 6H), 2.60 (br, 2H), 3.93 (br, 2H, J=9.0 Hz), 7.24 (s, 2H), 8.31 (s, 2H).

The amine from above was dissolved in isopropanol (2.3 mL) and treated with trimethylsilylisocyanate (64 µL, 0.47 mmol) at room temperature for 16 hours. The solution was then concentrated under reduced pressure and the crude material purified by column chromatography with silica gel (40:1 THF-Et$_2$O/NH$_4$OH) to afford [4-meso-(3,5,3",5"-tetramethyl-3',4',5',6'-tetrahydro-2'H-[2,2';6',2"]terpyridin-1'-yl)-butyl]-urea as a colorless oil (46 mg, 33%).

Using General Procedure B: The above material (45 mg, 0.11 mmol) was converted to the HBr salt to provide COMPOUND 61 (44 mg) as a white solid. $^1$H NMR (D$_2$O) δ 1.02 (qt, 2H, J=6.9 Hz), 1.13 (qt, 2H, J=6.6 Hz), 1.46 (m, 2H), 1.65 (m, 1H), 1.90 (m, 1H), 2.07 (d, 2H, J=12.6 Hz), 2.16 (br, 2H), 2.46 (s, 6H), 2.52 (s, 6H), 2.74 (m, 2H), 4.47 (d, 2H, J=9.9 Hz), 8.23 (s, 2H), 8.46 (s, 2H). $^{13}$C NMR (D$_2$O) δ 16.91 (2C), 17.57 (2C), 20.26, 22.48, 26.85, 32.71 (2C), 39.11, 53.26, 58.16 (2C), 136.00 (2C), 137.38 (2C), 138.98 (2C), 150.01 (2C), 152.09 (2C), 162.21. ES-MS m/z 410 (M$^+$H). Anal. Calcd. for C$_{24}$H$_{35}$N$_5$O.3.1HBr.5.0H$_2$O: C, 38.41; H, 6.46; N, 9.33; Br, 33.01. Found: C, 38.29; H, 6.30; N, 9.10; Br, 33.17.

EXAMPLE 62

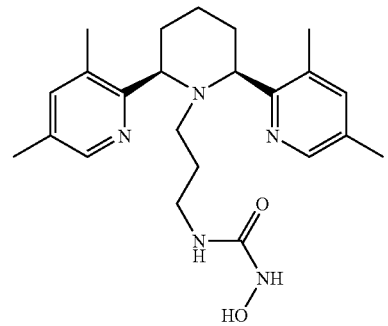

Compound 62: N-[3-meso-(3,5,3",5"-tetramethyl-3',4',5' 6'-tetrahydro-2'H-[22';6',2"]terpyridine-1'-yl)-propyl]-N'-hydroxyurea Using General Procedure A, a solution of meso-3,5,3",5"-tetramethyl-3',4',5',6'-tetrahydro-2'H-[2,2';6',2"]terpyridine (172 mg, 0.58 mmol) in DMF (3 mL) was added 2-(3-bromopropyl)-isoindole-1,3-dione (203 mg, 0.76 mmol), KI (19 mg, 0.12 mmol), and DIPEA (0.20 mL, 1.2 mmol) and the mixture stirred at 60° C. overnight. This gave, after work-up and column chromatography with silica gel (20:1:0.2 $CH_2Cl_2$/MeOH/$NH_4OH$), 2-[3-meso-(3,5,3",5"-tetramethyl-3',4',5',6'-tetrahydro-2'H-[2,2';6',2"]terpyridine-1'-yl)-propyl]-isoindole-1,3-dione (259 mg, 92%). $^1$H NMR ($CDCl_3$) δ 1.16 (br, 1H), 1.60 (br, 3H), 2.00 (m, 3H), 2.15 (s, 6H), 2.24 (m, 2H), 2.38 (s, 6H), 2.57 (br, 1H), 3.03 (br, 2H), 3.96 (br, 2H), 7.02 (s, 2H), 7.70 (m, 4H), 8.18 (s, 2H).

A solution of the above compound (259 mg, 0.54 mmol) in EtOH (5.4 mL) was treated with hydrazine monohydrate (0.26 mL, 5.4 mmol) and stirred at room temperature for 16 hours. $CH_2Cl_2$ (10 mL) was added and the white mixture filtered to remove the solids. The filtrate was then concentrated under reduced pressure and dried in vacuo. This afforded, after column chromatography with silica gel (20:1:0.1 $CH_2Cl_2$/$CH_3OH$/$NH_4OH$), 3-meso-(3,5,3",5"-tetramethyl-3',4',5',6'-tetrahydro-2'H-[2,2';6',2"]terpyridine-1'-yl) propylamine as a sticky white solid (0.15 g, 78%).

A solution of the above amine (146 mg, 0.41 mmol) and 1,1-carbonyldiimidazole (67 mg, 0.41 mmol) in THF (4.0 mL) was stirred for 45 minutes at room temperature. The solvent was then removed under reduced pressure and the residue dissolved in DMF (2 mL). The solution was then treated with $NH_2OH.H_2O$ (115 mg, 1.6 mmol) and DIPEA (0.36 mL, 2.1 mmol) and stirred at room temperature for 18 hours. The reaction was partitioned between $CH_2Cl_2$ (15 mL) and brine (10 mL) and separated. The organic phase was then washed several times with brine (4×10 mL) and the organic phase dried ($Na_2SO_4$) and concentrated under reduced pressure to afford, after column chromatography with silica gel (20:1:0.1 $CH_2Cl_2$:MeOH/$NH_4OH$), COMPOUND 62 as a white solid (84 mg, 49%). $^1$H NMR ($CDCl_3$) δ 0.44 (br, 2H), 1.60 (br, 3H), 1.95 (br, 3H), 2.27 (s, 6H), 2.39 (s, 6H), 2.50 (br, 2H), 2.60 (br, 2H), 3.72 (br, 2H), 6.86 (br, 1H), 7.26 (s, 2H), 7.77 (br, 1H), 8.30 (s, 2H), 10.41 (br, 1H). $^{13}$C NMR ($CDCl_3$) δ 18.31 (2C), 19.31 (2C), 25.37, 26.80, 32.96 (2C), 38.86, 52.34, 64.61 (2C), 130.57 (2C), 131.90 (2C), 139.85 (2C), 147.68 (2C), 157.58 (2C), 162.29. ES-MS m/z 412 (M$^+$H). Anal. Calcd. for $C_{23}H_{33}N_5O_2.0.3H_2O$: C, 66.26; H, 8.12; N, 16.80. Found: C, 66.30; H, 7.96; N, 16.90.

EXAMPLE 63

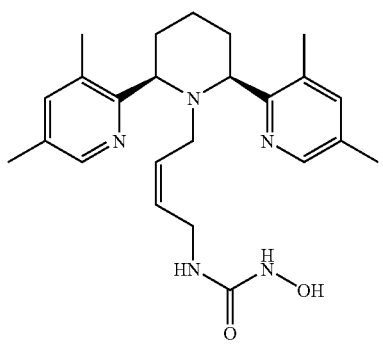

Compound 63: N-[4-meso-(3,5,3",5"-Tetramethyl-3',4',5',6'-tetrahydro-2'H-[2,2';6',2"]terpyridine-1'-yl)-cis-but-2-enyl]-N'-hydroxyurea Following General Procedure A, a solution of meso-3,5,3",5"-tetramethyl-3',4',5',6'-tetrahydro-2'H-[2,2';6',2"]terpyridine (150 mg, 0.51 mmol) in $CH_3CN$ (2.5 mL) was added cis-(4-chloro-but-2-enyl)-carbamic acid tert-butyl ester (115 mg, 0.56 mmol), KI (8 mg, 0.05 mmol), and DIPEA (0.13 mL, 0.76 mmol) and the mixture stirred at 60° C. overnight. This gave, after work-up and column chromatography with silica gel (50:1:0.1 $CH_2Cl_2$/MeOH/$NH_4OH$), [4-meso-(3,5,3",5"-tetramethyl-3',4',5',6'-tetrahydro-2'H-[2,2';6',2"]terpyridin-1'-yl)-cis-but-2-enyl]-carbamic acid tert-butyl ester (213 mg, 90%).

A solution of the above compound (0.213 g, 0.46 mmol) in $CH_2Cl_2$ (1.5 mL) was treated with TFA (1.0 mL) for 1 hour. 15% aqueous NaOH solution (~3 mL) was then added slowly until the acid content was neutralized and the solution became basic (pH=8 to 12). The phases were then separated and the aqueous extracted with $CH_2Cl_2$ (2×10 mL). The combined organics were then dried ($Na_2SO_4$) and concentrated under reduced pressure to give 4-meso-(3,5,3",5"-tetramethyl-3',4',5',6'-tetrahydro-2'H-[2,2';6',2"]terpyridin-1'-yl)-cis-but-2-enylamine (184 mg, excess) which was used immediately in the next reaction.

A solution of the above amine and 1,1-carbonyldiimidazole (80 mg, 0.501 mmol) in THF (5.0 mL) was stirred for 45 minutes at room temperature. The solvent was then removed under reduced pressure and the residue dissolved in DMF (2 mL). The solution was then treated with $NH_2OH.H_2O$ (137 mg, 2.0 mmol) and DIPEA (0.43 mL, 2.5 mmol) and stirred at room temperature for 18 hours. The reaction was partitioned between $CH_2Cl_2$ (15 mL) and brine (10 mL) and separated. The organic phase was then washed several times with brine (4×10 mL) and the organic phase dried ($Na_2SO_4$) and concentrated under reduced pressure to afford, after column chromatography with silica gel (20:1:0.1 $CH_2Cl_2$:MeOH/$NH_4OH$), COMPOUND 63 as a white solid (51 mg, 24%). $^1$H NMR ($CDCl_3$) δ 1.54 (br, 1H), 1.64 (br, 2H), 1.92 (br, 3H), 2.23 (s, 6H), 2.37 (s, 6H), 2.96 (br, 2H), 3.03 (br, 2H), 5.30 (br, 2H), 5.73 (br, 1H), 7.26 (s, 2H), 8.27 (br, 2H), 10.44 (br, 1H). $^{13}$C NMR ($CDCl_3$) δ 17.85 (2C), 18.70 (2C), 25.15, 32.90 (2C), 35.83, 46.73, 61.43 (2C), 126.95, 128.48, 130.04, 130.35 (2C), 139.49 (3C), 147.18 (2C), 157.10 (2C), 161.56. ES-MS m/z 424 (M$^+$H). Anal. Calcd. for $C_{24}H_{33}N_5O_2.0.5CH_2Cl_2$: C, 63.14; H, 7.35; N, 15.03. Found: C, 63.42; H, 7.56; N, 15.01.

EXAMPLE 64

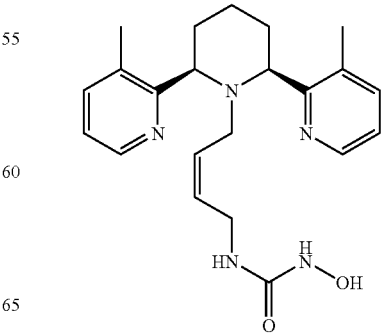

Compound 64: N-[4-meso-(3,3"-Dimethyl-3',4',5',6'-tetrahydro-2'H-[2,2';6',2"]terpyridine-1'-yl)-cis-but-2-enyl]-N'-hydroxyurea Following General Procedure A, a solution of meso-3,3"-dimethyl-3',4',5',6'-tetrahydro-2'H-[2,2';6',2"]terpyridine (133 mg, 0.50 mmol) in CH$_3$CN (5 mL) was added cis-(4-chloro-but-2-enyl)-carbamic acid tert-butyl ester (113 mg, 0.55 mmol), KI (8 mg, 0.05 mmol), and DIPEA (0.13 mL, 0.76 mmol) and the mixture stirred at 60° C. overnight. This gave, after work-up and column chromatography with silica gel (20:1:0.1 CH$_2$Cl$_2$/MeOH/NH$_4$OH), [4-meso-(3,3"-dimethyl-3',4',5',6'-tetrahydro-2'H-[2,2';6',2"]terpyridin-1'-yl)-cis-but-2-enyl]-carbamic acid tert-butyl ester (202 mg, 93%). $^1$H NMR (CDCl$_3$) δ 1.39 (s, 9H), 1.60 (m, 1H), 1.73 (br, 2H), 2.00 (br, 3H), 2.45 (br, 5H), 2.57 (s, 3H), 2.68 (br, 1H), 2.89 (br, 2H), 4.02 (br, 2H), 5.17 (br, 1H), 5.42 (br, 1H), 7.08 (m, 2H), 7.41 (m, 2H), 8.47 (br, 2H).

A solution of the above compound (0.20 g, 0.46 mmol) in CH$_2$Cl$_2$ (1.5 mL) was treated with TFA (1.0 mL) for 1 hour. 15% aqueous NaOH solution (~3 mL) was then added slowly until the acid content was neutralized and the solution became basic (pH=8 to 12). The phases were then separated and the aqueous extracted with CH$_2$Cl$_2$ (2×10 mL). The combined organics were then dried (Na$_2$SO$_4$) and concentrated under reduced pressure to give 4-meso-(3,3"-dimethyl-3',4', 5',6'-tetrahydro-2'H-[2,2';6',2"]terpyridin-1'-yl)-cis-but-2-enylamine (151 mg, 98%) which was used immediately in the next reaction.

A solution of the above amine and 1,1-carbonyldiimidazole (148 mg, 0.44 mmol) in THF (4.5 mL) was stirred for 45 minutes at room temperature. The solvent was then removed under reduced pressure and the residue dissolved in DMF (2 mL). The solution was then treated with NH$_2$OH.H$_2$O (122 mg, 1.8 mmol) and DIPEA (0.38 mL, 2.2 mmol) and stirred at room temperature for 18 hours. The reaction was partitioned between CH$_2$Cl$_2$ (15 mL) and brine (10 mL) and separated. The organic phase was then washed several times with brine (4×10 mL) and the organic phase dried (Na$_2$SO$_4$) and concentrated under reduced pressure to afford, after column chromatography with silica gel (20:1:0.1 CH$_2$Cl$_2$:MeOH/NH$_4$OH), COMPOUND 64 as a white solid (117 mg, 67%). $^1$H NMR (CDCl$_3$) δ 1.53 (m, 1H), 1.67 (m, 2H), 1.92 (m, 3H), 2.40 (s, 6H), 2.88 (br, 2H), 2.98 (br, 2H), 4.02 (br, 2H), 5.28 (br, 1H), 5.40 (m, 1H), 5.62 (br, 1H), 7.05 (m, 2H), 7.46 (d, 2H, J=7.0 Hz), 8.44 (d, 2H, J=3.5 Hz). $^{13}$C NMR (CDCl$_3$) δ 19.24 (2C), 25.46, 33.15 (2C), 36.03, 47.26, 62.35 (2C), 122.41 (2C), 127.25, 129.05, 131.21 (2C), 139.36 (2C), 147.16 (2C), 160.31 (2C), 161.98. ES-MS m/z 396 (M$^+$H). Anal. Calcd. for C$_{22}$H$_{29}$N$_5$O$_2$.1.5H$_2$O.0.2C$_3$H$_4$N$_2$: C, 62.24; H, 7.58; N, 17.34. Found: C, 62.34; H, 7.59; N, 17.31.

EXAMPLE 65

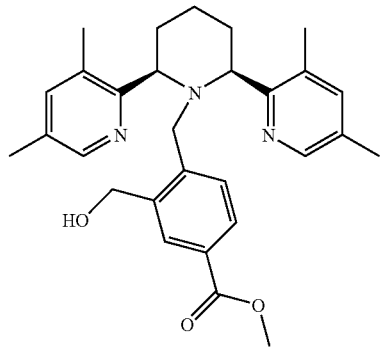

Compound 65: 3-Hydroxymethyl-4-meso-(3,5,3",5"-tetramethyl-3',4',5',6'-tetrahydro-2'H-[2,2';6',2"]terpyridin-1'-ylmethyl)-benzoic acid methyl ester A solution of meso-3,5,3",5"-tetramethyl-1',2',3',4',5',6'-hexahydro-[2,2';6',2"]terpyridine (0.44 g, 1.5 mmol), 2-bromomethyl-5-cyano-benzoic acid methyl ester (0.49 g, 1.9 mmol), and KI (49 mg, 0.30 mmol) in anhydrous DMF (7.5 mL) was treated with DIPEA (0.52 mL, 3.0 mmol) and stirred at 60° C. for 16 hours. The mixture was then concentrated under reduced pressure and the residue dissolved in EtOAc (20 mL). The organic solution was washed with brine (5×15 mL), dried (MgSO$_4$), and concentrated under reduced pressure. This afforded, after purification by column chromatography with silica gel (25:1 CH$_2$Cl$_2$/MeOH), 5-cyano-2-meso-(3,5,3",5"-tetramethyl-3',4',5',6'-tetrahydro-2'H-[2,2';6',2"]terpyridin-1'-ylmethyl)-benzoic acid methyl ester as a light beige-colored solid (0.60 g, 86%). $^1$H NMR (CDCl$_3$) δ 1.64 (br, 3H), 2.05 (br, 1H), 2.13 (s, 6H), 2.30 (br, 2H), 2.37 (s, 6H), 3.85 (s, 3H), 3.91 (s, 2H), 4.06 (d, 2H, J=12.0 Hz), 6.97 (s, 2H), 7.36 (d, 1H, J=7.5 Hz), 7.56 (s, 1H), 7.90 (d, 1H, J=6.0 Hz), 8.03 (s, 2H).

The alkylated product from above (0.60 g, 1.3 mmol) was dissolved in THF (15 mL) and MeOH (15 mL), cooled to 0° C., and treated with solid LiBH$_4$ (0.33 g, 15.4 mmol). After vigorous bubbling subsided, the mixture was let warm to room temperature over 1 hour while stirring. The excess LiBH$_4$ was quenched with 1N NaOH solution (5 mL) plus brine (25 mL). The aqueous phase was then extracted with CH$_2$Cl$_2$ (3×30 mL) and the combined organics dried (Na$_2$SO$_4$) and concentrated under reduced pressure to give, after column chromatographic purification on a silica gel plate (50:1:0.1 CH$_2$Cl$_2$/MeOH/NH$_4$OH), 3-hydroxymethyl-4-meso-(3,5,3",5"-tetramethyl-3',4',5',6'-tetrahydro-2'H-[2,2';6',2"]terpyridin-1'-ylmethyl)-benzonitrile as a fluffy white solid (0.45 g, 80%).

The compound from above (0.44 g, 1.0 mmol) was dissolved in MeOH (2.5 mL) and water (2.5 mL) and treated with NaOH pellets (0.40 g, 10 mmol) at 100° C. for 16 hours. The reaction was cooled to room temperature and 4N HCl added (~2 mL) until the solution pH=5. Brine (10 mL) was added and the aqueous extracted several times with CH$_2$Cl$_2$ (5×15 mL). The combined organics were dried (Na$_2$SO$_4$) and concentrated under reduced pressure to afford the desired 3-hydroxymethyl-4-meso-(3,5,3",5"-tetramethyl-3',4',5',6'-tetrahydro-2'H-[2,2';6',2"]terpyridin-1'-ylmethyl)-benzoic acid plus ~15% of inseparable amide side product (0.37 g, 86%).

The above mixture (0.37 g, 0.8 mmol) was then dissolved in MeOH (9 mL) and treated with c. H$_2$SO$_4$ (55 μL, 1.0 mmol) at 85° C. for 16 hours. The reaction was cooled to room temperature and 15% NaOH solution added (~1-2 mL) until the solution was basic pH=8-12. Brine (10 mL) was added and the aqueous extracted with $CH_2Cl_2$ (3×15 mL). The combined organics were dried ($Na_2SO_4$) and concentrated under reduced pressure to afford, after column chromatography with silica gel (50:1:0.1 $CH_2Cl_2$/MeOH/$NH_4OH$), COMPOUND 65 as a white solid (0.26 g, 69%). $^1H$ NMR ($CDCl_3$) δ 1.64 (br, 3H), 2.08 (s, 6H), 2.11 (br, 1H), 2.38 (m, 2H), 2.46 (s, 6H), 3.68 (br, 2H), 3.81 (s, 3H), 4.03 (d, 2H, J=11.1 Hz), 4.46 (s, 2H), 6.77 (d, 1H, J=7.5 Hz), 7.03 (s, 2H), 7.31 (d, 1H, J=7.5 Hz), 7.59 (s, 1H), 8.00 (s, 2H). $^{13}C$ NMR ($CDCl_3$) δ 17.66 (2C), 18.89 (2C), 25.42, 28.73 (2C), 51.80, 62.59 (2C), 66.69 (2C), 127.21, 127.46, 128.57 (2C), 130.13, 130.99 (2C), 131.42, 138.56, 138.72 (2C), 144.76, 146.76 (2C), 156.30 (2C), 167.06. ES-MS m/z 474 ($M^+H$). Anal. Calcd. for $C_{29}H_{35}N_3O_3.0.2CH_2Cl_2$: C, 71.49; H, 7.27; N, 8.57. Found: C, 71.76; H, 7.39; N, 8.52.

EXAMPLE 66

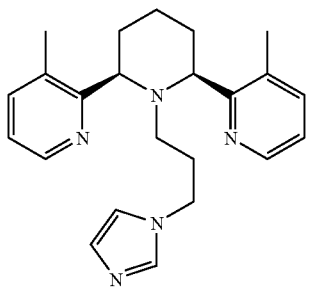

Compound 66: 1'-(2-imidazol-1-yl-ethyl)-3,3"-dimethyl-1',2',3',4',5',6'-hexahydro-[2,2';6',2"]terpyridine (HBr Salt)

To a solution of imidazole (1.33 g, 19.54 mmol) in THF (40 mL) was added NaH (60%, 0.94 g, 23.45 mmol) and 1,2-dibromoethane (5.1 mL, 58.61 mmol) and the reaction mixture was stirred overnight. Then the mixture was quenched with $H_2O$ (25 mL) and extracted with $CH_2Cl_2$ (2×30 mL). The combined organic layers were dried ($MgSO_4$), filtered, and concentrated to afford a pale yellow oil (1.31 g), which was used without any further purification.

A mixture of the above bromide (1.31 g, 7.48 mmol), meso-4-(3,3'-dimethyl-3',4',5',6'-tetrahydro-2'H-[2,2';6',2"]terpyridin-1'-yl)-butylamine (0.67 g, 2.49 mmol), DIPEA (0.65 mL, 3.74 mmol), and KI (41 mg, 0.25 mmol) in DMF (5 mL) were stirred according to General Procedure A. Purification by flash column chromatography on silica gel using MeOH/$NH_4OH$/$CH_2Cl_2$ (2:1:97), followed by purification by radial chromatography on silica gel (1 mm plate; using $CH_2Cl_2$,MeOH/$NH_4OH$; 50:1:1→25:1:1) afforded 1'-(2-imidazol-1-yl-ethyl)-3,3"-dimethyl-1',2',3',4',5',6'-hexahydro-[2,2';6',2']terpyridine as a yellow oil (38 mg, 1% (over two steps)). $^1H$ NMR ($CDCl_3$) δ 1.61-1.73 (m, 2H), 2.22-2.35 (m, 2H), 2.48 (s, 6H), 2.69 (s, 4H, J=9.0 Hz), 2.88 (s, 2H), 4.19 (d, 2H, J=12.0 Hz), 5.90 (s, 1H), 6.52 (s, 1H), 6.67 (s, 1H), 7.14 (dd, 2H, J=7.5, 4.8 Hz), 7.47 (dd, 2H, J=7.7, 0.6 Hz), 8.48 (d, 2H, J=3.9 Hz).

To a solution of the above amine (38 mg, 0.11 mmol) in HOAc (2 mL) was added a HBr saturated solution of HOAc (2 mL) according to General Procedure B. After drying in vacuo overnight, a sticky orange solid (60 mg) was isolated. $^1H$ NMR ($D_2O$) δ 1.52-1.64 (m, 2H), 1.71-1.84 (m, 1H), 1.97-2.02 (m, 1H), 2.20 (d, 2H, J=12.0 Hz), 2.61 (s, 6H), 2.89 (t, 2H, J=7.5 Hz), 4.21 (t, 2H, J=7.5 Hz), 4.71 (s, 2H), 7.06 (s, 1H), 7.34 (s, 1H), 7.95 (dd, 2H, J=7.8, 6.0 Hz), 8.47 (s, 1H), 8.50 (d, 2H, J=6.9 Hz), 8.71 (d, 2H, J=5.7 Hz). $^{13}C$ NMR ($D_2O$) δ 17.18, 22.15, 32.65, 44.27, 52.06, 58.56, 120.77, 121.79, 126.49, 135.07, 137.21, 140.37, 150.07, 153.40. ES-MS m/z 362 $[M^+H]^+$. Anal. Calcd. for $C_{22}H_{27}N_5.3.4HBr.3.2H_2O.0.5C_4H_{10}O$: C, 39.42; H, 5.76; N, 9.58; Br, 37.15. Found: C, 39.50; H, 5.70; N, 9.66; Br, 37.10.

EXAMPLE 67

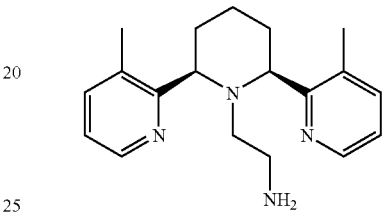

Compound 67: 2-(3,3"-Dimethyl-3',4',5',6'-tetrahydro-2'H-[2,2'°;6',2"]terpyridin-1'-yl)-ethylamine To a solution of the N-(2-hydroxy-ethyl)-2-nitro-benzenesulfonamide (2.0 g, 8.12 mmol) and $Et_3N$ (1.35 mL, 9.74 mmol) in $CH_2Cl_2$ (20 mL) at −20° C. was added a solution of MsCl (0.63 mL, 8.12 mol) in $CH_2Cl_2$ (5 mL) dropwise (via syringe pump) over 45 min. After addition, the mixture was stirred for 20 min at −20° C. Then the reaction was washed with saturated $NH_4Cl$ (2×50 mL) and brine (2×50 mL), dried ($MgSO_4$), filtered, and concentrated to afford a yellow oil (2.0 g, 86%). $^1H$ NMR ($CDCl_3$) δ 3.03 (s, 3H), 3.51 (q, 2H, J=6.0 Hz), 4.30 (t, 2H, J=4.5 Hz), 5.82 (t, 1H, J=6.0 Hz), 7.76-7.79 (m, 2H), 7.90-7.91 (m, 1H), 8.13-8.16 (m, 1H).

To a solution of the above methanesulfonic acid 2-(2-nitro-benzenesulfonylamine)-ethyl ester (2.03 g, 6.95 mmol) in benzene (20 mL) was added a solution of KOH (1.95 g, 34.73 mmol) in $H_2O$ (8 mL) rapidly. After 2 h, $H_2O$ (15 mL) was added and the phases were separated. The organic layer was dried ($MgSO_4$), filtered, and concentrated to afford 1-(2-nitro-benzenesulfonyl)-aziridine as a yellow oil (0.88 g, 55%). $^1H$ NMR ($CDCl_3$) δ 2.63 (s, 4H), 7.74-7.80 (m, 3H), 8.20-8.22 (m, 1H).

A solution of meso-4-(3,3'-dimethyl-3',4',5',6'-tetrahydro-2'H-[2,2';6',2"]terpyridin-1'-yl)-butylamine (550 mg, 2.06 mmol), nosyl aziridine (470 mg, 2.06 mmol), and DIPEA (0.57 mL, 3.30 mmol) in THF (10 mL) was stirred at room temperature for 3 d. Then the mixture was concentrated in vacuo, and the residue was dissolved in $CH_2Cl_2$ (20 mL) and washed with saturated $NaHCO_3$ (3×20 mL). The organic layer was dried ($MgSO_4$), filtered, and concentrated to afford a yellow solid. Purification by flash column chromatography on silica gel using 5% MeOH/$CH_2Cl_2$ afforded the product impurely as a yellow solid (650 mg, 64%), which was used without further purification.

To a solution of the above amine (650 mg, 1.31 mmol) in $CH_3CN$ (13 mL) was added $K_2CO_3$ (1.09 g, 7.86 mmol) and thiophenol (0.74 mL, 7.21 mmol). After 2 h, the mixture was diluted with $CH_2Cl_2$ (20 mL) and $H_2O$ (20 mL). The aqueous layer was extracted with CH$_2$Cl$_2$ (2×20 mL). The combined organic layers were dried (MgSO$_4$), filtered, and concentrated to afford a bright yellow oil. Purification by flash column chromatography on silica gel using MeOH/CH$_2$Cl$_2$ (2%→5%) afforded the product as a yellow foam (309 mg, 48% (over two steps)). $^1$H NMR (CDCl$_3$) δ 1.62 (m, 2H), 1.70-1.78 (m, 3H), 1.91-1.93 (m, 1H), 2.15-2.20 (m, 2H), 2.39-2.44 (m, 8H), 4.07 (d, 2H, J=9.0 Hz), 7.18 (dd, 2H, J=6.0, 3.0 Hz), 7.53 (d, 2H, J=6.0 Hz), 8.60 (d, 2H, J=3.0 Hz), 9.36 (br s, 2H). $^{13}$C NMR (CDCl$_3$) d 19.22, 25.12, 30.06, 34.19, 35.53, 49.86, 66.77, 123.06, 127.53, 127.86, 129.43, 131.37, 139.75, 140.12, 140.48, 147.47, 160.07. ES-MS m/z 311 [M$^+$H]$^+$. Anal. Calcd. for C$_{19}$H$_{26}$N$_4$O.0.8CH$_2$Cl$_2$.1.3H$_2$O: C, 59.19; H, 7.58; N, 13.94. Found: C, 59.46; H, 7.59; N, 14.10.

EXAMPLE 68

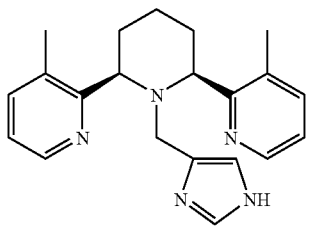

Compound 68: 1'-(1H-imidazol-4-ylmethyl)-3,3''-dimethyl-1',2',3',4',5',6'-hexahydro-[2,2';6',2'']terpyridine To a solution of 4-(hydroxymethyl)imidazole hydrochloride salt (526 mg, 3.91 mmol) in DMF (5 mL) was added DIPEA (2.04 mL, 11.73 mmol) and SEM-chloride (0.82 mL, 4.69 mmol). After 3 h, the reaction mixture was diluted with EtOAc (25 mL) and washed with water (2×20 mL) and brine (2×20 mL). The organic layer was dried (MgSO$_4$), filtered, and concentrated to afford a yellow oil. Purification by flash column chromatography on silica gel using MeOH/NH$_4$OH/CH$_2$Cl$_2$ (3:1:96) afforded [3-(2-trimethylsilanyloxyethoxymethyl)-3H-imidazol-4-yl]-methanol as a yellow oil (354 mg, 40%). $^1$H NMR (CDCl$_3$) δ −0.01 (s, 9H), 0.88-0.94 (m, 2H), 2.60-2.62 (br m, 1H), 3.45-3.53 (m, 2H), 4.61 and 4.67 (br s, total 2H), 5.23 and 5.36 (s total 2H), 6.99 and 7.04 (s, total 1H), 7.55 and 7.56 (s, total 1H).

To a solution of the above alcohol (354 mg, 1.55 mmol) in CH$_2$Cl$_2$ at 0° C. was added Et$_3$N (0.43 mL, 3.10 mmol) and MsCl (0.13 mL, 2.33 mmol) according to General Procedure F. No further purification afforded a yellow oil (270 mg).

A suspension of the above mesylate (270 mg, 0.88 mmol), meso-4-(3,3'-dimethyl-3',4',5',6'-tetrahydro-2'H-[2,2';6',2''] terpyridin-1'-yl)-butylamine (236 mg, 0.88 mmol), DIPEA (0.23 mL, 1.32 mmol), and KI (15 mg, 0.09 mmol) in DMF (10 mL) was stirred together according to General Procedure A. Purification by flash column chromatography using MeOH/NH$_4$OH/CH$_2$Cl$_2$ (2:1:97) afforded the product as a yellow oil (110 mg).

A solution of the above amine (110 mg, 0.23 mmol) in 6N HCl (10 mL) was stirred at 60° C. After 3 h, the reaction mixture was cooled and basified to pH=10-11 with solid K$_2$CO$_3$. Then it was extracted with CH$_2$Cl$_2$ (4×30 mL). The combined organic layers were dried (MgSO$_4$), filtered, and concentrated to afford a pale yellow solid. Purification by radial chromatography on silica gel (1 mm plate; using CH$_2$Cl$_2$/MeOH/NH$_4$OH; 50:1:1→25:1:1) afforded the product as a white solid (34 mg, 43%). $^1$H NMR (CDCl$_3$) δ 1.44-1.57 (m, 1H), 1.73 (d, 2H, J=12.0 Hz), 1.89-2.04 (m, 3H), 2.47 (br s, 6H), 3.31 (s, 2H), 3.84 (br d, 2H, J=12.0 Hz), 6.02 (br s, 1H), 7.07 (br s, 2H), 7.41-7.43 (m, 3H), 8.42 (d, 2H, J=3.0 Hz). $^{13}$C NMR (CDCl$_3$) δ 19.34, 25.26, 31.80, 32.36, 46.07, 70.19, 121.87, 122.53, 126.77, 135.13, 137.96, 147.04, 160.63. ES-MS m/z 348 [M$^+$H]$^+$. Anal. Calcd. for C$_{21}$H$_{25}$N$_5$.0.8H$_2$O: C, 69.70; H, 7.41; N, 19.35. Found: C, 69.78; H, 7.41; N, 19.01.

EXAMPLE 69

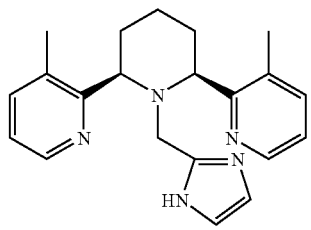

Compound 69: 1'(1H-imidazol-2-ylmethyl)-3,3''-dimethyl-1',2'3',4',5',6'-hexahydro-[2,2';6',2'']terpyridine To a suspension of 2-imidazolecarboxaldehyde (1.01 g, 10.51 mmol) in CH$_2$Cl$_2$ (25 mL) was added Et$_3$N (2.9 mL, 21.02 mmol) and tosyl chloride (3.01 g, 15.77 mmol) and the reaction mixture was heated to reflux overnight. Then the mixture was cooled and washed with saturated NH$_4$Cl (4×30 mL). The organic layer was dried (MgSO$_4$), filtered, and concentrated to afford a dark brown oil. Purification by flash column chromatography on silica gel using 2% MeOH/CH$_2$Cl$_2$ afforded 1-(toluene-4-sulfonyl)-1H-imidazole-2-carbaldehyde as a yellow oil (1.53 g, 58%). $^1$H NMR (CDCl$_3$) δ 2.45 (s, 3H), 7.31 (s, 1H), 7.49 (d, 2H, J=6.0 Hz), 7.83 (s, 1H), 8.00 (d, 2H, J=7.5 hz), 9.78 (s, 1H).

To a solution of the above aldehyde (1.53 g, 6.11 mmol) in CH$_2$Cl$_2$ (50 mL) at 0° C. was added TFA (5 mL) as described in J. Med. Chem. (1997) 40:2196. Purification by flash column chromatography using EtOAc/hexane (1:1) afforded [1-(toluene-4-sulfonyl)-1H-imidazol-2-yl]-methanol as a white solid (0.55 g, 36%). $^1$H NMR (CDCl$_3$) δ 2.45 (s, 3H), 3.03 (br s, 1H), 4.84 (s, 2H), 6.99 (d, 1H, J=3.0 Hz), 7.35 (s, 1H), 7.39 (d, 2H, J=3.0 Hz), 7.83 (d, 2H, J=9.0 Hz).

To a solution of the above alcohol (0.55 g, 2.17 mmol) and CBr$_4$ (1.08 g, 3.26 mmol) in CH$_2$Cl$_2$ (25 mL) at 0° C. was added a solution of triphenylphosphine (0.68 g, 2.60 mmol) in CH$_2$Cl$_2$ (10 mL) as described in J. Med. Chem. (1997) 40, 14:2196. Purification by flash column chromatography using 25% EtOAc/hexanes afforded 2-bromomethyl-1-(toluene-4-sulfonyl)-1H-imidazole as a yellow oil (0.31 g, 45%). $^1$H NMR (CDCl$_3$) δ 2.45 (s, 3H), 4.81 (s, 2H), 7.04 (s, 1H), 7.37 (d, 2H, J=9.0 Hz), 7.42 (s, 1H), 7.92 (d, 2H, J=9.0 Hz).

A mixture of the above bromide (310 mg, 0.98 mmol), meso-4-(3,3'-dimethyl-3',4',5',6'-tetrahydro-2'H-[2,2';6',2''] terpyridin-1'-yl)-butylamine (88 mg, 0.33 mmol), DIPEA (0.23 mL, 1.32 mmol), and KI (5 mg, 0.03 mmol) in DMF (5 mL) was stirred together according to General Procedure A. Purification by flash column chromatography on silica gel using MeOH/CH$_2$Cl$_2$ (2%→5%) afforded the product as a yellow oil (76 mg, 46%).

To a solution of the above tosylate (76 mg, 0.15 mmol) in MeOH (1 mL) was added HOBT (82 mg, 0.61 mmol) and the reaction mixture was stirred overnight. Then the mixture was concentrated to afford a brown oil. Purification by radial chromatography on silica gel (1 mm plate; using $CH_2Cl_2$/MeOH/$NH_4OH$; 50:1:1→10:1:1) afforded the product as a yellow oil (32 mg, 59%). $^1H$ NMR ($CDCl_3$) δ 1.54-1.63 (m, 1H), 1.73 (d, 2H, J=16.0 Hz), 1.91-1.21 (m, 3H), 2.44 (s, 6H), 3.40 (s, 2H), 3.96 (d, 2H, J=9.0 Hz), 6.49 (br s, 1H), 6.67 (br s, 1H), 6.94-6.99 (m, 2H), 7.37 (d, 2H, J=9.0 Hz), 8.35 (d, 2H, J=3.0 Hz). $^{13}C$ NMR ($CDCl_3$) δ 19.42, 20.27, 33.11, 53.77, 65.87, 122.32, 131.49, 139.03, 147.13, 160.37. ES-MS m/z 347 $[M^+H]^+$. Anal. Calcd. for $C_{21}H_{25}N_5.1.1H_2O$: C, 68.68; H, 7.46; N, 19.07. Found: C, 68.49; H, 7.37; N, 19.27.

EXAMPLE 70

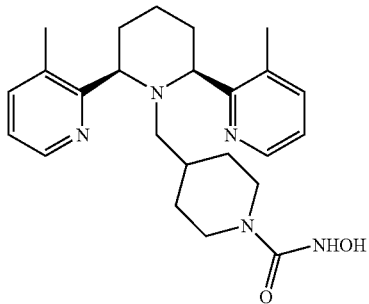

Compound 70: 4-(3,3"-dimethyl-3',4',5',6'-tetrahydro-2'H-[2,2';6',2"]terpyridin-1'-ylmethyl)-piperidine-1-hydroxyurea To a solution of ethyl isonipectotate (2.0 mL, 12.99 mmol) in $CH_2Cl_2$ (20 mL) was added $Et_3N$ (3.6 mL, 25.98 mmol) and p-toluenesulfonyl chloride (3.71 g, 19.48 mmol) and the reaction mixture was stirred overnight. Then the mixture was diluted with $CH_2Cl_2$ (10 mL) and washed with saturated $NH_4Cl$ (3×30 mL). The organic layer was dried ($MgSO_4$), filtered, and concentrated to afford a yellow solid. Purification by flash column chromatography on silica gel using hexanes/EtOAc (3:1) afforded 1-(toluene-4-sulfonyl)-piperidine-4-carboxylic acid ethyl ester as a white solid (3.45 g, 85%).

To a solution of the above ester (1.29 g, 4.79 mmol) in $CH_2Cl_2$ (20 mL) at 0° C. was added a solution of $LiAlH_4$ in THF (1.0 M, 13.9 mL, 13.87 mmol) and the mixture was heated to reflux. After 1 h, the mixture was cooled back down to 0° C. and quenched with $H_2O$ (0.51 mL), 15% NaOH (0.51 mL), and $H_2O$ (1.53 mL). After stirring for 30 min, the reaction mixture was dried ($MgSO_4$), filtered, and concentrated to afford [1-(toluene-4-sulfonyl)-piperidin-4-yl]-methanol as a clear oil (1.24 g, 100%). $^1H$ NMR ($CDCl_3$) δ 1.31-1.43 (m, 4H), 1.79 (d, 2H, J=12.0 Hz), 2.24 (t, 2H, J=12.0 Hz), 2.43 (s, 3H), 3.47 (d, 2H, J=6.0 Hz), 3.81 (d, 2H, J=12.0 Hz), 7.32 (d, 2H, J=6.0 Hz), 7.64 (d, 2H, J=6.0 Hz).

To a solution of the above alcohol (1.24 g, 4.79 mmol) in $CH_2Cl_2$ (20 mL) at 0° C. was added $Et_3N$ (1.3 mL, 9.58 mmol) and MsCl (0.56 mL, 7.18 mmol) according to General Procedure F. No further purification afforded a pale yellow solid (1.49 g, 90%).

The above mesylate (485 mg, 1.40 mmol), meso-4-(3,3'-dimethyl-3',4',5',6'-tetrahydro-2'H-[2,2';6',2"]terpyridin-1'-yl)-butylamine (311 mg, 1.16 mmol), DIPEA (0.30 mL, 1.71 mmol), and KI (20 mg, 0.12 mmol) in DMF (5 mL) was stirred together according to General Procedure A. Purification by flash column chromatography on silica gel using MeOH/$NH_4OH$/$CH_2Cl_2$ (2:1:97) afforded 3,3"-dimethyl-1'-[1-(toluene-4-sulfonyl)-piperidin-4-ylmethyl]-1',2',3',4',5',6'-hexahydro-[2,2';6',2']terpyridine as a tan foam (385 mg, 77%). $^1H$ NMR ($CDCl_3$) δ 0.11-0.22 (m, 2H), 1.00 (d, 2H, J=15.0 Hz), 1.51-1.69 (m, 5H), 2.04-2.08 (m, 1H), 2.25-2.36 (m, 4H), 2.45 (s, 3H), 2.50 (s, 6H), 3.18 (d, 2H, J=12.0 Hz), 3.64 (s, 1H), 4.10 (d, 2H, J=12.0 Hz), 7.01 (dd, 2H, J=6.0, 3.0 Hz), 7.25 (d, 2H, J=7.5 Hz), 7.35 (d, 2H, J=7.5 Hz), 7.45 (d, 2H, J=6.0 Hz), 8.33 (d, 2H, J=6.0 Hz).

The above tosylate (348 mg, 0.67 mmol) in HBr saturated HOAc (4 mL) was stirred overnight at 70° C. Then the reaction mixture was cooled and concentrated and the residue was dissolved in a minimum amount of $H_2O$ and basified to pH=11 using 10N NaOH. The aqueous phase was extracted with $CH_2Cl_2$ (5×20 mL). The combined organic layers were dried ($MgSO_4$), filtered, and concentrated to afford a brown oil. Purification by flash column chromatography on silica gel using MeOH/$NH_4OH$/$CH_2Cl_2$ (2:1:97) afforded 3,3'-dimethyl-1'-piperidin-4-ylmethyl-1',2',3',4',5',6'-hexahydro-[2,2';6',2"]terpyridine as a yellow oil (80 mg, 33%).

To a solution of the above amine (71 mg, 0.19 mmol) in THF (5 mL) was added hydroxyurea 4-nitrol-phenyl ester (46 mg, 0.23 mmol) and the reaction mixture was stirred at 70° C. After 2 h, the reaction was concentrated under reduced pressure. Purification by radial chromatography on silica gel (1 mm plate; using $CH_2Cl_2$/MeOH/$NH_4OH$; 50:1:1→25:1:1) afforded the product as a white solid (16 mg, 20%). $^1H$ NMR ($CDCl_3$) δ −0.46 (br m, 1H), 0.04 (br m, 1H), 1.07 (d, 2H, J=12.0 Hz), 1.55-1.71 (m, 3H), 2.01-2.35 (m, 12H), 2.50 (s, 6H), 3.45 (d, 2H, J=12.0 Hz), 4.12 (d, 2H, J=9.0 Hz), 6.47 (s, 1H), 7.09 (d, 2H, J=6.0, 3.0 Hz), 7.42 (d, 2H, J=6.0 Hz), 8.41 (d, 2H, J=6.0 Hz), $^{13}C$ NMR ($CDCl_3$) δ 0.39, 19.06, 25.74, 26.56, 29.73, 36.44, 43.64, 44.44, 53.82, 65.60, 122.55, 132.61, 138.26, 146.65, 160.35, 160.85. ES-MS m/z 424 $[M^+H]^+$. Anal. Calcd. for $C_{24}H_{33}N_5O_2.1.2CH_2Cl_2$: C, 57.60; H, 6.79; N, 13.33. Found: C, 57.90; H, 6.82; N, 13.40.

EXAMPLE 71

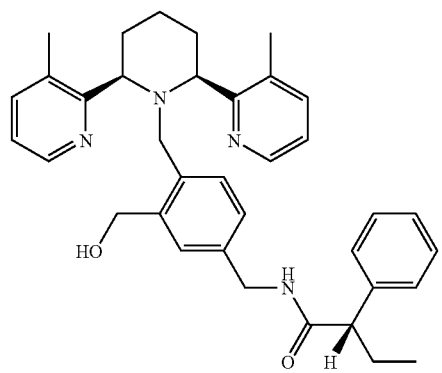

Compound 71: N-[4-(3,3"-dimethyl-3',4',5',6'-tetrahydro-2'H-[2,2';6',2"]-terpyridin-1'-ylmethyl)-3-hydroxymethyl-benzyl]-2-phenyl-butyramide To a solution of 3,3"-dimethyl-1',2',3',4',5',6'-hexahydro-[2,2';6',2"]terpyridine (0.500 g, 1.87 mmol) dissolved in CH<sub>3</sub>CN (10 mL) was added 2-bromomethyl-5-cyano-benzoic acid methyl ester (0.500 g, 1.96 mmol) and K$_2$CO$_3$ (0.720 g, 5.61 mmol). The mixture was stirred for 15 hours at 80° C. under a positive pressure of N$_2$. The mixture was concentrated in vacuo, quenched with saturated aqueous NaCl (25 mL) and extracted with CH$_2$Cl$_2$ (3×30 mL). The combined organic extracts were dried (Na$_2$SO$_4$), filtered, and concentrated in vacuo to give a brown oil which was used without purification.

The brown oil from the previous step was dissolved in MeOH (10 mL) followed by the slow addition of LiBH$_4$ (0.411 g, 18.7 mmol) to ensure the reaction mixture did not bubble over. The mixture was stirred at room temperature for 16 hours. The mixture was concentrated in vacuo, redissolved in CH$_2$Cl$_2$ (30 mL) and quenched with saturated aqueous NaHCO$_3$ (30 mL). The resulting mixture was extracted with CH$_2$Cl$_2$ (3×40 mL) and the combined organic extracts were dried (Na$_2$SO$_4$), filtered, and concentrated in vacuo to afford a yellow foam. Purification via column chromatography on silica gel (CH$_2$Cl$_2$:MeOH:NH$_4$OH, 92:5:3, v/v/v) afforded 4-(3,3"-dimethyl-3',4',5',6'-tetrahydro-2'H-[2,2';6',2"]terpyridin-1'-ylmethyl)-3-hydroxymethyl-benzonitrile as a white foam (0.610 g, 80%, 2-steps). $^1$H NMR (CDCl$_3$) δ 1.58-1.69 (m, 3H), 2.05 (m, 1H), 2.29-2.41 (m, 2H), 2.48 (s, 6H), 3.67 (s, 2H), 4.11 (d, 2H, J=12.0 Hz), 4.44 (s, 2H), 5.13 (br s, 1H), 6.85 (dd, 2H, J=6.0, 4.5 Hz), 6.92 (s, 2H), 7.23 (s+d, 3H), 8.16 (d, 2H, J=3.0 Hz).

To a solution of 4-(3,3"-dimethyl-3',4',5',6'-tetrahydro-2'H-[2,2';6',2"]terpyridin-1'-ylmethyl)-3-hydroxymethyl-benzonitrile (0.610 g, 1.48 mmol) dissolved in MeOH (12 mL) ammonia gas was bubbled for 10 minutes. A pre-washed mixture of Raney Nickel (~1.5 grams) was added to the nitrile and the mixture was shaken on the hydrogenator at 45 psi for 2.5 hours. The mixture was filtered through a sintered glass funnel containing a celite plug and the filtrated was concentrated in vacuo to a green foam. Purification by column chromatography on silica gel (CH$_2$Cl$_2$:MeOH:NH$_4$OH, 87:8:5, v/v/v) afforded [5-aminomethyl-2-(3,3"-dimethyl-3',4',5',6'-tetrahydro-2'H-[2,2';6',2"]-terpyridin-1'-ylmethyl)-phenyl]-methanol as a white foam (0.540 g, 88%). $^1$H NMR (CDCl$_3$) δ 1.25 (br s, 1H), 1.62-1.72 (m, 3H), 2.03 (m, 1H), 2.32 (m, 2H), 2.49 (s, 6H), 2.81 (br s, 1H), 3.55 (s, 2H), 3.62 (s, 1H), 4.01 (d, 2H, J=9.0 Hz), 4.34 (s, 2H), 5.18 (br s, 1H), 6.59 (d, 1H, J=9.0 Hz), 6.72 (d, 1H, J=9.0 Hz), 6.83 (m, 3H), 7.23 (d, 2H, J=9.0 Hz), 8.22 (d, 2H, J=3.0 Hz).

[5-Aminomethyl-2-(3,31"-dimethyl-3',4',5',6'-tetrahydro-2'H-[2,2';6',2"]terpyridin-1'-ylmethyl)-phenyl]-methanol (0.121 g, 0.29 mmol), S-(+)-2-phenylbutyric acid (54 µL, 0.35 mmol), HOBT (0.047 g, 0.35 mmol), EDCI (0.067 g, 0.35 mmol) and DIPEA (61 µL, 0.35 mmol) in CH$_2$Cl$_2$ (8 mL) were reacted according to General Procedure G. Purification by column chromatography on silica gel (CH$_2$Cl$_2$:MeOH: NH$_4$OH, 94:5:1, v/v/v) afforded N-[4-(3,3"-dimethyl-3',4',5',6'-tetrahydro-2'H-[2,2';6',2"]-terpyridin-1'-ylmethyl)-3-hydroxymethyl-benzyl]-2-phenyl-butyramide as a white solid (0.120 g, 73%). $^1$H NMR (CDCl$_3$) δ 0.86 (t, 3H, J=7.5 Hz), 1.59-1.76 (m, 3H), 2.04 (m, 1H), 2.32 (m, 2H), 2.49 (s, 6H), 3.62 (s, 2H), 4.00-4.09 (m, 4H), 4.32 (s, 2H), 5.07 (br s, 1H), 5.35 (br s, 1H), 6.44 (d, 1H, J=7.5 Hz), 6.63 (d, 2H, J=9.0 Hz), 6.75 (m, 2H), 7.13-7.33 (m, 7H), 8.22 (d, 2H, J=3.0 Hz). HPLC: 94%. ES-MS m/z 563 [M+H]+, 585 [M+Na]+.

EXAMPLE 72

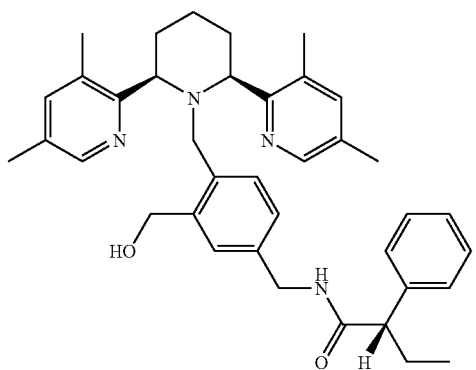

Compound 72: N-[3-hydroxymethyl-4-(3,5,3",5"-tetramethyl-3',4',5',6'-tetrahydro-2'H-[2,2';6',2"] terpyridin-1'-ylmethyl)-benzyl]-2-phenyl-butyramide To a solution of 3,5,3',5"-tetramethyl-1',2',3',4',5',6'-hexahydro-[2,2';6',2"]-terpyridine (0.130 g, 0.44 mmol) dissolved in CH$_3$CN (5 mL) was added 2-bromomethyl-5-cyano-benzoic acid methyl ester (0.117 g, 0.46 mmol) and K$_2$CO$_3$ (0.169 g, 1.32 mmol). The mixture was stirred for 15 hours at 80° C. under a positive pressure of N$_2$. The mixture was concentrated in vacuo, quenched with saturated aqueous NaCl (25 mL) and extracted with CH$_2$Cl$_2$ (3×30 mL). The combined organic extracts were dried (Na$_2$SO$_4$), filtered, and concentrated in vacuo to give a yellow oil which was used without purification.

The yellow oil from the previous step was dissolved in MeOH (5 mL) followed by the slow addition of LiBH$_4$ (0.097 g, 4.41 mmol) to ensure the reaction mixture did not bubble over. The mixture was stirred at room temperature for 16 hours. The mixture was concentrated in vacuo, redissolved in CH$_2$Cl$_2$ (30 mL) and quenched with saturated aqueous NaHCO$_3$ (30 mL). The resulting mixture was extracted with CH$_2$Cl$_2$ (3×40 mL) and the combined organic extracts were dried (Na$_2$SO$_4$), filtered, and concentrated in vacuo to afford a yellow oil. Purification via column chromatography on silica gel (CH$_2$Cl$_2$:MeOH:NH$_4$OH, 92:5:3, v/v/v) afforded 3-hydroxymethyl-4-(3,5,3",5"-tetramethyl-3',4',5',6'-tetrahydro-2'H-[2,2';6',2"]terpyridin-1'-ylmethyl)-benzonitrile as a yellow oil (0.060 g, 31%, 2-steps). $^1$H NMR (CDCl$_3$) δ 1.58-1.69 (m, 3H), 2.05 (m, 1H), 2.14 (s, 6H), 2.26-2.35 (m, 2H), 2.43 (s, 6H), 3.63 (s, 2H), 4.00 (d, 2H, J=12.0 Hz), 4.44 (s, 2H), 5.26 (br s, 1H), 6.82 (d, 1H, J=9.0 Hz), 6.92 (d, 1H, J=9.0 Hz), 7.05 (s, 2H), 7.26 (s, 1H), 8.01 (s, 2H).

To a solution of 3-hydroxymethyl-4-(3,5,3",5"-tetramethyl-3',4',5',6'-tetrahydro-2'H-[2,2';6',2"]terpyridin-1'-ylmethyl)-benzonitrile (0.060 g, 0.14 mmol) dissolved in MeOH (7 mL) ammonia gas was bubbled for 10 minutes. A pre-washed mixture of Raney Nickel (~0.5 gram) was added to the nitrile and the mixture was shaken on the hydrogenator at 40 psi for 2 hours. The mixture was filtered through a sintered glass funnel containing a celite plug and the filtrated was concentrated in vacuo to give a green foam. Purification by column chromatography on silica gel (CH$_2$Cl$_2$:MeOH: NH$_4$OH, 87:8:5, v/v/v) afforded [5-aminomethyl-2-(3,5,3", 5"-tetramethyl-3',4',5',6'-tetrahydro-2'H-[2,2';6',2"]terpyridin-1'-ylmethyl)-phenyl]-methanol as a pale yellow foam (0.061 g, 99%). $^1$H NMR (CDCl$_3$) δ 1.52-1.62 (m, 3H), 1.98 (m, 1H), 2.10 (s, 6H), 2.20-2.30 (m, 2H), 2.37 (s, 6H), 3.50 (s, 2H), 3.57 (s, 1H), 3.88 (d, 2H, J=9.0 Hz), 4.27 (s, 2H), 6.59 (d, 1H, J=9.0 Hz), 6.68 (d, 1H, J=9.0 Hz), 6.89 (s, 1H), 7.03 (s, 2H), 8.03 (s, 2H).

[5-Aminomethyl-2-(3,5,3",5"-tetramethyl-3',4',5',6'-tetrahydro-2'H-[2,2';6',2"]-terpyridin-1'-ylmethyl)-phenyl]-methanol (0.061 g, 0.14 mmol), S-(+)-2-phenylbutyric acid (22 μL, 0.16 mmol), HOBT (0.022 g, 0.16 mmol), EDCI (0.032 g, 0.16 mmol) and DIPEA (29 μL, 0.16 mmol) in CH$_2$Cl$_2$ (8 mL) were reacted according to General Procedure G. Purification by column chromatography on silica gel (CH$_2$Cl$_2$:MeOH:NH$_4$OH, 94:5:1, v/v/v) afforded N-[3-hydroxymethyl-4-(3,5,3",5"-tetramethyl-3',4',5',6'-tetrahydro-2'H-[2,2';6',2"]terpyridin-1'-ylmethyl)-benzyl]-2-phenyl-butyramide as a white solid (0.045 g, 55%). $^1$H NMR (CDCl$_3$) δ 0.86 (t, 3H, J=7.5 Hz), 1.66-1.76 (m, 3H), 2.10 (s*m, 7H), 2.32 (m, 2H), 2.42 (s, 6H), 3.65 (br s, 2H), 3.92 (m, 4H), 4.35 (s, 2H), 5.46 (br s, 1H), 6.45 (d, 1H, J=7.5 Hz), 6.60 (d, 1H, J=9.0 Hz), 6.68 (s, 1H), 7.00 (s, 2H), 7.13-7.33 (m, 7H), 8.00 (s, 2H). HPLC: 93%. ES-MS m/z 591 [M$^+$H]$^+$, 613 [M$^+$Na]$^+$.

EXAMPLE 73

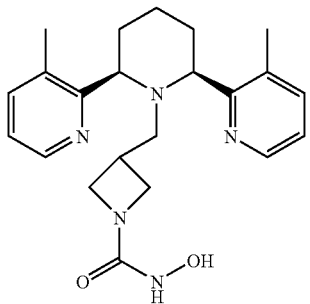

Compound 73: 3-(3,3"-Dimethyl-3',4',5',6'-tetrahydro-2'H-[2,2°;6',2"]terpyridin-1'-ylmethyl)-azetidine-1-carboxylic Acid Hydroxyamide Tert-butyl 3-(aminomethyl)-1-azetidinecarboxylate (J. Med. Chem., (2001) 44:94-104) (441 mg, 2.35 mmol) was dissolved in CH$_2$Cl$_2$ (2 mL) and TFA (1.5 mL) and the mixture was stirred for 2 hours at room temperature. The volatiles were removed under reduced pressure and the residue was dissolved in dry MeOH (5 mL). Solid NaHCO$_3$ was added (~500 mg) and the mixture was stirred for 17 hours. MeOH was removed, CH$_2$Cl$_2$ (50 mL) was added and the mixture was filtered through a plug of Celite. The filtrate was concentrated and the residue was dissolved in DMF (15 mL). DIPEA (0.817 mL, 4.70 mmol) and 2-nitrobenzenesulfonyl chloride (580 mg, 2.58 mmol) were added and the mixture was stirred for 2 hours. The mixture was concentrated and the residue was purified by column chromatography on silica gel (100% EtOAc) to provide [1-(2-nitro-benzenesulfonyl)-azetidin-3-yl]-methanol (167 mg, 26%). $^1$H NMR (CDCl$_3$) δ 2.73-2.80 (m, 1H), 3.76 (dd, 2H, J=5.4, 5.7 Hz), 3.90 (dd, 2H, J=5.7, 8.1 Hz), 4.17 (dd, 2H, J=8.1, 8.1 Hz).

To a 0° C. solution of [1-(2-nitro-benzenesulfonyl)-azetidin-3-yl]-methanol (165 mg, 0.606 mmol) in EtOAc (15 mL) was added Et$_3$N (0.101 mL, 0.727 mmol) then mesyl chloride (0.052 mL, 0.666 mmol). The reaction mixture was stirred for 1 hour at room temperature. The precipitate was filtered through a plug of Celite and was washed with EtOAc. The filtrate was concentrated and the crude mesylate was dissolved in DMF (5 mL). To this solution was added DIPEA (0.211 mL, 1.20 mmol) and 3,3'-dimethyl-1',2',3'4',5',6'-hexahydro-[2,2';6',2"]terpyridine (162 mg, 0.606 mmol) and the mixture was heated at 80° C. for 17 hours. Saturated NaHCO$_3$ (15 mL) was added and the mixture was extracted with CH$_2$Cl$_2$ (3×30 mL). The combined organic extracts were dried (MgSO$_4$), filtered and concentrated. The crude material was purified by radial chromatography on silica gel (Et$_2$O saturated with NH$_4$OH) to give 3,3'-dimethyl-1'-[1-(2-nitro-benzenesulfonyl)-azetidin-3-ylmethyl]-1',2',3'4',5',6'-hexahydro-[2,2';6',2"]terpyridine (168 mg, 53%).

A mixture of 3,3'-dimethyl-1'-[1-(2-nitro-benzenesulfonyl)-azetidin-3-ylmethyl]-1',2',3'4',5',6'-hexahydro-[2,2';6', 2"]terpyridine (168 mg, 0.322 mmol), thiophenol (0.3 mL), K$_2$CO$_3$ (500 mg) in CH$_3$CN (5 mL) were stirred at room temperature for 17 hours. The volatiles were removed under reduced pressure and saturated NaHCO$_3$ (15 mL) was added and the mixture was extracted with CH$_2$Cl$_2$ (3×30 mL). The combined organic extracts were dried (MgSO$_4$), filtered and concentrated. The crude material was subjected to column chromatography on silica gel (10:1:0.1 CH$_2$Cl$_2$:CH$_3$OH: NH$_4$OH; then 10:1:0.5) to provide 1'-azetidin-3-ylmethyl-1', 2',3'4',5',6'-hexahydro-[2,2';6',2"]terpyridine (74 mg, 80% pure by LC/MS).

To a 0° C. solution of 1'-azetidin-3-ylmethyl-1',2',3'4',5',6'-hexahydro-[2,2';6',2"]terpyridine from above (74 mg, 0.219 mmol) in toluene (2.5 mL) and DIPEA (0.095 mL, 0.5 mmol) was added phosgene solution in toluene (20 wt %, 0.12 mL, 0.26 mmol). The reaction mixture was warmed to room temperature and was stirred for 1.5 hours. The volatiles were removed under reduced pressure and the remaining yellow solid was dissolved in DMF (5 mL). DIPEA (0.40 mL) and NH$_2$OH.H$_2$O (100 mg, 1.56 mmol) were added and the mixture was stirred for 17 hours at room temperature. Saturated NaHCO$_3$ (15 mL) was added and the mixture was extracted with CH$_2$Cl$_2$ (3×30 mL). The combined organic extracts were dried (MgSO$_4$), filtered and concentrated. The crude material was purified by radial chromatography (10:1:0.2 CH$_2$Cl$_2$: CH$_3$OH:NH$_4$OH) on silica gel to provide COMPOUND 73 (27 mg, 31%) as a clear film. $^1$H NMR (CDCl$_3$) δ 1.16-1.19 (m, 1H), 1.53-1.65 (m, 3H), 1.94-2.11 (m, 3H), 2.42 (s, 6H), 2.41-2.43 (m, 2H), 3.01-3.06 (m, 2H), 3.45 (t, 2H, J=8.4 Hz), 3.60 (br s, 1H), 3.88 (d, 2H, J=10.2 Hz), 7.10 (dd, 2H, J=4.2, 7.5 Hz), 7.45 (d, 2H, J=7.5 Hz), 8.41 (d, 2H, J=4.2 Hz); $^{13}$C NMR (CDCl$_3$) δ 19.2, 25.2, 29.2, 30.8, 55.0, 57.4, 65.5, 122.7, 131.4, 139.2, 147.2, 160.6, 163.5; ES-MS m/z 396 (M$^+$H). Anal. Calcd. for C$_{22}$H$_{29}$N$_5$O$_2$.0.1H$_2$O.1.2 CH$_2$Cl$_2$: C, 55.82; H, 6.38; N, 14.03. Found: C, 55.75; H, 6.35; N, 14.08.

EXAMPLE 74

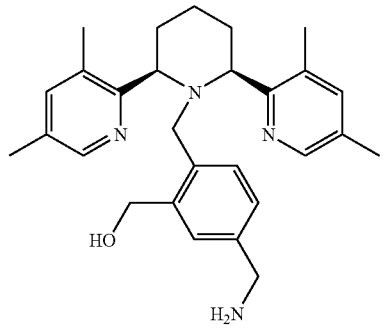

Compound 74: Meso-2'β,6'β-[5-aminomethyl-2-(3,5,3",5"-tetramethyl-3',4',5',6'-tetrahydro-2'H-[2,2';6',2"]terpyridin-1'-ylmethyl)-phenyl]-methanol Following the General Procedure A, meso-2'β,6'β-[3,5,3",5"-tetramethyl-1',2',3',4',5',6'-hexahydro-[2,2';6'2"]terpyridine] (0.1903 g, 0.64 mmol), 2-bromomethyl-5-cyano-benzoic acid methyl ester (0.1630 g, 0.64 mmol), KI (0.0100 g, 0.06 mmol), DIPEA (0.22 mL, 1.29 mmol), and DMF (6.4 mL) were stirred at 60° C. for 17 hours. Purification of the crude material by column chromatography on silica gel (50:1:1 $CH_2Cl_2$—MeOH—$NH_4OH$) provided 0.2682 g (89%) of meso-2'β,6'β-[5-cyano-2-(3,5,3",5"-tetramethyl-3',4',5',6'-tetrahydro-2'H-[2,2';6'2"]terpyridin-1'-ylmethyl)-benzoic acid methyl ester] as a brown oil. $^1$H NMR ($CDCl_3$) δ 1.63-1.67 (m, 3H), 2.00-2.05 (m, 1H), 2.12 (s, 6H), 2.21-2.31 (m, 2H), 2.36 (s, 6H), 3.84 (s, 3H), 3.90-3.94 (m, 2H), 4.05-4.08 (m, 2H), 6.96 (s, 2H), 7.37 (d, 1H, J=9.0 Hz), 7.56 (d, 1H, J=3.0 Hz), 7-0.90 (s, 1H), 8.02 (s, 2H).

To a solution of meso-2'β,6'β-[5-cyano-2-(3,5,3",5"-tetramethyl-3',4',5',6'-tetrahydro-2'H-[2,2';6'2"]terpyridin-1'-ylmethyl)-benzoic acid methyl ester] (0.2682 g, 0.57 mmol) in THF (6 mL) at 0° C. under Ar was added dropwise 1.0 M $LiAlH_4$ in THF (5.7 mL, 5.72 mmol). The mixture was stirred at room temperature for 2 hours, then distilled water (0.3 mL) was added, followed by 15% NaOH (1 mL), and distilled water (3 mL), and stirred for 15 minutes. The mixture was filtered through celite with $CH_2Cl_2$ and concentrated. Purification of the crude material by column chromatography on silica gel (25:1:1 $CH_2Cl_2$—MeOH—$NH_4OH$) provided 0.1435 g (54%) of COMPOUND 74 as a white solid. $^1$H NMR ($CDCl_3$) δ 1.58-1.62 (m, 4H), 2.01-2.07 (m, 2H), 2.10 (s, 6H), 2.31-2.35 (m, 2H), 2.45 (s, 6H), 3.58 (d, 4H, J=10.8 Hz), 4.36 (s, 2H), 6.57-6.67 (m, 2H), 6.85 (s, 1H), 7.02 (s, 2H), 8.01 (s, 2H). $^{13}$C NMR ($CDCl_3$) δ 18.08, 19.26, 25.84, 29.08, 46.30, 52.52, 62.98, 67.18, 125.22, 125.72, 127.84, 129.13, 131.23, 131.41, 138.04, 138.94, 140.91, 146.94, 157.02. ES-MS m/z 445.5 ($M^+H$). Anal. Calcd. for $C_{28}H_{36}N_4O·0.2CH_2Cl_2·0.3H_2O$: C, 72.53; H, 7.99; N, 12.00. Found: C, 72.91; H, 8.07; N, 11.91.

EXAMPLE 75

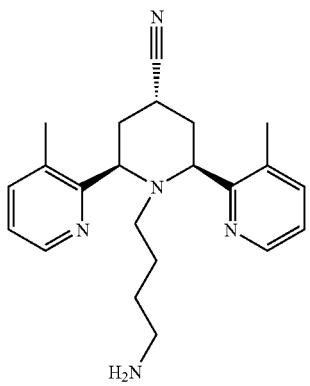

Compound 75: Meso-2'β,4'α,6'β-[1'-(4-amino-butyl)-3,3"-dimethyl-1',2',3',4',5',6'-hexahydro-[2,2';6',2"]terpyridine-4'-carbonitrile]

To a solution of meso-2'β,6'β-[3,3"-dimethyl-2',3',5',6'-tetrahydro-1'H-[2,2';6'2"]terpyridin-4'-one] (1.0760 g, 3.8 mmol) in MeOH (38 mL) under Ar was added $NaBH_4$ (0.3631 g, 9.6 mmol), and stirred at room temperature for 3.5 hours. The mixture was then concentrated, and saturated $NaHCO_3$ (40 mL) was added and extracted with $CH_2Cl_2$ (3×60 mL). The combined organic extracts were dried ($Na_2SO_4$), filtered, and concentrated to provide 1.0466 g (92%) of meso-2'β,4'β,6'β-[3,3"-dimethyl-1',2',3',4',5',6'-hexahydro-[2,2';6'2"]terpyridin-4'-ol] as a: yellow solid. $^1$H NMR ($CDCl_3$) δ 1.43-1.55 (m, 2H), 1.81-1.97 (m, 2H), 2.14-2.18 (m, 2H), 2.36 (s, 6H), 3.97-4.07 (m, 1H), 4.19-4.20 (m, 2H), 7.00-7.07 (m, 2H), 7.38-7.42 (m, 2H), 8.44 (d, 2H, J=6.0 Hz).

To a solution of meso-2'β,4'β,6'β-[3,3"-dimethyl-1',2',3',4',5',6'-hexahydro-[2,2';6'2"]terpyridin-4'-ol] (1.0466 g, 3.48 mmol) in THF (20 mL) were added DIPEA (1.80 mL, 10.44 mmol) and $Boc_2O$ (1.5484 g, 6.96 mmol) in THF (15 mL). The mixture was stirred at 50° C. for 16 hours, then concentrated. Saturated $NaHCO_3$ (40 mL) was added and extracted with $CH_2Cl_2$ (3×60 mL). The combined organic extracts were washed with brine (2×25 mL), dried ($Na_2SO_4$), filtered, and concentrated. Purification of the crude material by column chromatography on silica gel (50:1:1 $CH_2Cl_2$—MeOH—$NH_4OH$) provided 0.8317 g (62%) of meso-2'β,4'β,6'β-[4'-hydroxy-3,3"-dimethyl-3',4',5',6'-tetrahydro-2'H-[2,2';6'2"]terpyridine-1'-carboxylic acid tert-butyl ester]. $^1$H NMR ($CDCl_3$) δ 1.17 (s, 9H), 2.19 (t, 4H, J=6.6 Hz), 2.40 (s, 6H), 4.17-4.20 (m, 1H), 5.38 (t, 2H, J=6.3 Hz), 6.05 (d, 1H, J=10.2 Hz), 6.94-6.98 (m, 2H), 7.34-7.36 (m, 2H), 8.11 (d, 2H, J=3.9 Hz).

To a solution of meso-2'β,4'β,6'β-[4'-hydroxy-3,3"-dimethyl-3',4',5',6'-tetrahydro-2'H-[2,2';6'2"]terpyridine-1'-carboxylic acid tert-butyl ester] (0.8317 g, 2.17 mmol) and $Et_3N$ (0.45 mL, 3.26 mmol) in $CH_2Cl_2$ (22 mL) at 0° C. under Ar was added MsCl (0.20 mL, 2.60 mmol). The mixture was stirred at 0° C. for 30 minutes, then at room temperature for 2 hours, and quenched with saturated $NaHCO_3$ (15 mL) and extracted with $CH_2Cl_2$ (3×50 mL). The combined organic extracts were dried ($Na_2SO_4$), filtered, and concentrated to provide 1.0185 g (100%) of meso-2'β,4'β,6'β-[4'-methanesulfonyloxy-3,3"-dimethyl-3',4',5',6'-tetrahydro-2'H-[2,2';6'2"]terpyridine-1'-carboxylic acid tert-butyl ester] as an orange solid. $^1$H NMR ($CDCl_3$) δ 1.20 (s, 9H), 2.37 (s, 6H), 2.41-2.45 (m, 2H), 2.88-2.99 (m, 2H), 3.07 (s, 3H), 5.07-5.14 (m, 1H), 5.39-5.44 (m, 2H), 6.94-6.98 (m, 2H), 7.33-7.35 (m, 2H), 8.09 (d, 2H, J=6.0 Hz).

To a solution of meso-2'β,4'β,6'β-[4'-methanesulfonyloxy-3,3"-dimethyl-3',4',5',6'-tetrahydro-2'H-[2,2';6'2"]terpyridine-1'-carboxylic acid tert-butyl ester] (1.0185 g, 2.21 mmol) in DMSO (11 mL) was added NaCN (2.2398 g, 44.22 mmol), and stirred at 80° C. for 17 hours. The mixture was concentrated, and saturated $NaHCO_3$ (40 mL) was added and extracted with $CH_2Cl_2$ (3×100 mL). The combined organic extracts were washed with brine (3×40 mL), dried ($Na_2SO_4$), filtered, and concentrated. Purification of the crude material by column chromatography on silica gel (4:1 hexanes-EtOAc, then 100:1:1 $CH_2Cl_2$—MeOH—$NH_4OH$) provided 0.4933 g (57%) of meso-2'β,4'α,6'β-[4'-cyano-3,3"-dimethyl-3',4',5',6'-tetrahydro-2'H-[2,2';6'2"]terpyridine-1'-carboxylic acid tert-butyl ester] as a beige solid. $^1$H NMR ($CDCl_3$) δ 1.56 (s, 9H), 1.97-2.07 (m, 2H), 2.15 (s, 6H), 2.79-2.84 (m, 2H), 5.13-5.23 (m, 1H), 5.74 (s, 2H, J=6.0 Hz), 6.66-6.70 (m, 2H), 7.00 (d, 2H, J=9.0 Hz), 7.94 (d, 2H, J=6.0 Hz).

To a solution of the above nitrile (0.3118 g, 0.79 mmol) in $CH_2Cl_2$ (5 mL) was added TFA (5 mL) and stirred at room temperature for 3 hours, then concentrated. Distilled water (5 mL) and 10 N NaOH (3 mL) were added and extracted with $CH_2Cl_2$ (3×50 mL). The combined organic extracts were dried ($Na_2SO_4$), filtered, and concentrated. Purification of the crude material by column chromatography on silica gel (100:1:1 $CH_2Cl_2$—MeOH—$NH_4OH$) provided 0.1304 g (56%) of meso-2'β,4'α,6'β-[3,3"-dimethyl-1',2',3',4',5',6'-hexahydro-[2,2';6'2"]terpyridine-4'-carbonitrile] as an orange oil. $^1$H NMR (CDCl$_3$) δ 1.92-2.02 (m, 4H), 2.43 (s, 6H), 2.80-2.88 (m, 1H), 3.42 (s, 1H), 4.58-4.61 (m, 2H), 6.98-7.09 (m, 2H), 7.42-7.45 (m, 2H), 8.42 (d, 2H, J=6.0 Hz).

Following the General Procedure A, meso-2'β,4'α,6'β-[3,3"-dimethyl-1',2',3',4',5',6'-hexahydro-[2,2';6'2"]terpyridine-4'-carbonitrile] (0.1304 g, 0.45 mmol), 2-(4-bromo-butyl)-isoindole-1,3-dione (0.1383 g, 0.49 mmol), KI (0.0075 g, 0.05 mmol), DIPEA (0.16 mL, 0.90 mmol), and DMF (5 mL) were stirred at 60° C. for 16 hours. Purification of the crude material by column chromatography on silica gel (100:1:1 $CH_2Cl_2$—MeOH—$NH_4OH$) provided 0.1064 g (48%) of meso-2'β,4'α,6'β-[1'-[4-(1,3-dioxo-1,3-dihydro-isoindol-2-yl)-butyl]-3,3"-dimethyl-1',2',3',4',5',6'-hexahydro-[2,2';6'2"]terpyridine-4'-carbonitrile] as a white solid. $^1$H NMR (CDCl$_3$) δ 0.25-0.27 (m, 2H), 0.77-0.82 (m, 2H), 1.85 (d, 2H, J=14.7 Hz), 2.35 (t, 2H, J=7.5 Hz), 2.50 (s, 6H), 2.54-2.63 (m, 2H), 3.11 (t, 2H, J=7.2 Hz), 3.35-3.36 (m, 1H), 4.57 (d, 2H, J=12.0 Hz), 6.94-6.98 (m, 2H), 7.27-7.29 (m, 2H), 7.71-7.75 (m, 2H), 7.79-7.82 (m, 2H), 8.36 (d, 2H, J=3.0 Hz).

To a solution of meso-2'β,4'α,6'β-[1'-[4-(1,3-dioxo-1,3-dihydro-isoindol-2-yl)-butyl]-3,3"-dimethyl-1',2',3',4',5',6'-hexahydro-[2,2';6'2"]terpyridine-4'-carbonitrile] (0.1064 g, 0.22 mmol) in EtOH (2.2 mL) was added hydrazine monohydrate (0.10 mL, 2.16 mmol) and stirred at room temperature for 16 hours, then concentrated. Purification of the crude material by column chromatography on silica gel (50:1:1, then 30:1:1 $CH_2Cl_2$—MeOH—$NH_4OH$) provided 0.0313 g (39%) of COMPOUND 75 as a colorless oil. $^1$H NMR (CDCl$_3$) δ 0.46-0.48 (m, 2H), 0.63-0.73 (m, 2H), 1.89 (d, 2H, J=13.8 Hz), 2.12 (t, 2H, J=6.9 Hz), 2.26 (t, 2H, J=7.8 Hz), 2.48-2.52 (m, 2H), 2.53 (s, 6H), 2.90-3.10 (bs, 1H), 3.31-3.33 (m, 1H), 4.55 (d, 2H, J=11.1 Hz), 7.09-7.13 (m, 2H), 7.46 (d, 2H, J=7.5 Hz), 8.44 (d, 2H, J=3.9 Hz). $^{13}$C NMR (CDCl$_3$) δ 18.94, 25.19, 27.10, 29.26, 31.27, 41.77, 45.81, 59.61, 122.46, 122.81, 132.75, 138.64, 146.88, 158.33. ES-MS m/z 364.4 (M$^+$H). Anal. Calcd. for $C_{22}H_{29}N_5 \cdot 0.3CH_2Cl_2$: C, 68.86; H, 7.67; N, 18.00. Found: C, 69.22; H, 7.88; N, 18.15.

EXAMPLE 76

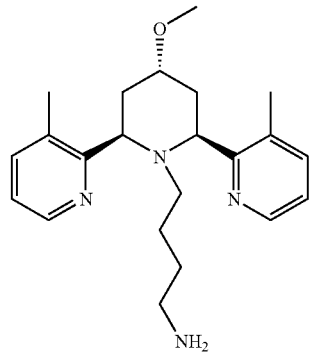

Compound 76: Meso-2'β,4'α,6'β-[4-(4'-methoxy-3,3"-dimethyl-3',4',5',6'-tetrahydro-2'H-[2,2';6',2"]terpyridin-1'-yl)-butylamine To a solution of meso-2'β,6'β-[3,3"-dimethyl-2',3',5',6'-tetrahydro-1'H-[2,2';6'2"]terpyridin-4'-one] (3.5417 g, 12.6 mmol) in THF (90 mL) under Ar at −78° C. was slowly added L-selectride (13.8 mL, 13.8 mmol), and was stirred for 30 minutes (*Tetrahedron: Asymmetry* (1999) 10:2225-2235). MeOH (35 mL) was added, and at room temperature distilled water (70 mL) was added and extracted with $CH_2Cl_2$ (3×150 mL). The combined organic extracts were dried ($Na_2SO_4$), filtered, and concentrated to provide 5.37 g (100%) of a 1:1 mixture of meso-2'β,4'β,6'β-[3,3"-dimethyl-1',2',3',4',5',6'-hexahydro-[2,2';6'2"]terpyridin-4'-ol] and meso-2'β,4'α,6'β-[3,3"-dimethyl-1',2',3',4',5',6'-hexahydro-[2,2';6'2"]terpyridin-4'-ol] as a sticky orange oil. $^1$H NMR (CDCl$_3$) δ 1.43-1.55 (m, 2H), 1.81-1.97 (m, 2H), 2.14-2.18 (m, 2H), 2.36 (s, 6H), 3.97-4.07 (m, 1H), 4.19-4.20 (m, 2H), 7.00-7.07 (m, 2H), 7.38-7.42 (m, 2H), 8.44-8.45 (m, 2H).

To a solution of a 1:1 mixture of meso-2'β,4'β,6'β-[3,3"-dimethyl-1',2',3',4',5',6'-hexahydro-[2,2';6'2"]terpyridin-4'-ol] and meso-2'β,4'α,6'β-[3,3"-dimethyl-1',2',3',4',5',6'-hexahydro-[2,2';6'2"]terpyridin-4'-ol] in THF (90 mL) was added DIPEA (4.36 mL, 25.2 mmol) and Boc$_2$O (3.3407 g, 15.1 mmol) and stirred at 50° C. for 16 hours. The mixture was concentrated, and saturated $NaHCO_3$ (75 mL) was added and extracted with $CH_2Cl_2$ (3×100 mL). The combined organic extracts were washed with brine (2×75 mL), dried ($Na_2SO_4$), filtered, and concentrated. Purification of the crude material by column chromatography on silica gel (1:1 hexanes-EtOAc) provided 1.2984 g (27%) of meso-2'β,4'β,6'β-[4'-hydroxy-3,3"-dimethyl-3',4',5',6'-tetrahydro-2'H-[2,2';6'2"]terpyridine-1'-carboxylic acid tert-butyl ester as a yellow solid and 0.8605 g (18%) of meso-2'β,4'α,6'β-[4'-hydroxy-3,3"-dimethyl-3',4',5',6'-tetrahydro-2'H-[2,2';6'2"]terpyridine]-1'-carboxylic acid tert-butyl ester a pale yellow solid. $^1$H NMR (CDCl$_3$) δ 1.17 (s, 9H), 2.19 (t, 4H, J=6.6 Hz), 2.40 (s, 6H), 4.17-4.20 (m, 1H), 5.38 (t, 2H, J=6.3 Hz), 6.05 (d, 1H, J=10.2 Hz), 6.94-6.98 (m, 2H), 7.34-7.36 (m, 2H), 8.11 (d, 2H, J=3.9 Hz) and $^1$H NMR (CDCl$_3$) δ 1.50 (s, 9H), 1.67-1.76 (m, 2H), 2.21 (s, 6H), 2.69-2.76 (m, 2H), 5.62-5.67 (m, 1H), 5.80-5.83 (m, 2H), 6.68-6.72 (m, 2H), 6.97-7.05 (m, 2H), 7.99 (d, 2H, J=3 Hz), respectively.

To a solution of meso-2'β,4'α,6'β-[4'-hydroxy-3,3''-dimethyl-3',4',51,6'-tetrahydro-2'H-[2,2';6'2'']terpyridine]-1'-carboxylic acid tert-butyl ester (0.1427 g, 0.37 mmol) in THF (4 mL) was added 60% NaH in mineral oil (0.0224 g, 0.56 mmol) and stirred at room temperature for 1 hour. MeI (0.05 mL, 0.75 mL) was added and stirred for 16 hours, and concentrated. Purification of the crude material by column chromatography on silica gel (NH$_4$OH saturated Et$_2$O) provided 0.1034 g (70%) of meso-2'β,4'α,6'β-[4'-methoxy-3,3''-dimethyl-1',2',3',4',5',6'-hexahydro-[2,2';6'2'']terpyridine] as a yellow oil. $^1$H NMR (CDCl$_3$) δ 1.35 (s, 9H), 1.69-1.78 (m, 2H), 2.29 (s, 6H), 2.64-2.72 (m, 2H), 3.44-3.51 (m, 3H), 4.79-4.83 (m, 1H), 5.66 (t, 2H, J=4.5 Hz), 6.78-6.82 (m, 2H), 7.15 (d, 2H, J=9.0 Hz), 8.06 (d, 2H, J=3.0 Hz).

To a solution of meso-2'β,4'α,6'β-[4'-methoxy-3,3''-dimethyl-1',2',3',4',5',6'-hexahydro-[2,2';6'2'']terpyridine] (0.1236 g, 0.31 mmol) in CH$_2$Cl$_2$ (3 mL) was added TFA (3 mL), and stirred at room temperature for 2.5 hours. The mixture was concentrated, and distilled water (2 mL) and 10 N NaOH (3 mL) were added and extracted with CH$_2$Cl$_2$ (3×15 mL). The combined organic extracts were dried (Na$_2$SO$_4$), filtered, and concentrated to provide 0.0666 g (72%) of meso-2'β,4'α,6'β-[4'-methoxy-3,3''-dimethyl-1',2',3',4',5',6'-hexahydro-[2,2';6'2'']terpyridin] as a yellow oil. $^1$H NMR (CDCl$_3$) δ 1.73-1.82 (m, 4H), 2.03-2.07 (m, 1H), 2.39 (s, 6H), 3.49 (s, 3H), 3.92-3.94 (m, 1H), 4.61 (d, 2H, J=12.0 Hz), 7.01-7.05 (m, 2H), 7.39 (d, 2H, J=6.0 Hz), 8.44 (d, 2H, J=6.0 Hz).

To a solution of meso-2'β,4'α,6'β-[4'-methoxy-3,3''-dimethyl-1',2',3',4',5',6'-hexahydro-[2,2';6'2'']terpyridin] (0.0666 g, 0.22 mmol) in DMF (3 mL) was added 2-(4-bromo-butyl)-isoindole-1,3-dione, KI (0.0033 g, 0.02 mmol), and DIPEA (0.08 mL, 0.44 mmol), and was stirred at 60° C. for 24 hours. The reaction mixture was concentrated, and saturated NaHCO$_3$ (5 mL) was added and extracted with CH$_2$Cl$_2$ (3×20 mL). The combined organic extracts were washed with brine (2×15 mL), dried (Na$_2$SO$_4$), filtered, and concentrated. Purification of the crude material by column chromatography on silica gel (50:1:1 CH$_2$Cl$_2$—MeOH—NH$_4$OH) provided 0.1006 g (92%) of meso-2'β,4'α,6'β-[2-[4-(4'-methoxy-3,3''-dimethyl-3',4',5',6'-tetrahydro-2'H-[2,2';6',2'']terpyridin-1'-yl)-butyl]-isoindole-1,3-dione] as a white sticky foam.

To a solution of meso-2'β,4'α,6'β-[2-[4-(4'-methoxy-3,3''-dimethyl-3',4',5',6'-tetrahydro-2'H-[2,2';6',2'']terpyridin-1'-yl)-butyl]-isoindole-1,3-dione] (0.1006 g, 0.20 mmol) in EtOH (2 mL) was added hydrazine monohydrate (0.1 mL, 2.02 mmol), and stirred at room temperature for 16 hours. The reaction mixture was concentrated, and purification of the crude material by column chromatography on silica gel (50:1:1 then 25:1:1 CH$_2$Cl$_2$—MeOH—NH$_4$OH) provided 0.0471 g (60%) of COMPOUND 76 as a colorless oil. $^1$H NMR (CDCl$_3$) δ 0.40-0.42 (m, 2H), 0.62-0.71 (m, 2H), 1.88 (d, 2H, J=13.5 Hz), 2.09-2.13 (m, 2H), 2.45-2.40 (m, 4H), 2.53 (s, 6H), 3.39 (s, 3H), 3.82 (s, 1H), 4.57 (d, 2H, J=12.0 Hz), 7.04-7.08 (m, 2H), 7.41 (d, 2H, J=7.5 Hz), 8.42 (d, 2H, J=3.9 Hz). $^{13}$C NMR (CDCl$_3$) δ 19.07, 25.21, 31.12, 31.36, 41.82, 45.66, 56.39, 57.65, 75.10, 122.26, 132.79, 138.31, 146.69, 160.04. ES-MS m/z 369.4 (M$^+$H). Anal. Calcd. for C$_{22}$H$_{32}$N$_4$O.0.1CH$_2$Cl$_2$.1.0H$_2$O: C, 67.20; H, 8.73; N, 14.18. Found: C, 67.46; H, 8.80; N, 14.07.

EXAMPLE 77

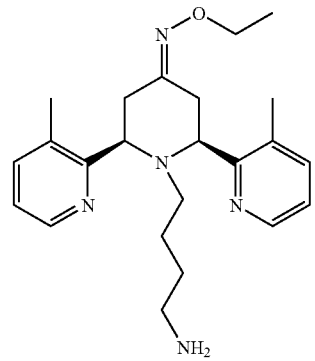

Compound 77: Meso-2'β,6'β-[1'-(4-amino-butyl)-3,3''-dimethyl-2',3',5',6'-tetrahydro-1'H-[2,2';6',2''] terpyridin-4'-one O-ethyl-oxime]

To a solution of meso-2'β,6'β-[3,3''-dimethyl-2',3',5',6'-tetrahydro-1' H-[2,2';6'2'']terpyridin-4'-one] (0.3065 g, 1.1 mmol) in MeOH (22 mL) was added O-ethylhydroxylamine hydrochloride and stirred at room temperature for 24 hours. Saturated NaHCO$_3$ was added, extracted with CH$_2$Cl$_2$ (3×30 mL), and the combined organic extracts were dried (Na$_2$SO$_4$), filtered, and concentrated to provide 0.4528 g (100%) of meso-2'β,6'β-[3,3''-dimethyl-2',3',5',6'-tetrahydro-1'H-[2,2';6',2'']terpyridin-4'-one O-ethyl-oxime] as a yellow oil. $^1$H NMR (CDCl$_3$) δ 1.27 (t, 3H, J=7.5 Hz), 1.71 (s, 1H), 2.10-2.18 (m, 1H), 2.39 (s, 6H), 2.43-2.53 (m, 2H), 3.30-3.41 (m, 1H), 3.44-3.49 (m, 1H), 4.09-4.16 (m, 2H), 4.28-4.35 (m, 2H), 7.05-7.09 (m, 2H), 7.43 (d, 2H, J=9.0 Hz), 8.46 (d, 2H, J=6.0 Hz).

To a solution of meso-2'β,6'β-[3,3''-dimethyl-2',3',5',6'-tetrahydro-1'H-[2,2';6',2'']terpyridin-4'-one O-ethyl-oxime] (0.4528 g, 1.40 mmol) in DMF (14 mL) was added 2-(4-bromo-butyl)-isoindole-1,3-dione (0.4329 g, 1.54 mmol), KI (0.0232 g, 0.14 mmol), and DIPEA (0.49 mL, 2.80 mmol), and was stirred at 60° C. for 20 hours. The reaction mixture was concentrated, and saturated NaHCO$_3$ (15 mL) was added and extracted with CH$_2$Cl$_2$ (3×40 mL). The combined organic extracts were dried (Na$_2$SO$_4$), filtered, and concentrated. Purification of the crude material by column chromatography on silica gel (4:1 hexanes-EtOAc) provided 0.2813 g of meso-2'β,6'β-[2-[4-(4'-ethoxyimino-3,3''-dimethyl-3',4',5',6'-tetrahydro-2'H-[2,2';6',2'']terpyridin-1'-yl)-butyl]-isoindole-1,3-dione] as a yellow foam.

To a solution of meso-2'β,6'β-[2-[4-(4'-ethoxyimino-3,3''-dimethyl-3',4',5',6'-tetrahydro-2'H-[2,2';6',2'']terpyridin-1'-yl)-butyl]-isoindole-1,3-dione] (0.2813 g, 0.54 mmol) in EtOH (5 mL) was added n-butyl amine (0.53 mL, 5.35 mmol), and was stirred at 80° C. for 16 hours before it was concentrated. Purification of the crude material by column chromatography on silica gel (50:1:1 then 15:1:1 CH$_2$Cl$_2$—MeOH—NH$_4$OH) provided 0.1325 g (23% over 2 steps) of COMPOUND 77 as a pale yellow oil. $^1$H NMR (CDCl$_3$) δ 0.22-0.25 (bs, 2H), 0.58-0.63 (m, 2H), 1.23 (t, 3H, J=6.9 Hz), 2.04 (t, 2H, J=6.6 Hz), 2.33-2.44 (m, 3H), 2.51 (s, 6H), 2.77-2.87 (m, 1H), 3.09-3.29 (m, 2H), 4.04-4.10 (m, 2H), 4.28-4.38 (m, 2H), 7.09-7.11 (m, 2H), 7.43 (d, 2H, J=7.2 Hz), 8.41-8.42 (m, 2H). $^{13}$C NMR (CDCl$_3$) δ 14.88, 18.75, 26.22, 31.04, 32.01, 41.68, 42.60, 63.32, 64.49, 69.00, 122.34, 122.71, 133.11, 133.25, 137.88, 138.25, 146.44, 146.50, 157.83, 157.87, 159.50. ES-MS m/z 396.4 (M$^+$H). Anal. Calcd. for C$_{23}$H$_{33}$N$_5$O·0.7H$_2$O: C, 67.68; H, 8.49; N, 17.16. Found: C, 67.74; H, 8.37; N, 16.98.

EXAMPLE 78

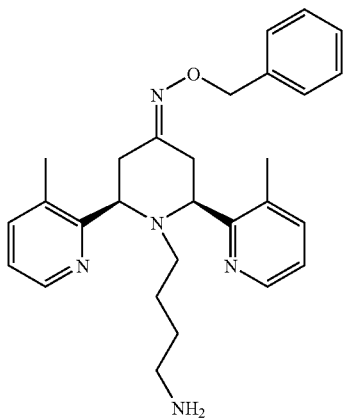

Compound 78: Meso-2'β,6'β-[1'-(4-amino-butyl-3,3"-dimethyl-2',3',5',6'-tetrahydro-1'H-[2,2';6',2"]terpyridin-4'-one O-benzyl-oxime]

To a solution of meso-2'β,6'β-[3,3"-dimethyl-2',3',5',6'-tetrahydro-1'H-[2,2';6'2"]terpyridin-4'-one] (0.2902 g, 1.0 mmol) in MeOH (20 mL) was added O-benzylhydroxylamine hydrochloride (0.1811 g, 1.1 mmol) and stirred at room temperature for 22 hours. Saturated NaHCO$_3$ (15 mL) was added, extracted with CH$_2$Cl$_2$ (3×40 mL), and the combined organic extracts were dried (Na$_2$SO$_4$), filtered, and concentrated to provide 0.4358 g (100%) of meso-2'β,6'β-[3,3"-dimethyl-2',3',5',6'-tetrahydro-1'H-[2,2';6',2"]terpyridin-4'-one O-benzyl-oxime] as a yellow oil. $^1$H NMR (CDCl$_3$) δ 2.13-2.21 (m, 1H), 2.37 (s, 6H), 2.40-2.59 (m, 2H), 3.22 (bs, 1H), 3.49-3.54 (m, 1H), 4.30 (d, 2H, J=22.8 Hz), 5.13 (s, 2H), 7.06-7.09 (m, 2H), 7.32-7.43 (m, 7H), 8.45 (d, 2H, J=6.0 Hz).

To a solution of meso-2'β,6'β-[3,3"-dimethyl-2',3',5',6'-tetrahydro-1'H-[2,2';6',2"]terpyridin-4'-one O-benzyl-oxime] (0.4358 g, 1.13 mmol) in DMF (11 mL) was added 2-(4-bromo-butyl)-isoindole-1,3-dione (0.3498 g, 1.24 mmol), KI (0.0188 g, 0.11 mmol), and DIPEA (0.39 mL, 2.26 mmol), and was stirred at 60° C. for 19 hours. The reaction mixture was concentrated, and saturated NaHCO$_3$ (15 mL) was added and extracted with CH$_2$Cl$_2$ (3×40 mL). The combined organic extracts were dried (Na$_2$SO$_4$), filtered, and concentrated. Purification of the crude material by column chromatography on silica gel (4:1 hexanes-EtOAc) provided 0.4436 g of meso-2'β,6'β-[2-[4-(4'-benzyloxyimino-3,3"-dimethyl-3',4',5',6'-tetrahydro-2'H-[2,2';6',2"]terpyridin-1'-yl)-butyl]-isoindole-1,3-dione] as an orange foam.

To a solution of meso-2'β,6'β-[2-[4-(4'-benzyloxyimino-3,3"-dimethyl-3',4',5',6'-tetrahydro-2'H-[2,2';6',2"]terpyridin-1'-yl)-butyl]-isoindole-1,3-dione] (0.4436 g, 0.75 mmol) in EtOH (8 mL) was added n-butyl amine (0.75 mL, 7.55 mmol), and was stirred at 80° C. for 16 hours before it was concentrated. Purification of the crude material by column chromatography on silica gel (50:1:1 then 20:1:1 CH$_2$Cl$_2$—MeOH—NH$_4$OH) provided 0.1276 g (24% over 2 steps) of COMPOUND 78 as a pale yellow oil. $^1$H NMR (CDCl$_3$) δ 0.19-0.22 (bs, 2H), 0.56-0.66 (m, 2H), 2.04 (t, 2H, J=6.9 Hz), 2.36-2.46 (m, 3H), 2.51 (s, 6H), 2.87 (t, 1H, J=13.2 Hz), 3.16 (t, 1H, J=13.8 Hz), 3.32 (d, 1H, J=14.4 Hz), 4.27-4.39 (m, 2H), 5.08 (s, 2H), 7.08-7.12 (m, 2H), 7.28-7.44 (m, 7H), 8.41 (d, 2H, J=4.2 Hz). $^{13}$C NMR (CDCl$_3$) δ 18.83, 25.75, 27.15, 31.14, 32.76, 41.75, 43.58, 62.91, 64.20, 75.69, 122.78, 127.97, 128.44, 128.63, 130.31, 132.91, 133.01, 138.41, 146.66, 146.71, 157.95, 160.30. ES-MS m/z 458.4 (M$^+$H). Anal. Calcd. for C$_{28}$H$_{35}$N$_5$O·0.9H$_2$O: C, 70.98; H, 7.83; N, 14.78. Found: C, 70.87; H, 7.62; N, 14.58.

EXAMPLE 79

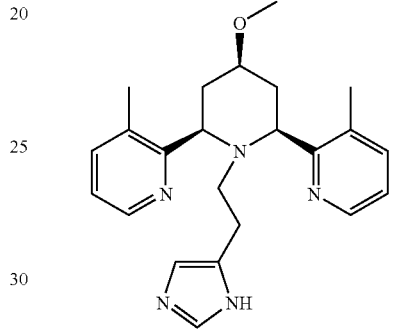

Compound 79: Meso-2'β,4'β,6'β-{1'-[2-(3H-imidazol-4-yl)-ethyl]-4'-methoxy-3,3"-dimethyl-1' 2',3,4',5',6'-hexahydro-[2,2';6',2"]terpyridine To a solution of meso-2'β,6'β-[3,3"-dimethyl-2',3',5',6'-tetrahydro-1'H-[2,2';6'2"]terpyridin-4'-one] (1.0760 g, 3.8 mmol) in MeOH (38 mL) under Ar was added NaBH$_4$ (0.3631 g, 9.6 mmol), and stirred at room temperature for 3.5 hours. The mixture was then concentrated, and saturated NaHCO$_3$ (40 mL) was added and extracted with CH$_2$Cl$_2$ (3×60 mL). The combined organic extracts were dried (Na$_2$SO$_4$), filtered, and concentrated to provide 1.0466 g (92%) of meso-2'β,4'β,6'β-[3,3"-dimethyl-1',2',3',4',5',6'-hexahydro-[2,2';6'2"]terpyridin-4'-ol] as a yellow solid. $^1$H NMR (CDCl$_3$) δ1.43-1.55 (m, 2H), 1.81-1.97 (m, 2H), 2.14-2.18 (m, 2H), 2.36 (s, 6H), 3.97-4.07 (m, 1H), 4.19-4.20 (m, 2H), 7.00-7.07 (m, 2H), 7.38-7.42 (m, 2H), 8.44 (d, 2H, J=6.0 Hz).

To a solution of meso-2'β,4'β,6'β-[3,3"-dimethyl-1',2',3',4',5',6'-hexahydro-[2,2';6'2"]terpyridin-4'-ol] (1.0466 g, 3.48 mmol) in THF (20 mL) were added DIPEA (1.80 mL, 10.44 mmol) and Boc$_2$O (1.5484 g, 6.96 mmol) in THF (15 mL). The mixture was stirred at 50° C. for 16 hours, then concentrated. Saturated NaHCO$_3$ (40 mL) was added and extracted with CH$_2$Cl$_2$ (3×60 mL). The combined organic extracts were washed with brine (2×25 mL), dried (Na$_2$SO$_4$), filtered, and concentrated. Purification of the crude material by column chromatography on silica gel (50:1:1 CH$_2$Cl$_2$—MeOH—NH$_4$OH) provided 0.8317 g (62%) of meso-2'β,4'β,6'β-[4'-hydroxy-3,3"-dimethyl-3',4',5',6'-tetrahydro-2'H-[2,2';6'2"]terpyridine-1'-carboxylic acid tert-butyl ester]. $^1$H NMR (CDCl$_3$) δ 1.17 (s, 9H), 2.19 (t, 4H, J=6.6 Hz), 2.40 (s, 6H), 4.17-4.20 (m, 1H), 5.38 (t, 2H, J=6.3 Hz), 6.05 (d, 1H, J=10.2 Hz), 6.94-6.98 (m, 2H), 7.34-7.36 (m, 2H), 8.11 (d, 2H, J=3.9 Hz).

To a solution of meso-2'β,4'α,6'β-[4'-hydroxy-3,3''-dimethyl-3',4',5',6'-tetrahydro-2'H-[2,2';6'2'']terpyridine]-1'-carboxylic acid tert-butyl ester (0.5194 g, 1.36 mmol) in DMF (5 mL) was added 60% NaH in mineral oil (0.0816 g, 2.04 mmol) and stirred at room temperature for 1 hour. MeI (0.17 mL, 2.72 mL) was added and stirred for 3.5 hours, and concentrated. Purification of the crude material by column chromatography on silica gel (50:1:1 CH$_2$Cl$_2$—MeOH—NH$_4$OH) provided 0.4289 g (79%) of meso-2'β,4'β,6'β-[4'-methoxy-3,3''-dimethyl-1',2',3',4',5',6'-hexahydro-[2,2';6'2'']terpyridine] as a beige solid. ES-MS m/z 398.3 (M$^+$H).

To a solution of the above material (0.2435 g, 0.82 mmol) in DMF (8 mL) were added 5-(2-chloro-ethyl)-1H-imidazole (0.1606 g, 1.23 mmol), DIPEA (0.29 mL, 1.64 mmol), and KI (0.0133 g, 0.08 mmol) and stirred at 80° C. for 48 hours. The mixture was concentrated and saturated NaHCO$_3$ (15 mL) was added and extracted with CH$_2$Cl$_2$ (3×30 mL). The combined organic extracts were washed with brine (2×30 mL), dried (Na$_2$SO$_4$), filtered, and concentrated. Purification of the crude material by column chromatography on silica gel (25:1:1 CH$_2$Cl$_2$—MeOH—NH$_4$OH) followed by another column (50:1:1 CH$_2$Cl$_2$—MeOH—NH$_4$OH) provided 39.9 mg (11%) of COMPOUND 79 as a light beige solid. $^1$H NMR (CDCl$_3$) δ 1.74 (s, 1H), 2.03-2.05 (m, 4H), 2.41 (s, 6H), 2.50-2.52 (m, 2H), 2.63 (s, 1H), 3.35 (s, 3H), 3.49-3.50 (m, 1H), 4.04-4.05 (m, 2H), 6.11 (s, 1H), 7.04-7.06 (m, 2H), 7.33 (s, 1H), 7.39 (d, 2H, J=6.9 Hz), 8.35-8.36 (m, 2H). $^{13}$C NMR (CDCl$_3$) 19.08, 23.69, 36.45, 49.86, 55.70, 62.59, 68.86, 118.64, 122.62, 131.69, 134.50, 139.08, 140.32, 147.05, 159.35. ES-MS m/z 392.2 (M$^+$H). Anal. Calcd. for C$_{23}$H$_{29}$N$_5$O.0.4CH$_2$Cl$_2$: C, 66.06; H, 7.06; N, 16.46. Found: C, 66.38; H, 7.31; N, 16.32.

EXAMPLE 80

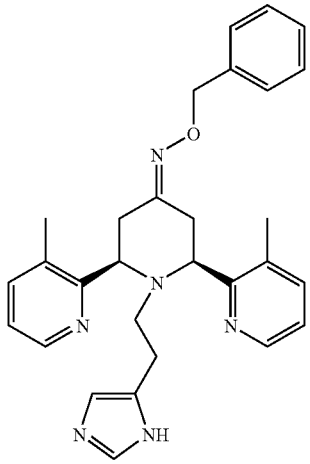

Compound 80: Meso-2'β,6'β-{1'-[2-(3H-imidazol-4-yl)-ethyl]-3,3''-dimethyl-2',3',5',6'-tetrahydro-1'H-[2,2';6',2'']terpyridin-4'-one O-benzyl-oxime}

To a solution of meso-2'β,6'β-[3,3''-dimethyl-2',3',5',6'-tetrahydro-1'H-[2,2';6',2'']terpyridin-4'-one O-benzyl-oxime] (0.1449 g, 1.11 mmol) in DMF (7 mL) was added 5-(2-chloro-ethyl)-1H-imidazole (0.0966 g, 0.74 mmol), KI (0.0123 g, 0.07 mmol), and DIPEA (0.25 mL, 1.48 mmol), and was stirred at 80° C. for 19 hours. The reaction mixture was concentrated, and saturated NaHCO$_3$ (15 mL) was added and extracted with CH$_2$Cl$_2$ (3×30 mL). The combined organic extracts were washed with brine (2×25 mL), dried (Na$_2$SO$_4$), filtered, and concentrated. Purification of the crude material by column chromatography on silica gel (100:1:1 then 10:1:1 CH$_2$Cl$_2$—MeOH—NH$_4$OH) followed by radial chromatography (25:1:1 CH$_2$Cl$_2$—MeOH—NH$_4$OH) provided 19.6 mg (5%) of COMPOUND 80 as a yellow oil. $^1$H NMR (CDCl$_3$) δ 1.58-1.59 (m, 1H), 2.39-2.43 (m, 2H), 2.44 (s, 6H), 2.68 (t, 2H, J=7.5 Hz), 2.84 (t, 1H, J=12.3 Hz), 3.10 (t, 1H, J=12.3 Hz), 3.30 (d, 1H, J=14.7 Hz), 4.22-4.33 (m, 2H), 5.08 (s, 2H), 6.13 (s, 1H), 7.09 (t, 2H, J=6.3 Hz), 7.27-7.34 (m, 7H), 7.42 (d, 2H, J=7.5 Hz), 8.40-8.41 (m, 2H). $^{13}$C NMR (CDCl$_3$) δ 18.94, 25.27, 28.56, 34.04, 46.33, 63.05, 64.34, 75.79, 119.70, 122.96, 128.07, 128.46, 128.69, 132.54, 132.68, 134.42, 138.37, 138.83, 146.90, 158.01, 159.27. ES-MS m/z 481.5 (M$^+$H). Anal. Calcd. for C$_{29}$H$_{32}$N$_6$O.0.4H$_2$O.0.3CH$_2$Cl$_2$: C, 68.56; H, 6.56; N, 16.37. Found: C, 68.87; H, 6.53; N, 16.65.

EXAMPLE 81

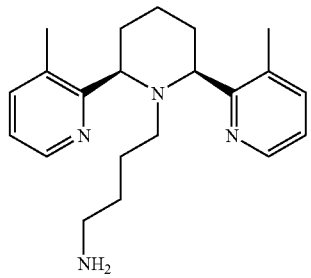

2-(4-Bromo-butyl)-isoindole-1,3-dione

To a hot solution (90° C.) of dibromobutane (1.50 kg, 6.95 mol) in dimethylformamide (1.7 L) was added potassium phthalimide (329 g, 1.74 mol). The solution was stirred at 90° C. for 5 hours. The solution was cooled to room temperature prior to the addition of water (900 mL). The layers were separated and the aqueous layer was extracted with CH$_2$Cl$_2$ (2×500 mL). The combined organic portions were washed with a saturated aqueous solution of NaHCO$_3$ (1.0 L). The organic layer was dried (MgSO$_4$) and concentrated under reduced pressure. Hexane (3.0 L) was added to the residue and the solid (mostly diphthalimide side product) was filtered. Hexane (1.0 L) was added to the filtrate and the resulting mixture was placed at −20° C. for 1.5 hours. the precipitate was filtered and dried under vacuum to afford 285 g (58%) of 2-(4-bromo-butyl)-isoindole-1,3-dione as white solid. $^1$H NMR (CDCl$_3$) δ 1.75-7.95 (m, 4H), 3.44 (t, 2H, J=6.5 Hz), 3.71 (t, 2H, J=6.5 Hz), 7.65-7.75 (m, 2H), 7.80-7.90 (m, 2H). $^{13}$C NMR (CDCl$_3$) δ 27.64, 30.22, 33.26, 37.35, 123.68, 132.42, 134.42, 168.79.

4-(3,3''-Dimethyl-3',4',5',6'-tetrahydro-2'H-cis-[2,2'; 6',2'']terpyridin-1'-yl)-butylamine To a solution of 3-methyl-pyridine-2-carbaldehyde (19.4 g, 160 mmol) in MeOH (200 mL) was added NH$_4$OAc (9.27 g, 120 mmol) followed by the slow addition (a period of approx. 15 minutes) of 1,3-acetonedicarboxylic acid (11.7 g, 80.2 mmol). After the vigorous bubbling subsided, the solution was allowed to stir for 1.5 hour. The solvent was then removed under reduced pressure and CH$_2$Cl$_2$ (300 mL) and saturated aqueous solution of Na$_2$CO$_3$ (200 mL) were added.

The layers were separated and the aqueous phase extracted with CH$_2$Cl$_2$ (2×300 mL). The combined organic extracts were dried (MgSO$_4$) and concentrated under reduced pressure. The crude product was purified by chromatography on silica gel (1:1 EtOAc:hexane, slowly increased gradient to 100% EtOAc). The fractions containing the desired product were concentrated under reduced pressure. The residue was recrystallized in EtOAc to provide 9.25 g, (41%) of 3,3"-dimethyl-2',3',5',6'-tetrahydro-1'H-[2,2';6',2"]terpyridin-4'-one as yellow solid. $^1$H NMR (CDCl$_3$) δ 2.37 (s, 6H), 2.50-2.60 (m, 2H), 2.75-2.90 (m, 2H), 3.37 (t, 1H, J=12.5 Hz), 4.40-4.55 (m, 2H), 7.10 (dd, 2H, J=7.6, 4.8 Hz), 7.44 (d, 2H, J=7.6 Hz), 8.47 (br d, 2H).

To a solution of 3,3"-dimethyl-2',3',5',6'-tetrahydro-1'H-[2,2';6',2"]terpyridin-4'-one (9.6 g, 34.1 mmol) in diethylene glycol (170 mL) was added hydrazine monohydrate (90 mL, 2.89 mol) and potassium hydroxide pellets (57.4 g, 1.02 mol) and the reaction stirred at 125° C. for 2 hours. 50 mL of hydrazine distilled off and water (200 mL) was added the remaining mixture. The solution was extracted with CH$_2$Cl$_2$ (4×300 mL). The combined organic extracts were dried (MgSO$_4$) and concentrated under reduced pressure. The residue was dissolved in EtOAc (500 mL) and washed with a saturated solution of NaHCO3 (3×100 mL) to remove the residual diethylene glycol. The organic extract was dried (MgSO$_4$) and concentrated under reduced pressure to afford 8.82 g (97%) of 3,3"-dimethyl-1',2',3',4',5',6'-hexahydro-[2,2';6',2"]terpyridine as yellow solid. $^1$H NMR (CDCl$_3$) δ 1.50-1.65 (m, 2H), 1.75-1.95 (m, 3H), 2.13 (m, 1H), 2.37 (s, 6H), 3.09 (br t, 1H), 4.15-4.25 (m, 2H), 7.02 (dd, 2H, J=7.5, 4.8 Hz) 7.38 (d, 2H, J=7.5 Hz), 8.46 (br d, 2H).

A solution of 3,3"-dimethyl-1',2',3',4',5',6'-hexahydro-[2,2';6',2"]terpyridine (17.3 g, 64.7 mmol), 2-(4-bromo-butyl)-isoindole-1,3-dione (20.1 g, 71.2 mmol), potassium iodide (1.08 g, 6.47 mmol), and diisopropylethylamine (22.5 mL, 129 mmol) in acetonitrile (650 mL) was stirred at 60° C. for 19.5 hours. The mixture was concentrated under reduced pressure. The residue was purified by chromatography on silica gel (90:10:1 diethylether: methanol: ammonium hydroxide and slowly increased amount of methanol to 80:20:1). The fractions containing the desired product were concentrated, dissolved in ethanol (300 mL), and treated with hydrazine hydrate (30 mL). The solution was stirred at 50° C. for 17.5 hours. The mixture was filtered through a glass frit and concentrated in vacuo. The residue was taken up in CH$_2$Cl$_2$ (200 mL) and was washed with 1N aqueous sodium hydroxide (80 mL). The layers were separated and the aqueous layer was extracted with CH$_2$Cl$_2$ (3×150 mL). The combined organic extracts were dried (MgSO$_4$) and concentrated under reduced pressure. The residue was then purified by chromatography on silica gel (85:15:1 diethylether: methanol: ammonium hydroxide and slowly increased to 50:50:1). The product was dissolved in CH$_2$Cl$_2$ (150 mL) and was filtered on a glass frit to remove all silica carried from the column. The filtrate was concentrated to afford 14.2 g of material that was redissolved in methanol (45 mL). A solution of methanol (20 mL) saturated with HCl was added and the resulting mixture was stirred for 15 minutes. The solution was added dropwise to 1.5 L of diethylether. The solid was carefully filtrated under an atmosphere of N$_2$ to afford 11.7 g (35% over 3 steps) of 4-(3,3"-dimethyl-3',4',5',6'-tetrahydro-2'H-cis-[2,2';6',2"]terpyridin-1'-yl)-butylamine as a yellow solid. $^1$H NMR (D$_2$O) δ 1.10-1.2 (m, 2H), 1.25-1.40 (m, 2H), 1.40-1.60 (m, 2H), 1.70 (m, 1H), 1.95 (m, 1H), 2.05-2.20 (m, 2H), 2.20-2.30 (m, 2H), 2.59 (s, 6H), 2.65-2.80 (m, 2H), 4.55-4.65 (m, 2H), 7.85-7.95 (m, 2H), 8.42 (d, 2H, J=8.0 Hz), 8.67 (d, 2H, J=5.5 Hz) $^{13}$C NMR (CDCl$_3$) δ 17.2, 20.2, 22.5, 25.1, 32.6, 39.4, 52.4, 57.9, 126.0, 136.9, 139.8, 149.6, 154.5; ES-MS m/z 339.4 (M$^+$H). Anal. Calcd. for C$_{21}$H$_{30}$N$_4$.3.3HCl.2.9H$_2$O: C, 49.35; H, 7.71; N, 10.96; Cl, 22.89. Found: C, 49.61; H, 7.45; N, 10.90; Cl, 22.67.

EXAMPLE 82

Cyclocondensation Formation of (2S, 6R)-4-oxo-2,6-diphenylpiperidine

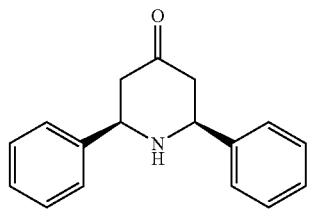

To a solution of benzaldehyde (21.20 g, 200 mmol) in methanol (800 mL) was added ammonium acetate (8.47 g, 110 mmol) followed by the slow addition (over a period of approx. 20 minutes, controlling gas evolution) of 1,3-acetonedicarboxylic acid (14.60 g, 100 mmol). After the vigorous bubbling subsided, the solution was allowed to stir for 2 hours. The solvent was then removed under reduced pressure and CH$_2$Cl$_2$ (500 mL) and saturated aqueous solution of Na$_2$CO$_3$ (300 mL) was added. The layers were separated and the aqueous phase extracted with CH$_2$Cl$_2$ (2×400 mL). The combined organic extracts were dried over anhydrous MgSO$_4$ and were concentrated under reduced pressure. The crude product was purified by silica gel flash column chromatography (3:1 EtOAc: hexanes as an eluent, with 1:1 EtOAc: hexanes used to elute the product). The fractions containing the desired product were concentrated under reduced pressure to give the desired 4-oxo-2,6-diphenylpiperidine (10.3 g, 41%) as a yellow oil. The spectral data was consistent with that of the literature values (Pandiarajan, K., et al., *Indian J. Chem. Sect. B.* (1987) 26B:624-627). $^1$H NMR (CDCl$_3$) δ 1.83 (br s, 1H, NH), 2.30 (m, 2H), 2.43 (m, 2H), 4.22 (dd, 2H, J=3.9, 10.8 Hz), 7.39 (m, 10H).

EXAMPLE 83

Cyclocondensation Formation of (2S, 6R)-4-oxo-2,6-di-(pyridin-4-yl)-piperidine

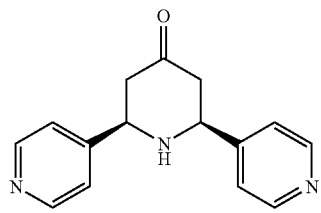

To a solution of 4-pyridine carboxaldehyde (3.21 g, 30.0 mmol) in methanol (60 mL) was added ammonium acetate (1.27 g, 16.5 mmol) followed by the slow addition (over 10 minutes) of 1,3-acetonedicarboxylic acid (2.19 g, 15 mmol).

After the vigorous bubbling subsided, the solution was allowed to stir for 2 hours. The solvent was then removed under reduced pressure and CH$_2$Cl$_2$ (50 mL) and saturated aqueous solution of Na$_2$CO$_3$ (30 mL) was added. The layers were separated and the aqueous phase extracted with CH$_2$Cl$_2$ (2×40 mL). The combined organic extracts were dried over anhydrous MgSO$_4$ and were concentrated under reduced pressure. The crude product was purified by silica gel flash column chromatography (5% methanol in dichloromethane as an eluent). The fractions containing the desired product were concentrated under reduced pressure to give the desired 4-oxo-2,6-diphenylpiperidine (630 mg, 17%) as a yellow oil. $^1$H NMR (CDCl$_3$) δ 2.35 (m, 2H), 2.43 (m, 2H), 4.20 (dd, 2H, J=3.3, 11.4 Hz), 5.15 (br s, 1H, NH), 7.38 (d, 4H, J=7.5 Hz), 8.58 (d, 4H, J=7.5 Hz). MS (m/z): 254.1 (M+H$^+$).

It is understood that the foregoing detailed description and accompanying Examples are merely illustrative, and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. U.S. patents and publications referenced herein are incorporated by reference.

The invention claimed is:

1. A method of making a compound of formula (3)

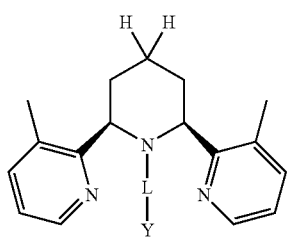

(3)

comprising contacting a compound of formula (4)

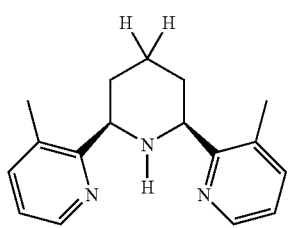

(4)

with a compound of the formula

X-L-Y wherein X is a leaving group;
L is —(CH$_2$)$_4$—; and
Y is phthalimide.

2. The method of claim 1, wherein X is halo.
3. The method of claim 1, wherein X is bromo.
4. The method of claim 1 further comprising reacting the compound of formula (3) with hydrazine hydrate to obtain a compound of formula (5)

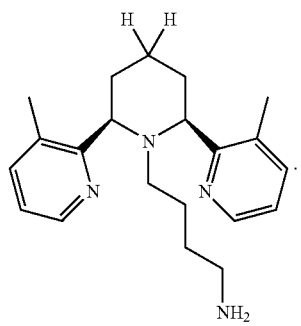

(5)

5. The method of claim 1, wherein the compound of formula (4) is prepared by reacting a compound of formula (6)

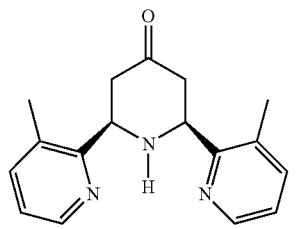

(6)

with hydrazine monohydrate in the presence of potassium hydroxide.

6. A method to prepare a compound of the formula (5)

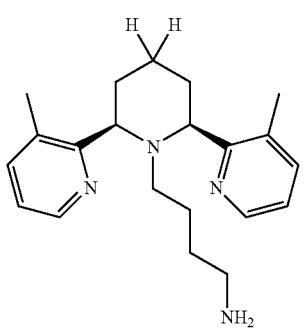

(5)

comprising the steps of:

reacting a compound of the formula (6)

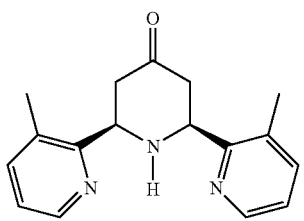

(6)

with hydrazine monohydrate in the presence of potassium hydroxide, to obtain a compound of formula (4)

111
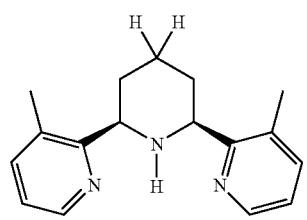
(4)
followed by
reacting the compound of formula (4) with 2-(4-bromo-butyl)-isoindole-1,3-dione, to obtain a compound of formula (7); and
112
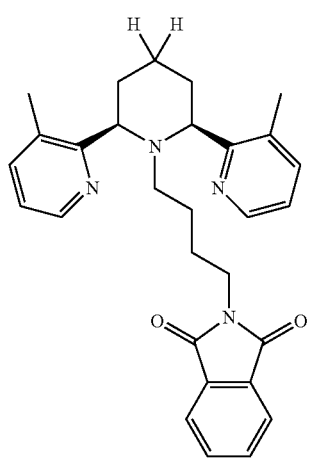
(7)
deprotecting the compound of formula (7) with hydrazine hydrate.
* * * * *